(12) United States Patent
Ahmed et al.

(10) Patent No.: US 11,883,387 B2
(45) Date of Patent: Jan. 30, 2024

(54) PQSR INVERSE AGONISTS

(71) Applicant: HELMHOLTZ-ZENTRUM FÜR INFEKTIONSFORSCHUNG GMBH, Braunschweig (DE)

(72) Inventors: Ahmed S. A. Ahmed, Braunschweig (DE); Martin Empting, Braunschweig (DE); Mostafa Hamed, Braunschweig (DE); Rolf W. Hartmann, Braunschweig (DE); Jörg Haupenthal, Braunschweig (DE); Thomas Hesterkamp, Braunschweig (DE); Ahmed A. M. Kamal, Braunschweig (DE); Christine K. Maurer, Braunschweig (DE); Teresa Röhrig, Braunschweig (DE); Christian Schütz, Braunschweig (DE); Samir Yahiaoui, Braunschweig (DE); Michael Zender, Braunschweig (DE)

(73) Assignee: Helmholtz-Zentrum Für Infektionsforschung GmbH, Braunschweig (DE)

( * ) Notice: Subject to any disclaimer, the term of this patent is extended or adjusted under 35 U.S.C. 154(b) by 295 days.

(21) Appl. No.: 17/257,804

(22) PCT Filed: Jul. 3, 2019

(86) PCT No.: PCT/EP2019/067899
§ 371 (c)(1),
(2) Date: Jan. 4, 2021

(87) PCT Pub. No.: WO2020/007938
PCT Pub. Date: Jan. 9, 2020

(65) Prior Publication Data
US 2021/0353606 A1 Nov. 18, 2021

(30) Foreign Application Priority Data
Jul. 3, 2018 (EP) ..................... 18181475

(51) Int. Cl.
*A61K 31/4439* (2006.01)
*A61P 31/04* (2006.01)
*A61K 31/444* (2006.01)
*A61K 31/506* (2006.01)
*A61K 45/06* (2006.01)
*C07D 401/12* (2006.01)
*C07D 401/14* (2006.01)
*C07D 403/12* (2006.01)
*C07D 405/14* (2006.01)
*C07D 413/12* (2006.01)
*C07D 417/12* (2006.01)
*C07D 417/14* (2006.01)
*C07D 471/04* (2006.01)

(52) U.S. Cl.
CPC ........ *A61K 31/4439* (2013.01); *A61K 31/444* (2013.01); *A61K 31/506* (2013.01); *A61K 45/06* (2013.01); *A61P 31/04* (2018.01); *C07D 401/12* (2013.01); *C07D 401/14* (2013.01); *C07D 403/12* (2013.01); *C07D 405/14* (2013.01); *C07D 413/12* (2013.01); *C07D 417/12* (2013.01); *C07D 417/14* (2013.01); *C07D 471/04* (2013.01)

(58) Field of Classification Search
CPC .............. A61K 31/4439; A61K 31/444; A61K 31/506; A61P 31/04; C07D 213/74; C07D 401/12; C07D 401/14; C07D 403/12; C07D 405/14; C07D 413/12; C07D 417/12; C07D 417/14; C07D 471/04
See application file for complete search history.

(56) References Cited

U.S. PATENT DOCUMENTS

2017/0226089 A1 8/2017 Chen et al.

FOREIGN PATENT DOCUMENTS

| CN | 108003151 A | 5/2018 |
|---|---|---|
| WO | 2012/116010 A2 | 8/2012 |
| WO | 2014/176258 A1 | 10/2014 |
| WO | 2016/007837 A1 | 1/2016 |
| WO | 2016/040764 A1 | 3/2016 |
| WO | 2016/112088 A1 | 7/2016 |

OTHER PUBLICATIONS

Zhang, Y. et al., "Enhanced Octadecane Dispersion and Biodegradation by a Pseudomonas Rhamnolipid Surfactant (Biosurfactant)", Applied and Environmental Microbiology (Oct. 1992) vol. 58, No. 10, pp. 3276-3282.

Maurer, C. et al., "Development and validation of a UHPLC-MS/MS procedure for quantification of the Pseudomonas Quinolone Signal in bacterial culture after acetylation for characterization of new quorum sensing inhibitors", Journal of Pharmaceutical and Biomedical Analysis (2013), http://dx.doi.org/10.1016/j.jpba.2013.07.047, 34 pages.

(Continued)

*Primary Examiner* — Kortney L. Klinkel
*Assistant Examiner* — Padmaja S Rao
(74) *Attorney, Agent, or Firm* — Fox Rothschild LLP

(57) ABSTRACT

The present invention relates to a compound according to general formula (I), which acts as an inhibitor of PqsR (the currently only known receptor for the *Pseudomonas* Quinolone Signal (PQS)); to a pharmaceutical composition containing one or more of the compound(s) of the invention; to a combination preparation containing at least one compound of the invention and at least one further active pharmaceutical ingredient; and to uses of said compound(s), including the use as a medicament, e.g. the use in the treatment or prophylaxis of a bacterial infection, especially a *Pseudomonas aeruginosa* or *Burkholderia* infection.

(I)

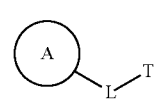

17 Claims, No Drawings

(56) References Cited

OTHER PUBLICATIONS

Ilangovan, A. et al., "Structural Basis for Native Agonist and Synthetic Inhibitor Recognition by the Pseudomonas aeruginosa Quorum Sensing Regulator PqsR (MvfR)", PLOS Pathogens (Jul. 2013) vol. 9, Issue 7, e1003508, 18 pages.
Lu, C. et al., "Overcoming the Unexpected Functional Inversion of a PqsR Antagonist in Pseudomonas aeruginosa: An In Vivo Potent Antivirulence Agent Targeting pqs Quorum Sensing", Angew. Chem. Int. Ed. (2014) 53, 1109-1112.
Lu, C. et al., "Discovery of Antagonists of PqsR, a Key Player in 2-Alkyl-4-quinolone-Dependent Quorum Sensing in Pseudomonas aeruginosa", Chemistry & Biology 19, 381-390 (Mar. 23, 2012).
Zender, M. et al., "Discovery and Biophysical Characterization of 2-Amino-Oxadiazoles as Novel Antagonists of PqsR, an Important Regulator of Pseudomonas aeruginosa Virulence", Journal of Medicinal Chemistry (Aug. 6, 2013) 52 pages.
Klein, T. et al., "Identification of Small-Molecule Antagonists of the Pseudomonas aeruginosa Transcriptional Regulator PqsR: Biophysically Guided Hit Discovery and Optimization", ACS Chem. Biol., dx.doi.org/10.1021/cb300208g (Jun. 20, 2012) 6 pages.
Coleman, J.P. et al., "Pseudomonas aeruginosa PqsA Is an Anthranilate-Coenzyme A Ligase", Journal of Bacteriology (Feb. 2008) vol. 190, No. 4, pp. 1247-1255.
Storz, M.P. et al., "Validation of PqsD as an Anti-biofilm Target in Pseudomonas aeruginosa by Development of Small-Molecule Inhibitors", Journal of the American Chemical Society (2012) 134, pp. 16143-16146, dx.doi.org/10.1021/ja3072397.
Lesic, B. et al., "Inhibitors of Pathogen Intercellular Signals as Selective Anti-Infective Comounds", PLoS Pathogens (Sep. 2007) vol. 3, Issue 9, pp. 1229-1239.
Pistorius, D. et al., "Biosynthesis of 2-Alkyl-4(1H)-Quinolones in Pseudomonas aeruginosa:: Potential for Therapeutic Interference wiht Pathogenicity" ChemBioChem (2011), 12, pp. 850-853.
Calfee, M.W. et al., "Interference with Pseudomonas quinolone signal synthesis inhibits virulence factor expression by Pseudomonas aeruginosa", PNAS (Sep. 25, 2001) vol. 98, No. 20, pp. 11633-11637.
Weidel, E. et al., "Structure Optimization of 2-Benzamidobenzoic Acids as PqsD Inhibitors for Pseudomonas aeruginosa Infections and Elucidation of Binding Mode by SPR, STD NMR and Molecular Docking", J. Med. Chem. (Jul. 8, 2013) 37 pages.
Sahner, J.H. et al., "Combining In Silico and Biophysical Methods for the Development of Pseudomonas aeruginosa Quorum Sensing Inhibitors # An Alternative Approach for Structure-Based Drug Design", J. Med. Chem. (Oct. 1, 2013) 29 pages.
Storz, M.P. et al., "Biochemical and Biophysical Analysis of a Chiral PqsD Inhibitor Revealing Tight-binding Behavior and Enantiomers with Contrary Thermodynamic Signatures", ACS Chem. Biol. (2013) 8, pp. 2794-2801, dx.doi.org/10.1021/cb400530d.
Hinsberger, S. et al., "Benzamidobenzoic acids as potent PqsD inhibitors for the treatment of Pseudomonas aeruginosa infections", European Journal of Medicinal Chemistry, 76 (2014) pp. 343-351.
Jakobsen, T.H. et al., "Ajoene, a Sulfer-Rich Molecule from Garlic, Inhibits Genes Controlled by Quorum Sensing", Antimicrobial Agents and Chemotherapy (Feb. 6, 2012) pp. 2314-2325.
Rasmussen, T.B. et al., "Identity and effects of quorum-sensing inhibitors produced by Penicillium species", Microbiology (2005) 151, pp. 1325-1340.
Hentzer, M. et al., "Inhibition of quorum sensing in Pseudomonas aeruginosa biofilim bacteria by a halogenated furanone compound", Microbiology (2002) 148, pp. 87-102.
Hentzer, M. et al., "Attenuation of Pseudomonas aeruginosa virulence by quorum sensing inhibitors", The EMBO Journal, vol. 22, No. 15, pp. 3803-3815 (2003).
O'Loughlin, C.T. et al., "A quorum-sensing inhibitor blocks Pseudomonas aeruginosa virulence and biofilm formation", PNAS (Oct. 29, 2013) vol. 110, No. 44, pp. 17981-17986.
Yang, L. et al., "Computer-Aided Identification of Recognized Drugs as Pseudomonas aeruginosa Quorum-Sensing Inhibitors", Antimicrobial Agents and Chemotherapy (Jun. 2009) vol. 53, No. 6, pp. 2432-2443.
Frei, R. et al., "2-Aminobenzimidazole Derivatives Strongly Inhibit and Disperse Pseudomonas aeruginosa Biofilms", Angew. Chem. Int. Ed. (2012) 51, pp. 1-5.
Seenaiah Dandu et al: "Synthesis and antimicrobial activity of pyrimidinyl bis(benzazoles)", Medicinal Chemistry Research, Birkhaeuser, Boston, US, vol. 26, No. 2 (Dec. 21, 2016) pp. 431-441, XP036140806, ISSN: 1054-2523, DOI: 10.1007/S00044-016-1758-9 (retrieved on Dec. 21, 2016) table 1; compounds 5b, 5c.
Database Registry (Online) Chemical Abstracts Service, Columbus, Ohio, US (Feb. 17, 2014) XP002785624, Database accession No. 1546402-30-5 abstract.
International Search Report for International Patent Application No. PCT/EP2019/067899, dated Sep. 17, 2019, 5 pages.

PQSR INVERSE AGONISTS

CROSS-REFERENCES TO RELATED APPLICATIONS

This application is a U.S. national phase application, pursuant to 35 U.S.C. § 371, of PCT/EP2019/067899, filed Jul. 3, 2019, designating the United States, which claims priority to European Application No. 18181475.7, filed Jul. 3, 2018. The entire contents of the aforementioned patent applications are incorporated herein by this reference.

FIELD OF THE INVENTION

The present invention relates to a compounds according to general formula (I), which acts as an inverse of PqsR (the currently only known receptor for the *Pseudomonas* Quinolone Signal (PQS), sometimes also referred to as MvfR); to a pharmaceutical composition containing one or more of the compound(s) of the invention; to a combination preparation containing at least one compound of the invention and at least one further active pharmaceutical ingredient; and to uses of said compound(s), including the use as a medicament, e.g. the use in the treatment or prophylaxis of a bacterial infection, especially a *Pseudomonas aeruginosa* or *Burkholderia* infection.

BACKGROUND OF THE INVENTION

In view of the rapid decline in the effectiveness of antibiotics due to the emergence of resistance, there is a need for a constant supply of new compounds for effective treatment of infections. The development of antimicrobial resistance is mainly attributed to the overuse of antibiotics interfering with essential metabolic processes in bacteria. Moreover, bacteria living in biofilms, sessile cell communities embedded in a matrix of extracellular polymeric substances showing reduced metabolic activity and growth rate, exhibit up to 1000 fold higher resistance against antibiotics than free-living bacteria. Thus, novel therapeutic approaches that aim at reducing bacterial pathogenicity by interfering with bacterial virulence and biofilm formation instead of their metabolic activity are considered as highly favourable and are urgently needed.

The opportunistic pathogen *P. aeruginosa* causes severe and fatal infections including such of the urinary tract, of the gastrointestinal tract, of chronic and burnt wounds, of the eyes, of the ears, and of the lungs. Its pathogenicity is strongly related to the expression of virulence factors causing progressive tissue damage and biofilm formation hindering a successful drug therapy. The regulation of pathogenicity is based on a cell-density dependent intercellular communication system known as quorum sensing (QS).

*P. aeruginosa* uses as signal molecules N-acyl-L-homoserine lactones (AHLs) for the las and rhl QS systems and 2-alkyl-4-(1H)-quinolones (AQs) for the pqs QS system. The latter is restricted to *Pseudomonas* and *Burkholderia* species allowing for selective therapy with pqs QS inhibitors. While *Pseudomonas* and *Burkholderia* both produce 2-heptyl-4-hydroxyquinoline (HHQ), *Pseudomonas* uniquely uses the *Pseudomonas* quinolone signal (PQS) as signal molecule. PQS and its biosynthetic precursor HHQ serve as the natural ligands and agonists of the key DNA-binding receptor PqsR. This transcriptional regulator fine-tunes a large set of genes, notably such involved in the biosynthesis of HHQ and in the production of virulence factors such as pyocyanin and lectins. Regarding biofilms, the production of extracellular DNA (eDNA) and lectins, both main biofilm matrix components, is controlled by the pqs QS system. A pqsR mutant of *P. aeruginosa* is pqs QS-deficient, does not produce any pyocyanin or lectin A, shows reduced eDNA production, and displays reduced pathogenicity in mice.

To date, a number of compounds have been discovered that target QS in *P. aeruginosa*. The majority of these compounds has been reported to interfere with the AHL-based QS systems in *Pseudomonas* either via direct interaction with the receptors LasR [1, 2] or RhlR [3], at the posttranscriptional level [4-6], or at superior regulatory systems [7]. However, except an extract from *Allium sativum* (garlic), that exhibited no significant improvement of lung function in a clinical trial, these QS inhibitors have been only used in preclinical studies. Whereas AHL-mediated QS is widespread among Gram-negative bacteria, interference with pqs QS allows for selective therapy avoiding adverse effects on beneficial bacterial consortia present in the host. A few pqs QS inhibitors have been described acting as blockers of the signal molecule biosynthesis [8-16] or as antagonists of the receptor PqsR [17-21]. A QS inhibitor based on anthranilate structure, methyl anthranilate, was shown to inhibit PQS formation and the production of the virulence factor elastase at millimolar concentrations [12]. QS inhibitors targeting the enzyme PqsA were able to reduce the production of signal molecules HHQ and PQS ($IC_{50}$: ~100 µM for 6FABA) [14, 16, 22] and enhanced the survival rate of *Pseudomonas*-infected mice in a thermal injury mice model [14]. However, high concentrations were necessary to obtain an in cellulo or in vivo effect. Inhibitors of the enzyme PqsD were able to reduce the biovolume of a *P. aeruginosa* biofilm [15], however, did not exhibit any anti-virulence properties (no effect on virulence factor pyocyanin, no effect on the survival of *Pseudomonas*-infected *Galleria mellonella* larvae; unpublished data). Zender [18] and Klein [17] reported PqsR antagonists affecting the production of virulence factor pyocyanin, however with moderate potency ($IC_{50}$ values in the double-digit micromolar range). Furthermore, these compounds did not inhibit biofilm formation (unpublished data). Quinazoline-based PqsR antagonists developed in the group of Paul Williams [21] were reported to exhibit anti-virulence activity. However, the most promising compound was only moderately active in reducing pyocyanin production ($IC_{50}$~50 µM in a less PQS- and pyocyanin-producing *P. aeruginosa* strain). A reduction in biomass of a *P. aeruginosa* biofilm by this compound was observed, however at an unknown concentration. Another potent antagonist of PqsR is 2-heptyl-6-nitro-4-oxo-1,4-dihydroquinoline-3-carboxamide and was developed in the group of Anke Steinbach and Rolf W. Hartmann[20]. 2-heptyl-6-nitro-4-oxo-1,4-dihydroquinoline-3-carboxamide is highly affine to PqsR ($IC_{50}$=35 nM in *E. coli* reporter gene assay, $IC_{50}$=400 nM in *P. aeruginosa* reporter gene assay), strongly reduces signal molecule production (HHQ production by 54% and PQS by 37% at 15 µM), and shows excellent anti-virulence potency in cellulo (inhibition of virulence factor pyocyanin production: $IC_{50}$=2 µM) and in in vivo animal infection models. Further reported PqsR-targeting compounds have been described by the working group of Laurance Rahme (DOI: 10.1371/journal.ppat.1004321; WO2012116010) and in follow-up patents by Spero Therapeutics (WO2014176258, WO2016040764, WO2016007837, WO2016112088). These compound classes show activity against pyocyanin and alkylquinolone production in the nanomolar range. The compounds commonly referred to as M64 and SPR-00305

(205 in WO2016112088) suffer from pharmakokinetic drawbacks (e.g. low metabolic stability).

All in all, the hitherto known compounds show a number of deficiencies hampering their utility as a drug, including low metabolic stability, low bioavailability/solubility, low selectivity and toxicity.

In view of the deficits of the prior art compounds and the severe conditions associated with antibiotic resistant microorganisms, both acute and chronic, there is a need for novel anti-pathogenic compounds exhibiting both anti-virulence and anti-biofilm activity, especially compounds having inverse agonistic activity on PqsR to thereby permit an effective treatment of bacterial infections.

SUMMARY AND DESCRIPTION OF THE INVENTION

The present invention was made in view of the prior art and the needs described above, and, therefore, the object of the present invention is to provide novel PqsR inverse agonists according to general formula (I), preferably PqsR inverse agonists having one or more improved properties, e.g. biofilm inhibition (biovolume reduction and/or eDNA suppression), high antivirulence activity, an improved pharmacokinetic and/or physiochemical property, including bioavailability, solubility, and metabolic stability. Other objects of the present invention are to provide a pharmaceutical composition comprising at least one PqsR inverse agonist as described herein; a combination preparation containing at least one compound of the invention and at least one further active pharmaceutical ingredient; and uses of the compound(s) of the invention, including the use as a medicament, e.g. the use in the treatment or prophylaxis of a bacterial infection, especially a *Pseudomonas aeruginosa* or *Burkholderia* infection.

These objects are solved by the subject matter of the attached claims as will become apparent upon reference to the following description and definitions.

The present invention relates to:
[1] A compound having the formula (I):

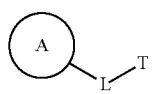

or a pharmacologically acceptable salt thereof, wherein
A represents a group:

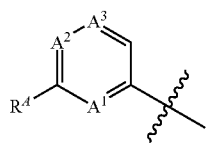

wherein
$A^1$ and $A^2$ each, independently of one another, represents N or CH;
$A^3$ is N or C—$R^{43}$;
$R^{43}$ represents a hydrogen atom, a halogen atom, $CF_3$, CN, C(=O)$NH_2$, C(=O)OH, $CH_2OH$, $CH_2NH_2$, OH, OMe, or $NH_2$;
at least one of $A^1$, $A^2$ and $A^3$ being N;
$R^4$ represents $CF_3$, CN, Cl, $NO_2$ or F;

L is a group represented by formula (L-1) or (L-2):

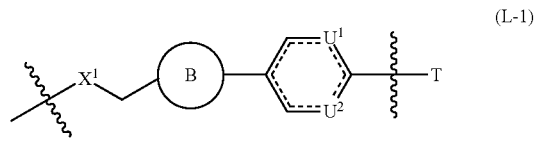

wherein
$X^1$ is NH or S;
ring B is a partially unsaturated or aromatic, 5-membered heterocyclic ring represented by formula (B-1) or 6-membered heterocyclic ring represented by formula (B-2):

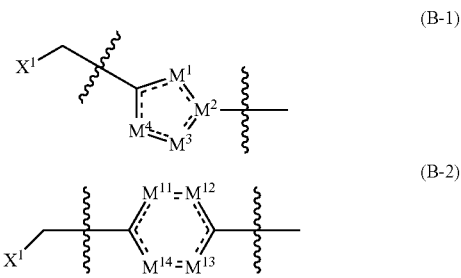

wherein
$M^1$, $M^3$ and $M^4$ each, independently of one another, represents CH, N, NH, O, or S;
$M^2$ represents C or N;
$M^{11}$, $M^{12}$, $M^{13}$, and $M^{14}$ each, independently of one another, represents CH or N;
at least one of $M^1$, $M^2$, $M^3$, $M^4$, M, $M^{12}$, $M^{13}$, and $M^{14}$ being a group with a heteroatom as defined above;
$U^1$ and $U^2$ each, independently of one another, represents N or C($R^1$);
$R^1$, at each occasion independently, represents a hydrogen atom, a halogen atom, OH, CN, $CF_3$, $CH_2$—OH, $OCH_3$, $OCF_3$; or an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group;
each " ---- ", independently of one another, represents a single bond or a double bond, wherein at least one " --- " in each of the rings of formulae (L-1), (B-1) and (B-2) is a double bond;

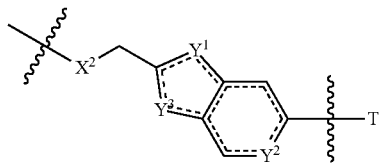

wherein
$X^2$ is NH, O, or S;
$Y^1$ and $Y^3$ each, independently of one another, represents CH, N, NH, O, or S;
$Y^2$ represents N or C($R^{11}$);
$R^{11}$ represents a hydrogen atom, a halogen atom, OH, CN, $CF_3$, $CH_2$—OH, $OCH_3$, $OCF_3$; or an alkyl, alkenyl, alkynyl, heteroalkyl, cycloalkyl, heterocycloalkyl, alkylcycloalkyl, heteroalkylcycloalkyl, heteroaryl, aralkyl or heteroaralkyl group;

each " ---- ", independently of one another, represents a single bond or a double bond, wherein at least one " --- " in the ring of formula (L-2) is a double bond;

T is $R^2$ or a group: —Y—$R^3$, wherein $R^2$ is a hydrogen atom, a halogen atom, CN, $CF_3$, $CH_2$—OH; $NR^{T1}R^{T2}$; or an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which groups may optionally be substituted;

$R^{T1}$ and $R^{T2}$ each, independently of one another, represents a hydrogen atom or a ($C_1$-$C_3$)alkyl group, which may be substituted by one or more, identical or different, group(s) selected from a halogen atom, OH, =O, and $NH_2$;

Y is —O— or —S—; and $R^3$ is a hydrogen atom; or an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which groups may optionally be substituted.

More specifically, the present invention is directed to:

[1A] a compound having the formula (I):

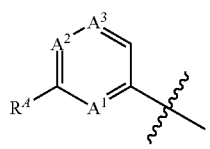
(I)

or a pharmacologically acceptable salt thereof,
wherein
A represents a group:

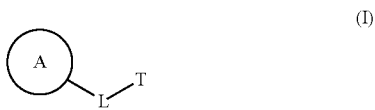

wherein
said group A is as defined in (i) or (ii):
(i) $A^1$ is CH; $A^2$ is N;
$A^3$ is N or C—$R^{43}$
$R^{43}$ represents a hydrogen atom, a halogen atom, $CF_3$, CN, C(=O)$NH_2$, C(=O)OH, $CH_2$OH, $CH_2NH_2$, OH, OMe, or $NH_2$; and
$R^A$ represents $CF_3$, CN, Cl, $NO_2$ or F; or
(ii) $A^1$ is N; $A^2$ is N; $A^3$ is C—$NH_2$; and $R^A$ represents $CF_3$, CN, Cl, $NO_2$ or F;

L is a group represented by formula (L-1) or (L-2):

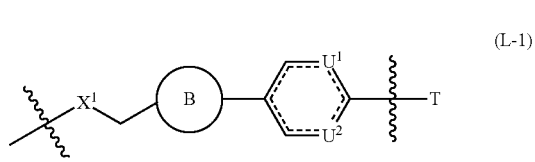
(L-1)

wherein
$X^1$ is NH or S;
ring B is a partially unsaturated or aromatic, 5-membered heterocyclic ring represented by formula (B-1) or 6-membered heterocyclic ring represented by formula (B-2):

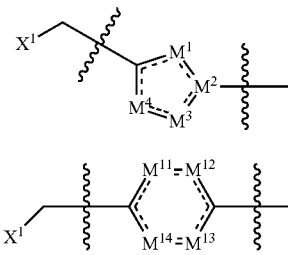
(B-1)

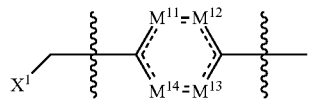
(B-2)

wherein
the ring represented by formula (B-1) is:
(i) a ring, wherein $M^1$ is CH; $M^2$ is C or N; and each of $M^3$ and $M^4$, independently of one another, is N or NH; or
(ii) a ring, wherein $M^1$ is S; $M^2$ is C; and each of $M^3$ and $M^4$, independently of one another, is CH or N;

$M^{11}$, $M^{12}$, $M^{13}$, and $M^{14}$ each, independently of one another, represents CH or N;

at least one of $M^{11}$, $M^{12}$, $M^{13}$, and $M^{14}$ being a group with a heteroatom as defined above;

$U^1$ and $U^2$ each, independently of one another, represents N or C($R^1$);

$R^1$, at each occasion independently, represents a hydrogen atom, a halogen atom, OH, CN, $CF_3$, $CH_2$—OH, $OCH_3$, $OCF_3$; or an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group;

each " ---- " of one another, represents a single bond or a double bond, wherein at least one " --- " in each of the rings of formulae (L-1), (B-1) and (B-2) is a double bond;

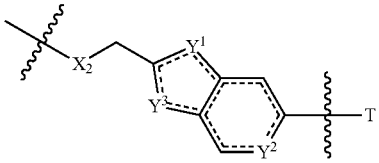
(L-2)

wherein
$X^2$ is NH, O or S;
$Y^1$ represents N, NH, S or O;
$Y^2$ represents N or C($R^{11}$)
$Y^3$ represents N or NH;
$R^{11}$ represents a hydrogen atom, a halogen atom, OH, CN, $CF_3$, $CH_2$—OH, $OCH_3$, $OCF_3$; or an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group;

each " ---- ", independently of one another, represents a single bond or a double bond, wherein at least one " --- " in the ring of formula (L-2) is a double bond;

T is $R^2$ or a group: —Y—$R^3$, wherein
$R^2$ is a hydrogen atom, a halogen atom, CN, $CF_3$, $CH_2$—OH; $NR^{T1}R^{T2}$; or an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which groups may optionally be substituted;

$R^{T1}$ and $R^{T2}$ each, independently of one another, represents a hydrogen atom or a $(C_1-C_3)$alkyl group, which may be substituted by one or more, identical or different, group(s) selected from a halogen atom, OH, =O, and NH$_2$;

Y is —O— or —S—; and $R^3$ is a hydrogen atom; or an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which groups may optionally be substituted.

Compounds are usually described herein using standard nomenclature or the definitions presented below. For compounds having asymmetric centers, it should be understood that, unless otherwise specified, all of the optical isomers and mixtures thereof are encompassed. Compounds with two or more asymmetric elements can also be present as mixtures of diastereomers. In addition, compounds with carbon-carbon double bonds may occur in Z- and E-forms, with all isomeric forms of the compounds being included in the present invention unless otherwise specified. Where a compound exists in various tautomeric forms, a recited compound is not limited to any one specific tautomer, but rather is intended to encompass all tautomeric forms. It will be apparent that the compound of the invention may, but need not, be present as a hydrate, solvate or non-covalent complex. In addition, the various crystal forms and polymorphs are within the scope of the present invention, as are prodrugs of the compound of the invention. Recited compounds are further intended to encompass compounds in which one or more atoms are replaced with an isotope, i.e., an atom having the same atomic number but a different mass number. By way of general example, and without limitation, isotopes of hydrogen include tritium and deuterium and isotopes of carbon include $^{11}C$, $^{13}C$, and $^{14}C$.

Compounds according to the formulas provided herein, which have one or more stereogenic center(s), have an enantiomeric excess of at least 50%. For example, such compounds may have an enantiomeric excess of at least 60%, 70%, 80%, 85%, 90%, 95%, or 98%. Some embodiments of the compounds have an enantiomeric excess of at least 99%. It will be apparent that single enantiomers (optically active forms) can be obtained by asymmetric synthesis, synthesis from optically pure precursors or by resolution of the racemates. Resolution of the racemates can be accomplished, for example, by conventional methods such as crystallization in the presence of a resolving agent, or chromatography, using, for example a chiral HPLC column.

The compound according to the invention is described herein using a general formula that includes variables such as, e.g. A, $A^1$-$A^3$, L, T, $M^1$-$M^4$, $M^{11}$-$M^{14}$, $R^4$, $R^{43}$, $R^1$-$R^3$, $R^{T1}$-$R^{T2}$, $R^{E1}$-$R^{E3}$, and $R^{G1}$-$R^{G3}$, $U^1$-$U^2$, $X^1$-$X^2$, Y and $Y^1$-$Y^3$. Unless otherwise specified, each variable within such a formula is defined independently of any other variable, and any variable that occurs more than one time in a formula is defined independently at each occurrence. Thus, for example, if a group is shown to be substituted with 0-2 R*, the group may be unsubstituted, or substituted with 1 or 2 group(s) R*, wherein R* at each occurrence is selected independently from the corresponding definition of R*. Also, combinations of substituents and/or variables are permissible only if such combinations result in stable compounds, i.e., compounds that can be isolated, characterized and tested for biological activity.

As used herein a wording defining the limits of a range of length such as, e. g., "from 1 to 5" means any integer from 1 to 5, i. e. 1, 2, 3, 4 and 5. In other words, any range defined by two integers explicitly mentioned is meant to comprise and disclose any integer defining said limits and any integer comprised in said range. For example, the term "$C_1$-$C_3$" refers to 1 to 3, i.e. 1, 2 or 3, carbon atoms; and the term "$C_1$-$C_6$" refers to 1 to 6, i.e. 1, 2, 3, 4, 5 or 6, carbon atoms. Further, the prefix "$(C_{x-y})$" as used herein means that the chain, ring or combination of chain and ring structure as a whole, indicated in direct association of the prefix, may consist of a minimum of x and a maximum of y carbon atoms (i.e. x<y), wherein x and y represent integers defining the limits of the length of the chain (number of carbon atoms) and/or the size of the ring (number of carbon ring atoms).

A "pharmacologically acceptable salt" of a compound disclosed herein is an acid or base salt that is generally considered in the art to be suitable for use in contact with the tissues of human beings or animals without excessive toxicity or carcinogenicity, and preferably without irritation, allergic response, or other problem or complication. Such pharmaceutical salts include mineral and organic acid salts of basic residues such as amines, as well as alkali or organic salts of acidic residues such as carboxylic acids.

Suitable pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—(CH$_2$)$_n$—COOH where n is any integer from 0 to 4 (i.e., 0, 1, 2, 3, or 4) and the like. Similarly, pharmaceutically acceptable cations include, but are not limited to sodium, potassium, calcium, aluminum, lithium and ammonium. Those of ordinary skill in the art will recognize further pharmacologically acceptable salts for the compounds provided herein. In general, a pharmacologically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in water or in an organic solvent, or in a mixture of the two. Generally, the use of nonaqueous media, such as ether, ethyl acetate, ethanol, isopropanol or acetonitrile, is preferred.

A "substituent," as used herein, refers to a molecular moiety that is covalently bonded to an atom within a molecule of interest. For example, a substituent on a ring may be a moiety such as a halogen atom, an alkyl, haloalkyl, hydroxy, cyano, or amino group, or any other substituent described herein that is covalently bonded to an atom, preferably a carbon or nitrogen atom, that is a ring member.

The term "substituted," as used herein, means that any one or more hydrogen atom(s) on the designated atom or group (e.g. alkyl, alkoxy, alkoxyalkyl, cycloalkyl, heterocycloalkyl, heteroaryl) is replaced with a selection from the indicated substituents, provided that the designated atom's normal valence or the group's number of possible sites for substitution is not exceeded, and that the substitution results in a stable compound, i.e. a compound that can be isolated, characterized and tested for biological activity. When a substituent is oxo, i.e., =O, then 2 hydrogens on the atom are replaced. An oxo group that is a substituent of an aromatic carbon atom results in a conversion of —CH— to —C(=O)— and may lead to a loss of aromaticity. For example, a pyridyl group substituted by oxo is a pyridone. The indication mono-, di-, tri or tetrasubstituted denotes groups having one (mono), two (di), three (tri) or four substituents, provided that the substitution does not exceeded the number of possible sites for substitution and results in a stable compound. For example, a monosubstituted imidazolyl group may be an (imidazolidin-2-on)yl group and a disubstituted isoxazolyl group may be a ((3,5-dimethyl)isoxazolyl) group.

As used herein, "comprising", "including", "containing", "characterized by", and grammatical equivalents thereof are inclusive or open-ended terms that do not exclude additional, unrecited elements or method steps. Yet, "Comprising", etc. is also to be interpreted as including the more restrictive terms "consisting essentially of" and "consisting of", respectively.

As used herein, "consisting of" excludes any element, step, or ingredient not specified in the claim.

When trade names are used herein, it is intended to independently include the trade name product formulation, the generic drug, and the active pharmaceutical ingredient(s) of the trade name product.

In general, unless defined otherwise, technical and scientific terms used herein have the same meaning as commonly understood by one of ordinary skill in the art to which this invention belongs, and are consistent with general textbooks and dictionaries.

The expression "optionally substituted" refers to groups in which one or more hydrogen atoms, e.g. 1 to 6 hydrogen atoms, have been replaced each independently of the others by fluorine, chlorine, bromine or iodine atoms; or by OH, =O, SH, =S, $NH_2$, =NH, CN or $NO_2$ groups. This expression refers furthermore to groups in which one or more hydrogen atoms have been replaced each independently of the others by unsubstituted $C_1$-$C_6$alkyl, ($C_1$-$C_6$) haloalkyl (e.g. a fluoromethyl, trifluoromethyl, chloromethyl, (1- or 2-)haloethyl (e.g. (1- or 2-) chloroethyl), or (2- or 3-) halopropyl (e.g. (2- or 3-) fluoropropyl) group), ($C_1$-$C_6$) hydroxyalkyl (e.g. a hydroxymethyl, (1- or 2-)hydroxyethyl, or (2- or 3-) hydroxypropyl group), unsubstituted $C_2$-$C_6$alkenyl, unsubstituted $C_2$-$C_6$alkynyl, unsubstituted $C_1$-$C_6$heteroalkyl, unsubstituted $C_3$-$C_{10}$cycloalkyl, unsubstituted $C_2$-$C_9$heterocycloalkyl, unsubstituted $C_6$-$C_{10}$aryl, unsubstituted $C_1$-$C_9$heteroaryl, unsubstituted $C_7$-$C_{12}$aralkyl or unsubstituted $C_2$-$C_{11}$ heteroaralkyl groups.

The expression alkyl or alkyl group denotes a saturated, straight-chain or branched hydrocarbon group that contains from 1 to 20 carbon atoms, preferably from 1 to 12 carbon atoms, more preferably from 1 to 6 carbon atoms, or the number of carbon atoms indicated in the prefix. If an alkyl is substituted, the substitution may take place, independently of one another, by mono-, di-, or tri-substitution of individual carbon atoms of the molecule, e.g. 1, 2, 3, 4, 5, 6, or 7 hydrogen atom(s) may, at each occasion independently, be replaced by a selection from the indicated substituents. The foregoing also applies if the alkyl group forms a part of a group, e.g. haloalkyl, hydroxyalkyl, alkylamino, alkoxy, or alkoxyalkyl. Examples of an alkyl group include methyl, ethyl, propyl, iso-propyl, n-butyl, iso-butyl, sec-butyl, tert-butyl, n-pentyl, iso-pentyl, n-hexyl, 2,2-dimethylbutyl, or n-octyl, and examples of a substituted alkyl group or a group where the alkyl forms a part of a group, include haloalkyl, e.g. a trifluoromethyl or a difluoromethyl group; hydroxyalkyl, e.g. hydroxymethyl or 2-hydroxyethyl group, and a methoxymethyl group. The term "($C_{1-6}$) alkyl" includes, for example, $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$—, $H_3C$—$CH_2$—$CH(CH_2CH_3)$—, —$CH_2CH_2CH_2CH_2CH_2CH_3$, —$CH(CH_3)CH_2CH_2CH_2CH_3$, ($H_3CH_2C$)$CH(CH_2CH_2CH_3)$—, —$C(CH_3)_2(CH_2CH_2CH_3)$, —$CH(CH_3)CH(CH_3)CH_2CH_3$, and —$CH(CH_3)CH_2CH(CH_3)_2$.

The expression alkenyl refers to an at least partially unsaturated, straight-chain or branched hydrocarbon group that contains one or more double bond(s) and from 2 to 20 carbon atoms, preferably from 2 to 12 carbon atoms, more preferably from 2 to 6 carbon atoms, for example an ethenyl (vinyl), propenyl (allyl), iso-propenyl, butenyl, isoprenyl or hex-2-enyl group. Preferably, an alkenyl group has one or two, especially one, double bond(s).

The expression alkynyl refers to an at least partially unsaturated, straight-chain or branched hydrocarbon group that contains one or more triple bond(s) and from 2 to 20 carbon atoms, preferably from 2 to 12 carbon atoms, more preferably from 2 to 6, e.g. 2, 3 or 4, carbon atoms, for example an ethynyl (acetylenyl), propynyl, butynyl or propargyl group. Preferably, an alkynyl group has one or two, especially one, triple bond(s).

The expression alkoxy or alkoxy group refers to an alkyl group singular bonded to oxygen, i.e. —O-alkyl. The term "($C_1$-$C_6$) alkoxy" includes, for example, methoxy, ethoxy, n-propoxy, isopropoxy, n-butoxy, sec-butoxy, isobutoxy, tert-butoxy, n-pentyloxy, tert-amyloxy- or n-hexyloxy, and accordingly ($C_1$-$C_3$)alkoxy includes methoxy, ethoxy, n-propoxy, or isopropoxy.

The expression alkoxyalkyl or alkoxyalkyl group refers to an alkyl group singular bonded to one or more alkoxy group(s), e.g. -alkyl-O-alkyl or -alkyl-O-alkyl-O-alkyl. The term "($C_2$-$C_5$) alkoxyalkyl" includes, for example, methoxymethyl, methoxyethoxymethyl, and 1-ethoxyethyl.

The expression haloalkyl or haloalkyl group refers to an alkyl group in which one, two, three or more hydrogen atoms have been replaced independently of each other by a halogen atom. The term "($C_1$-$C_3$) haloalkyl" includes, for example, fluoromethyl, difluoromethyl, trifluoromethyl, chloromethyl, dichloromethyl, bromomethyl, dibromomethyl, iodomethyl, (1- or 2-)haloethyl (e.g. (1- or 2-)fluoroethyl or (1- or 2-)chloroethyl), (2- or 3-) halopropyl (e.g. (2- or 3-) fluoropropyl or (2- or 3-) chloropropyl).

The expression hydroxyalkyl or hydroxyalkyl group refers to an alkyl group in which one, two, three or more hydrogen atoms have been replaced independently of each other by a hydroxy (OH) group. The term "($C_1$-$C_4$) hydroxyalkyl" includes, for example, hydroxymethyl, hydroxyethyl, hydroxypropyl and hydroxybutyl.

As used herein, the expression heteroalkyl or heteroalkyl group refers to an alkyl group, straight chain or branched as defined above, in which one or more, preferably 1, 2, 3 or 4, carbon atom(s) has/have been replaced, each independently of one another, by an oxygen, nitrogen, selenium, silicon or sulphur atom, preferably by an oxygen, sulphur or nitrogen atom, C(O), OC(O), C(O)O, C(O)NH, NH, SO, $SO_2$ or by a CH=CH group, wherein said heteroalkyl group may be substituted. For example, a "($C_1$-$C_4$)heteroalkyl group" contains from 1 to 4, e.g. 1, 2, 3 or 4, carbon atoms and 1, 2, 3 or 4, preferably 1, 2 or 3, heteroatoms selected from oxygen, nitrogen and sulphur (especially oxygen and nitrogen). Examples of an heteroalkyl group include alkylamino, dialkylamino, alkylaminoalkyl, dialkylaminoalkyl, acyl, acylalkyl, alkoxycarbonyl, acyloxy, acyloxyalkyl, carboxyalkylamide, alkoxycarbonyloxy, alkylcarbamoyl, alkylamido, alkylcarbamoylalkyl, alkylamidoalkyl, alkylcarbamoyloxyalkyl, alkylureidoalkyl, alkoxy, alkoxyalkyl, or alkylthio group. The expression alkylthio or alkylthio group refers to an alkyl group, in which one or more non-adjacent $CH_2$ group(s) are replaced by sulfur, wherein the alkyl moiety of the alkylthio group may be substituted. Specific examples of a heteroalkyl group include acyl, methoxy, trifluoromethoxy, ethoxy, n-propyloxy, isopropyloxy, tert-butyloxy, methoxymethyl, ethoxymethyl, methoxyethyl, methylamino, ethylamino, dimethylamino, diethylamino, isopropylethylamino, methylaminomethyl, ethylaminomethyl, diisopropylaminoethyl, dimethylaminomethyl, dimethylaminoethyl, acetyl, propionyl, butyryloxy, acetyloxy, methoxycarbonyl, ethoxycarbonyl, isobutyrylaminomethyl, N-ethyl-N-methylcarbamoyl, N-methylcarbamoyl, cyano, nitrile, isonitrile, thiocyanate, isocyanate, isothiocyanate and alkylnitrile.

The expression cycloalkyl or cycloalkyl group refers to a saturated carbocyclic ring group comprising one or more rings (preferably 1 or 2) and containing from 3 to 14 ring carbon atoms, preferably from 3 to 10 (more preferably 3, 4, 5, 6 or 7) ring carbon atoms; the cycloalkyl group may be substituted and can be bonded as a substituent via every suitable position of the ring system. Examples of cycloalkyl include monocyclic hydrocarbon rings, bicyclic hydrocarbon rings and spiro-hydrocarbon rings. In a bicyclic cycloalkyl group, two rings are joined together so that they have at least two carbon atoms in common. In a spiro-hydrocarbon ring, 2 or 3 rings are linked together by one common atom carbon atom (spiro-atom). If a cycloalkyl is substituted, the substitution may take place, independently of one another, by mono- or di-substitution of individual ring carbon atoms of the molecule, and the cycloalkyl group as a whole may carry 1, 2, 3, or 4 substituents from the indicated selection of substituents, i.e. 1, 2, 3, or 4 hydrogen atom(s) of the carbon ring atoms may, at each occasion independently, be replaced by a substituent selected from the indicated list of substituents thereby resulting in a mono-, di-, tri-, or tetra-substituted cycloalkyl group. Examples of cycloalkyl include cyclopropyl, cyclobutyl, cyclopentyl, cyclohexyl, cycloheptyl, bicyclo[2.2.0]hexyl, bicyclo[3.2.0]heptyl, bicyclo[3.2.1]octyl, bicyclo[2.2.2]octyl, bicyclo[4.3.0]nonyl (octahydroindenyl), bicyclo[4.4.0]decyl (decahydronaphthyl), bicyclo[2.2.1]heptyl (norbornyl), bicyclo[4.1.0]heptyl (norcaranyl), bicyclo[3.1.1]heptyl (pinanyl), spiro[2.5]octyl, and spiro[3.3]heptyl. If a cycloalkyl is partially unsaturated, the group contains one, two or more double bonds, such as, for example, a cycloalkenyl group, including cyclopropenyl, cyclobutenyl, cyclopentenyl, cyclohexenyl, cycloheptenyl, cyclobutadienyl, cyclopentadienyl, cyclohexadienyl, bicyclo[2.2.1]heptadienyl, and spiro[4,5]decenyl.

The expression heterocycloalkyl or heterocycloalkyl group refers to a cycloalkyl group, saturated or partially unsaturated, as defined above, in which one or more, preferably 1, 2 or 3, ring carbon atom(s) has/have been replaced each independently of one another by an oxygen, nitrogen or sulphur atom, preferably oxygen or nitrogen, or by NO, SO or $SO_2$; the heterocycloalkyl may be substituted and can be bonded as a substituent via every suitable position of the ring system; at least one carbon atom must be present between two oxygen atoms and between two sulphur atoms or between an oxygen and a sulphur atom; and the ring as a whole must have chemical stability. A heterocycloalkyl group has preferably 1 or 2 ring(s) containing from 3 to 10 (more preferably 3, 4, 5, 6 or 7, and most preferably 5, 6 or 7) ring atoms. Examples of heterocycloalkyl include aziridinyl, oxiranyl, thiiranyl, oxaziridinyl, dioxiranyl, azetidinyl, oxetanyl, thietanyl, diazetidinyl, dioxetanyl, dithietanyl, pyrrolidinyl, tetrahydrofuranyl, thiolanyl, azolyl, thiazolyl, isothiazolyl, imidazolidinyl, pyrazolidinyl, oxazolidinyl, isoxazolidinyl, thiazolidinyl, isothiazolidinyl, dioxolanyl, dithiolanyl, piperazinyl, morpholinyl, thiomorpholinyl, trioxanyl, azepanyl, oxepanyl, thiepanyl, homopiperazinyl, urotropinyl, oxazolidinonyl, dihydropyrazolyl, dihydropyrrolyl, dihydropyrazinyl, dihydropyridyl, dihydropyrimidinyl, dihydrofuryl, dihydropyranyl, and examples of substituted heterocycloalkyl include lactam, lactone and cyclic imide ring systems.

The expression alkylcycloalkyl refers to a group containing both cycloalkyl and also an alkyl, alkenyl or alkynyl group in accordance with the above definitions, for example alkylcycloalkyl, cycloalkylalkyl, alkylcycloalkenyl, alkenylcycloalkyl and alkynylcycloalkyl groups. An alkylcycloalkyl group preferably contains a cycloalkyl group that contains one or two ring systems having from 3 to 10 (preferably 3, 4, 5, 6 or 7) carbon atoms, and one or two alkyl, alkenyl or alkynyl groups having 1 or 2 to 6 carbon atoms, the cyclic groups being optionally substituted.

The expression heteroalkylcycloalkyl refers to alkylcycloalkyl groups as defined above in which one or more (preferably 1, 2 or 3) carbon atoms have been replaced each independently of the others by an oxygen, nitrogen, silicon, selenium, phosphorus or sulphur atom (preferably oxygen, sulphur or nitrogen). A heteroalkylcycloalkyl group preferably contains 1 or 2 ring systems having from 3 to 10 (preferably 3, 4, 5, 6 or 7) ring atoms, and one or two alkyl, alkenyl, alkynyl or heteroalkyl groups having from 1 or 2 to 6 carbon atoms. Examples of such groups are alkylheterocycloalkyl, alkylheterocycloalkenyl, alkenylheterocycloalkyl, alkynylhetero-cycloalkyl, heteroalkylcycloalkyl, heteroalkylheterocycloalkyl and heteroalkylheterocycloalkenyl, the cyclic groups being optionally substituted and saturated or mono-, di- or tri-unsaturated.

The expressions aryl, Ar or aryl group refer to an aromatic group that contains one or more aromatic rings containing from 6 to 14 ring carbon atoms ($C_6$-$C_{14}$), preferably from 6 to 10 ($C_6$-$C_{10}$), more preferably 6 ring carbon atoms; the aryl may be substituted and can be bonded as a substituent via every suitable position of the ring system. Examples of aryl include phenyl, naphthyl, bi-phenyl, indanyl, indenyl, anthracenyl, phenanthrenyl, tetrahydronaphthyl and fluorenyl.

The expression heteroaryl or heteroaryl group refers to an aromatic group that contains one or more aromatic rings containing from 5 to 14 ring atoms, preferably from 5 to 10 (more preferably 5 or 6) ring atoms, and contains one or more (preferably 1, 2, 3 or 4) oxygen, nitrogen, phosphorus or sulphur ring atoms (preferably O, S or N); the heteroaryl may be substituted and can be bonded as a substituent via every suitable position of the ring system. Examples of an unsubstituted heteroaryl group include 2-pyridyl, 2-imidazolyl, 3-phenylpyrrolyl, thiazolyl, oxazolyl, triazolyl, tetrazolyl, isoxazolyl, indazolyl, indolyl, benzimidazolyl, pyridazinyl, quinolinyl, purinyl, carbazolyl, acridinyl, pyrimidyl, 2,3'-bifuryl, 3-pyrazolyl and isoquinolinyl.

The expression aralkyl refers to a group containing both aryl and also alkyl, alkenyl, alkynyl and/or cycloalkyl groups in accordance with the above definitions, such as, for example, arylalkyl, arylalkenyl, arylalkynyl, arylcycloalkyl, arylcycloalkenyl, alkylarylcycloalkyl and alkylarylcycloalkenyl groups. Specific examples of aralkyls are toluene, xylene, mesitylene, styrene, benzyl chloride, o-fluorotoluene, 1H-indene, tetralin, dihydronaphthalene, indanone, phenylcyclopentyl, cumene, cyclohexylphenyl, fluorene and indan. An aralkyl group preferably contains one or two aromatic ring systems (1 or 2 rings) containing from 6 to 10 carbon atoms and one or two alkyl, alkenyl and/or alkynyl groups containing from 1 or 2 to 6 carbon atoms and/or a cycloalkyl group containing 5 or 6 ring carbon atoms.

The expression heteroaralkyl refers to an aralkyl group as defined above in which one or more (preferably 1, 2, 3 or 4) carbon atoms have been replaced each independently of the others by an oxygen, nitrogen, silicon, selenium, phosphorus, boron or sulphur atom (preferably oxygen, sulphur or nitrogen), that is to say to groups containing both aryl or heteroaryl and also alkyl, alkenyl, alkynyl and/or heteroalkyl and/or cycloalkyl and/or heterocycloalkyl groups in accordance with the above definitions. A heteroaralkyl group preferably contains one or two aromatic ring systems (1 or 2 rings) containing from 5 or 6 to 10 ring carbon atoms and one or two alkyl, alkenyl and/or alkynyl groups containing 1 or 2 to 6 carbon atoms and/or a cycloalkyl group containing 5 or 6 ring carbon atoms, 1, 2, 3 or 4 of those carbon atoms having been replaced each independently of the others by oxygen, sulphur or nitrogen atoms. Examples of heteroaralkyl groups are arylheteroalkyl, arylheterocycloalkyl, arylheterocycloalkenyl, arylalkylheterocycloalkyl, arylalkenylheterocycloalkyl, arylalkynylheterocycloalkyl, arylalkyl-heterocycloalkenyl, heteroarylalkyl, heteroarylalkenyl, heteroarylalkynyl, heteroarylheteroalkyl, heteroarylcycloalkyl, heteroarylcycloalkenyl, heteroarylheterocycloalkyl, hetero-arylheterocycloalkenyl, heteroarylalkylcycloalkyl, heteroarylalkylheterocycloalkenyl, heteroaryl-heteroalkyl-cycloalkyl, heteroarylheteroalkylcycloalkenyl, heteroalkyl-heteroarylalkyl and hetero-arylheteroalkylheterocycloalkyl groups, the cyclic groups being saturated or mono-, di- or tri-unsaturated. Specific examples are a tetrahydroisoquinolinyl, benzoyl, 2- or 3-ethylindolyl, 4-methylpyridino, 2-, 3- or 4-methoxyphenyl, 4-ethoxyphenyl, 2-, 3- or 4-carboxyphenylalkyl group.

The expression heterocycle denotes ring systems, which include the above defined heterocycloalkyl and heteroaryl ring systems, e.g. a partially unsaturated heterocycle is synonymous with a partially unsaturated heterocycloalkyl and an aromatic heterocycle is synonymous with a heteroaryl. The heterocycle may be substituted and can be bonded as a substituent via every suitable position of the ring system. Examples of a partially unsaturated or aromatic heterocycle include oxetenyl, thietenyl, azetinyl, 2,3-dihydrofuranyl, 2,5-dihydrofuranyl, 2,5-dihydrothiophenyl, 2,5-dihydro-1H-pyrrolyl, furanyl, thiophenyl, pyrrolyl, benzo[b]furanyl, benzo[b]thiophenyl, indolyl, benzo[c]pyrrolyl, benzo[a]pyrrolyl, imidazolyl, pyrazolyl, oxazolyl, isoxazolyl, thiazolyl, isothiazolyl, 1,2,3-triazolyl, 1,2,4-triazolyl, tetrazolyl, dihydropyridinyl, oxazinyl, pyridinyl, dihydropyranyl, azepinyl, tetrahydropyranyl, dihydrothiopyranyl, quinolinyl, isoquinolinyl, quinazolinyl, pyridazinyl, pyrimidinyl, pyrazinyl, purinyl, and pteridinyl.

The general term ring as used herein, unless defined otherwise, includes the cyclic groups defined herein above, e.g. a cycloalkyl group, heterocycloalkyl group, aryl group, heteroaryl group, and heterocycle.

The expression halogen or halogen atom as used herein means fluorine, chlorine, bromine, or iodine.

The expression heteroatom as used herein, preferably denotes an oxygen, nitrogen or sulphur atom, more preferably a nitrogen or oxygen atom.

The expression "alkylene" (or alkanediyl functional group) refers to an unsubstituted, saturated, straight chain hydrocarbon group that contains the indicated number of carbon atoms (in the form of methylene ($CH_2$) groups) and has the free valencies at the terminal methylene groups, for example a butylene —$(CH_2)_4$—, n-pentylene —$(CH_2)_5$—, n-hexylene —$(CH_2)_6$—, or n-octylene —$(CH_2)_8$— group.

The expression "alkenylene" refers to an at least partially unsaturated alkanediyl functional group as defined above that contains one or more double bond(s) (i.e. the methylene groups of the alkanediyl functional group are interrupted by —CH=CH— and/or terminated by —$CH_2$—CH=).

The expression "alkynylene" refers to an at least partially unsaturated alkanediyl functional group as defined above that contains one or more triple bond(s) (i.e. the methylene groups of the alkanediyl functional group are interrupted by —CH≡CH— and/or terminated by —$CH_2$—C≡).

The term "PqsR inverse agonist", as used herein, refers to a compound of general formula (I) provided herein, as well as to salts and preferably pharmaceutically acceptable salts thereof. It will be apparent that such compounds may be further substituted as indicated.

The activity and more specifically the bioactivity of the compounds according to the present invention can be assessed using appropriate assays known to those skilled in the art, e.g. in vitro or in vivo assays. For instance, the PqsR inverse agonistic activity may be determined by E. coli-based p-galactosidase reporter gene assay, or evaluated in PQS assay, pyocyanin virulence assay and biofilm assay, as provided in more detail in the Examples below.

Preferably, the present invention relates to one or more of the following:

[2] The compound according to [1] above, or a pharmacologically acceptable salt thereof, wherein $A^2$ is N;

[3] the compound according to [1] or [2], or a pharmacologically acceptable salt thereof, wherein $A^1$ is C—H;

[4] the compound according to any one of [1] to [3], or a pharmacologically acceptable salt thereof, wherein $A^3$ is C—H, C—Cl, C—$NH_2$, C—CN or C—$CF_3$;

[5] the compound according to any one of [1] to [4], or a pharmacologically acceptable salt thereof, wherein $A^1$ is CH, $A^2$ is N, and $A^3$ is C—H, C—Cl, C—$NH_2$, C—CN or C—$CF_3$;

[6] the compound according to any one of [1] to [4], or a pharmacologically acceptable salt thereof, wherein $A^1$ is N, $A^2$ is N, and $A^3$ is C—$NH_2$;

[7] the compound according to any one of [1] to [6], or a pharmacologically acceptable salt thereof, wherein $R^4$ is $CF_3$, CN, or Cl; and more preferably $CF_3$ or CN;

[8] the compound according to any one of [1] to [6], or a pharmacologically acceptable salt thereof, wherein A is a group selected from the groups:

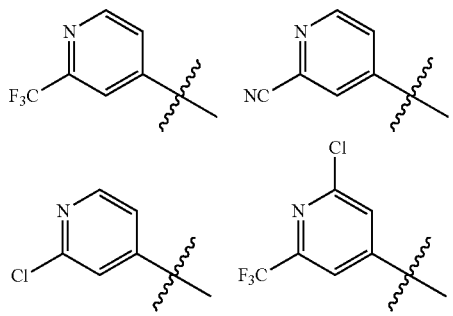

-continued

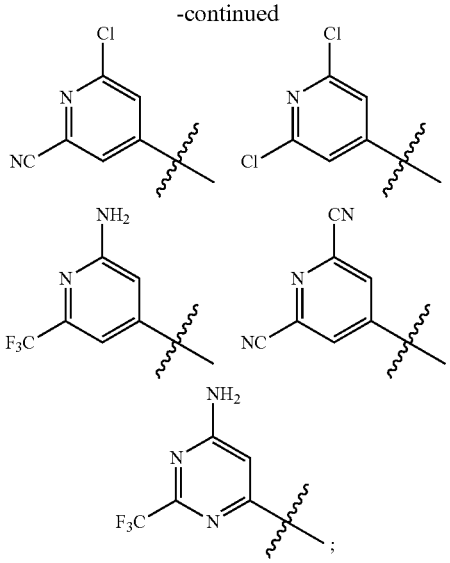

[8A] the compound according to any one of [1], [1A] and 2 to [6], or a pharmacologically acceptable salt thereof, wherein A is a group selected from the groups:

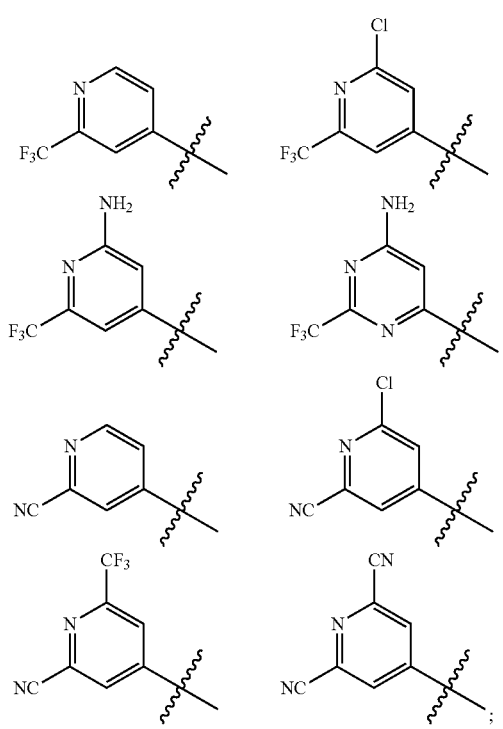

[9] the compound according to any one of [1], [1A] and [2] to [8A], or a pharmacologically acceptable salt thereof, wherein L is a group of formula (L-1);
[10] the compound according to [9], or a pharmacologically acceptable salt thereof, wherein $X^1$ is NH;
[11] the compound according to [9], or a pharmacologically acceptable salt thereof, wherein $X^1$ is S;
[12] the compound according to any one of [9] to [11], or a pharmacologically acceptable salt thereof, wherein the ring B is a ring represented by formula (B-1);
[13] the compound according to [12], or a pharmacologically acceptable salt thereof, wherein the ring represented by formula (B-1) is (i) a ring, wherein $M^1$ is CH and each of $M^2$, $M^3$ and $M^4$ is N; or (ii) a ring, wherein $M^1$ is S, $M^2$ is C, $M^3$ is N and $M^4$ is CH;
[14] the compound according to any one of [9] to [13], or a pharmacologically acceptable salt thereof, wherein the group represented by formula (L-1) contains one of the following groups as a partial structure:

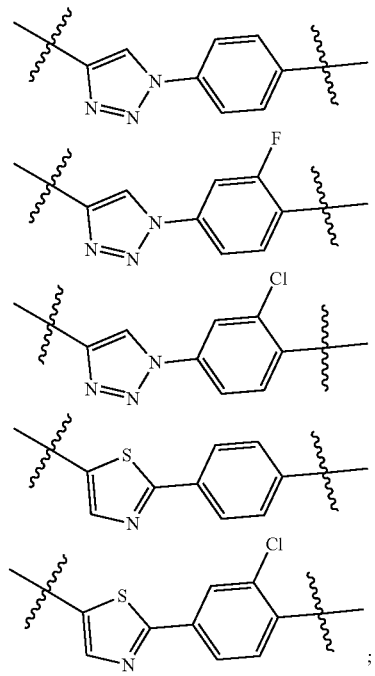

[15] the compound according to any one of [9] to [11], or a pharmacologically acceptable salt thereof, wherein the ring B is a ring represented by formula (B-2);
[16] the compound according to [15], or a pharmacologically acceptable salt thereof, wherein the ring represented by formula (B-2) is (i) a ring, wherein $M^{11}$ is N and each of $M^{12}$, $M^{13}$ and $M^{14}$ is CH; or (ii) a ring, wherein $M^{11}$ and $M^{14}$ are CH, and $M^{12}$ and $M^{13}$ are N; and more preferably a ring according to (ii);
[17] the compound according to any one of [9] to [11], [15] and [16], or a pharmacologically acceptable salt thereof, wherein the group represented by formula (L-1) contains one of the following groups as a partial structure:

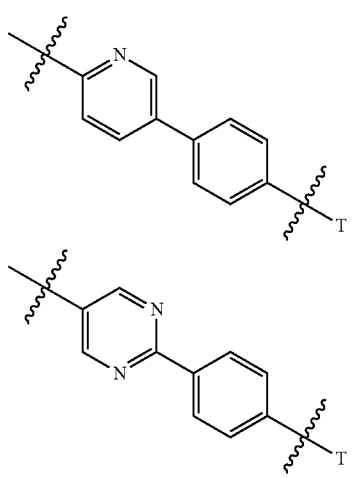

-continued

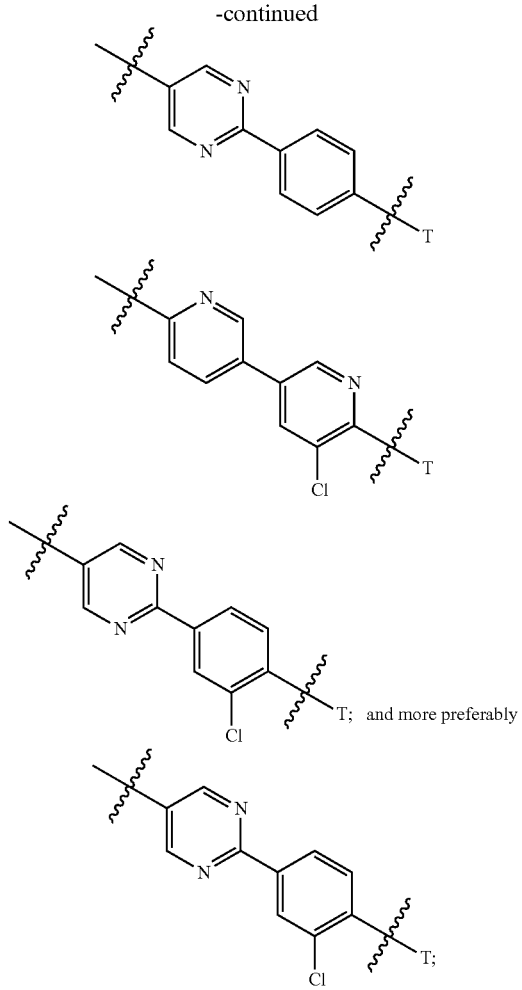

T; and more preferably

[18] the compound according to any one of [1], [1A] and [2] to [8A], or a pharmacologically acceptable salt thereof, wherein L is a group of formula (L-2);

[19] the compound according to [18], or a pharmacologically acceptable salt thereof, wherein $X^2$ is S or NH, and more preferably S;

[20] the compound according to [18] or [19], or a pharmacologically acceptable salt thereof, wherein the group represented by formula (T-2) is a group selected from:

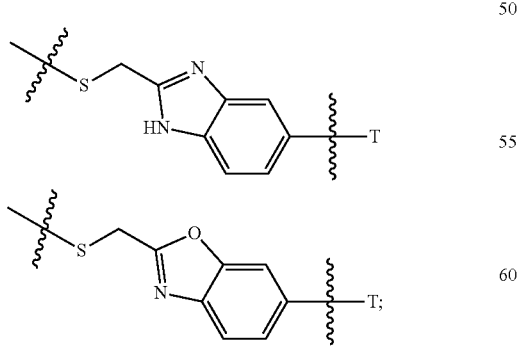

[20A] the compound according to [18] or [19], or a pharmacologically acceptable salt thereof, wherein the group represented by formula (L-2) is a group selected from:

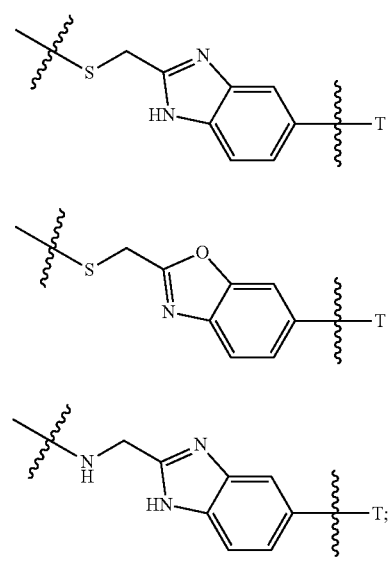

and more preferably

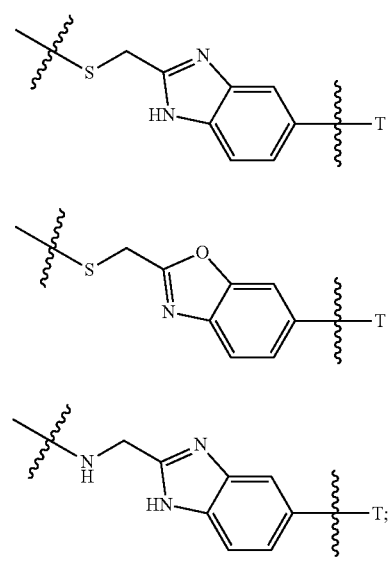

[21] the compound according to any one of [1] to [20], or a pharmacologically acceptable salt thereof, wherein T is selected from:

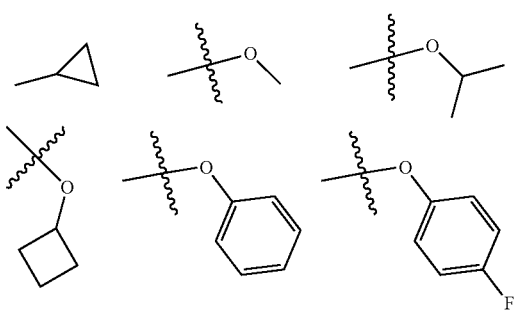

[21A] the compound according to any one of [1] to [20A], or a pharmacologically acceptable salt thereof, wherein T is selected from:

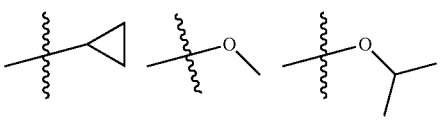

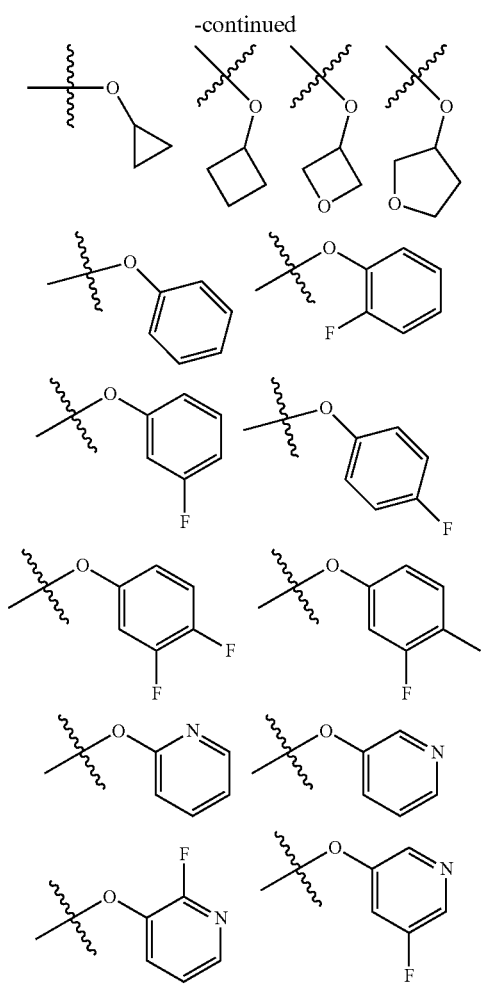

and Cl, and more preferably a group selected from:

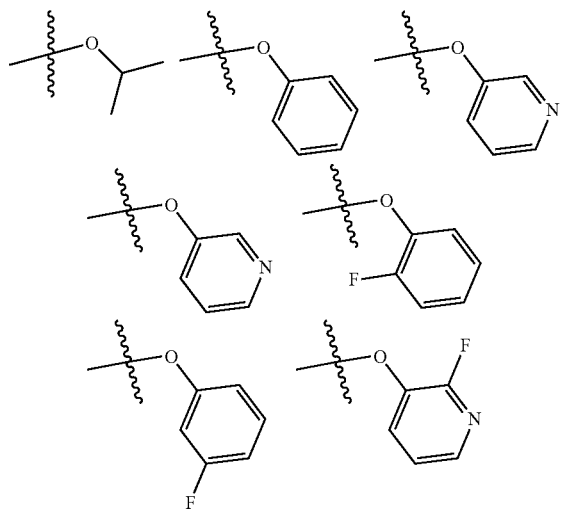

and Cl;

[22] the compound according to any one of [18] to [21], or a pharmacologically acceptable salt thereof, wherein the group A is selected from:

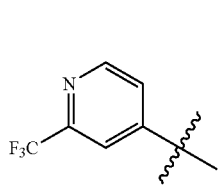 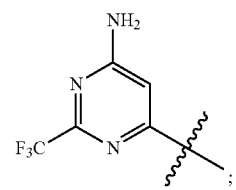

and T is:

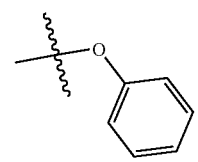 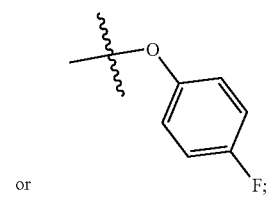

or F;

[22A] the compound according to any one of [18] to [21A], or a pharmacologically acceptable salt thereof, wherein the group A is selected from:

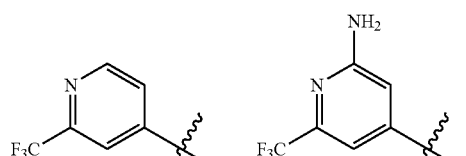

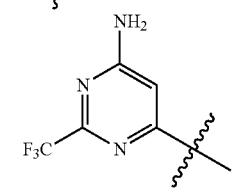

and more preferably
and T is:

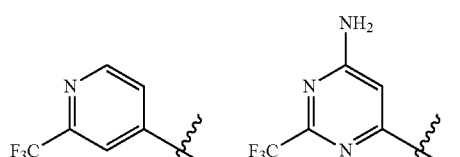

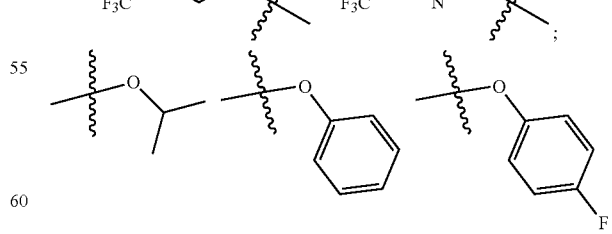

or Cl;

[23] the compound according to claim 14, or a pharmacologically acceptable salt thereof, wherein the group A is:

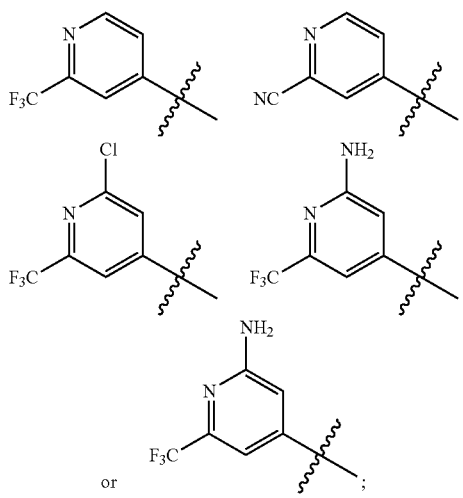

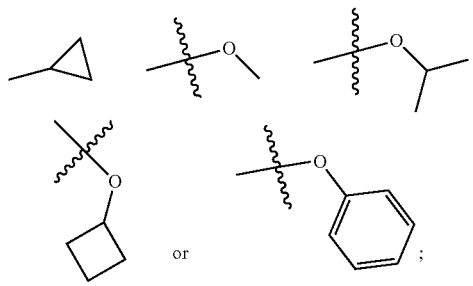

and
T is:

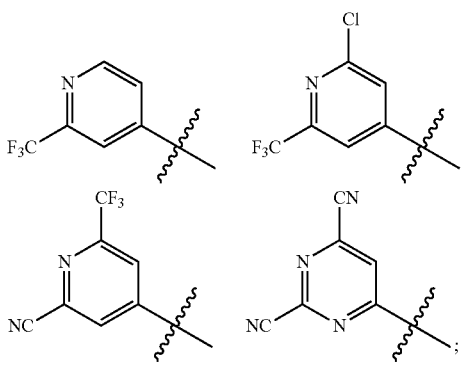

[23A] the compound according to claim 14, or a pharmacologically acceptable salt thereof, wherein the group A is:

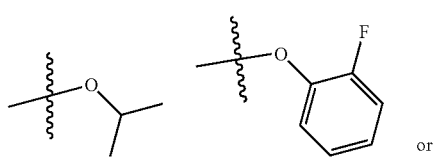

and
T is:

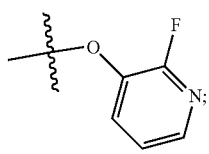

-continued

[24] the compound according to [17], or a pharmacologically acceptable salt thereof, wherein the group A is:

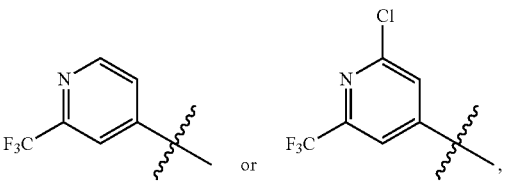 [SMILES: *c1ccnc(C(F)(F)F)c1 ; *c1cc(Cl)nc(C(F)(F)F)c1]

and preferably

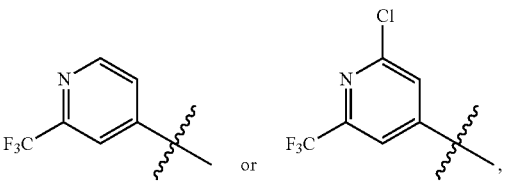 [SMILES: *c1ccnc(C(F)(F)F)c1 ; *c1cc(Cl)nc(C(F)(F)F)c1]

and
T is:

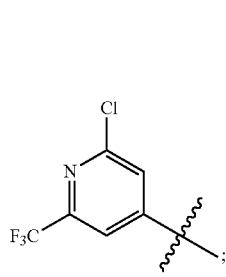 [SMILES: *c1cc(Cl)nc(C(F)(F)F)c1]

or Cl, and preferably

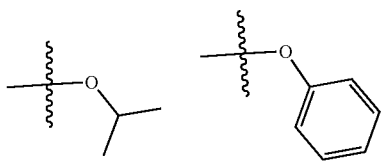

[25] the compound according to any one of [1] to [24], or a pharmacologically acceptable salt thereof, wherein the compound is selected from the group consisting of:

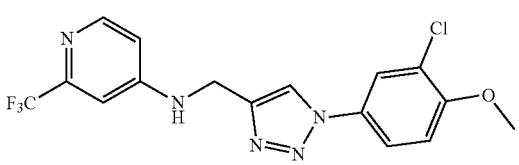

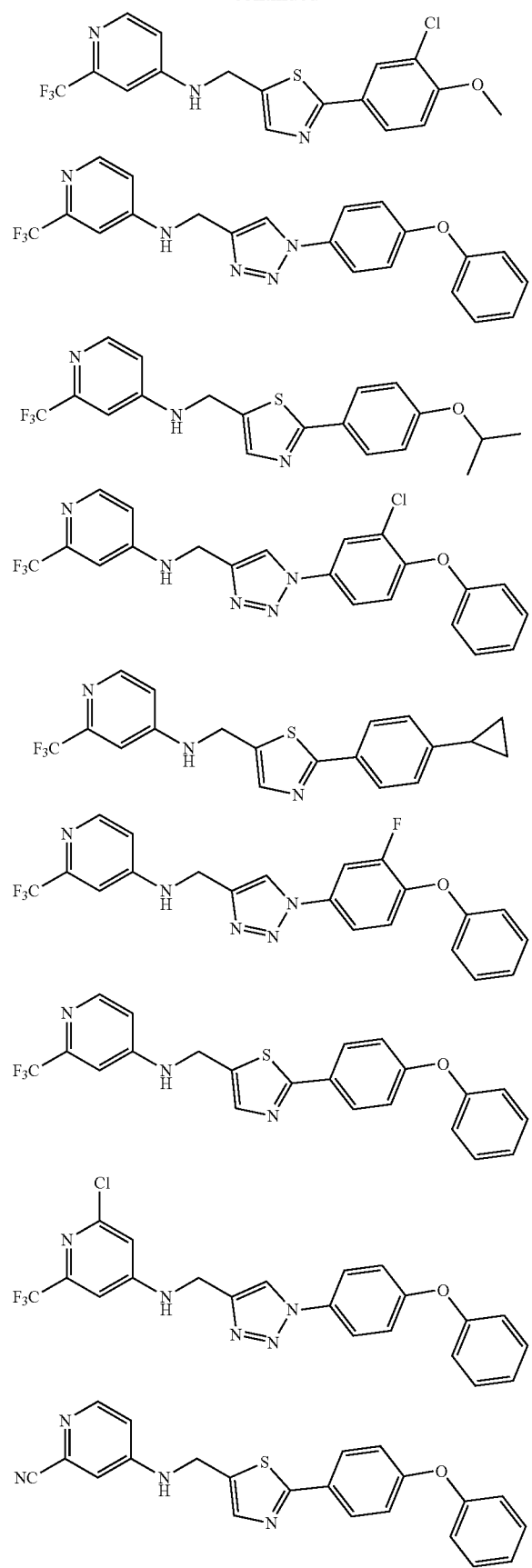
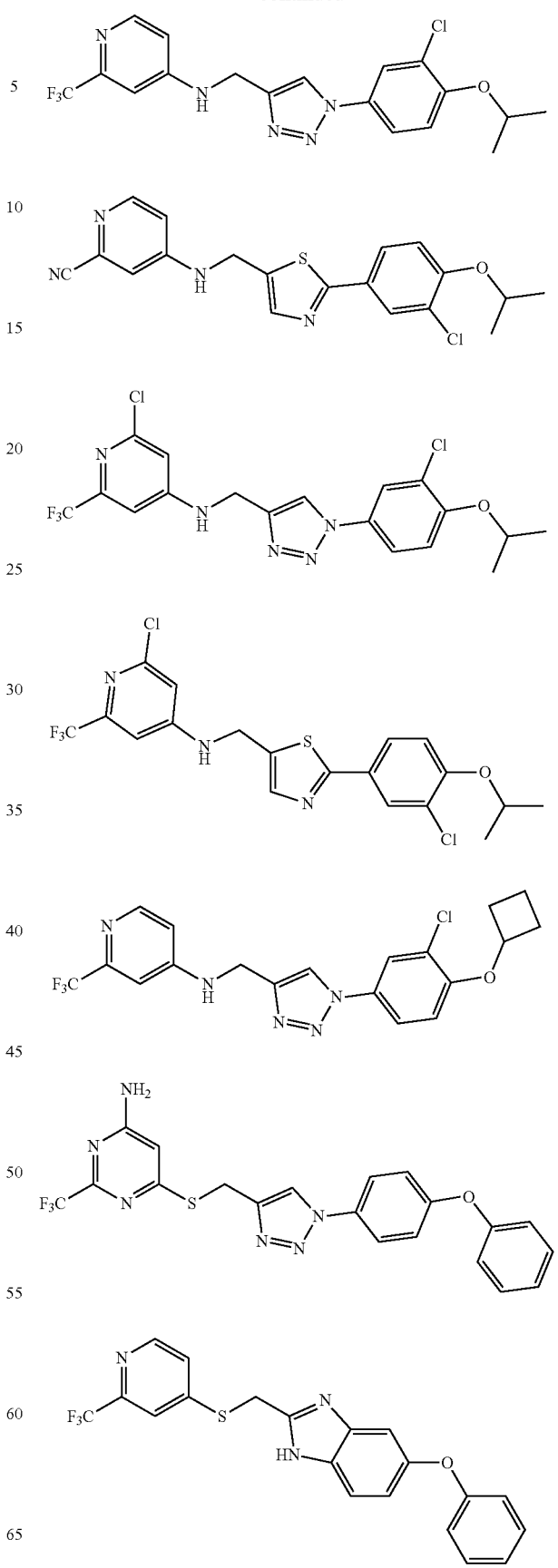

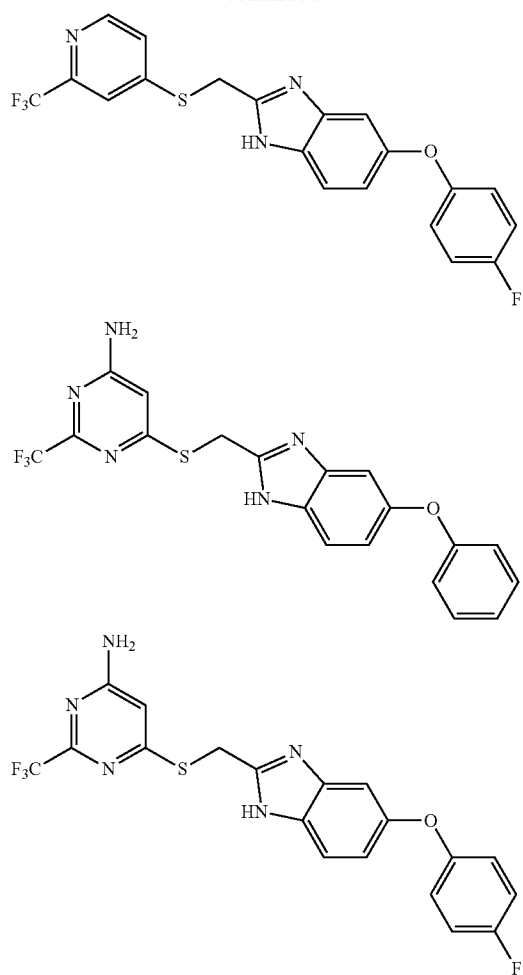
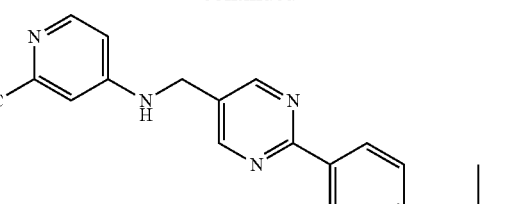
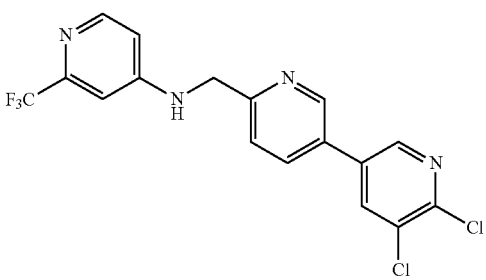
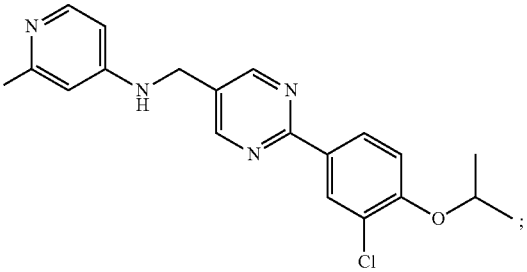
[26] the compound according to any one of [1], [1A] and [2] to [24], or a pharmacologically acceptable salt thereof, wherein the compound is selected from the group consisting of:

-continued
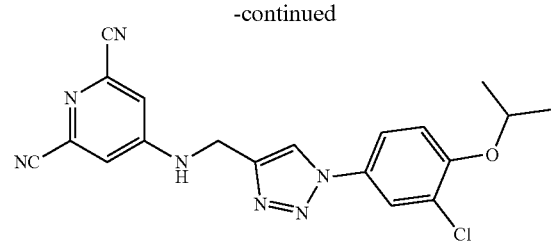
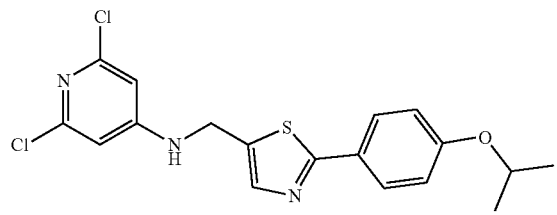
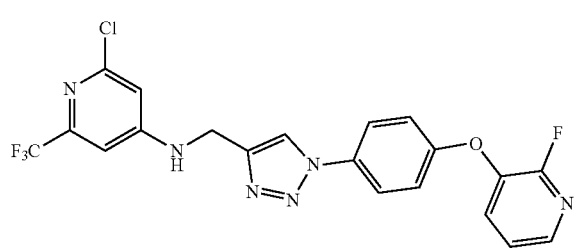
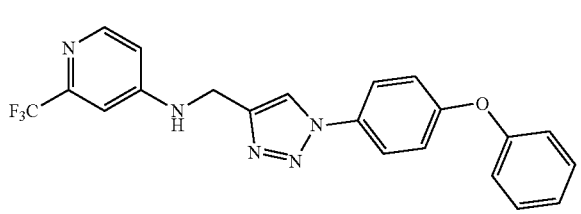
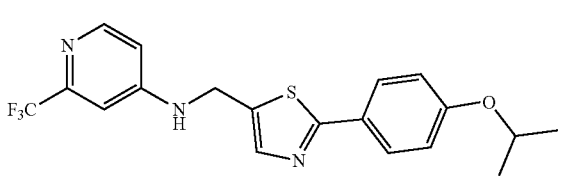
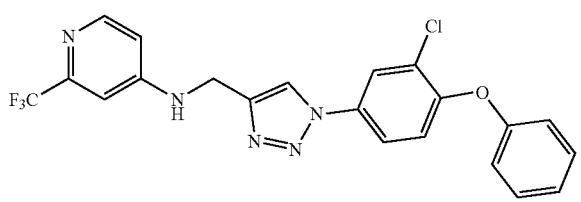
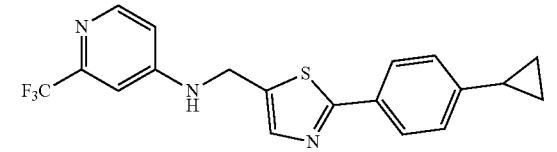
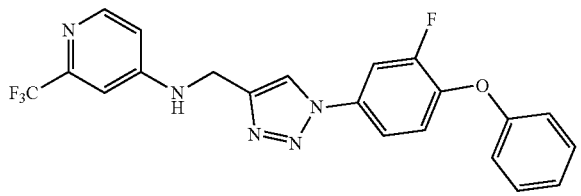
-continued
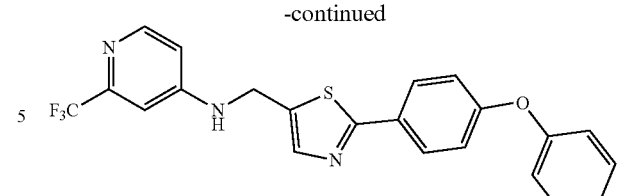
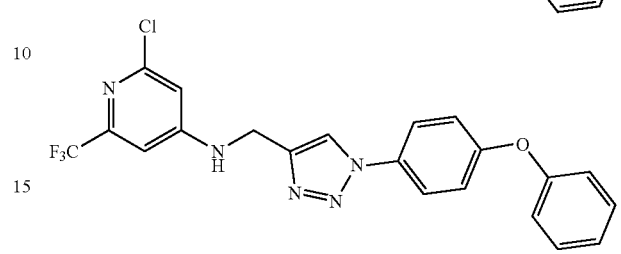
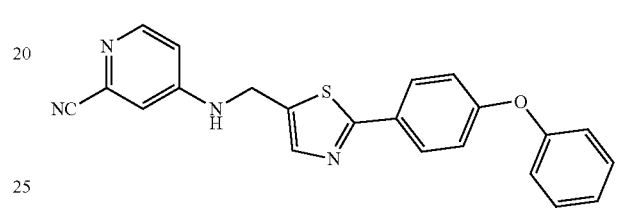
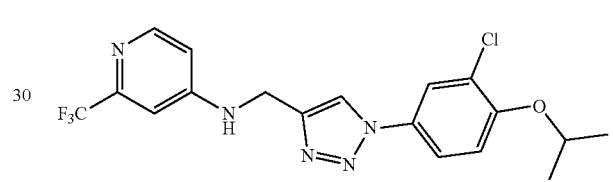
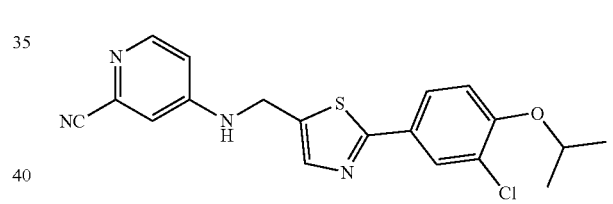
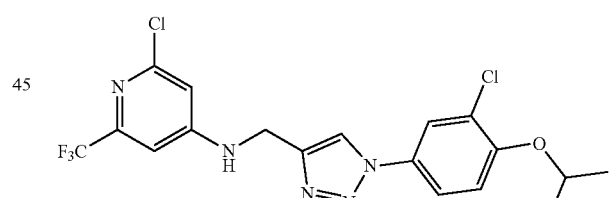
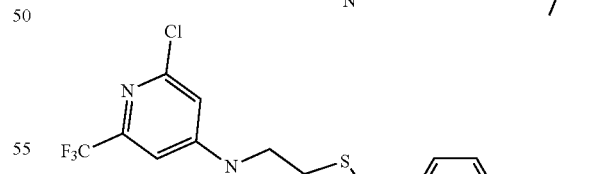
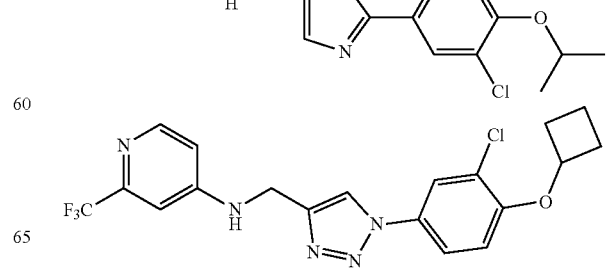

-continued
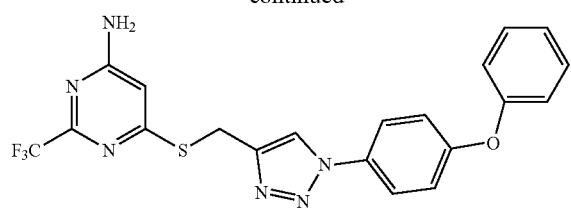
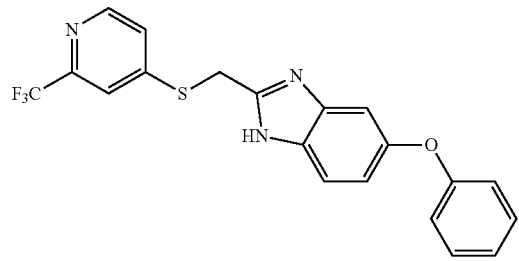
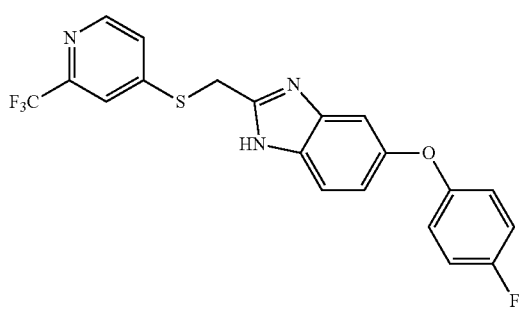
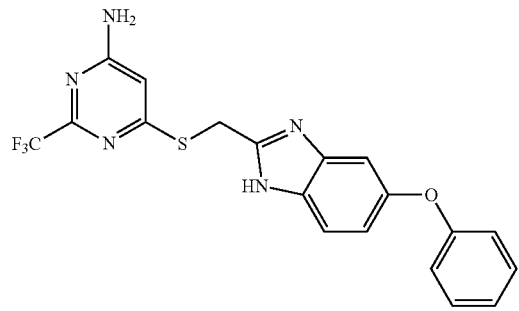
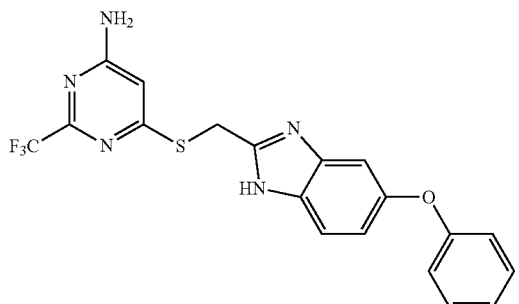
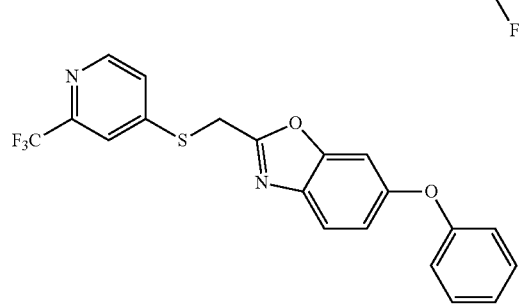
-continued
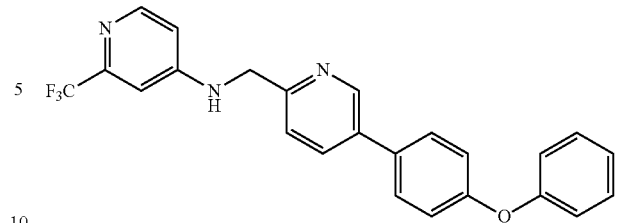
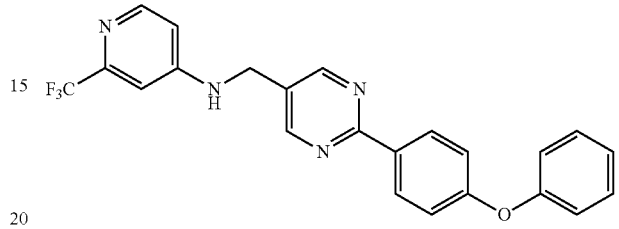
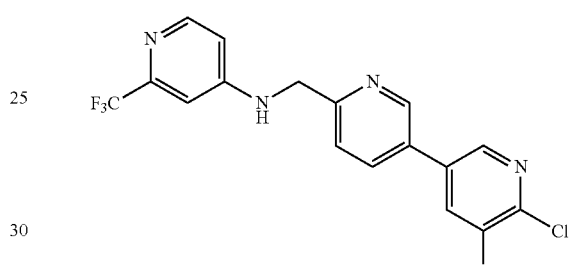
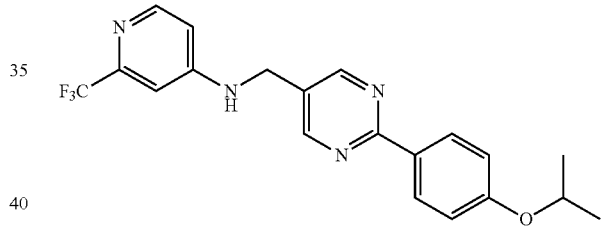
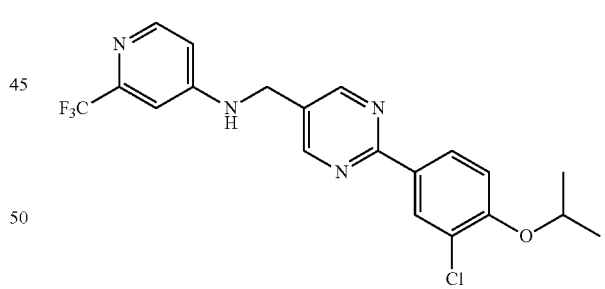
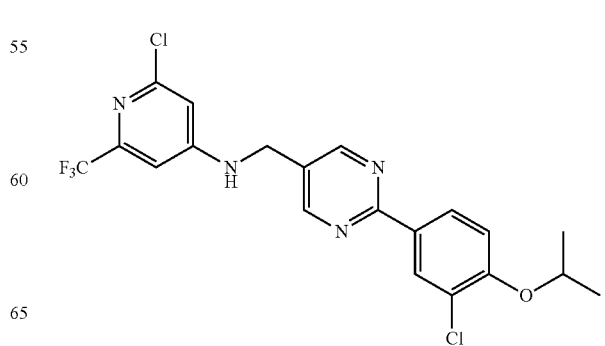

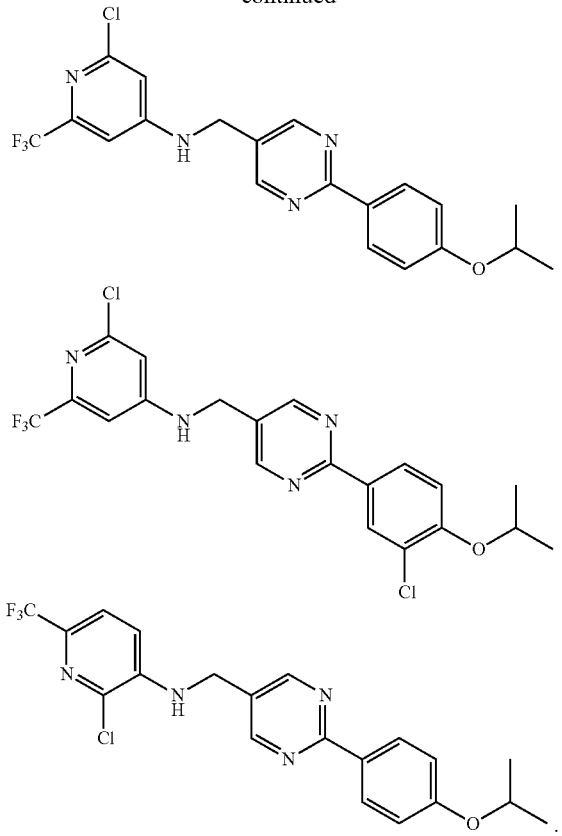

Compounds including suitable combinations of preferred embodiments, i.e. [2] to [25] or [26], of the compound according to general formula (I), or a salt thereof, are particularly preferred; e.g. a compound or salt thereof including a combination of [1], [8], [14] and [21]; or [1A], [8A], [14] and [21A]; as disclosed herein. In other words, the present invention specifically encompasses all possible combinations of [1] to [24] or [1A] to [24] as indicated above, which result in a stable compound.

A compound of formula (I) can be obtained by chemical synthesis in a number of ways well known to one skilled in the art of organic synthesis using usual chemical reaction and synthesis methods. For example, the compounds can be obtained based on the materials and the reaction conditions for the preparation of compounds of formula (I) provided in the examples below.

The therapeutic use of a compound of formula (I), its pharmacologically acceptable salts, solvates or hydrates and also formulations and pharmaceutical compositions which contain the same are within the scope of the present invention. Accordingly, the present invention relates to a compound or a pharmaceutical composition of the invention for use as a medicament. The present invention also relates to the use of those compounds of formula (I) as active ingredients in the preparation or manufacture of a medicament.

A pharmaceutical composition according to the present invention comprises at least one compound of formula (I) and, optionally, one or more carrier substance(s), excipient(s) and/or adjuvant(s). Pharmaceutical compositions may additionally comprise, for example, one or more of water, buffers (e.g., neutral buffered saline or phosphate buffered saline), ethanol, mineral oil, vegetable oil, dimethylsulfoxide, carbohydrates (e.g., glucose, mannose, sucrose or dextrans), mannitol, proteins, adjuvants, polypeptides or amino acids such as glycine, antioxidants, chelating agents such as EDTA or glutathione and/or preservatives. Furthermore, one or more other active ingredients may (but need not) be included in the pharmaceutical compositions provided herein. For instance, the compounds of the invention may advantageously be employed in combination with another antibiotic or antifungal agent, an anti-viral agent, an antihistamine, a non-steroidal anti-inflammatory drug, a disease modifying anti-rheumatic drug, another cytostatic drug, a drug with smooth muscle activity modulatory activity or mixtures of the aforementioned.

Pharmaceutical compositions may be formulated for any appropriate route of administration, including, for example, topical such as, e.g., transdermal or ocular, oral, buccal, nasal, vaginal, rectal or parenteral administration. The term parenteral as used herein includes subcutaneous, intradermal, intravascular such as, e.g., intravenous, intramuscular, spinal, intracranial, intrathecal, intraocular, periocular, intraorbital, intrasynovial and intraperitoneal injection, as well as any similar injection or infusion technique. Within the invention, compositions provided herein may be formulated as a lyophilizate. Formulation for topical administration may be preferred for certain conditions such as, e.g., in the treatment of skin conditions such as burns or itch.

Carrier substances are, for example, cyclodextrins such as hydroxypropyl O-cyclodextrin, micelles, liposomes, nanoparticles such as solid lipid nanoparticles, excipients and/or adjuvants. Customary excipients include, for example, inert diluents such as, e.g., calcium carbonate, sodium carbonate, lactose, calcium phosphate or sodium phosphate, granulating and disintegrating agents such as, e.g., corn starch or alginic acid, binding agents such as, e.g., starch, gelatin or acacia, and lubricating agents such as, e.g., magnesium stearate or stearic acid. Examples of adjuvants are aluminum hydroxide, aluminum phosphate, calcium phosphate hydroxide, paraffin oil, squalene, thimerosal, detergents, Freund's complete adjuvant, or Freund's incomplete adjuvant.

For the prevention and/or treatment of bacterial infections, especially P. aeruginosa or Burkholderia infections, the dose of the biologically active compound according to the invention may vary within wide limits and may be adjusted to individual requirements. Active compounds according to the present invention are generally administered in a therapeutically effective amount. The expression "therapeutically effective amount" denotes a quantity of the compound(s) that produces a result that in and of itself helps to ameliorate, heal, or cure the respective condition or disease. Preferred doses range from about 0.1 mg to about 140 mg per kilogram of body weight per day (about 0.5 mg to about 7 g per patient per day). The daily dose may be administered as a single dose or in a plurality of doses. The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination (i.e. other drugs being used to treat the patient) and the severity of the particular disease undergoing therapy.

The invention further relates to a combination preparation containing at least one compound according to the invention and at least one further active pharmaceutical ingredient. The combination preparation of the invention for use as a medicament, in particular for use in the treatment or prophylaxis of bacterial infections, such as a *P. aeruginosa* or *Burkholderia* infection.

Preferably, in the combination preparation of the invention the further active pharmaceutical ingredient is another antibiotic, including classical antibiotics and anti-virulence compounds such as quorum sensing and adhesion inhibitors. The other antibiotic can be selected from the group consisting of (a) β-lactam antibiotics, including penams, carbapenams, oxapenams, penems, carbapenems, monobactams, cephems, carbacephems, oxacephems, and monobactams; (b) aminoglycoside antibiotics, including Amikacin, Arbekacin, Astromicin, Bekanamycin, Dibekacin, Framycetin, Gentamicin, Hygromycin B, Isepamicin, Kanamycin, Neomycin, Netilmicin, Paromomycin, Paromomycin sulfate, Ribostamycin, Sisomicin, Spectinomycin, Streptomycin, Tobramycin, and Verdamicin; (c) quinolone antibiotics, including Ciprofloxacin, Enoxacin, Gatifloxacin, Grepafloxacin, Levofloxacin, Lomefloxacin, Moxifloxacin, Nalidixic acid, Norfloxacin, Ofloxacin, Sparfloxacin, Temafloxacin, and Trovafloxacin; and (d) cationic peptidic antibiotics, including Polymyxins (e.g. Collistin), LL-37, and POL7080.

Preferred compounds of the invention will have certain pharmacological properties. Such properties include, but are not limited to oral bioavailability, such that the preferred oral dosage forms discussed above can provide therapeutically effective levels of the compound in vivo.

The compound according to the invention as well as the pharmaceutical composition according to the invention can be used as a medicament, which can be administered to a patient (e.g. parenterally to a human or another mammal), and will be present within at least one body fluid or tissue of the patient. As used herein, the term "treatment" encompasses both disease-modifying treatment and symptomatic treatment, either of which may be prophylactic, i.e., before the onset of symptoms, in order to prevent, delay or reduce the severity of symptoms, or therapeutic, i.e., after the onset of symptoms, in order to reduce the severity and/or duration of symptoms. In particular, the conditions or diseases that can be ameliorated, prevented or treated using a compound of formula (I) or a pharmaceutical composition according to the invention include bacterial infections, in particular antimicrobial activity against Gram-negative bacteria, especially infections with *Pseudomonas aeruginosa* strains (such as PAO1, PA14, MHH9639, MHH11444, and further clinical isolates exhibiting an intact pqs QS system) including such of the urinary tract, of the gastrointestinal tract, of chronic and burnt wounds, of the eyes, of the ears, and of the lungs or infections with *Burkholderia* species (such as *B. cenocepacia* and *B. pseudomallei*). Accordingly, the present invention also provides methods for treating a subject, e.g. patients, suffering from said diseases. Patients may include but are not limited to primates (especially humans), domesticated companion animals (such as dogs, cats, horses) and livestock (such as cattle, pigs, sheep, chicken), with dosages as described herein.

That is to say, the present invention also includes a method for treating a respiratory condition, including cystic fibrosis (CF), chronic obstructive pulmonary disease (COPD) and primary ciliary dyskinesia, in a subject, the method comprising:

administering to said subject an effective amount of the compound according to any one of claims 1 to 10, of the pharmaceutical composition according to claim 11, or of the combination preparation of claim 12, thereby treating the respiratory condition.

The invention further relates to a coating for medicinal devices, e.g. catheters, implants, or tubings, containing at least one compound according to the present invention.

The present invention is now further illustrated by the following examples from which further features, embodiments and advantages of the present invention may be taken. However, the invention should not be construed to be limited to the examples, but encompasses the subject-matter as defined in the claims.

EXAMPLES

Materials and Methods

A. Chemicals and Analytical Methods Used for Organic Synthesis $^1$H and $^{13}$C NMR spectra were recorded on a Bruker DRX-500 instrument. Chemical shifts are given in parts per million (ppm) with the solvent resonance as internal standard for spectra obtained in $CDCl_3$, $MeOH$-$d_4$ and $DMSO$-$d_6$. All coupling constants (J) are given in hertz. Mass spectrometry (LC/MS) was performed on a MSQ® electro spray mass spectrometer (Thermo Fisher). The system was operated by the standard software Xcalibur®. A RP C18 NUCLEODUR® 100-5 (125×3 mm) column (Macherey-Nagel GmbH) was used as stationary phase with water/acetonitrile mixtures as eluent. All solvents were HPLC grade. Reagents were used as obtained from commercial suppliers without further purification. Flash chromatography was performed on silica gel 60, 70-230 mesh (Fluka) and the reaction progress was determined by thin-layer chromatography (TLC) analyses on silica gel 60, $F_{254}$ (Merck). Visualization was accomplished with UV light and staining with basic potassium permanganate ($KMnO_4$). The melting points were measured using melting point apparatus SMP3 (Stuart Scientific). The apparatus is uncorrected.

Specific examples for the preparation of compounds of formula (I) are provided in the following examples. Unless otherwise specified all starting materials and reagents are of standard commercial grade, and are used without further purification, or are readily prepared from such materials by routine methods. Those skilled in the art of organic synthesis will recognize that starting materials and reaction conditions may be varied including additional steps employed to produce compounds encompassed by the present invention.

B. Chemicals, Bacterial Strains and Media Used in Biological Experiments.

Yeast extract was purchased from Fluka (Neu-Ulm, Germany), peptone from casein from Merck (Darmstadt, Germany), and Bacto™ Tryptone from BD Biosciences (Heidelberg, Germany). Salts and organic solvents of analytical grade were obtained from VWR (Darmstadt, Germany).

*P. aeruginosa* strain PA14 (PA14) was stored in glycerol stocks at −80° C.

The following media were used: Luria Bertani broth (LB) and PPGAS medium.[23]

Example 1. Compounds 001 to 053

1.1 Preparation of N-((1-(4-Phenoxyphenyl)-1H-1,2,3-triazol-4-yl)methyl)-2-(trifluoromethyl) pyridin-4-amine (001)

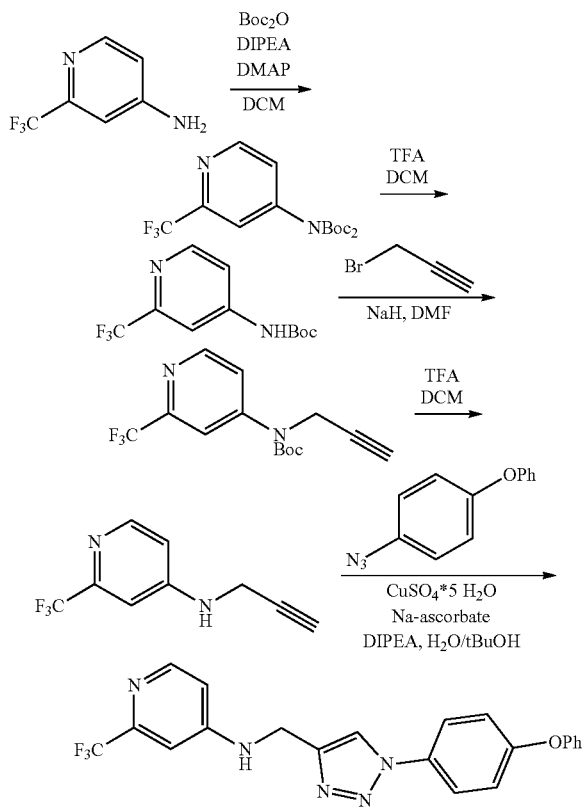

Step A. Di-tert-butyl(2-(trifluoromethyl)pyridin-4-yl)dicarbamate

To a solution of 2-trifluoromethyl-4-aminopyridine (3.24 g, 20.0 mmol) in DCM (60 mL) were added Boc$_2$O (9.82 g, 45.0 mmol), DIPEA (7.66 mL, 44.0 mmol) and DMAP (806 mg, 6.60 mmol). The reaction mixture was stirred for 18 h at r.t. and saturated NH$_4$Cl solution was added followed by extraction with EtOAc. The combined organic layers were washed with Brine, dried over Na$_2$SO$_4$, filtrated and evaporated under reduced pressure. The crude product was used without any further purification.

LC-MS: m/z: 363 (M+H)+. 1H-NMR (300 MHz, CDCl3): δ [ppm]=8.72 (d, J=5.4 Hz, 1H), 7.52 (d, J=1.7 Hz, 1H), 7.31 (dd, J=5.3 Hz, J=1.8 Hz, 1H), 1.47 (s, 18H).

Step B. Tert-butyl (2-(trifluoromethyl)pyridin-4-yl)carbamate

Ditert-butyl(2-(trifluoromethyl)pyridin-4-yl)dicarbamate (2.17 g, 6.00 mmol) was dissolved in DCM/TFA 9:1 (12 mL) and stirred for 16 h at r.t. until the starting material was fully consumed (TLC control). Saturated Na$_2$CO$_3$ solution was added followed by extraction with DCM. The combined organic layers were dried over Na$_2$SO$_4$ filtrated and concentrated in vacuo. The desired compound (1.49 g, 5.70 mmol, >98%) was used without further purification.

LC-MS: m/z: 207 (M+H-tBu)$^+$. $^1$H-NMR (300 MHz, CDCl$_3$): δ [ppm]=8.53 (d, J=5.6 Hz, 1H), 7.78 (d, J=2.0 Hz, 1H), 7.44 (dd, J=5.5 Hz, J=2.1 Hz, 1H), 6.92 (bs, 1H), 1.53 (s, 9H).

Step C. Tert-butyl prop-2-yn-1-yl(2-(trifluoromethyl)pyridin-4-yl)carbamate A solution of tert-butyl(2-(trifluoromethyl)pyridin-4-yl)carbamate (1.49 g, 5.70 mmol) was cooled to 0° C. and NaH (60 wt %) (273 mg, 6.83 mmol) were added portionwise under vigorous stirring. After 30 min. the reaction mixture was warmed to r.t. and propargylbromide (0.56 mL, 7.40 mmol) was added dropwise and stirred for 3 h at r.t. Addition of saturated NH$_4$Cl solution and extraction with Et$_2$O followed by washing the combined organic layers with saturated LiCl solution yielded the crude product after drying over Na$_2$SO$_4$, filtration and concentration in vacuo, which was purified by automate column chromatography. The title compound (1.22 g, 4.05 mmol, 71%) was isolated as a yellow solid.

LC-MS: m/z: 245 (M+H-tBu)$^+$. $^1$H-NMR (300 MHz, CDCl$_3$): δ [ppm]=8.63 (d, J=5.5, 1 H), 7.85 (d, J=2.0 Hz, 1H), 7.55 (dd, J=5.5 Hz, J=2.1 Hz, 1H), 4.48 (d, J=2.3 Hz, 2H), 2.25 (t, J=2.4 Hz, 1H).

Step D. N-(prop-2-yn-1-yl)-2-(trifluoromethyl)pyridin-4-amine tert-butyl prop-2-yn-1-yl(2-(trifluoromethyl)pyridin-4-yl)carbamate (1.21 g, 4.03 mmol) was dissolved in DCM (1 mL) and TFA (1 mL) was added. After stirring at r.t. for 18 h the mixture was cooled to 0° C. and saturated Na$_2$CO$_3$ solution was added. The reaction mixture was extracted with DCM and the combined organic layers were washed with Brine, dried over Na$_2$SO$_4$, filtered and concentrated under reduced pressure. Automated flash chromatography led to the title compound (820 mg, 4.03 mmol, >98%) as a white solid.

LC-MS: m/z: 201 (M+H)$^+$. $^1$H-NMR (300 MHz, CDCl$_3$): δ [ppm]=8.31 (d, J=6.5 Hz, 1H), 7.72 (bs, 1H), 7.16 (d, J=2.1 Hz, 1H), 6.89 (dd, J=6.5 Hz, J=2.3 Hz, 1H), 4.10 (d, J=2.4 Hz, 2H), 2.33 (t, J=2.6 Hz, 1H).

Step E. N-((1-(4-Phenoxyphenyl)-1H-1,2,3-triazol-4-yl)methyl)-2-(trifluoromethyl) pyridin-4-amine (001)

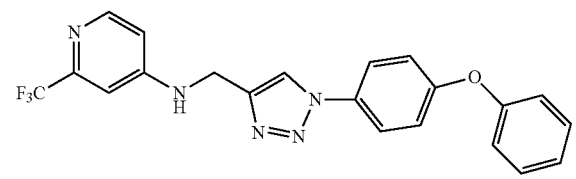 [SMILES: FC(F)(F)c1cc(NCc2cn(-c3ccc(Oc4ccccc4)cc3)nn2)ccn1]

N-(Prop-2-yn-1-yl)-2-(trifluoromethyl)pyridin-4-amine (20 mg, 100 μmol) was dissolved in tBuOH/H$_2$O (1 mL) followed by the addition of 1-azido-4-phenoxybenzene (21 mg, 100 μmol) and DIPEA (17.5 μL, 100 μmol). The reaction mixture was purged with Argon and Cu$_2$SO$_4$*5H$_2$O (10 mol %) and Na-ascorbate (10 mol %) were added. After stirring for 15 h at 40° C. saturated NH$_4$Cl solution was added and the reaction mixture was extracted with EtOAc. The combined organic layers were washed with Brine, dried over Na$_2$SO$_4$, filtered and concentrated under reduced pressure. The title compound (40 mg, 98 µmol), 98%) was yielded after prep-HPLC purification as a white solid.

LC-MS: m/z: 412 (M+H)$^+$. $^1$H-NMR (300 MHz, DMSO-d$_6$): δ [ppm]=4.53 (d, J=5.7 Hz, 2H 6-H), 6.83 (dd, J=5.7 Hz, J 2.2 Hz, 1H), 7.06 (d, J=2.2 Hz, 1H), 7.11 (m, 2H), 7.21 (sh, 3H, 14-H), 7.45 (m, 2H), 7.64 (m, 1H), 7.89 (m, 2H), 8.20 (d, J=5.7 Hz, 1H), 8.72 (s, 1H).

1.2 Compounds 002 to 053

Compounds 002 to 053 described below are further representative examples of compounds according to general formula (I) of the present invention. These compounds have been synthesized based on the procedure described above for Compound 001.

N-((1-(3-(Morpholinomethyl)phenyl)-1H-1,2,3-triazol-4-yl)methyl)-2-(trifluoromethyl)pyridin-4-amine (002)

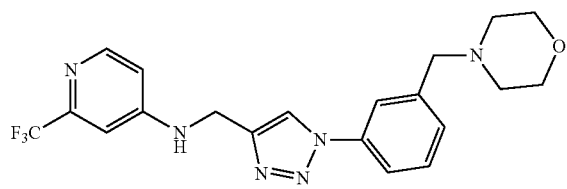 [SMILES: FC(F)(F)c1cc(NCc2cn(-c3cccc(CN4CCOCC4)c3)nn2)ccn1]

LC-MS: m/z: 419 (M+H)$^+$.

N-((1-(3-Chlorophenyl)-1H-1,2,3-triazol-4-yl)methyl)-2-(trifluoromethyl)pyridin-4-amine (003)

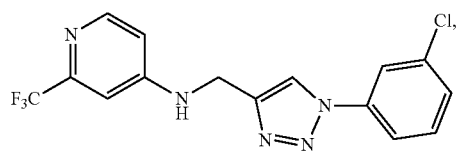 [SMILES: FC(F)(F)c1cc(NCc2cn(-c3cccc(Cl)c3)nn2)ccn1]

LC-MS: m/z: 354 (M+H)$^+$.

Phenyl(4-(4-(((2-(trifluoromethyl)pyridin-4-yl)amino)methyl)-1H-1,2,3-triazol-1-yl)phenyl)methanone (004)

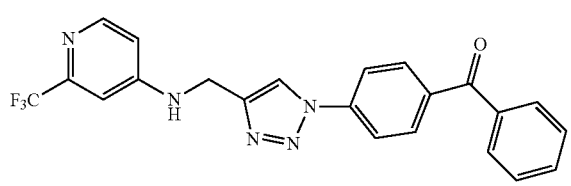 [SMILES: O=C(c1ccccc1)c1ccc(-n2cc(CNc3ccnc(C(F)(F)F)c3)nn2)cc1]

LC-MS: m/z: 424 (M+H)$^+$.

N-((1-(3,4-Dichlorophenyl)-1H-1,2,3-triazol-4-yl)methyl)-2-(trifluoromethyl)pyridin-4-amine (005)

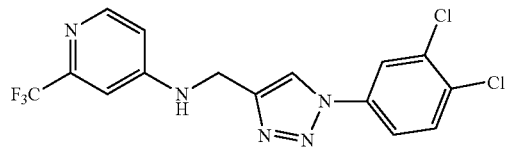 [SMILES: FC(F)(F)c1cc(NCc2cn(-c3ccc(Cl)c(Cl)c3)nn2)ccn1]

LC-MS: m/z: 388 (M+H)$^+$.

N-((1-(4-Methoxyphenyl)-1H-1,2,3-triazol-4-yl)methyl)-2-(trifluoromethyl)pyridin-4-amine (006)

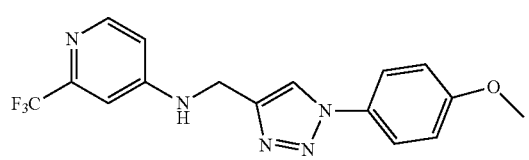 [SMILES: COc1ccc(-n2cc(CNc3ccnc(C(F)(F)F)c3)nn2)cc1]

LC-MS: m/z: 350 (M+H)$^+$.

2-Iodo-N-((1-(4-phenoxyphenyl)-1H-1,2,3-triazol-4-yl)methyl)-6-(trifluoromethyl)pyridin-4-amine (007)

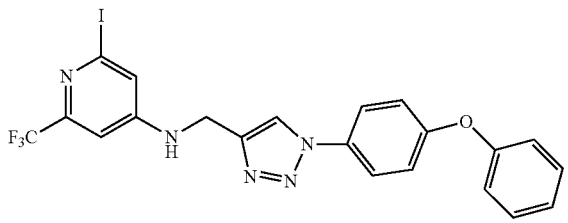 [SMILES: FC(F)(F)c1cc(NCc2cn(-c3ccc(Oc4ccccc4)cc3)nn2)cc(I)n1]

LC-MS: m/z: 538 (M+H)$^+$. $^1$H-NMR (300 MHz, CDCl$_3$): δ [ppm]=4.57 (d, J=5.4 Hz, 2H, 6-H), 5.30-5.33 (m, 1H, NH), 6.89 (d, J=2.1 Hz, 1H, 2-H), 6.99-7.09 (m, 3H, 14-H, 16-H), 7.11 (d, J=2.1 Hz, 1H, 4-H), 7.13-7.17 (m, 2H, 11-H), 7.17-7.24 (m, 2H), 7.33-7.43 (m, 3H, 15-H, NH), 7.63-7.68 (m, 2H, 10-H), 7.88 (s, 1H, 8-H).

N-((1-(4-chlorophenyl)-1H-1,2,3-triazol-4-yl)methyl)-2-(trifluoromethyl)pyridin-4-amine (008)

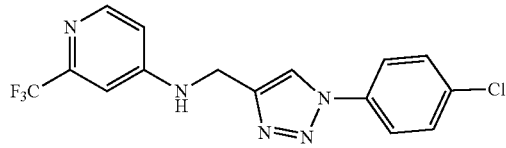 [SMILES: FC(F)(F)c1cc(NCc2cn(-c3ccc(Cl)cc3)nn2)ccn1]

LC-MS: m/z: 354 (M+H)$^+$.

N-((1-(3-Fluorophenyl)-1H-1,2,3-triazol-4-yl)methyl)-2-(trifluoromethyl)pyridin-4-amine (009)

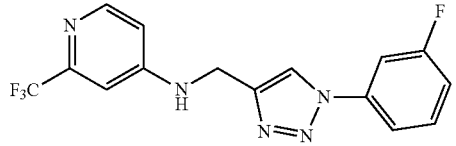 [SMILES: Fc1cccc(-n2cc(CNc3ccnc(C(F)(F)F)c3)nn2)c1]

LC-MS: m/z: 338 (M+H)$^+$.

N-((1-(4-Fluorophenyl)-1H-1,2,3-triazol-4-yl)methyl)-2-(trifluoromethyl)pyridin-4-amine (010)

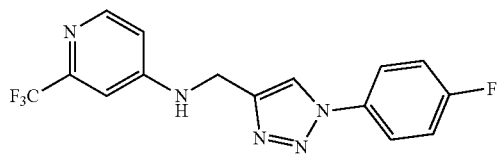 [SMILES: Fc1ccc(-n2cc(CNc3ccnc(C(F)(F)F)c3)nn2)cc1]

LC-MS: m/z: 338 (M+H)$^+$.

N-((1-(3-(Trifluoromethoxy)phenyl)-1H-1,2,3-triazol-4-yl)methyl)-2-(trifluoromethyl)pyridin-4-amine (011°)

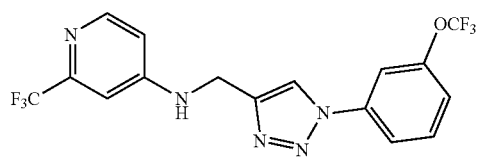 [SMILES: FC(F)(F)Oc1cccc(-n2cc(CNc3ccnc(C(F)(F)F)c3)nn2)c1]

LC-MS: m/z: 404 (M+H)$^+$.

N-((1-(4-(Trifluoromethoxy)phenyl)-1H-1,2,3-triazol-4-yl)methyl)-2-(trifluoromethyl)pyridin-4-amine (012)

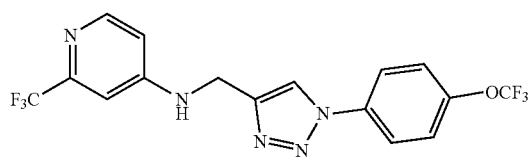 [SMILES: FC(F)(F)Oc1ccc(-n2cc(CNc3ccnc(C(F)(F)F)c3)nn2)cc1]

LC-MS: m/z: 404 (M+H)$^+$.

4-(4-(((2-(trifluoromethyl)pyridin-4-yl)amino)methyl)-1H-1,2,3-triazol-1-yl)benzonitrile (013)

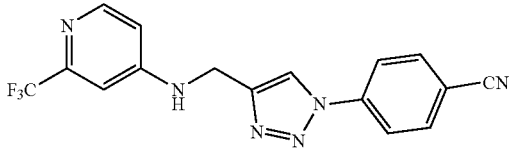 [SMILES: N#Cc1ccc(-n2cc(CNc3ccnc(C(F)(F)F)c3)nn2)cc1]

LC-MS: m/z: 345 (M+H)$^+$.

2-(Trifluoromethyl)-N-((1-(4-(trifluoromethyl)phenyl)-1H-1,2,3-triazol-4-yl)methyl)pyridin-4-amine (014)

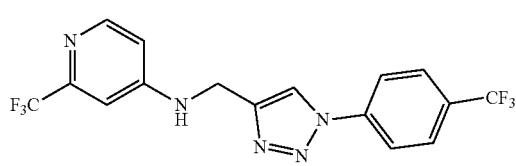 [SMILES: FC(F)(F)c1ccc(-n2cc(CNc3ccnc(C(F)(F)F)c3)nn2)cc1]

LC-MS: m/z: 388 (M+H)$^+$.

N-((1-(3-(Methylthio)phenyl)-1H-1,2,3-triazol-4-yl)methyl)-2-(trifluoromethyl)pyridin-4-amine (015)

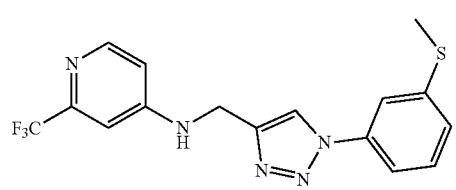 [SMILES: CSc1cccc(-n2cc(CNc3ccnc(C(F)(F)F)c3)nn2)c1]

LC-MS: m/z: 366 (M+H)$^+$.

N-((1-(4-(methylthio)phenyl)-1H-1,2,3-triazol-4-yl)methyl)-2-(trifluoromethyl)pyridin-4-amine (016)

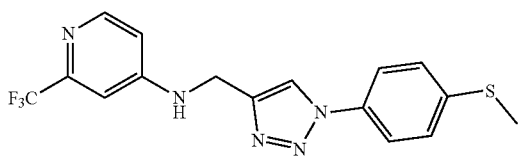

LC-MS: m/z: 366 (M+H)$^+$.

N-((1-(3-chloro-4-methoxyphenyl)-1H-1,2,3-triazol-4-yl)methyl)-2-(trifluoromethyl)pyridin-4-amine (017)

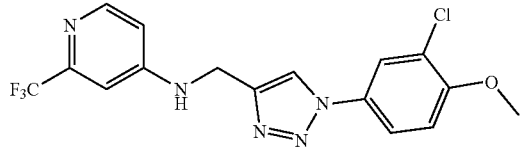

LC-MS: m/z: 384 (M+H)+.

N-((1-(4-(Phenylamino)phenyl)-1H-1,2,3-triazol-4-yl)methyl)-2-(trifluoromethyl)pyridin-4-amine (018)

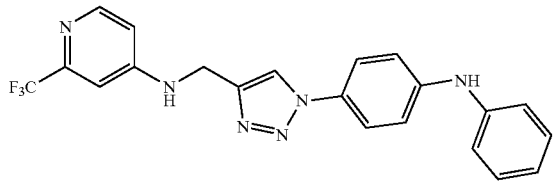 [SMILES: FC(F)(F)c1cc(NCc2cn(-c3ccc(Nc4ccccc4)cc3)nn2)ccn1]

LC-MS: m/z: 411 (M+H)+.

N-((1-(4-(Morpholinomethyl)phenyl)-1H-1,2,3-triazol-4-yl)methyl)-2-(trifluoromethyl)pyridin-4-amine (019)

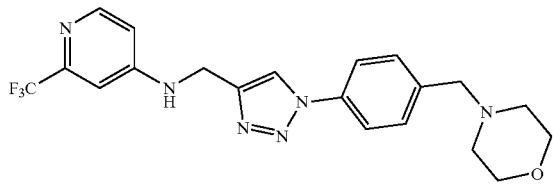 [SMILES: FC(F)(F)c1cc(NCc2cn(-c3ccc(CN4CCOCC4)cc3)nn2)ccn1]

LC-MS: m/z: 419 (M+H)+.

N-((1-(3,4-Difluorophenyl)-1H-1,2,3-triazol-4-yl)methyl)-2-(trifluoromethyl)pyridin-4-amine (020)

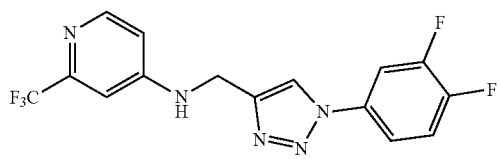

LC-MS: m/z: 356 (M+H)+.

N-((1-(4-phenoxyphenyl)-1H-1,2,3-triazol-4-yl)methyl)-5-(trifluoromethyl)pyridin-3-amine (021)

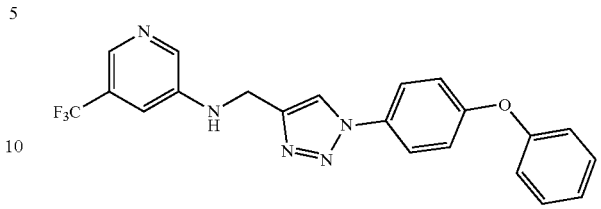

LC-MS: m/z: 412 (M+H)+. $^1$H NMR (300 MHz, CDCl$_3$) δ 8.21 (s, 1H), 7.80 (s, 1H), 7.58 (d, J=8.9 Hz, 2H), 7.32 (t, J=7.8 Hz, 2H), 7.09 (dd, J=20.6, 8.2 Hz, 5H), 6.99 (d, J=7.9 Hz, 2H), 4.62 (s, 1H), 4.51 (d, J=5.2 Hz, 2H).

N-((1-(3-Chloro-4-(trifluoromethoxy)phenyl)-1H-1,2,3-triazol-4-yl)methyl)-2-(trifluoromethyl) pyridin-4-amine (022)

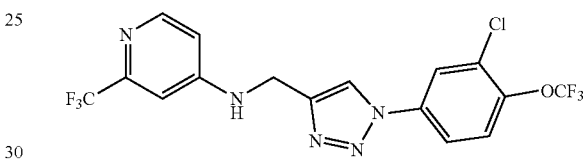

LC-MS: m/z: 438 (M+H)+. $^1$H-NMR (300 MHz, CDCl$_3$): δ [ppm]=4.63 (d, J=5.6 Hz, 2H, 6-H), 5.25 (m, 1H, NH), 6.68 (dd, J=5.7 Hz, J=2.3 Hz, 1H, 4-H), 6.92 (d, J=2.3 Hz, 1H, 2-H), 7.51 (m, 1H, 13-H), 7.69 (dd, J=8.9 Hz, J=2.6 Hz, 1H, 14-H), 7.93 (m, 2H, 8-H, 10-H), 8.33 (d, J=5.7 Hz, 1H, 5-H).

N-((1-(4-Bromo-3-methoxyphenyl)-1H-1,2,3-triazol-4-yl)methyl)-2-(trifluoromethyl)pyridin-4-amine (023)

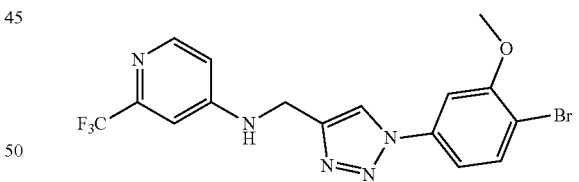

LC-MS: m/z: 429 (M+H)+.

N-((1-(4-Bromo-2-fluorophenyl)-1H-1,2,3-triazol-4-yl)methyl)-2-(trifluoromethyl)pyridin-4-amine (024)

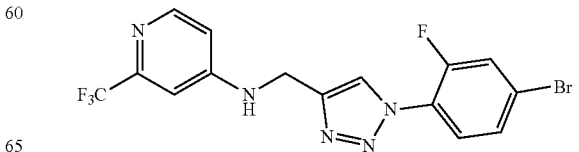

LC-MS: m/z: 416 (M+H)+.

N-((1-(4-(Pyridin-4-ylmethyl)phenyl)-1H-1,2,3-tri-azol-4-yl)methyl)-2-(trifluoromethyl)pyridin-4-amine (025)

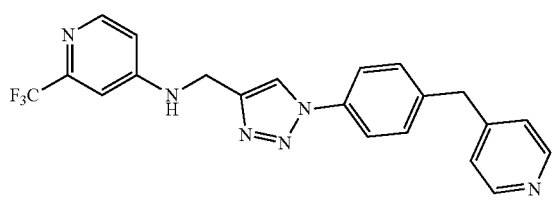 [SMILES: FC(F)(F)c1cc(NCc2cn(-c3ccc(Cc4ccncc4)cc3)nn2)ccn1]

LC-MS: m/z: 411 (M+H)+.

N-((1-(3-Fluoro-4-methoxyphenyl)-1H-1,2,3-triazol-4-yl)methyl)-2-(trifluoromethyl)pyridin-4amine (026)

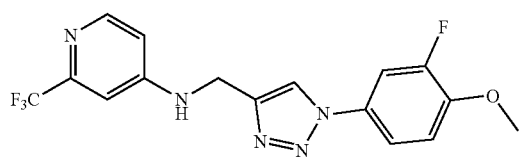 [SMILES: COc1ccc(-n2cc(CNc3ccnc(C(F)(F)F)c3)nn2)cc1F]

LC-MS: m/z: 368 (M+H)+.

N-((1-(3-Chloro-4-fluorophenyl)-1H-1,2,3-triazol-4-yl)methyl)-2-(trifluoromethyl)pyridin-4-amine (027)

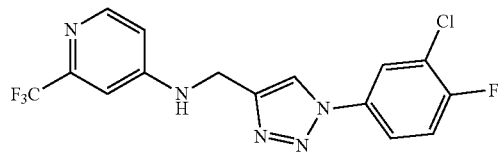 [SMILES: Fc1ccc(-n2cc(CNc3ccnc(C(F)(F)F)c3)nn2)cc1Cl]

LC-MS: m/z: 372 (M+H)+.

N-((1-(3-fluoro-4-phenoxyphenyl)-1H-1,2,3-triazol-4-yl)methyl)-2-(trifluoromethyl)pyridin-4-amine (028)

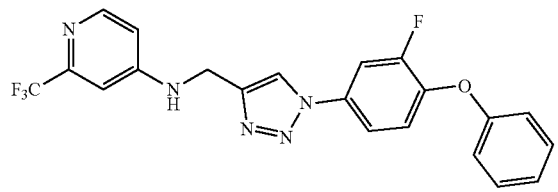 [SMILES: Fc1cc(-n2cc(CNc3ccnc(C(F)(F)F)c3)nn2)ccc1Oc1ccccc1]

LC-MS: m/z: 430 (M+H)+.

N-((1-(4-(Methyl(phenyl)amino)phenyl)-1H-1,2,3-triazol-4-yl)methyl)-2-(trifluoromethyl)pyridin-4-amine (029)

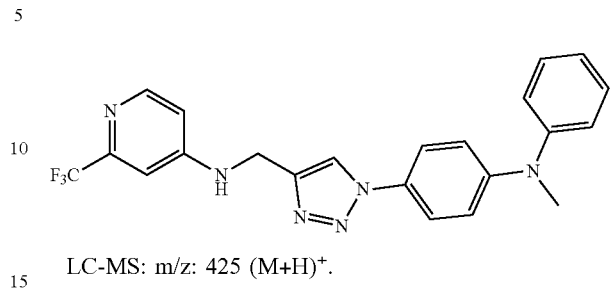

LC-MS: m/z: 425 (M+H)+.

N-((1-(4-(3-Chlorophenoxy)phenyl)-1H-1,2,3-tri-azol-4-yl)methyl)-2-(trifluoromethyl)pyridin-4-amine (030)

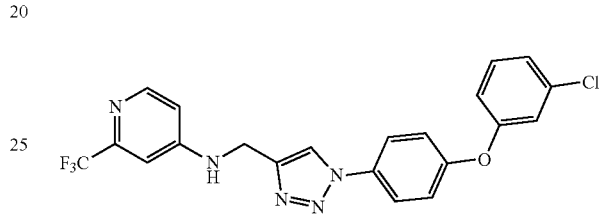

LC-MS: m/z: 446 (M+H)+.

N-((1-(3-Chloro-4-(pyridin-3-yloxy)phenyl)-1H-1,2,3-triazol-4-yl)methyl)-2-(trifluoromethyl)pyridin-4-amine (031)

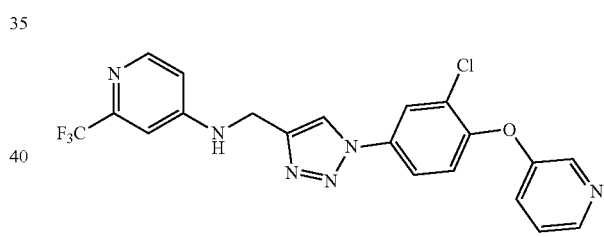

LC-MS: m/z: 447 (M+H)+. $^1$H-NMR (300 MHz, CDCl$_3$): δ [ppm]=4.62 (d, J=5.6 Hz, 2H), 5.54-5.58 (m, 1H), 6.66 (dd, J=5.7 Hz, J=2.2 Hz, 1H), 6.91 (d, J=2.1 Hz, 1H), 7.12 (d, J=8.8 Hz, 1H), 7.28-7.34 (m, 2H), 7.60 (dd, J=8.9 Hz, J=2.6 Hz, 1H) 7.88 (d, J=2.5 Hz, 1H), 7.93 (s, 1H), 8.29 (d, J 5.7 Hz, 1H), 8.40-8.44 (m, 2H).

2-Chloro-N-((1-(4-phenoxyphenyl)-1H-1,2,3-triazol-4-yl)methyl)-6-(trifluoromethyl)pyridin-4-amine (032)

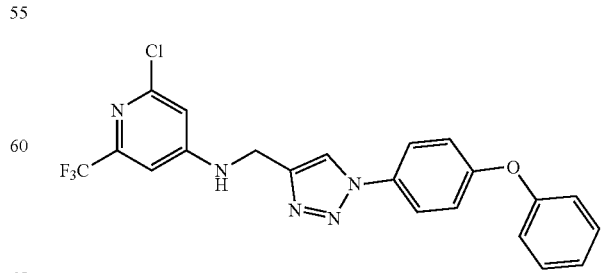

LC-MS: m/z: 446 (M+H)+. $^1$H-NMR (300 MHz, CDCl$_3$): δ [ppm]=4.60 (d, J=5.4 Hz, 2H), 5.35 (t, J=5.4 Hz, 1H), 6.69

(d, J=2.0 Hz, 1H), 6.86 (d, J=2.0 Hz, 1H), 7.06-7.09 (m, 2H), 7.12-7.17 (m, 2H), 7.17-7.22 (m, 1H), 7.38-7.43 (m, 2H), 7.63-7.68 (m, 2H), 7.88 (s, 1H).

N-((1-(4-(Pyridin-3-yloxy)phenyl)-1H-1,2,3-triazol-4-yl)methyl)-2-(trifluoromethyl)pyridin-4-amine (033)

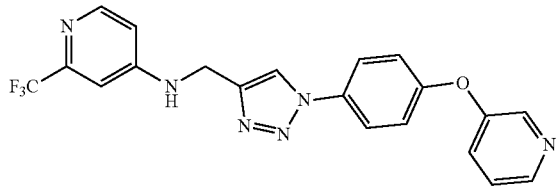 [SMILES: FC(F)(F)c1cc(NCc2cn(-c3ccc(Oc4cccnc4)cc3)nn2)ccn1]

LC-MS: m/z: 413 (M+H)⁺. ¹H-NMR (300 MHz, CDCl₃): δ [ppm]=4.64 (d, J=5.7 Hz, 2H), 5.16-5.18 (m, 1H), 6.68 (dd, J=5.8 Hz, J=2.3 Hz, 1H), 6.92 (d, J=2.3 Hz, 1H), 7.15 (d, J=8.9 Hz, 1H), 7.35 (m, 2H), 7.63 (dd, J=8.9 Hz, J=2.6 Hz, 1H), 7.90 (s, 1H), 7.92 (d, J=2.6 Hz, 1H), 8.35 (d, J=5.7 Hz, 1H), 8.45 (m, 2H).

N-((1-(3-Chloro-4-(pyridin-2-yloxy)phenyl)-1H-1,2,3-triazol-4-yl)methyl)-2-(trifluoromethyl)pyridin-4-amine (034)

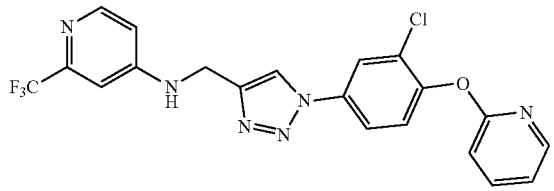 [SMILES: FC(F)(F)c1cc(NCc2cn(-c3ccc(Oc4ccccn4)c(Cl)c3)nn2)ccn1]

LC-MS: m/z: 447 (M+H)⁺. ¹H-NMR (300 MHz, CDCl₃): δ [ppm]=4.63 (d, J 5.5 Hz, 2H), 5.15-5.17 (m, 1H), 6.67-6.70 (dd, J=5.7 Hz, J=2.2 Hz, 1H), 6.93 (d, J=2.2 Hz, 1H), 7.04-7.09 (m, 2H), 7.39 (d, J=8.6 Hz, 1H), 7.67 (dd, J=8.6 Hz, J=2.3 Hz, 1H), 7.75-7.80 (m, 1H), 7.88 (d, J=2.6 Hz, 1H), 7.90 (s, 1H), 8.13-8.15 (m, 1H), 8.35 (d, J=5.6 Hz, 1H).

N-((1-(4-Isopropoxyphenyl)-1H-1,2,3-triazol-4-yl)methyl)-2-(trifluoromethyl)pyridin-4-amine (035)

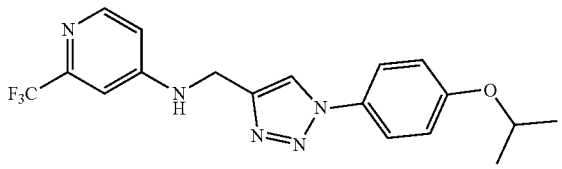 [SMILES: CC(C)Oc1ccc(-n2cc(CNc3ccnc(C(F)(F)F)c3)nn2)cc1]

LC-MS: m/z: 378 (M+H)⁺. ¹H-NMR (300 MHz, CDCl₃): δ [ppm]=1.37 (d, J=6.1 Hz, 6H), 4.54-4.65 (m, 3H), 5.20 (bs, 1H), 6.67 (dd, J=5.7 Hz, J=2.1 Hz, 1H), 6.92 (d, J=2.1 Hz, 1H), 7.00 (d, J=8.9 Hz, 2H), 7.57 (d, J=8.9 Hz, 2H), 7.83 (s, 1H), 8.33 (d, J=5.7 Hz).

N-((1-(3-Chloro-4-isopropoxyphenyl)-1H-1,2,3-triazol-4-yl)methyl)-2-(trifluoromethyl)pyridin-4-amine (036)

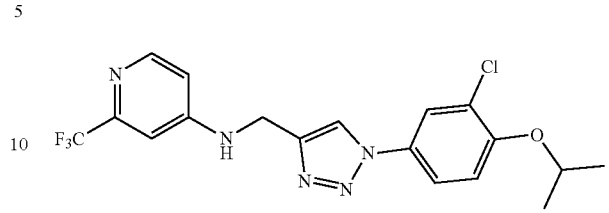

LC-MS: m/z: 412 (M+H)⁺. ¹H-NMR (300 MHz, CDCl₃): δ [ppm]=1.42 (d, J=5.9 Hz, 6H), 4.60 (d, J=5.3 Hz, 2H), 4.63 (d, J=5.9 Hz, 1H), 6.67 (d, J=5.7 Hz, 1H), 6.92 (s, 1H), 7.05 (d, J=8.9 Hz, 1H), 7.54 (m, 1H), 7.72 (m, 1H), 7.84 (s, 1H), 8.33 (d, J=5.7 Hz).

N-((1-(4-(4-Chlorophenoxy)phenyl)-1H-1,2,3-triazol-4-yl)methyl)-2-(trifluoromethyl)pyridin-4-amine (037)

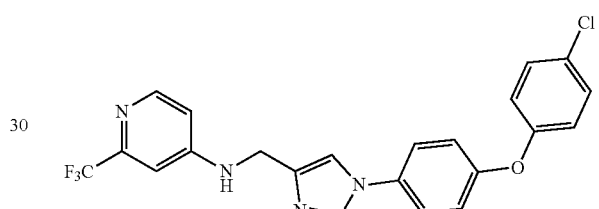

LC-MS: m/z 446 (M+H)⁺.

N-((1-(3-Chloro-4-(methylthio)phenyl)-1H-1,2,3-triazol-4-yl)methyl)-2-(trifluoromethyl)pyridin-4-amine (038)

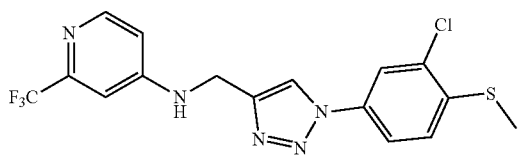 [SMILES: CSc1ccc(-n2cc(CNc3ccnc(C(F)(F)F)c3)nn2)cc1Cl]

LC-MS: m/z 400 (M+H)⁺.

N-((1-(4-Bromophenyl)-1H-1,2,3-triazol-4-yl)methyl)-2-(trifluoromethyl)pyridin-4-amine (039)

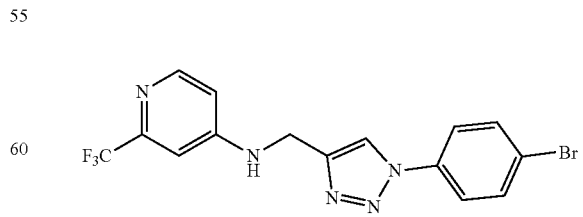

LC-MS: m/z 398 (M+H)⁺. ¹H-NMR (300 MHz, CDCl₃): δ [ppm]=4.63 (d, J=5.3 Hz, 2H), 5.18 (bs, 1H), 6.68 (m, 1H), 6.92 (s, 1H), 7.62 (m, 2H), 7.68 (m, 2H), 7.91 (s, 1H), 8.34 (m, 1H).

47

N-((1-(4-(1H-Indol-1-yl)phenyl)-1H-1,2,3-triazol-4-yl)methyl)-2-(trifluoromethyl)pyridin-4-amine (040)

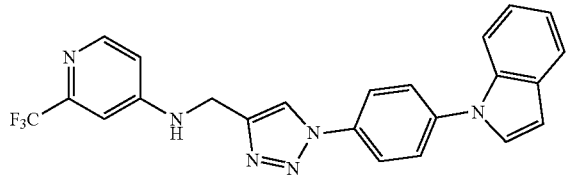

LC-MS: m/z 435(M+H)⁺. ¹H-NMR (300 MHz, CDCl₃): δ [ppm]=4.66 (d, J=5.5 Hz, 2H), 5.21 (bs, 1H), 6.70 (dd, J=5.7 Hz, J=2.1 Hz, 1H), 6.75 (d, J=3.5 Hz, 1H), 6.94 (d, J=2.3 Hz, 1H), 7.22 (m, 1H), 7.28 (m, 2H), 7.38 (d, J=3.4 Hz, 1H), 7.95 (d, J=8.2 Hz, 1H), 7.11 (m, 3H), 7.89 (d, J=8.9 Hz, 2H), 7.97 (s, 1H), 8.35 (d, J=5.7 Hz). 4-(((1-(4-Phenoxyphenyl)-1H-1,2,3-triazol-4-yl)methyl)amino)picolinonitrile (041)

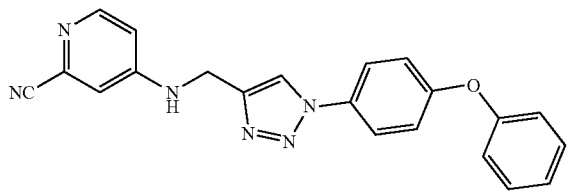 [SMILES: N#Cc1cc(NCc2cn(-c3ccc(Oc4ccccc4)cc3)nn2)ccn1]

LC-MS: m/z 369 (M+H)⁺. H NMR (500 MHz, Acetone) δ 8.39 (s, 1H), 8.05 (d, J=5.8 Hz, 1H), 7.75-7.70 (m, 2H), 7.34-7.28 (m, 2H), 7.11-7.02 (m, 4H), 6.97 (dd, J=8.6, 0.9 Hz, 2H), 6.79 (dd, J=5.8, 2.5 Hz, 1H), 6.75 (s, 1H), 4.52 (d, J=5.8 Hz, 2H).

2-Chloro-N-((1-(3-chloro-4-isopropoxyphenyl)-1H-1,2,3-triazol-4-yl)methyl)-6-(trifluoromethyl)pyridin-4-amine (042)

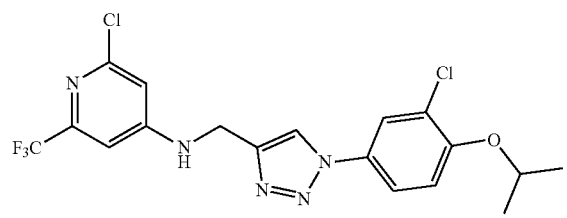 [SMILES: CC(C)Oc1ccc(-n2cc(CNc3cc(Cl)nc(C(F)(F)F)c3)nn2)cc1Cl]

LC-MS: m/z: 467 (M+H)⁺. ¹H-NMR (300 MHz, CDCl₃): δ [ppm]=1.43 (d, J=6.1 Hz, 6H), 4.59 (d, J=5.3 Hz, 2H), 4.64 (sept, J=6.1 Hz, 1H), 5.38 (bs, 1H), 6.69 (d, J=2.0 Hz, 1H), 6.86 (d, J=2.0 Hz, 1H), 7.07 (d, J=8.9 Hz, 1H), 7.56 (dd, J=8.9 Hz, J=2.6 Hz, 1H), 7.74 (d, J=2.6 Hz, 1H), 7.85 (s, 1H).

48

N-((1-(4-(1H-pyrrolo[2,3-c]pyridin-1-yl)phenyl)-1H-1,2,3-triazol-4-yl)methyl)-2-(trifluoromethyl)pyridin-4-amine (043)

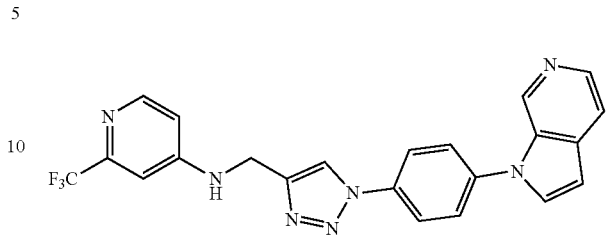

LC-MS: m/z 436 (M+H)⁺.

N-((1-(4-(1H-pyrrolo[2,3-b]pyridin-1-yl)phenyl)-1H-1,2,3-triazol-4-yl)methyl)-2-(trifluoromethyl)pyridin-4-amine (044)

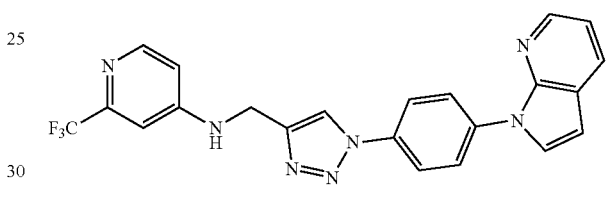

LC-MS: m/z 436 (M+H)⁺.

N-((1-(4-(1H-benzo[d]imidazol-1-yl)phenyl)-1H-1,2,3-triazol-4-yl)methyl)-2-(trifluoromethyl)pyridin-4-amine (045)

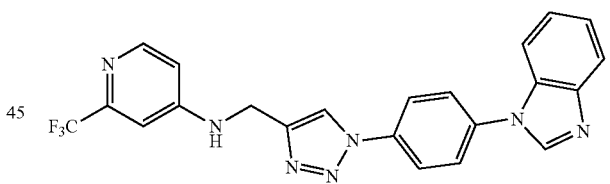

LC-MS: m/z 436 (M+H)⁺.

N-((1-(4-(1H-indazol-1-yl)phenyl)-1H-1,2,3-triazol-4-yl)methyl)-2-(trifluoromethyl)pyridin-4-amine (046)

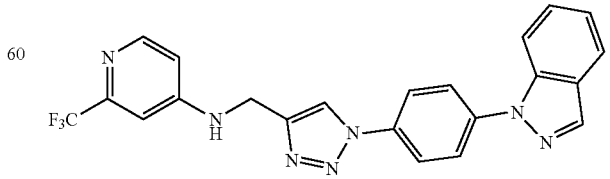

LC-MS: m/z 436 (M+H)⁺.

49

N-((1-(3-chloro-4-cyclobutoxyphenyl)-1H-1,2,3-triazol-4-yl)methyl)-2-(trifluoromethyl)pyridin-4-amine (047)

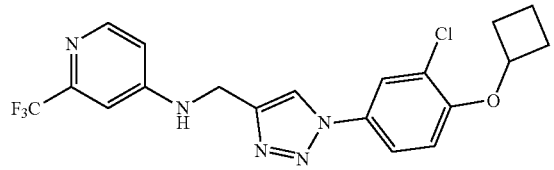 [SMILES: FC(F)(F)c1cc(NCc2cn(-c3ccc(OC4CCC4)c(Cl)c3)nn2)ccn1]

LC-MS: m/z 424 (M+H)⁺.

2,6-Dichloro-N-((1-(4-phenoxyphenyl)-1H-1,2,3-triazol-4-yl)methyl)pyridin-4-amine (048)

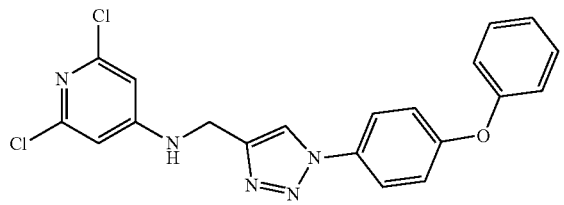 [SMILES: Clc1cc(NCc2cn(-c3ccc(Oc4ccccc4)cc3)nn2)cc(Cl)n1]

LC-MS: m/z 412 (M+H)⁺.

2-Chloro-N-((1-(4-phenoxyphenyl)-1H-1,2,3-triazol-4-yl)methyl)pyridin-4-amine (049)

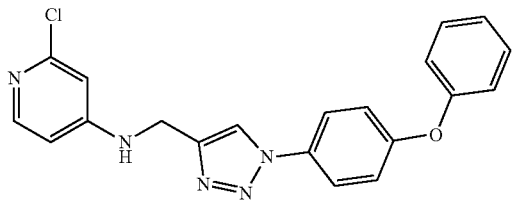 [SMILES: Clc1cc(NCc2cn(-c3ccc(Oc4ccccc4)cc3)nn2)ccn1]

LC-MS: m/z 378 (M+H)⁺.

4-(((1-(4-Phenoxyphenyl)-1H-1,2,3-triazol-4-yl)methyl)amino)-6-(trifluoromethyl)pyridin-2-ol (050)

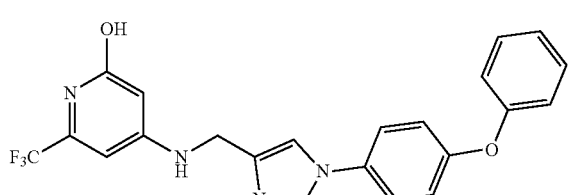

LC-MS: m/z 428 (M+H)⁺.

50

6-Chloro-4-(((1-(4-phenoxyphenyl)-1H-1,2,3-triazol-4-yl)methyl)amino)picolinonitrile (051)

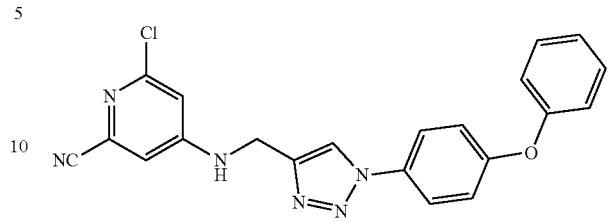

LC-MS: m/z 403 (M+H)⁺.

4-(((1-(4-Phenoxyphenyl)-1H-1,2,3-triazol-4-yl)methyl)amino)pyridine-2,6-dicarbonitrile (052)

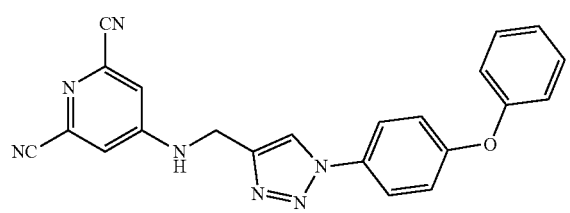 [SMILES: N#Cc1cc(NCc2cn(-c3ccc(Oc4ccccc4)cc3)nn2)cc(C#N)n1]

LC-MS: m/z 394 (M+H)⁺.

N-((1-(3-Chloro-4-phenoxyphenyl)-1H-1,2,3-triazol-4-yl)methyl)-2-(trifluoromethyl)pyridin-4-amine (053)

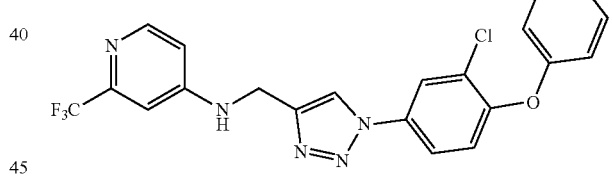

LC-MS: m/z: 446 (M+H)⁺. ¹H-NMR (300 MHz, CDCl₃): δ [ppm]=4.62 (d, J=5.6 Hz, 2H, 6-H). 5.31-5.34 (m, 1H, NH), 6.67 (d, J=5.7 Hz, J=2.3 Hz, 1H, 4-H), 6.92 (d, J=2.2 Hz, 1H, 2-H), 7.01-7.08 (m, 3H, 13-H/16-H), 7.16-7.23 (m, 1H, 18-H), 7.36-7.43 (m, 2H, 17-H), 7.54 (dd, J=8.9 Hz, J=2.6 Hz, 1H, 14-H), 7.85 (d, J=2.6 Hz, 13-H), 7.89 (s, 1H, 8-H), 8.32 (d, J=5.6 Hz, 1H, 5-H).

Example 2. Compounds 054 to 064

2.1 Preparation of 4-(((1-(4-phenoxyphenyl)-1H-1,2,3-triazol-4-yl)methyl)thio)-2-(trifluoromethyl)pyridine (054)

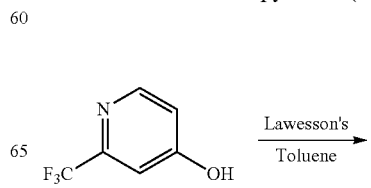

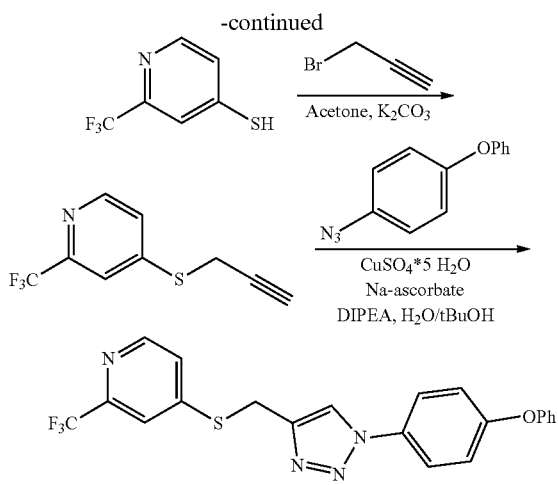

Step A. 2-(Trifluoromethyl)pyridine-4-thiol

A mixture of 2-(trifluoromethyl)pyridin-4-ol (100 mg, 0.613 mmol) and Lawesson's reagent (123.99 mg, 0.307 mmol) in toluene (10 mL) was refluxed for 2 hours. Excess solvent was evaporated under reduced pressure. The residue was purified by automate column chromatography to give the desired product (75 mg, 68% yield). LC-MS: m/z: 180 (M+H)$^+$.

Step B. 4-(prop-2-yn-1-ylthio)-2-(trifluoromethyl)pyridine

To a mixture of 2-(Trifluoromethyl)pyridine-4-thiol (60 mg, 0.335 mmol) and K$_2$CO$_3$ (55.54 mg, 0.402 mmol) in Acetone (10 ml) was added the propargyl bromide (47.8 mg, 30.45 µl, 0.402 mmol). The reaction was stirred for 1 hour at room temp. Excess solvent was evaporated under reduced pressure and to the remaining residue water (30 ml) was added and then extraction with Ethyl acetate. The organic solvent was then dried over anhydrous MgSO$_4$ and evaporated under reduced pressure. The residue was purified by automate column chromatography to give the desired product (55 mg, 75% yield). LC-MS: m/z: 218 (M+H)$^+$.

Step C. 4-(((1-(4-phenoxyphenyl)-1H-1,2,3-triazol-4-yl)methyl)thio)-2-(trifluoromethyl)pyridine (054)

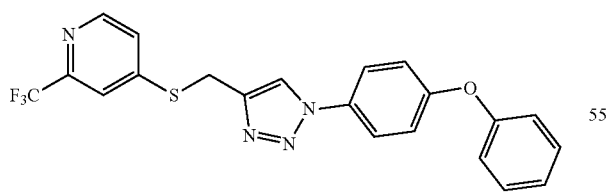

4-(prop-2-yn-1-ylthio)-2-(trifluoromethyl)pyridine (21.7 mg, 100 µmol) was dissolved in tBuOH/H$_2$O (1 mL) followed by the addition of 1-azido-4-phenoxybenzene (21 mg, 100 µmol) and DIPEA (17.5 µL, 100 µmol). The reaction mixture was purged with Argon and Cu$_2$SO$_4$*5H$_2$O (10 mol %) and Na-ascorbate (10 mol %) were added. After stirring for 15 h at 40° C. saturated NH$_4$Cl solution was added and the reaction mixture was extracted with EtOAc. The combined organic layers were washed with Brine, dried over Na$_2$SO$_4$, filtered and concentrated under reduced pressure. The title compound (35 mg, 83%) was yielded after prep-HPLC purification.

LC/MS: m/z 429.01 (M+H)$^+$. $^1$H-NMR (300 MHz, Chloroform-d) δ 8.51 (d, J=5.3 Hz, 1H), 7.89 (s, 1H), 7.67-7.55 (m, 3H), 7.47-7.32 (m, 3H), 7.22-7.01 (m, 5H), 4.44 (s, 2H).

2.2 Compounds 055 to 064

Compounds 055 to 064 described below are further representative examples of compounds according to general formula (I) of the present invention. These compounds have been synthesized based on the procedure described above for Compound 054.

4-(((1-(4-chlorophenyl)-1H-1,2,3-triazol-4-yl)methyl)thio)-2-(trifluoromethyl)pyridine (055)

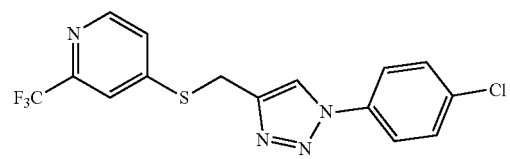 [SMILES: FC(F)(F)c1cc(SCc2cn(-c3ccc(Cl)cc3)nn2)ccn1]

LC/MS: m/z 371 (M+H)$^+$. $^1$H-NMR (300 MHz, DMSO-d6) δ 8.83 (s, 1H), 8.56 (d, J=5.3 Hz, 1H), 8.01-7.87 (m, 3H), 7.76-7.54 (m, 3H), 4.64 (s, 2H).

4-(((1-(3-Chlorophenyl)-1H-1,2,3-triazol-4-yl)methyl)thio)-2-(trifluoromethyl)pyridine (056)

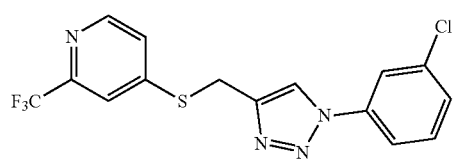 [SMILES: FC(F)(F)c1cc(SCc2cn(-c3cccc(Cl)c3)nn2)ccn1]

LC-MS: m/z: 371 (M+H)$^+$.

Phenyl(4-(4-(((2-(trifluoromethyl)pyridin-4-yl)thio)methyl)-1H-1,2,3-triazol-1-yl)phenyl)methanone (057)

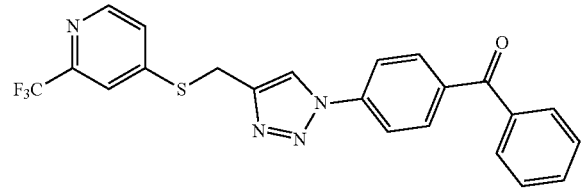 [SMILES: O=C(c1ccccc1)c1ccc(-n2cc(CSc3ccnc(C(F)(F)F)c3)nn2)cc1]

LC-MS: m/z: 441 (M+H)$^+$.

4-(((1-(4-Bromophenyl)-1H-1,2,3-triazol-4-yl)methyl)thio)-2-(trifluoromethyl)pyridine (058)

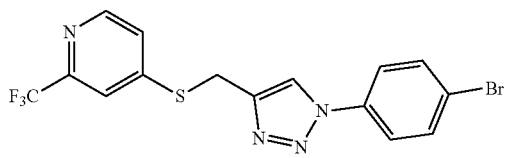

LC-MS: m/z: 415 (M+H)+.

4-(((1-(3,4-Dichlorophenyl)-1H-1,2,3-triazol-4-yl)methyl)thio)-2-(trifluoromethyl)pyridine (059)

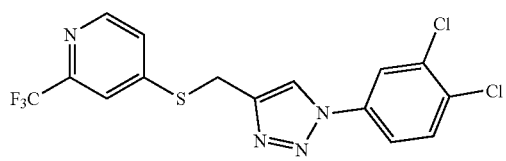 [SMILES: FC(F)(F)c1cc(SCc2cn(-c3ccc(Cl)c(Cl)c3)nn2)ccn1]

LC-MS: m/z: 405 (M+H)+.

4-(((1-(4-chlorophenyl)-1H-1,2,3-triazol-4-yl)methyl)thio)-2-(trifluoromethyl)pyrimidine (060)

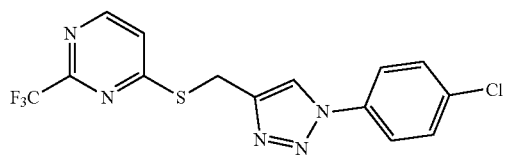 [SMILES: FC(F)(F)c1nccc(SCc2cn(-c3ccc(Cl)cc3)nn2)n1]

LC/MS: m/z 372 (M+H)+. $^1$H-NMR (300 MHz, Acetone-d6) δ 8.66 (d, J=5.5 Hz, 1H), 8.53 (s, 1H), 7.92-7.82 (m, 2H), 7.73 (dd, J=5.6, 0.6 Hz, 1H), 7.66-7.57 (m, 2H), 4.69 (d, J=0.7 Hz, 2H).

4-(((1-(4-phenoxyphenyl)-1H-1,2,3-triazol-4-yl)methyl)thio)-2-(trifluoromethyl)pyrimidine (061)

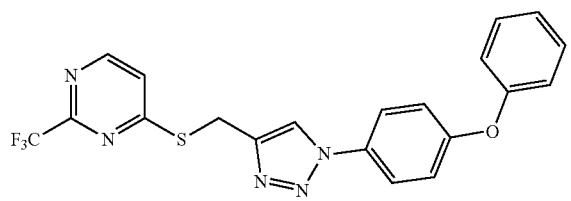 [SMILES: FC(F)(F)c1nccc(SCc2cn(-c3ccc(Oc4ccccc4)cc3)nn2)n1]

LC/MS: m/z 430 (M+H)+. $^1$H-NMR (300 MHz, Chloroform-d) δ 8.40 (d, J=5.5 Hz, 1H), 7.98 (s, 1H), 7.62-7.48 (m, 2H), 7.37-7.22 (m, 3H), 7.10-6.91 (m, 5H), 4.53 (s, 2H).

4-(((1-(4-methoxyphenyl)-1H-1,2,3-triazol-4-yl)methyl)thio)-2-(trifluoromethyl)pyridine (062)

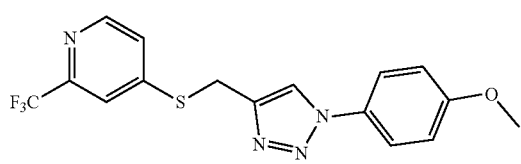 [SMILES: COc1ccc(-n2cc(CSc3ccnc(C(F)(F)F)c3)nn2)cc1]

LC-MS: m/z 367 (M+H)+.

4-(((1-(3-chloro-4-(trifluoromethoxy)phenyl)-1H-1,2,3-triazol-4-yl)methyl)thio)-2-(trifluoromethyl)pyridine (063)

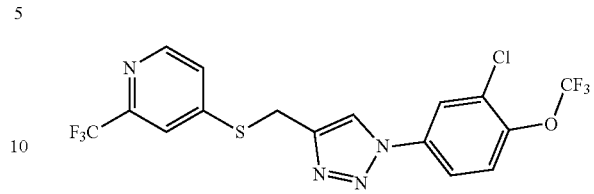

LC/MS: m/z 455.16 (M+H)+. $^1$H-NMR (300 MHz, DMSO-d6) δ 8.92 (s, 1H), 8.56 (d, J=5.3 Hz, 1H), 8.31 (d, J=2.6 Hz, 1H), 8.04 (dd, J=9.0, 2.6 Hz, 1H), 7.91 (d, J=1.7 Hz, 1H), 7.81 (dq, J=9.0, 1.4 Hz, 1H), 7.71 (dd, J=5.4, 1.8 Hz, 1H), 4.66 (s, 2H).

4-(((1-(3-fluoro-4-(trifluoromethoxy)phenyl)-1H-1,2,3-triazol-4-yl)methyl)thio)-2-(trifluoromethyl)pyridine (064)

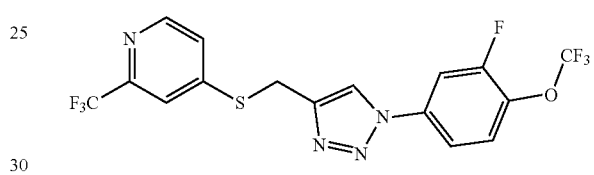

LC/MS: m/z 439.15 (M+H)+. $^1$H-NMR (500 MHz, Chloroform-d) δ 8.58-8.48 (m, 1H), 7.94 (t, J=0.7 Hz, 1H), 7.68 (dd, J=10.1, 2.5 Hz, 1H), 7.60-7.57 (m, 1H), 7.56-7.44 (m, 2H), 7.41 (dd, J=5.3, 1.8 Hz, 1H), 4.44 (d, J=0.8 Hz, 2H).

Example 3. Preparation of 6-(((1-(4-phenoxyphenyl)-1H-1,2,3-triazol-4-yl)methyl)thio)-2-trifluoromethyl)pyrimidin-4-amine (065)

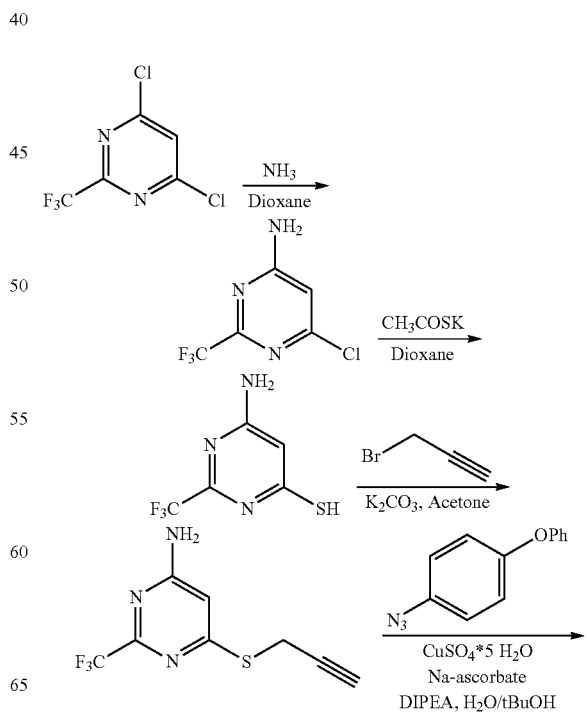

-continued

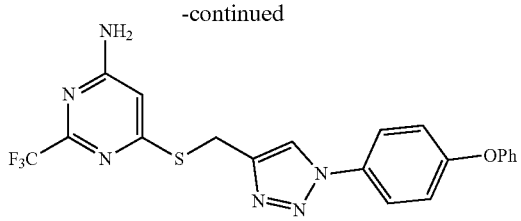

Step A.
6-Chloro-2-(trifluoromethyl)pyrimidin-4-amine

To 4,6-dichloro-2-(trifluoromethyl)pyrimidine (300 mg 1.38 mmol) in Dioxane (3 ml) was added ammonia solution (1 ml). The reaction was heated under microwave activation, at 100° C. for 20 min. After cooling, excess solvent was evaporated under reduced pressure. The obtained residue was taken to the next step without further purification. LC/MS: m/z 198 (M+H)+.

Step B.
6-Amino-2-(trifluoromethyl)pyrimidine-4-thiol

6-Chloro-2-(trifluoromethyl)pyrimidin-4-amine (50 mg, 0.221 mmol) and potassium thioacetate (37.9 mg, 0.331 mmol) in Dioxane (3 ml) were heated in microwave (Temp. 100-C, Hold time 10 min., Pressure 300, Power 150). After cooling, excess solvent was evaporated under reduced pressure. The reaction mixture was partitioned between ethyl acetate and water. The aqueous phase was extracted again with ethyl acetate. The organic solvent was then dried over MgSO4 and evaporated under reduced pressure. The combined organic layers were dried over anhydrous MgSO4 and evaporated under reduced pressure. The obtained residue was taken to the next step without further purification. LC/MS: m/z 196 (M+H)+.

Step C. 6-(prop-2-yn-1-ylthio)-2-(trifluoromethyl) pyrimidin-4-amine

To a mixture of 6-Amino-2-(trifluoromethyl)pyrimidine-4-thiol (50 mg, 0.25 mmol) and K2CO3 (42.49 mg, 0.307 mmol) in acetone (10 ml) was added the propargyl bromide (36.57 mg, 0.307 mmol). The reaction was stirred at room temp for 2 hours. Excess solvent was evaporated under reduced pressure and to the remaining residue, water (20 ml) was added and then extraction with ethyl acetate. The organic solvent was then dried over MgSO4 and evaporated under reduced pressure. The residue was purified by automate column chromatography to give the desired product (40 mg, 67% yield). LC/MS: m/z 234 (M+H)+.

Step D. Synthesis of 6-(((1-(4-phenoxyphenyl)-1H-1,2,3-triazol-4-yl)methyl)thio)-2-(trifluoromethyl) pyrimidin-4-amine (065)

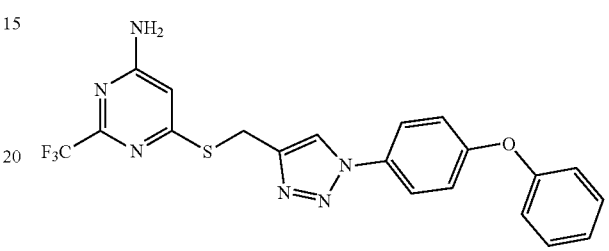

6-(prop-2-yn-1-ylthio)-2-(trifluoromethyl)pyrimidin-4-amine (19.5 mg, 100 μmol) was dissolved in tBuOH/H2O (1 mL) followed by the addition of 1-azido-4-phenoxybenzene (21 mg, 100 μmol) and DIPEA (17.5 μL, 100 μmol). The reaction mixture was purged with Argon and Cu2SO4*5H2O (10 mol %) and Na-ascorbate (10 mol %) were added. After stirring for 15 h at 40° C. saturated NH4Cl solution was added and the reaction mixture was extracted with EtOAc. The combined organic layers were washed with Brine, dried over Na2SO4, filtered and concentrated under reduced pressure. The title compound (25 mg, 67%) was yielded after prep-HPLC purification.

LC-MS: m/z: 445 (M+H)+. 1H NMR (500 MHz, Acetone) δ 8.28 (s, 1H), 7.70 (d, J=8.0 Hz, 2H), 7.30 (t, J=6.9 Hz, 2H), 7.14-6.87 (m, 5H), 6.64 (s, 2H), 6.51 (s, 1H), 4.41 (s, 2H).

Example 4: Compounds 066 and 067

4.1 Preparation of 2-(4-phenoxyphenyl)-5-(((2-(trifluoromethyl)pyridin-4-yl)thio)methyl) thiazole (066)

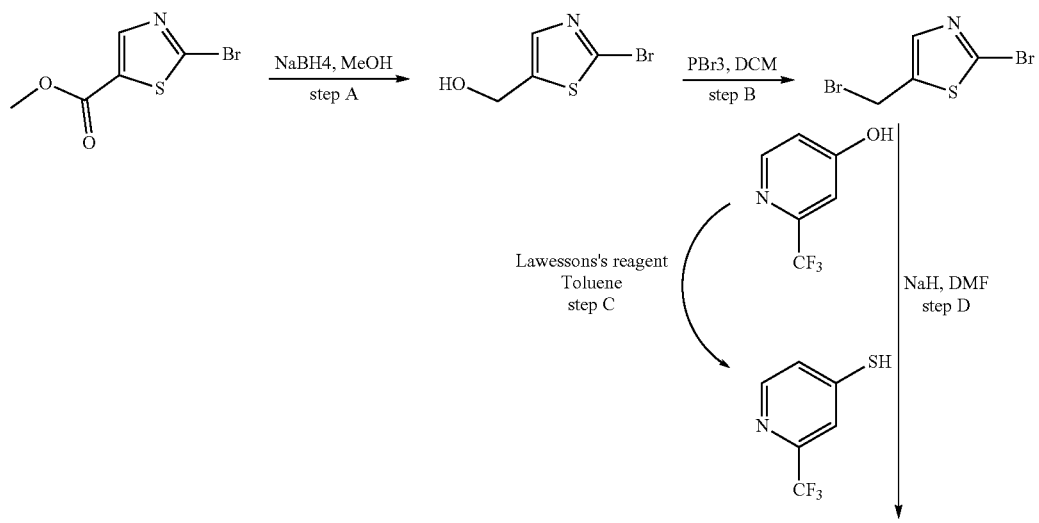
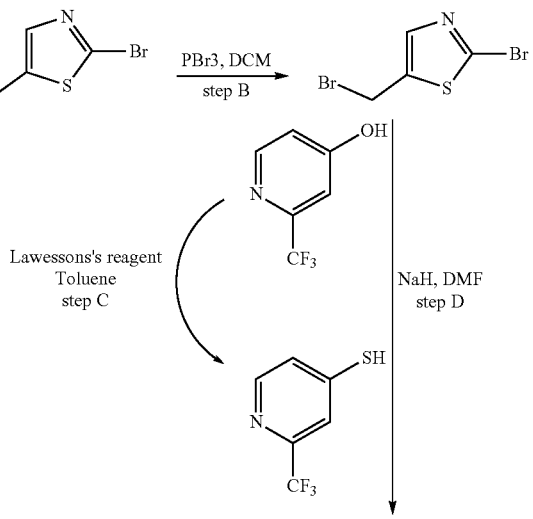

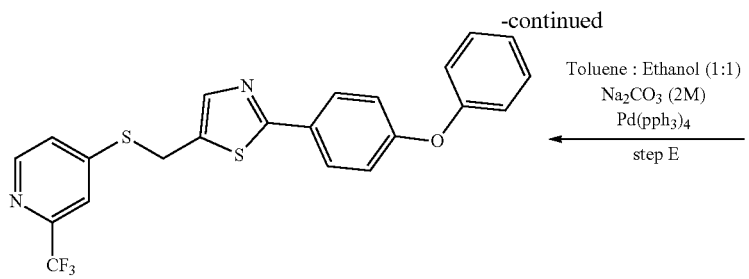

Step A. (2-Bromothiazol-5-yl)methanol

Methyl 2-bromothiazole-5-carboxylate (4.94 g, 23 mmol) was dissolved in 45 ml methanol and sodium borohydride (8.5 g, 23 mmol) was added slowly and stirred at rt for 1 hour then concentrated under reduced pressure. The residue was diluted with saturated aqueous $NaHCO_3$ and extracted with ethyl acetate. The combined organic layers were dried over anhydrous $MgSO_4$ und concentrated under reduced pressure. The crude product was directly used in the next step without any further purification. LC.MS: m/z 194.0 $(M+H)^+$.

Step B. 2-Bromo-5-(bromomethyl)thiazole

To (2-bromothiazol-5-yl)methanol (100 mg, 0.52 mmol) in DCM (10 ml) at 0° C. was added the Phosphorus tribromide (705 mg, 3.45 mmol). A precipitate was formed during the addition and the reaction was stirred at room temperature for 2 hours. The reaction was quenched with $NaHCO_3$ and extracted with DCM. The organic solvent was dried over anhydrous $MgSO_4$ then removed under reduced pressure. The crude product was directly used in the next step without any further purification.

Step C. 2-(Trifluoromethyl)pyridine-4-thiol

A mixture of 2-(trifluoromethyl)pyridin-4-ol (100 mg, 0.613 mmol) and Lawesson's reagent (123.99 mg, 0.307 mmol) in toluene (10 mL) was refluxed for 2 hours. Excess solvent was evaporated under reduced pressure. The residue was purified was purified by column chromatography (DCM) to give the desired product. LC.MS: m/z 180.08 $(M+H)^+$.

Step D. 2-Bromo-5-(((2-(trifluoromethyl)pyridin-4-yl)thio)methyl)thiazole

A mixture of 2-bromo-5-(bromomethyl)thiazole (160 mg, 0.62 mmol), 2-(trifluoromethyl)pyridine-4-thiol (75 mg, 0.42 mmol) and $K_2CO_3$ (60 mg, 0.42 mmol) in DMF (10 mL) was stirred overnight at rt. Excess solvent was evaporated under reduced pressure and to the remaining residue water (30 ml) was added and then extraction with DCM. The organic solvent was then dried over anhydrous $MgSO_4$ and evaporated under reduced pressure. The remaining residue was taken directly for the next step and used without further purification. LC.MS: m/z 354.81 $(M+H)^+$.

Step E. 2-(4-Phenoxyphenyl)-5-(((2-(trifluoromethyl)pyridin-4-yl)thio)methyl)thiazole (066)

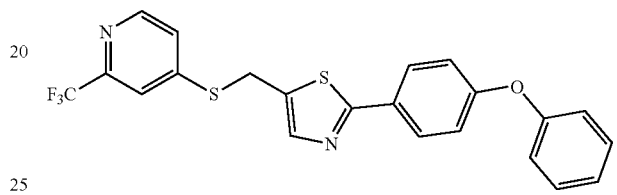

A mixture of 2-bromo-5-(((2-(trifluoromethyl)pyridin-4-yl)thio)methyl)thiazole (50 mg, 0.14 mmol), phenoxyphenyl boronic acid (45 mg, 0.21 mmol), sodium carbonate (2 M, 2 mL) and tetrakis(triphenylphosphine) palladium (0.07 mmol) was suspended in an oxygen-free toluene/ethanol (1:1, v:v, 15 mL) solution and refluxed for 4 h under nitrogen atmosphere. The reaction mixture was cooled to room temperature. The aqueous layer was extracted with ethyl acetate (3×10 mL). The organic layer was washed once with brine and once with water, dried over $MgSO_4$, filtered and the solution was concentrated under reduced pressure. The residue was purified by prep-HPLC using acetonitrile and water as eluent to afford the desired compound. $^1$H NMR (300 MHz, Acetone) δ 8.56 (d, J=5.3 Hz, 1H), 7.93 (d, J=8.8 Hz, 1H), 7.86 (s, 1H), 7.79 (d, J=1.5 Hz, 1H), 7.63 (dd, J=5.2, 1.7 Hz, 1H), 7.63 (dd, J=5.2, 1.7 Hz, 1H), 7.43 (dd, J=8.4, 7.5 Hz, 2H), 7.24-7.16 (m, 1H), 7.13-7.01 (m, 4H), 4.83 (d, J=0.7 Hz, 2H). LC.MS: m/z 445.12 $(M+H)^+$.

4.2 2-(4-Chlorophenyl)-5-(((2-(trifluoromethyl)pyridin-4-yl)thio)methyl) thiazole (067)

Compound 067 was synthesized based on the procedure described above for Compound 066.

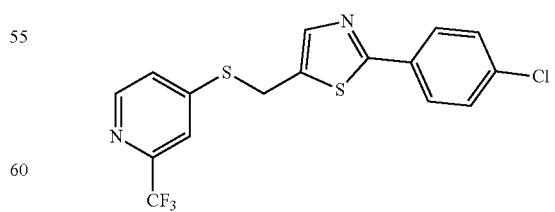

$^1$H NMR (300 MHz, $CDCl_3$) δ 8.45 (d, J=5.3 Hz, 1H), 7.74 (dd, J=8.8, 2.1 Hz, 2H), 7.66 (s, 1H), 7.45 (d, J=1.1 Hz, 1H), 7.32 (dd, J=8.8, 2.0 Hz, 2H), 7.22 (dd, J=5.2, 1.5 Hz, 1H), 4.40 (d, J=0.4 Hz, 2H). LC.MS: m/z 386.96 $(M+H)^+$.

Example 5: Compounds 068 and 069

5.1 Preparation of 6-(((2-(4-phenoxyphenyl)thiazol-5-yl)methyl)thio)-2-(trifluoromethyl) pyrimidin-4-amine (068)

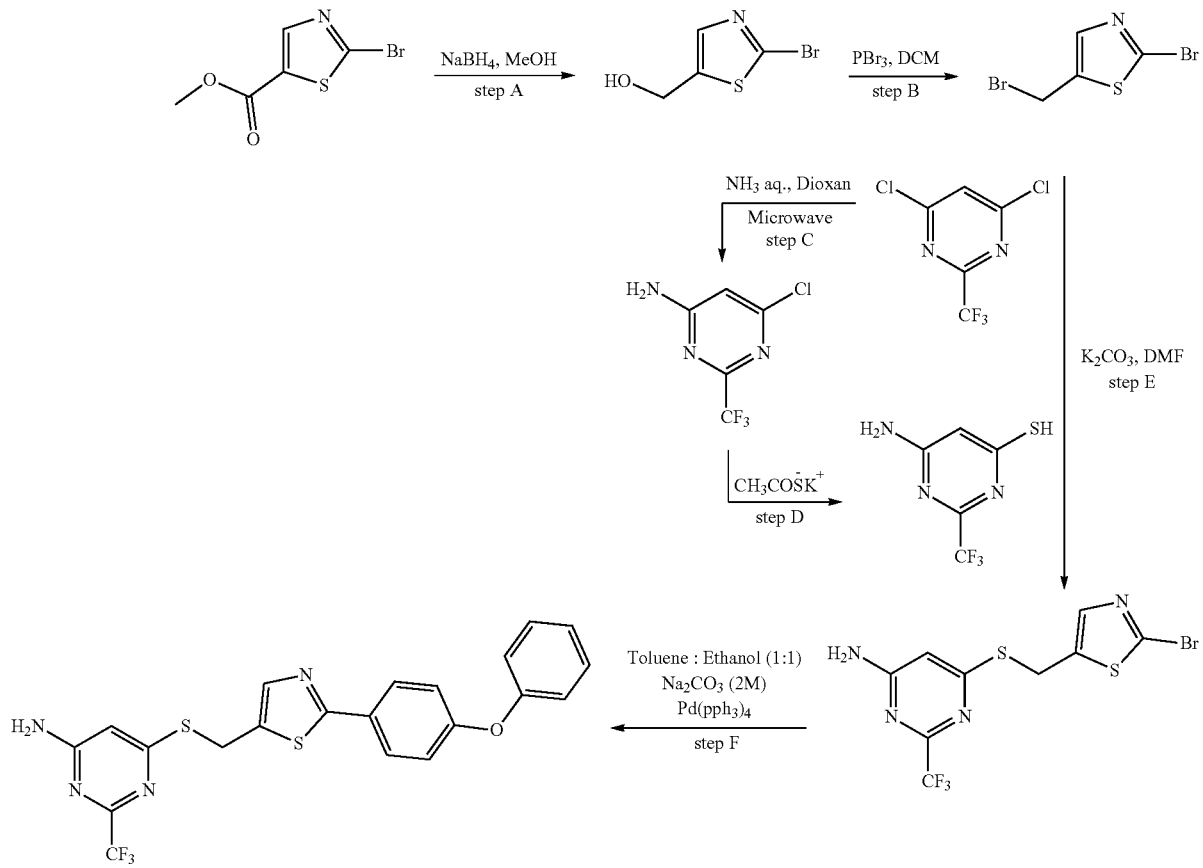

Step A. (2-Bromothiazol-5-yl)methanol

Methyl 2-bromothiazole-5-carboxylate (4.94 g, 23 mmol) was dissolved in 45 ml methanol and sodium borohydride (8.5 g, 23 mmol) was added slowly and stirred at rt for 1 hour then concentrated under reduced pressure. The residue was diluted with saturated aqueous $NaHCO_3$ and extracted with ethyl acetate. The combined organic layers were dried over anhydrous $MgSO_4$ und concentrated under reduced pressure. The crude product was directly used in the next step without any further purification. LC.MS: m/z 194.0 $(M+H)^+$.

Step B. 2-Bromo-5-(bromomethyl)thiazole

To (2-bromothiazol-5-yl)methanol (100 mg, 0.52 mmol) in DCM (10 ml) at OC was added the Phosphorus tribromide (705 mg, 3.45 mmol). A precipitate was formed during the addition and the reaction was stirred at room temperature for 2 hours. The reaction was quenched with $NaHCO_3$ and extracted with DCM. The organic solvent was dried over anhydrous $MgSO_4$ then removed under reduced pressure. The crude product was directly used in the next step without any further purification.

Step C.
6-Chloro-2-(trifluoromethyl)pyrimidin-4-amine

To 4,6-dichloro-2-(trifluoromethyl)pyrimidine (300 mg 1.38 mmol) in Dioxane (3 ml) was added ammonia solution (1 ml). The reaction was heated under microwave activation, at 100-C for 20 min. After cooling, excess solvent was evaporated under reduced pressure. The obtained residue was taken to the next step without further purification. LC.MS: m/z 198.07 $(M+H)^+$.

Step D.
6-Amino-2-(trifluoromethyl)pyrimidine-4-thiol

6-Chloro-2-(trifluoromethyl)pyrimidin-4-amine (50 mg, 0.221 mmol) and potassium thioacetate (37.9 mg, 0.331 mmol) in Dioxane (3 ml) were heated in microwave (Temp. 100-C, Hold time 10 min., Pressure 300, Power 150). After cooling, excess solvent was evaporated under reduced pressure. The reaction mixture was partitioned between ethyl acetate and water. The aqueous phase was extracted again with ethyl acetate. The organic solvent was then dried over $MgSO_4$ and evaporated under reduced pressure. The combined organic layers were dried over anhydrous MgSO$_4$ and evaporated under reduced pressure. The obtained residue was taken to the next step without further purification. LC.MS: m/z 196.10 (M+H)$^+$.

Step E. 6-(((2-Bromothiazol-5-yl)methyl)thio)-2-(trifluoromethyl)pyrimidin-4-amine A mixture of 2-bromo-5-(bromomethyl)thiazole (160 mg, 0.62 mmol), 6-Amino-2-(trifluoromethyl)pyrimidine-4-thiol (82 mg, 0.42 mmol) and K$_2$CO$_3$ (60 mg, 0.42 mmol) in DMF (10 mL) was stirred overnight at rt. Excess solvent was evaporated under reduced pressure and to the remaining residue water (30 ml) was added and then extraction with DCM. The organic solvent was then dried over anhydrous MgSO$_4$ and evaporated under reduced pressure. The obtained residue was purified using combi-flash (DCM: MeOH 0% to 5%). LC.MS: m/z 371.17 (M+H)$^+$.

Step F. 6-(((2-(4-phenoxyphenyl)thiazol-5-yl)methyl)thio)-2-(trifluoromethyl)pyrimidin-4-amine (068)

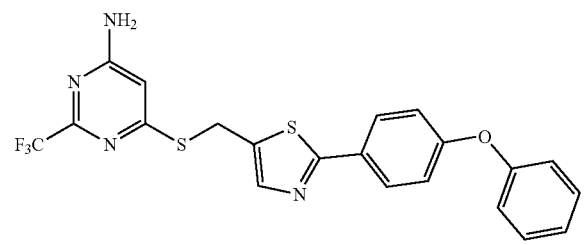 [SMILES: Nc1cc(SCc2cnc(-c3ccc(Oc4ccccc4)cc3)s2)nc(C(F)(F)F)n1]

A mixture of 6-(((2-bromothiazol-5-yl)methyl)thio)-2-(trifluoromethyl)pyrimidin-4-amine (52 mg, 0.14 mmol), phenoxyphenyl boronic acid (45 mg, 0.21 mmol), sodium carbonate (2 M, 2 mL) and tetrakis(triphenylphosphine) palladium (0.07 mmol) was suspended in an oxygen-free toluene/ethanol (1:1, v:v, 15 mL) solution and refluxed for 4 h under nitrogen atmosphere. The reaction mixture was cooled to room temperature. The aqueous layer was extracted with ethyl acetate (3×10 mL). The organic layer was washed once with brine and once with water, dried over MgSO$_4$, filtered and the solution was concentrated under reduced pressure. The residue was purified by prep-HPLC using acetonitrile and water as eluent to afford the desired compound. $^1$H NMR (500 MHz, Acetone) δ 7.94-7.88 (m, 2H), 7.78 (s, 1H), 7.45-7.40 (m, 2H), 7.20 (t, J=7.4 Hz, 1H), 7.06 (dt, J=11.4, 5.3 Hz, 4H), 6.82 (s, 2H), 6.61 (s, 1H), 4.73 (s, 2H). LC.MS: m/z 461.19 (M+H)$^+$.

5.2 6-(((2-(3-chloro-4-methoxyphenyl)thiazol-5-yl)methyl)thio)-2-(trifluoromethyl) pyrimidin-4-amine (069)

Compound 069 was synthesized based on the procedure described above for Compound 068.

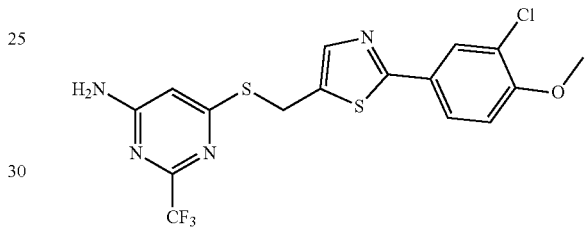

$^1$H NMR (500 MHz, Acetone) δ 7.94 (d, J=2.2 Hz, 1H), 7.80 (dd, J=8.6, 2.2 Hz, 1H), 7.77 (s, 1H), 7.20 (d, J=8.7 Hz, 1H), 6.80 (s, 2H), 6.61 (s, 1H), 4.73 (d, J=0.4 Hz, 2H), 3.96 (s, 3H). LC.MS: m/z 433.08 (M+H)$^+$.

Example 6: Preparation of N$^4$-((2-(3-chloro-4-methoxyphenyl)thiazol-5-yl)methyl)-2-(trifluoromethyl)pyrimidine-4,6-diamine (070)

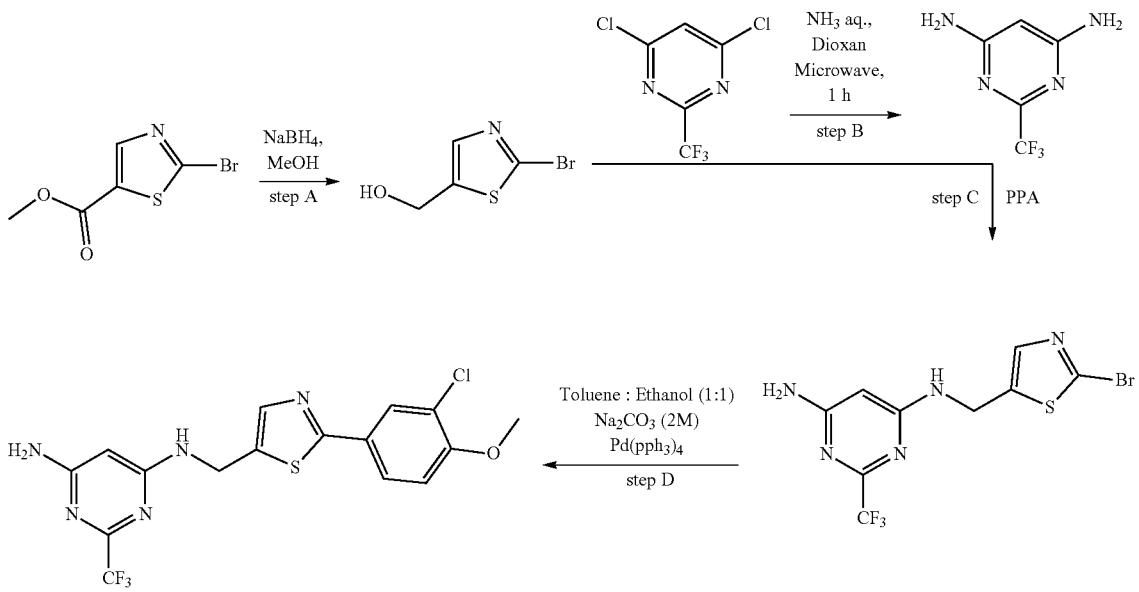

Step A. (2-Bromothiazol-5-yl)methanol

Methyl 2-bromothiazole-5-carboxylate (4.94 g, 23 mmol) was dissolved in 45 ml methanol and sodium borohydride (8.5 g, 23 mmol) was added slowly and stirred at rt for 1 hour then concentrated under reduced pressure. The residue was diluted with saturated aqueous NaHCO$_3$ and extracted with ethyl acetate. The combined organic layers were dried over anhydrous MgSO$_4$ und concentrated under reduced pressure. The crude product was directly used in the next step without any further purification. LC.MS: m/z 194.0 (M+H)$^+$.

Step B. 2-(trifluoromethyl)pyrimidine-4,6-diamine

To 4,6-dichloro-2-(trifluoromethyl)pyrimidine (300 mg 1.38 mmol) in Dioxane (3 ml) was added ammonia solution (3 ml). The reaction was heated under microwave activation, at 120° C. for 60 min. After cooling, excess solvent was evaporated under reduced pressure. The obtained residue was taken to the next step without further purification. LC.MS: m/z 179.08 (M+H)$^+$.

Step C. N$^4$-((2-Bromothiazol-5-yl)methyl)-2-(trifluoromethyl)pyrimidine-4,6-diamine To a mixture of (2-bromothiazol-5-yl)methanol (445 mg, 2.29 mmol) and 2-(trifluoromethyl)pyrimidine-4,6-diamine (612 mg, 3.44 mmol), polyphosphoric acid (2.29 g), was added and stirred at 130° C. for 4 h. The reaction mixture was poured into ice water and stirred for 1 h to give a fine precipitate. After filtration, the aqueous layer was extracted with ethyl acetate (3×10 mL). The organic solvent was then dried over anhydrous MgSO$_4$ and evaporated under reduced pressure. The remaining residue was taken directly for the next step and used without further purification. LC.MS: m/z 353.94 (M+H)$^+$.

Step D. N$^4$-((2-(3-chloro-4-methoxyphenyl)thiazol-5-yl)methyl)-2-(trifluoromethyl)-pyrimidine-4,6-diamine (070)

A mixture of N$^4$-((2-bromothiazol-5-yl)methyl)-2-(trifluoromethyl)pyrimidine-4,6-diamine (50 mg, 0.14 mmol), (3-chloro-4-methoxyphenyl)boronic acid (39 mg, 0.21 mmol), sodium carbonate (2 M, 2 mL) and tetrakis(triphenylphosphine) palladium (0.07 mmol) was suspended in an oxygen-free toluene/ethanol (1:1, v:v, 15 mL) solution and refluxed for 4 h under nitrogen atmosphere. The reaction mixture was cooled to room temperature. The aqueous layer was extracted with ethyl acetate (3×10 mL). The organic layer was washed once with brine and once with water, dried over MgSO$_4$, filtered and the solution was concentrated under reduced pressure. The residue was purified by prep-HPLC using acetonitrile and water as eluent to afford the desired compound. $^1$H NMR (500 MHz, Acetone) δ 7.82 (s, 1H), 7.69 (d, J=8.6 Hz, 1H), 7.60 (s, 1H), 7.08 (d, J=8.6 Hz, 1H), 6.84 (t, J=5.6 Hz, 1H), 5.99 (s, 2H), 5.62 (s, 1H), 4.66 (d, J=6.1 Hz, 2H), 3.84 (s, 3H). LC.MS: m/z 416.06 (M+H)$^+$.

Example 7: Compounds 071 to 096

7.1 Preparation of N-((2-(4-phenoxyphenyl)thiazol-5-yl)methyl)-2-(trifluoromethyl)pyridin-4-amine (071)

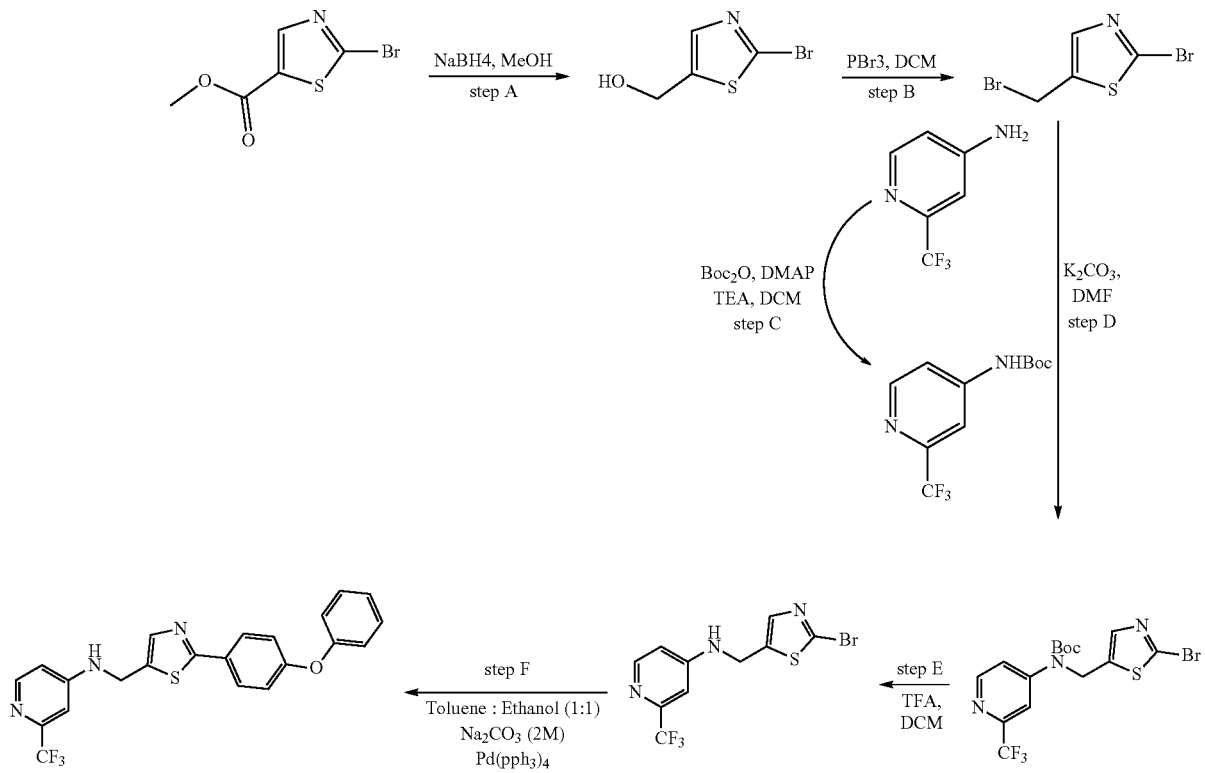

Step A. (2-Bromothiazol-5-yl)methanol

Methyl 2-bromothiazole-5-carboxylate (4.94 g, 23 mmol) was dissolved in 45 ml methanol and sodium borohydride (8.5 g, 23 mmol) was added slowly and stirred at rt for 1 hour then concentrated under reduced pressure. The residue was diluted with saturated aqueous NaHCO$_3$ and extracted with ethyl acetate. The combined organic layers were dried over anhydrous MgSO$_4$ und concentrated under reduced pressure. The crude product was directly used in the next step without any further purification. LC.MS: m/z 194.0 (M+H)$^+$.

Step B. 2-Bromo-5-(bromomethyl)thiazole

To (2-bromothiazol-5-yl)methanol (100 mg, 0.52 mmol) in DCM (10 ml) at OC was added the Phosphorus tribromide (705 mg, 3.45 mmol). A precipitate was formed during the addition and the reaction was stirred at room temperature for 2 hours. The reaction was quenched with NaHCO$_3$ and extracted with DCM. The organic solvent was dried over anhydrous MgSO$_4$ then removed under reduced pressure. The crude product was directly used in the next step without any further purification.

Step C. tert-Butyl (2-(trifluoromethyl)pyridin-4-yl)carbamate 2-(Trifluoromethyl)pyridin-4-amine (135 mg, 0.83 mmol), DMAP (10.25 mg, 0.08 mmol), Boc$_2$O (274.80 mg, 1.25 mmol) and Et$_3$N (152.83 μl, 1.09 mmol) were suspended in anhydrous DCM (3 mL) at rt, and stirred 2 h under argon atmosphere. The reaction mixture was diluted with CH$_2$C$_2$(25 mL) and washed with 0.1 N HCl (5 mL). The combined organic layers were dried over anhydrous MgSO$_4$ and concentrated under reduced pressure. The obtained residue was taken to the next step without further purification. $^1$H-NMR (300 MHz, CDCl$_3$): δ [ppm]=8.53 (d, J=5.6 Hz, 1H), 7.78 (d, J=2.0 Hz, 1H), 7.44 (dd, J=5.5 Hz, J=2.1 Hz, 1H), 6.92 (bs, 1H), 1.53 (s, 9H). LC.MS: m/z 207 (M+H-tBu)$^+$.

Step D. tert-Butyl ((2-bromothiazol-5-yl)methyl)(2-(trifluoromethyl)pyridin-4-yl)carbamate A mixture of 2-bromo-5-(bromomethyl)thiazole (160 mg, 0.62 mmol), tert-Butyl (2-(trifluoromethyl)pyridin-4-yl)carbamate (110 mg, 0.42 mmol) and K$_2$CO$_3$ (60 mg, 0.42 mmol) in DMF (10 mL) was stirred overnight at rt. Excess solvent was evaporated under reduced pressure and to the remaining residue water (30 ml) was added and then extraction with DCM. The organic solvent was then dried over anhydrous MgSO$_4$ and evaporated under reduced pressure. The remaining residue was taken directly for the next step and used without further purification. LC.MS: m/z 337.90 (M+H-tBu)$^+$.

Step E. N-((2-Bromothiazol-5-yl)methyl)-2-(trifluoromethyl)pyridin-4-amine

To crude tert-butyl ((2-bromothiazol-5-yl)methyl)(2-(trifluoromethyl)pyridin-4-yl)carbamate (57 mg, 0.13 mmol) dissolved in DCM (10 ml) was added TFA (2 ml). The reaction was stirred for 2 hours at room temp. Excess solvent was evaporated under reduced pressure and to the remaining residue was dissolved in DCM (10 ml×2) and evaporated again under reduced pressure. The remaining residue was taken directly for the next step and used without further purification. $^1$H NMR (500 MHz, Acetone) δ 8.19 (d, J=6.0 Hz, 1H), 7.55 (s, 1H), 7.22 (s, 1H), 7.06 (d, J=2.4 Hz, 1H), 6.84 (dd, J=6.0, 2.4 Hz, 1H), 4.74 (s, 1H). LC.MS: m/z 338.04 (M+H)$^+$.

Step F. N-((2-(4-Phenoxyphenyl)thiazol-5-yl)methyl)-2-(trifluoromethyl)pyridin-4-amine (071)

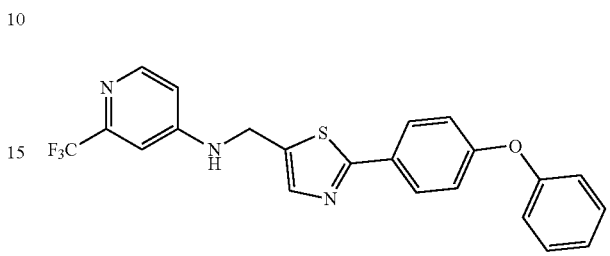

A mixture of N-((2-bromothiazol-5-yl)methyl)-2-(trifluoromethyl)pyridin-4-amine (47 mg, 0.14 mmol), phenoxyphenyl boronic acid (45 mg, 0.21 mmol), sodium carbonate (2 M, 2 mL) and tetrakis(triphenylphosphine) palladium (0.07 mmol) was suspended in an oxygen-free toluene/ethanol (1:1, v:v, 15 mL) solution and refluxed for 4 h under nitrogen atmosphere. The reaction mixture was cooled to room temperature. The aqueous layer was extracted with ethyl acetate (3×10 mL). The organic layer was washed once with brine and once with water, dried over MgSO$_4$, filtered and the solution was concentrated under reduced pressure. The residue was purified by prep-HPLC using acetonitrile and water as eluent to afford the desired compound. $^1$H NMR (300 MHz, Acetone) δ 8.11 (d, J=5.7 Hz, 1H), 7.85-7.77 (m, 2H), 7.70 (t, J=0.9 Hz, 1H), 7.35-7.26 (m, 2H), 7.11-7.03 (m, 1H), 7.00-6.89 (m, 5H), 6.84 (t, J=5.4 Hz, 1H), 6.76 (dd, J=5.7, 2.3 Hz, 1H), 4.69 (dd, J=6.0, 0.9 Hz, 2H). LC.MS: m/z 428.12 (M+H)$^+$.

7.2 Compounds 072 to 096

Compounds 072 to 096 described below are further representative examples of compounds according to general formula (I) of the present invention. These compounds have been synthesized based on the procedure described above for Compound 071.

N-((2-(4-Chlorophenyl)thiazol-5-yl)methyl)-2-(trifluoromethyl)pyridin-4-amine (072)

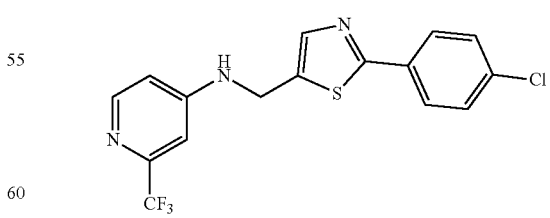

$^1$H NMR (300 MHz, CDCl$_3$) δ 8.35 (d, J=5.7 Hz, 1H), 7.89-7.77 (m, 2H), 7.75 (s, 1H), 7.46-7.36 (m, 2H), 6.91 (d, J=2.3 Hz, 1H), 6.65 (dd, J=5.7, 2.4 Hz, 1H), 4.87 (t, J=5.2 Hz, 1H), 4.66 (dd, J=5.7, 0.7 Hz, 2H). LC.MS: m/z 370.13 (M+H)$^+$.

N-((2-(6-Chloropyridin-3-yl)thiazol-5-yl)methyl)-2-(trifluoromethyl)pyridin-4-amine (073)

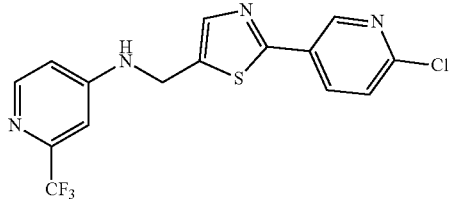 [SMILES: FC(F)(F)c1cc(NCc2cnc(-c3ccc(Cl)cc3)s2)ccn1]

¹H NMR (300 MHz, Acetone) δ 8.78 (dd, J=2.5, 0.6 Hz, 1H), 8.18 (dd, J=8.4, 2.5 Hz, 1H), 8.11 (d, J=5.7 Hz, 1H), 7.83 (s, 1H), 7.44 (dd, J=8.4, 0.7 Hz, 1H), 6.99 (d, J=2.3 Hz, 1H), 6.86 (t, J=6.3 Hz, 1H), 6.76 (dd, J=5.7, 2.4 Hz, 1H), 4.76 (dd, J=6.1, 1.0 Hz, 2H). LC.MS: m/z 371.03 (M+H)⁺.

N-((2-(4-Methoxy-3-methylphenyl)thiazol-5-yl)methyl)-2-(trifluoromethyl)pyridin-4-amine (074)

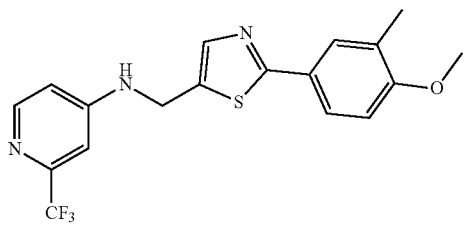 [SMILES: COc1ccc(-c2ncc(CNc3ccnc(C(F)(F)F)c3)s2)cc1C]

¹H NMR (300 MHz, Acetone) δ 8.11 (d, J=5.7 Hz, 1H), 7.65-7.56 (m, 3H), 6.97 (d, J=2.3 Hz, 1H), 6.87 (d, J=8.3 Hz, 1H), 6.84-6.78 (m, 1H), 6.75 (dd, J=5.7, 2.3 Hz, 1H), 4.66 (d, J=5.5 Hz, 2H), 3.76 (s, 3H). LC.MS: m/z 380.09 (M+H)⁺.

N-((2-(4-Methoxy-3,5-dimethylphenyl)thiazol-5-yl)methyl)-2-(trifluoromethyl)pyridin-4-amine (075)

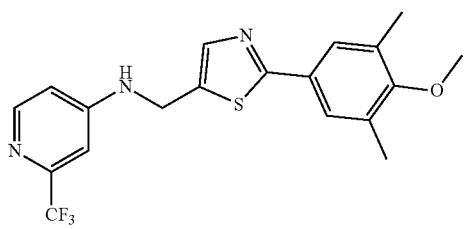 [SMILES: COc1c(C)cc(-c2ncc(CNc3ccnc(C(F)(F)F)c3)s2)cc1C]

¹H NMR (300 MHz, Acetone) δ 8.24 (d, J=5.7 Hz, 1H), 7.80 (s, 1H), 7.64-7.55 (m, 2H), 7.10 (d, J=2.3 Hz, 1H), 6.92 (t, J=5.6 Hz, 1H), 6.88 (dd, J=5.7, 2.3 Hz, 1H), 4.81 (d, J=5.9 Hz, 2H), 3.79-3.62 (m, 3H), 2.32-2.28 (m, 6H). LC.MS: m/z 394.09 (M+H)⁺.

4-(((2-(4-Phenoxyphenyl)thiazol-5-yl)methyl)amino)picolinonitrile (076)

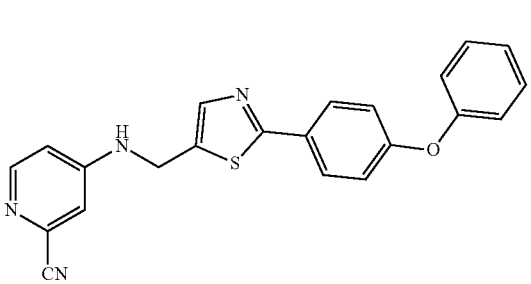 [SMILES: N#Cc1cc(NCc2cnc(-c3ccc(Oc4ccccc4)cc3)s2)ccn1]

¹H NMR (500 MHz, MeOD) δ 8.57 (s, 1H), 8.14 (d, J=5.1 Hz, 1H), 7.87 (d, J=7.9 Hz, 2H), 7.77 (s, 1H), 7.41 (t, J=6.7 Hz, 2H), 7.19 (t, J=6.6 Hz, 1H), 7.13 (s, 1H), 7.04 (dd, J=16.7, 7.8 Hz, 4H), 6.86 (d, J=3.1 Hz, 1H), 4.69 (s, 2H). LC.MS: m/z 385.11 (M+H)⁺.

4-(((2-(3-Chloro-4-methoxyphenyl)thiazol-5-yl)methyl)amino)picolinonitrile (077)

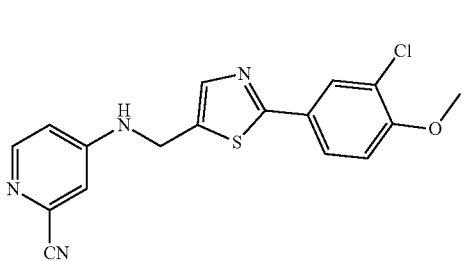 [SMILES: COc1ccc(-c2ncc(CNc3ccnc(C#N)c3)s2)cc1Cl]

¹H NMR (500 MHz, Acetone) δ 8.20 (d, J=5.8 Hz, 1H), 7.96 (d, J=2.2 Hz, 1H), 7.84 (dd, J=8.6, 2.1 Hz, 1H), 7.22 (d, J=8.7 Hz, 1H), 7.20 (d, J=2.4 Hz, 1H), 7.00 (s, 1H), 6.92 (dd, J=5.8, 2.5 Hz, 1H), 4.82 (dd, J=5.9, 0.8 Hz, 2H). LC.MS: m/z 357.06 (M+H)⁺.

N-((5-(4-Phenoxyphenyl)thiazol-2-yl)methyl)-2-(trifluoromethyl)pyridin-4-amine (078)

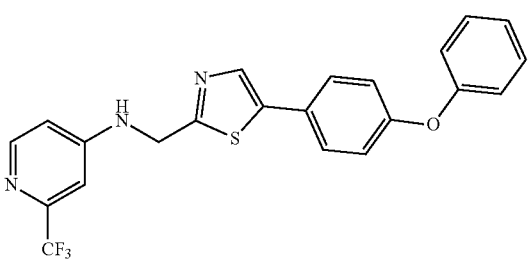 [SMILES: FC(F)(F)c1cc(NCc2ncc(-c3ccc(Oc4ccccc4)cc3)s2)ccn1]

LC.MS: m/z 428.01 (M+H)⁺.

69

N-((4-(4-Phenoxyphenyl)thiazol-2-yl)methyl)-2-(trifluoromethyl)pyridin-4-amine (079)

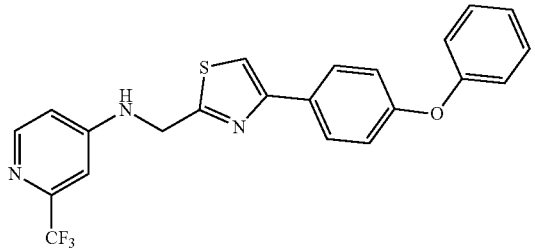 [SMILES: FC(F)(F)c1cc(NCc2nc(-c3ccc(Oc4ccccc4)cc3)cs2)ccn1]

¹H NMR (300 MHz, Acetone) δ 8.12 (d, J=5.7 Hz, 1H), 7.93-7.84 (m, 2H), 7.66 (s, 1H), 7.34-7.21 (m, 2H), 7.10-6.99 (m, 3H), 6.97-6.87 (m, 4H), 6.76 (dd, J=5.7, 2.3 Hz, 1H), 4.78 (d, J=6.2 Hz, 2H). LC.MS: m/z 428.00 (M+H)⁺.

N-((2-(4-Phenoxyphenyl)thiazol-4-yl)methyl)-2-(trifluoromethyl)pyridin-4-amine (080)

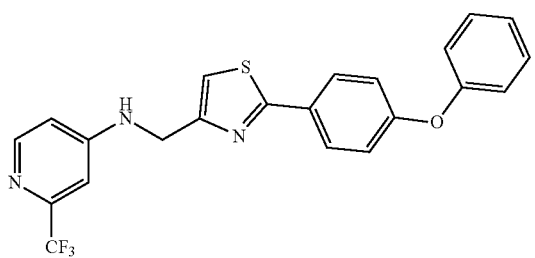 [SMILES: FC(F)(F)c1cc(NCc2csc(-c3ccc(Oc4ccccc4)cc3)n2)ccn1]

LC.MS: m/z 428.01 (M+H)⁺.

N-((2-(4-Cyclopropylphenyl)thiazol-4-yl)methyl)-2-(trifluoromethyl)pyridin-4-amine (081)

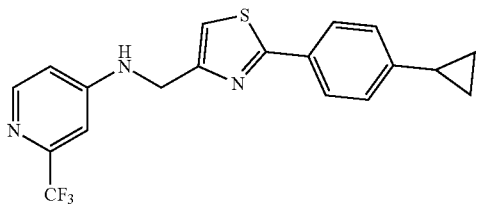 [SMILES: FC(F)(F)c1cc(NCc2csc(-c3ccc(C4CC4)cc3)n2)ccn1]

¹H NMR (500 MHz, MeOD) δ 8.46 (s, 1H), 8.05 (d, J=5.9 Hz, 1H), 7.64 (dd, J=5.6, 2.8 Hz, 2H), 7.03 (d, J=8.4 Hz, 1H), 6.92 (d, J=2.3 Hz, 1H), 6.70 (dd, J=5.9, 2.4 Hz, 1H), 4.58 (s, 1H), 3.21 (dt, J=3.2, 1.6 Hz, 1H), 1.86-1.78 (m, 1H), 0.94-0.87 (m, 1H), 0.64-0.59 (m, 1H). LC.MS: m/z 376.28 (M+H)⁺.

70

N-((2-(3-Chloro-4-isopropoxyphenyl)thiazol-4-yl)methyl)-2-(trifluoromethyl)pyridin-4-amine (082)

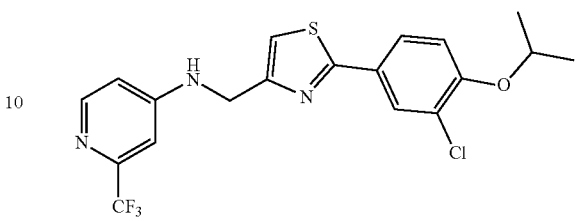

¹H NMR (500 MHz, Acetone) δ 8.24 (d, J=5.7 Hz, 1H), 7.95 (d, J=2.2 Hz, 1H), 7.82 (s, 1H), 7.79 (dd, J=8.6, 2.2 Hz, 1H), 7.21 (d, J=8.7 Hz, 1H), 7.11 (d, J=2.3 Hz, 1H), 6.92 (t, J=5.4 Hz, 1H), 6.88 (dd, J=5.7, 2.3 Hz, 1H), 4.82-4.69 (m, 2H), 1.37 (d, J=6.0 Hz, 7H). LC.MS: m/z 428.11 (M+H)⁺.

N-((2-(6-(4-Fluorophenoxy)pyridin-3-yl)thiazol-4-yl)methyl)-2-(trifluoromethyl)pyridin-4-amine (083)

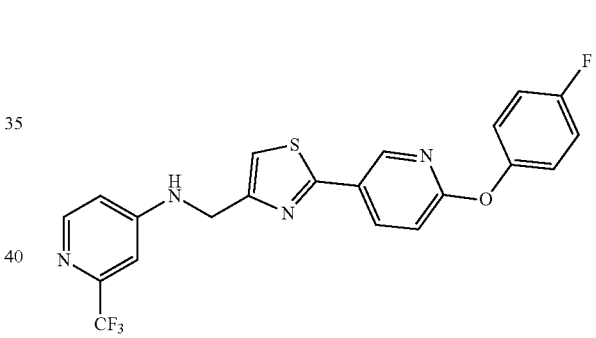

LC.MS: m/z 447.01 (M+H)⁺.

N-((2-(5-Chloro-6-methoxypyridin-3-yl)thiazol-4-yl)methyl)-2-(trifluoromethyl)pyridin-4-amine (084)

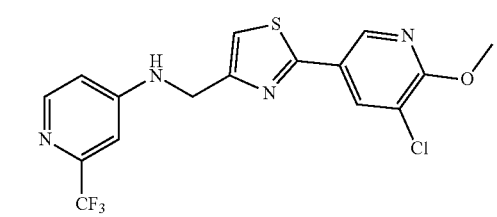 [SMILES: COc1ncc(-c2nc(CNc3ccnc(C(F)(F)F)c3)cs2)cc1Cl]

LC.MS: m/z 401.08 (M+H)⁺.

71

4-(4-(((2-(Trifluoromethyl)pyridin-4-yl)amino)methyl)thiazol-2-yl)benzonitrile (085)

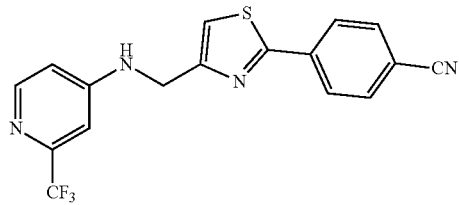 [SMILES: N#Cc1ccc(-c2nc(CNc3ccnc(C(F)(F)F)c3)cs2)cc1]

LC.MS: m/z 361.08 (M+H)$^+$.

N-((2-(4-Methoxyphenyl)thiazol-4-yl)methyl)-2-(trifluoromethyl)pyridin-4-amine (086)

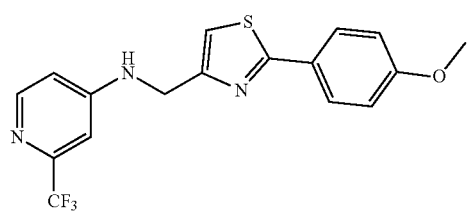 [SMILES: COc1ccc(-c2nc(CNc3ccnc(C(F)(F)F)c3)cs2)cc1]

LC.MS: m/z 366.15 (M+H)$^+$.

N-((2-(4-Isopropoxyphenyl)thiazol-4-yl)methyl)-2-(trifluoromethyl)pyridin-4-amine (087)

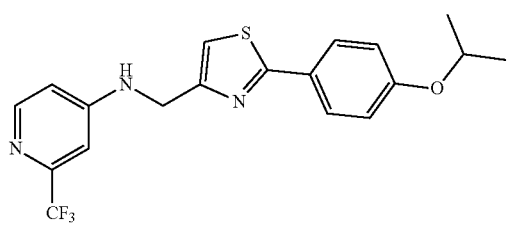 [SMILES: CC(C)Oc1ccc(-c2nc(CNc3ccnc(C(F)(F)F)c3)cs2)cc1]

LC.MS: m/z 394.15 (M+H)$^+$.

N-((2-(4-(4-Fluorophenoxy)phenyl)thiazol-4-yl)methyl)-2-(trifluoromethyl)pyridin-4-amine (088)

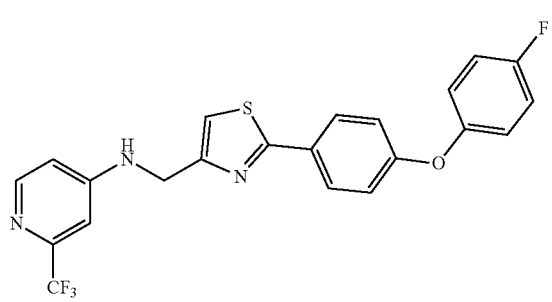 [SMILES: Fc1ccc(Oc2ccc(-c3nc(CNc4ccnc(C(F)(F)F)c4)cs3)cc2)cc1]

LC.MS: m/z 446.10 (M+H)$^+$.

72

N-((2-(3-Phenoxyphenyl)thiazol-4-yl)methyl)-2-(trifluoromethyl)pyridin-4-amine (089)

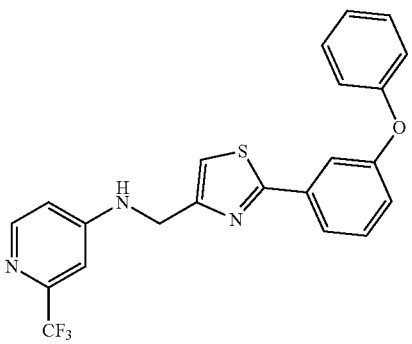 [SMILES: FC(F)(F)c1cc(NCc2csc(-c3cccc(Oc4ccccc4)c3)n2)ccn1]

LC.MS: m/z 428.14 (M+H)$^+$.

Cyclopropyl(3-(4-(((2-(trifluoromethyl)pyridin-4-yl)amino)methyl)thiazol-2-yl)phenyl)methanone (090)

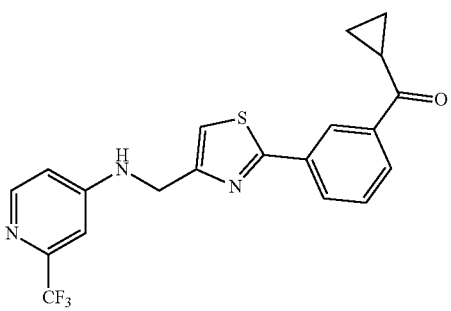 [SMILES: O=C(c1cccc(-c2nc(CNc3ccnc(C(F)(F)F)c3)cs2)c1)C1CC1]

LC.MS: m/z 404.12 (M+H)$^+$.

4-(((2-(3-Chloro-4-isopropoxyphenyl)thiazol-5-yl)methyl)amino)picolinonitrile (091)

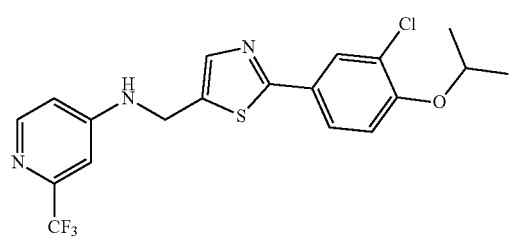 [SMILES: CC(C)Oc1ccc(-c2ncc(CNc3ccnc(C(F)(F)F)c3)s2)cc1Cl]

LC-MS: m/z 385 (M+H)$^+$.

2-Chloro-N-((2-(4-phenoxyphenyl)thiazol-5-yl)methyl)-6-(trifluoromethyl)pyridin-4-amine (092)

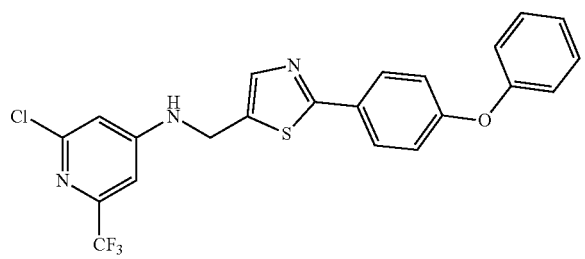 [SMILES: FC(F)(F)c1cc(NCc2cnc(-c3ccc(Oc4ccccc4)cc3)s2)cc(Cl)n1]

LC-MS: m/z 462 (M+H)⁺.

2-Chloro-N-((2-(4-phenoxyphenyl)thiazol-5-yl)methyl)pyridin-4-amine (093)

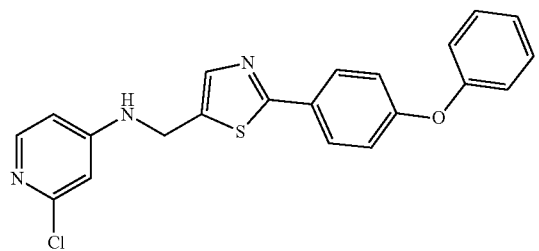 [SMILES: Clc1cc(NCc2cnc(-c3ccc(Oc4ccccc4)cc3)s2)ccn1]

LC-MS: m/z 394 (M+H)⁺.

2-Chloro-N-((2-(3-chloro-4-isopropoxyphenyl)thiazol-5-yl)methyl)-6-(trifluoromethyl)pyridin-4-amine (094)

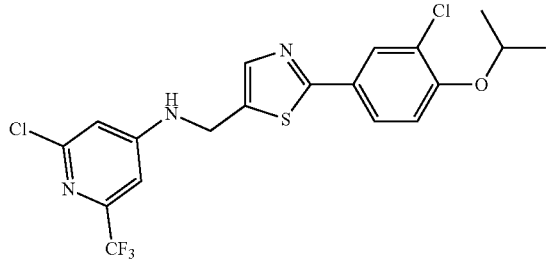 [SMILES: CC(C)Oc1ccc(-c2ncc(CNc3cc(Cl)nc(C(F)(F)F)c3)s2)cc1Cl]

LC-MS: m/z 462 (M+H)⁺.

N-((5-(4-Phenoxyphenyl)-4H-1,2,4-triazol-3-yl)methyl)-2-(trifluoromethyl)pyridin-4-amine (095)

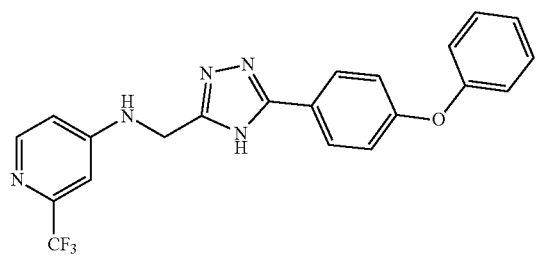 [SMILES: FC(F)(F)c1cc(NCc2nnc(-c3ccc(Oc4ccccc4)cc3)[nH]2)ccn1]

¹H NMR (300 MHz, Acetone) δ 8.22 (d, J=5.7 Hz, 1H), 8.10-8.03 (m, 2H), 7.48-7.39 (m, 2H), 7.33-7.27 (m, 1H), 7.23-7.15 (m, 2H), 7.12-7.05 (m, 4H), 6.90-6.85 (m, 3H), 4.65 (s, 2H). LC.MS: m/z 412.03 (M+H)⁺.

N-((3-(4-Phenoxyphenyl)-1H-pyrazol-5-yl)methyl)-2-(trifluoromethyl)pyridin-4-amine (096)

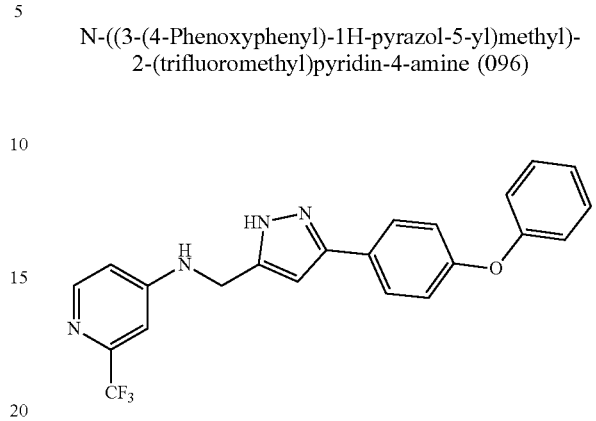

LC.MS: m/z 411.00 (M+H)⁺.

Example 8. Compounds 097 to 108

8.1 Preparation of N-((5-(4-phenoxyphenyl)pyridin-2-yl)methyl)-2-(trifluoromethyl)pyridin-4-amine (097)

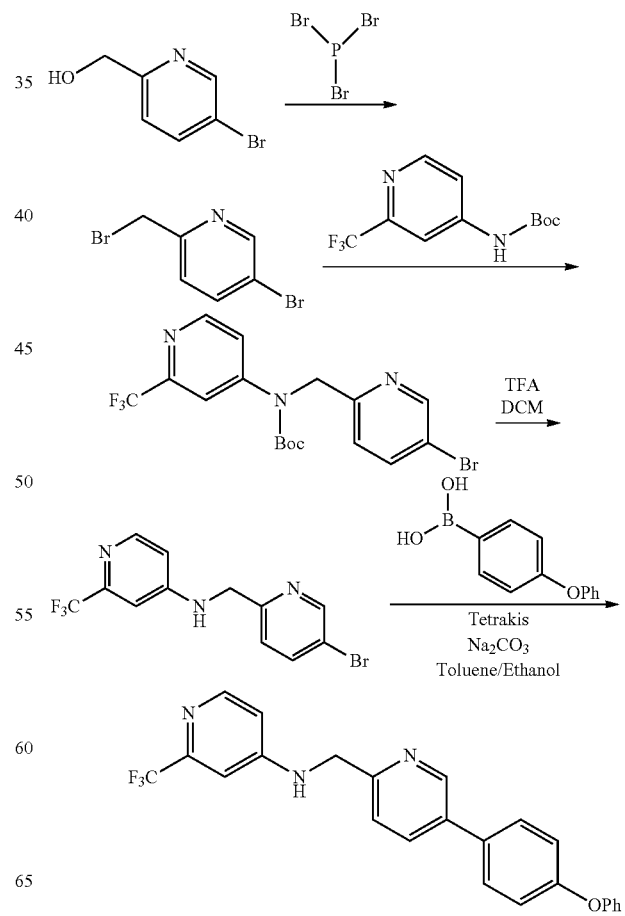

Step A. 5-bromo-2-(bromomethyl)pyridine

To (5-bromopyridin-2-yl)methanol (100 mg, 0.53 mmol) in DCM (10 ml) at OC was added the Phosphorus tribromide (720 mg, 2.65 mmol). The reaction was stirred at room temperature for 2 hours. The reaction was quenched with NaHCO$_3$ at OC and extracted with DCM. The organic solvent was dried over anhydrous MgSO$_4$ then removed under reduced pressure. The crude product was directly used in the next step without any further purification. LC/MS: m/z 252 (M+H)$^+$.

Step B. tert-butyl ((5-bromopyridin-2-yl)methyl)(2-(trifluoromethyl)pyridin-4-yl)carbamate To a stirred solution of tert-butyl (2-(trifluoromethyl)pyridin-4-yl)carbamate (30 mg, 0.114 mmol) and NaH (5.2 mg, 0.23 mmol) in DMF (10 ml) at 0° C. was added 5-bromo-2-(bromomethyl)pyridine (28.7 mg, 0.114 mmol). The reaction was stirred at room temp overnight. The reaction was then added on ice water followed by extraction with ethyl acetate. The organic solvent was then dried over MgSO$_4$ and evaporated under reduced pressure. Purification was done by automate column chromatography to give the desired product. LC/MS: m/z 432 (M+H)$^+$.

Step C. N-((5-bromopyridin-2-yl)methyl)-2-(trifluoromethyl)pyridin-4-amine tert-butyl ((5-bromopyridin-2-yl)methyl)(2-(trifluoromethyl)pyridin-4-yl)carbamate (30 mg, 0.069 mmol) was dissolved in DCM (5 mL) and TFA (1 mL) was added. After stirring at r.t. for 18 h the mixture was cooled to 0° C. and saturated Na$_2$CO$_3$ solution was added. The reaction mixture was extracted with DCM and the combined organic layers were washed with Brine, dried over Na$_2$SO$_4$, filtered and concentrated under reduced pressure. The crude product was directly used in the next step without any further purification. LC/MS: m/z 332 (M+H)$^+$.

Step D. N-((5-(4-phenoxyphenyl)pyridin-2-yl)methyl)-2-(trifluoromethyl)pyridin-4-amine (097)

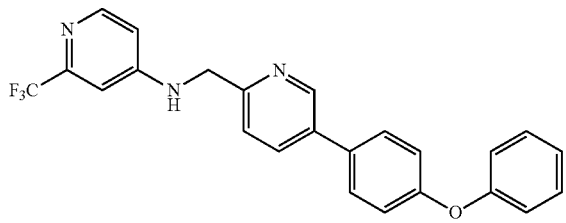

A mixture of N-((5-bromopyridin-2-yl)methyl)-2-(trifluoromethyl)pyridin-4-amine (20 mg, 0.06 mmol), phenoxyphenyl boronic acid (15.5 mg, 0.07 mmol), sodium carbonate (2 M, 2 mL) and tetrakis(triphenylphosphine) palladium (0.003 mmol) was suspended in an oxygen-free toluene/ethanol (1:1, v:v, 15 mL) solution and refluxed for 4 h under nitrogen atmosphere. The reaction mixture was cooled to room temperature and excess solvent was removed under reduced pressure. The aqueous layer was extracted with ethyl acetate (3×10 mL). The organic layer was washed once with brine and once with water, dried over MgSO$_4$, filtered and the solution was concentrated under reduced pressure. The residue was purified by prep-HPLC using acetonitrile and water as eluent to afford the desired compound.

LC-MS: m/z: 422 (M+H)$^+$. $^1$H NMR (300 MHz, CDCl$_3$) δ 8.73 (s, 1H), 8.25 (d, J=5.7 Hz, 1H), 7.81 (dd, J=8.1, 1.8 Hz, 1H), 7.51-7.45 (m, 2H), 7.34-7.27 (m, 3H), 7.10-6.99 (m, 5H), 6.87 (d, J=2.1 Hz, 1H), 6.59 (dd, J=5.6, 2.0 Hz, 1H), 5.86 (s, 1H), 4.48 (d, J=4.4 Hz, 2H).

8.2 Compounds 098 to 108

Compounds 098 to 108 described below are further representative examples of compounds according to general formula (I) of the present invention. These compounds have been synthesized based on the procedure described above for Compound 097.

N-((6'-Chloro-[3,3'-bipyridin]-6-yl)methyl)-2-(trifluoromethyl)pyridin-4-amine (098)

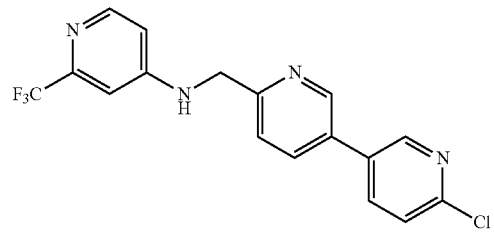 [SMILES: FC(F)(F)c1cc(NCc2ccc(-c3ccc(Cl)nc3)cn2)ccn1]

LC-MS: m/z: 365 (M+H)$^+$. $^1$H NMR (300 MHz, CDCl$_3$) δ 8.73 (s, 1H), 8.56 (s, 1H), 8.26 (d, J=5.5 Hz, 1H), 7.81 (t, J=8.3 Hz, 2H), 7.38 (dd, J=13.3, 8.2 Hz, 2H), 6.87 (s, 1H), 6.59 (d, J=5.1 Hz, 1H), 5.84 (s, 1H), 4.51 (d, J=4.6 Hz, 2H).

N-((5-(6-Chloropyridin-3-yl)pyrimidin-2-yl)methyl)-2-(trifluoromethyl)pyridin-4-amine (099)

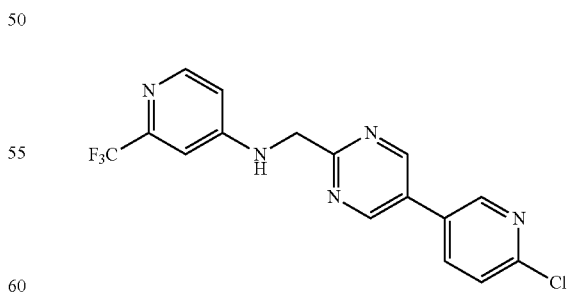

LC-MS: m/z: 366 (M+H)$^+$. $^1$H NMR (300 MHz, CDCl$_3$) δ 8.88 (s, 2H), 8.57 (d, J=2.5 Hz, 1H), 8.28 (d, J=5.7 Hz, 1H), 7.81 (dd, J=8.3, 2.6 Hz, 1H), 7.45 (d, J=8.3 Hz, 1H), 6.91 (d, J=2.3 Hz, 1H), 6.63 (dd, J=5.8, 2.3 Hz, 1H), 5.86 (s, 1H), 4.63 (d, J=4.9 Hz, 2H).

77

N-((6'-Phenoxy-[3,3'-bipyridin]-6-yl)methyl)-2-(trifluoromethyl)pyridin-4-amine (100)

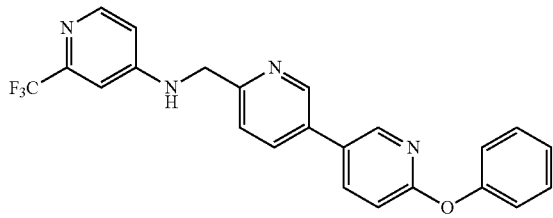

LC-MS: m/z: 423 (M+H)⁺. ¹H NMR (300 MHz, CDCl₃) δ 8.70 (d, J=2.1 Hz, 1H), 8.34 (d, J=2.5 Hz, 1H), 8.25 (d, J=5.7 Hz, 1H), 7.80 (ddd, J=13.8, 8.3, 2.4 Hz, 2H), 7.40-7.29 (m, 3H), 7.19-7.07 (m, 3H), 6.97 (d, J=8.5 Hz, 1H), 6.86 (d, J=2.3 Hz, 1H), 6.58 (dd, J=5.7, 2.3 Hz, 1H), 5.86 (t, J=4.2 Hz, 1H), 4.48 (d, J=4.9 Hz, 2H).

N-((5'-Chloro-6'-methoxy-[3,3'-bipyridin]-6-yl)methyl)-2-(trifluoromethyl)pyridin-4-amine (101)

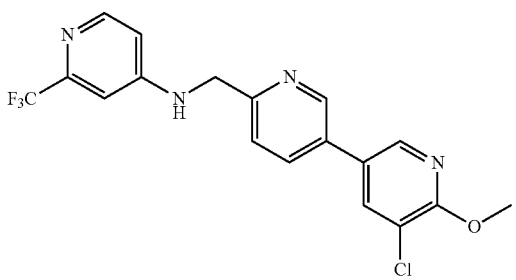 [SMILES: COc1ncc(-c2ccc(CNc3ccnc(C(F)(F)F)c3)nc2)cc1Cl]

LC-MS: m/z: 395 (M+H)⁺. ¹H NMR (300 MHz, CDCl₃) δ 8.68 (d, J=1.9 Hz, 1H), 8.23 (dd, J=9.7, 3.9 Hz, 2H), 7.81-7.73 (m, 2H), 7.32 (d, J=8.1 Hz, 1H), 6.87 (d, J=2.2 Hz, 1H), 6.59 (dd, J=5.6, 2.2 Hz, 1H), 5.89 (s, 1H), 4.49 (d, J=4.8 Hz, 2H), 4.01 (s, 3H).

N-((5',6'-Dichloro-[3,3'-bipyridin]-6-yl)methyl)-2-(trifluoromethyl)pyridin-4-amine (102)

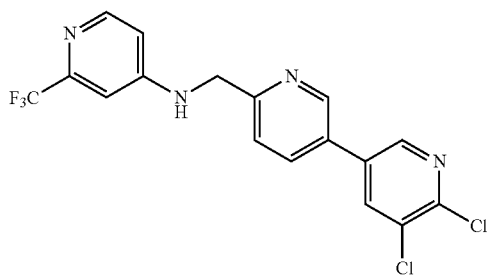 [SMILES: FC(F)(F)c1cc(NCc2ccc(-c3cnc(Cl)c(Cl)c3)cn2)ccn1]

LC-MS: m/z: 399 (M+H)⁺. ¹H NMR (300 MHz, CDCl₃) δ 8.72 (d, J=2.2 Hz, 1H), 8.46 (dd, J=2.2, 1.0 Hz, 1H), 8.25 (d, J=5.7 Hz, 1H), 7.91 (dd, J=2.2, 1.1 Hz, 1H), 7.82 (dd, J=8.1, 1.4 Hz, 1H), 7.37 (d, J=8.2 Hz, 1H), 6.87 (d, J=1.8 Hz, 1H), 6.59 (dd, J=5.6, 1.9 Hz, 1H), 5.86 (s, 1H), 4.52 (d, J=4.8 Hz, 2H).

78

N-((5-(3-Phenoxyphenyl)pyridin-2-yl)methyl)-2-(trifluoromethyl)pyridin-4-amine (103)

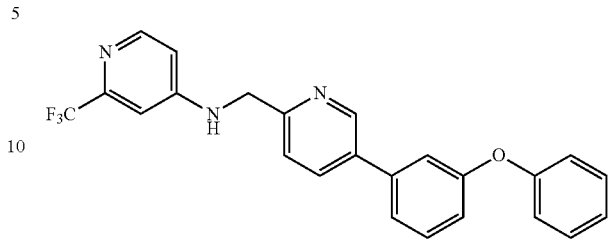

LC-MS: m/z: 422 (M+H)⁺. ¹H NMR (300 MHz, CDCl₃) δ 8.71 (d, J=1.7 Hz, 1H), 8.24 (d, J=5.7 Hz, 1H), 7.79 (dd, J=8.1, 2.3 Hz, 1H), 7.41-7.21 (m, 5H), 7.16 (t, J=1.9 Hz, 1H), 7.07 (t, J=7.4 Hz, 1H), 7.02-6.95 (m, 3H), 6.86 (d, J=2.1 Hz, 1H), 6.58 (dd, J=5.7, 2.2 Hz, 1H), 5.88 (s, 1H), 4.47 (d, J=4.7 Hz, 2H).

N-((5-(3-Chloro-4-methoxyphenyl)pyridin-2-yl)methyl)-2-(trifluoromethyl)pyridin-4-amine (104)

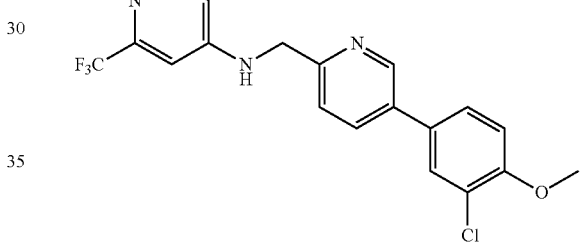

LC-MS: m/z: 394 (M+H)⁺. ¹H NMR (300 MHz, CDCl₃) δ 8.69 (s, 1H), 8.24 (d, J=5.4 Hz, 1H), 7.81-7.73 (m, 1H), 7.55-7.52 (m, 1H), 7.42-7.35 (m, 1H), 7.28 (d, J=7.7 Hz, 1H), 6.98 (dd, J=8.6, 1.5 Hz, 1H), 6.87 (s, 1H), 6.63-6.56 (m, 1H), 5.92 (s, 1H), 4.47 (d, J=3.9 Hz, 2H), 3.89 (d, J=1.7 Hz, 3H).

N-((2-(4-Phenoxyphenyl)pyrimidin-5-yl)methyl)-2-(trifluoromethyl)pyridin-4-amine (105)

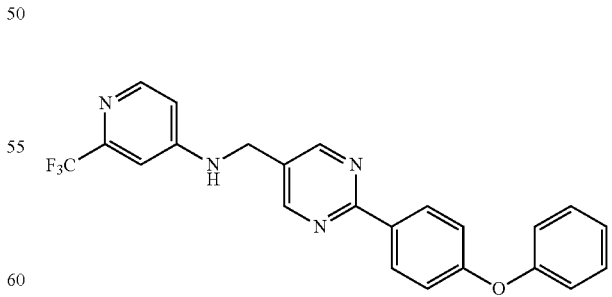

LC-MS: m/z: 423 (M+H)⁺. ¹H NMR (500 MHz, CDCl₃) δ 8.68 (s, 2H), 8.34 (d, J=8.1 Hz, 2H), 8.26 (d, J=5.6 Hz, 1H), 7.31 (t, J=7.5 Hz, 2H), 7.10 (t, J=7.4 Hz, 1H), 7.01 (d, J=8.1 Hz, 4H), 6.83 (s, 1H), 6.54 (d, J=5.6 Hz, 1H), 4.87 (s, 1H), 4.40 (d, J=5.4 Hz, 2H).

N-((2-(4-isopropoxyphenyl)pyrimidin-5-yl)methyl)-2-(trifluoromethyl)pyridin-4-amine (106)

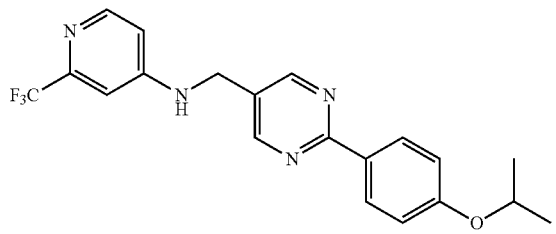 [SMILES: CC(C)Oc1ccc(-c2ncc(CNc3ccnc(C(F)(F)F)c3)cn2)cc1]

LC-MS: m/z: 389 (M+H)+. 1H NMR (500 MHz, CDCl3) δ 8.64 (s, 2H), 8.29 (d, J=8.4 Hz, 2H), 8.25 (d, J=5.7 Hz, 1H), 6.90 (d, J=8.4 Hz, 2H), 6.82 (s, 1H), 6.53 (d, J=5.6 Hz, 1H), 4.86 (t, J=4.9 Hz, 1H), 4.58 (hept, J=6.0 Hz, 1H), 4.36 (d, J=5.5 Hz, 2H), 1.31 (d, J=6.0 Hz, 6H).

N-((2-(4-Cyclopropylphenyl)pyrimidin-5-yl)methyl)-2-(trifluoromethyl)pyridin-4-amine (107)

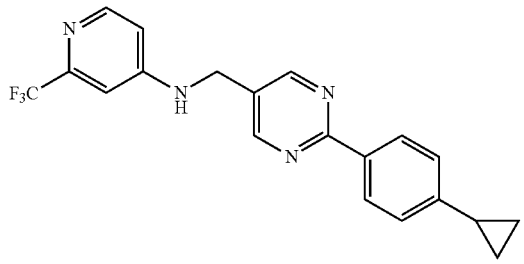 [SMILES: FC(F)(F)c1cc(NCc2cnc(-c3ccc(C4CC4)cc3)nc2)ccn1]

LC-MS: m/z: 371 (M+H)+. 1H NMR (500 MHz, CDCl3) δ 8.66 (s, 2H), 8.25 (t, J=6.3 Hz, 3H), 7.11 (d, J=8.0 Hz, 2H), 6.82 (s, 1H), 6.53 (d, J=5.6 Hz, 1H), 4.82 (s, 1H), 4.37 (d, J=5.5 Hz, 2H), 1.93-1.85 (m, 1H), 1.01-0.93 (m, 2H), 0.74-0.69 (m, 2H).

N-((2-(3-Chloro-4-isopropoxyphenyl)pyrimidin-5-yl)methyl)-2-(trifluoromethyl)pyridin-4-amine (108)

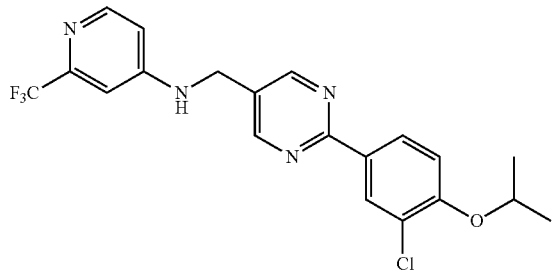

LC-MS: m/z: 423 (M+H)+. 1H NMR (500 MHz, Acetone) δ 8.75 (s, 2H), 8.33 (d, J=2.1 Hz, 1H), 8.23 (dd, J=8.7, 2.2 Hz, 1H), 8.10 (d, J=5.7 Hz, 1H), 7.12 (d, J=8.8 Hz, 1H), 6.96 (d, J=2.3 Hz, 1H), 6.77 (s, 1H), 6.72 (dd, J=5.7, 2.3 Hz, 1H), 4.68 (hept, J=6.1 Hz, 1H), 4.53 (d, J=5.9 Hz, 2H), 1.26 (d, J=6.0 Hz, 6H).

Example 9. Compounds 109 to 115

9.1 Preparation of 4-(((5-(4-phenoxyphenyl)pyridin-2-yl)methyl)thio)-2-(trifluoromethyl)-pyridine (109)

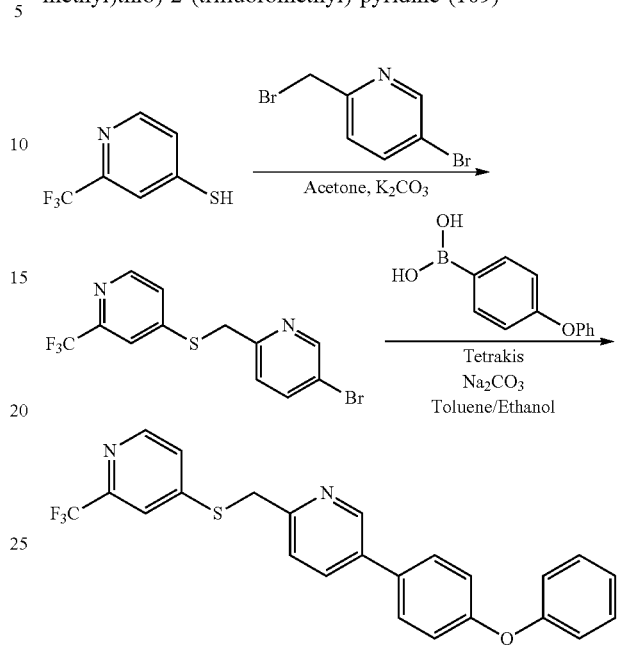

Step A. 4-(((5-bromopyridin-2-yl)methyl)thio)-2-(trifluoromethyl)pyridine

To a mixture of 2-(Trifluoromethyl)pyridine-4-thiol (60 mg, 0.335 mmol) and K2CO3 (55.54 mg, 0.402 mmol) in Acetone (10 ml) was added 5-bromo-2-(bromomethyl)pyridine (101 mg, 0.402 mmol). The reaction was stirred for 1 hour at room temp. Excess solvent was evaporated under reduced pressure and to the remaining residue water (30 ml) was added and then extraction with Ethyl acetate. The organic solvent was then dried over anhydrous MgSO4 and evaporated under reduced pressure. The residue was purified by automate column chromatography to give the desired product. LC-MS: m/z: 349 (M+H)+.

Step B. 4-(((5-(4-phenoxyphenyl)pyridin-2-yl)methyl)thio)-2-(trifluoromethyl)pyridine (109)

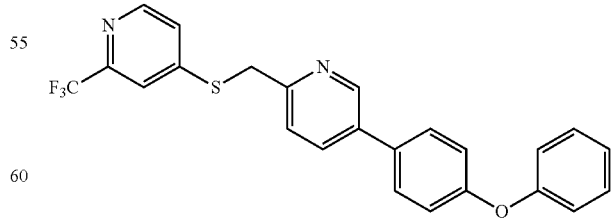

A mixture of 4-(((5-bromopyridin-2-yl)methyl)thio)-2-(trifluoromethyl)pyridine (21 mg, 0.06 mmol), phenoxyphenyl boronic acid (15.5 mg, 0.07 mmol), sodium carbonate (2 M, 2 mL) and tetrakis(triphenylphosphine) palladium (0.003 mmol) was suspended in an oxygen-free toluene/ethanol (1:1, v:v, 15 mL) solution and refluxed for 4 h under nitrogen atmosphere. The reaction mixture was cooled to room temperature and excess solvent was removed under reduced pressure. The aqueous layer was extracted with ethyl acetate (3×10 mL). The organic layer was washed once with brine and once with water, dried over MgSO$_4$, filtered and the solution was concentrated under reduced pressure. The residue was purified by prep-HPLC using acetonitrile and water as eluent to afford the desired compound.

LC-MS: m/z: 439 (M+H)$^+$. $^1$H NMR (300 MHz, CDCl$_3$) δ 8.70 (dd, J=2.3, 0.7 Hz, 1H), 8.41 (d, J=5.3 Hz, 1H), 7.77 (dd, J=8.1, 2.4 Hz, 1H), 7.57 (d, J=1.5 Hz, 1H), 7.48-7.40 (m, 3H), 7.31 (ddt, J=10.9, 7.6, 2.0 Hz, 3H), 7.11-6.97 (m, 5H), 4.36 (s, 2H).

9.2 Compounds 110 to 115

Compounds 110 to 115 described below are further representative examples of compounds according to general formula (I) of the present invention. These compounds have been synthesized based on the procedure described above for Compound 109. 4-((4-(6-Chloropyridin-3-yl)benzyl) thio)-2-(trifluoromethyl)pyridine (110)

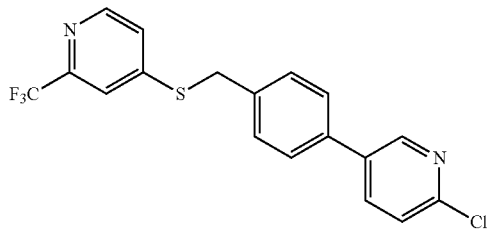

LC-MS: m/z: 381 (M+H)$^+$. $^1$H NMR (300 MHz, CDCl$_3$) δ 8.53 (d, J=2.1 Hz, 1H), 8.42 (d, J=5.3 Hz, 1H), 7.76 (dd, J=8.3, 2.6 Hz, 1H), 7.45 (dd, J=6.5, 1.4 Hz, 5H), 7.33 (dd, J=8.3, 0.6 Hz, 1H), 7.21 (dd, J=5.5, 1.9 Hz, 1H), 4.24 (s, 2H).

4-(((5-(4-Chlorophenyl)pyridin-2-yl)methyl)thio)-2-(trifluoromethyl)pyridine (111)

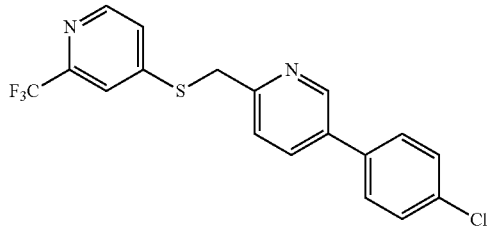 [SMILES: FC(F)(F)c1cc(SCc2ccc(-c3ccc(Cl)cc3)cn2)ccn1]

LC-MS: m/z: 381 (M+H)$^+$. $^1$H NMR (300 MHz, CDCl$_3$) δ 8.68 (d, J=2.3 Hz, 1H), 8.40 (d, J=5.3 Hz, 1H), 7.77 (dd, J=8.1, 2.3 Hz, 1H), 7.57 (s, 1H), 7.44-7.38 (m, 4H), 7.38-7.32 (m, 2H), 4.36 (s, 2H).

6-Chloro-6'-(((2-(trifluoromethyl)pyridin-4-yl)thio) methyl)-3,3'-bipyridine (112)

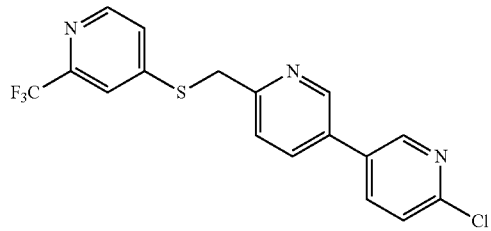 [SMILES: FC(F)(F)c1cc(SCc2ccc(-c3ccc(Cl)nc3)cn2)ccn1]

LC-MS: m/z: 382 (M+H)$^+$. $^1$H NMR (300 MHz, CDCl$_3$) δ 8.69 (d, J=2.0 Hz, 1H), 8.53 (d, J=2.4 Hz, 1H), 8.41 (d, J=5.3 Hz, 1H), 7.84-7.74 (m, 2H), 7.57 (d, J=1.4 Hz, 1H), 7.50 (d, J=8.1 Hz, 1H), 7.43-7.32 (m, 2H), 4.38 (s, 2H).

2-Chloro-5-(6-(((2-(trifluoromethyl)pyridin-4-yl) thio)methyl)pyridin-3-yl)pyrimidine (113)

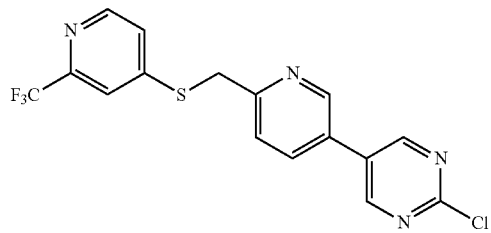 [SMILES: FC(F)(F)c1cc(SCc2ccc(-c3cnc(Cl)nc3)cn2)ccn1]

LC-MS: m/z: 383 (M+H)$^+$. $^1$H NMR (300 MHz, CDCl$_3$) δ 8.76 (s, 2H), 8.70 (d, J=1.6 Hz, 1H), 8.42 (d, J=5.3 Hz, 1H), 7.81 (dd, J=8.1, 2.4 Hz, 1H), 7.55 (d, J=8.2 Hz, 2H), 7.34 (dd, J=5.2, 1.6 Hz, 1H), 4.39 (s, 2H).

6-Phenoxy-6'-(((2-(trifluoromethyl)pyridin-4-yl) thio)methyl)-3,3'-bipyridine (114)

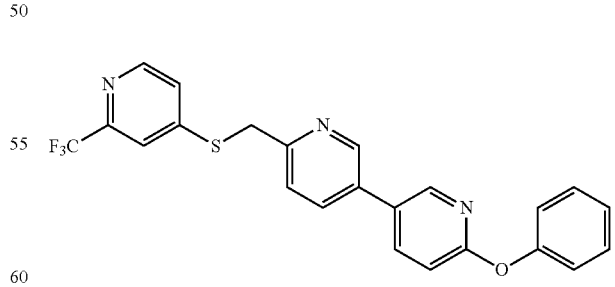

LC-MS: m/z: 440 (M+H)$^+$. $^1$H NMR (300 MHz, CDCl$_3$) δ 8.69-8.64 (m, 1H), 8.40 (d, J=5.3 Hz, 1H), 8.32 (dd, J=2.5, 0.6 Hz, 1H), 7.77 (ddd, J=15.6, 8.3, 2.5 Hz, 2H), 7.56 (d, J=1.1 Hz, 1H), 7.45 (d, J=8.1 Hz, 1H), 7.40-7.29 (m, 3H), 7.17-7.05 (m, 3H), 6.95 (dd, J=8.5, 0.6 Hz, 1H), 4.36 (s, 2H).

5-Chloro-6-methoxy-6'-(((2-(trifluoromethyl)pyridin-4-yl)thio)methyl)-3,3'-bipyridine (115)

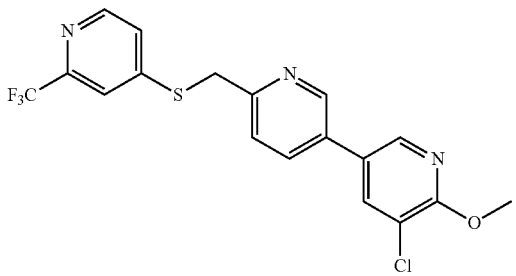 [SMILES: COc1ncc(-c2ccc(CSc3ccnc(C(F)(F)F)c3)nc2)cc1Cl]

LC-MS: m/z: 411 (M+H)+. 1H NMR (300 MHz, CDCl3) δ 8.66 (s, 1H), 8.41 (d, J=5.3 Hz, 1H), 8.20 (d, J=2.2 Hz, 1H), 7.81-7.70 (m, 2H), 7.57 (d, J=1.6 Hz, 1H), 7.46 (d, J=7.9 Hz, 1H), 7.34 (dd, J=5.3, 1.7 Hz, 1H), 4.37 (s, 2H), 4.01 (s, 3H).

Example 10: Compounds 116 to 118

10.1 Preparation of 5,6-dichloro-2-(((6-chloro-2-(trifluoromethyl)pyrimidin-4-yl)thio)methyl)-1H-benzo[d]imidazole (116) and 6-(((5,6-dichloro-1H-benzo[d]imidazol-2-yl)methyl)thio)-2-(trifluoromethyl)pyrimidin-4-amine (117)

solvent was then dried over anhydrous MgSO4 and evaporated under reduced pressure. The crude product was directly used in the next step without any further purification. LC.MS: m/z 234.96 (M+H)+.

Step B. 5,6-Dichloro-2-(((6-chloro-2-(trifluoromethyl pyrimidin-4-yl)thio)methyl)-1H-benzo[d]imidazole A mixture of (5,6-dichloro-1H-benzo[d]imidazol-2-yl)methanethiol (233 mg, 1 mmol), 4,6-dichloro-2-(trifluoromethyl)pyrimidine (217 mg 1 mmol), and K2CO3 (180 mg, 1.5 mmol) in DMF (10 mL) was stirred at rt for 2 h. Excess solvent was evaporated under reduced pressure and to the remaining residue water (30 ml) was added and then extraction with DCM. The organic solvent was then dried over anhydrous MgSO4 and evaporated under reduced pressure. The residue was purified by prep-HPLC using acetonitrile and water as eluent to afford the desired compound. 1H NMR (300 MHz, Acetone) δ 11.80 (s, 1H), 8.03 (s, 1H), 7.73 (s, 2H), 4.87 (s, 2H). LC.MS: m/z 414.98 (M+H)+.

Step C. 6-(((5,6-dichloro-1H-benzo[d]imidazol-2-yl)methyl)thio)-2-(trifluoromethyl)pyrimidin-4-amine, and 5,6-dichloro-2-(((6-methoxy-2-(trifluoromethyl)pyrimidin-4-yl)thio)methyl)-1H-benzo[d]imidazole To 5,6-dichloro-2-(((6-chloro-2-(trifluoromethyl)pyrimidin-4-yl)thio)methyl)-1H-benzo[d]imidazole (207 mg 0.5

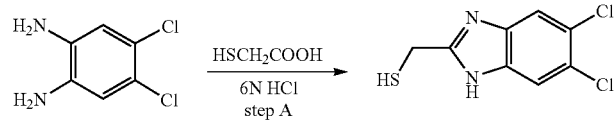

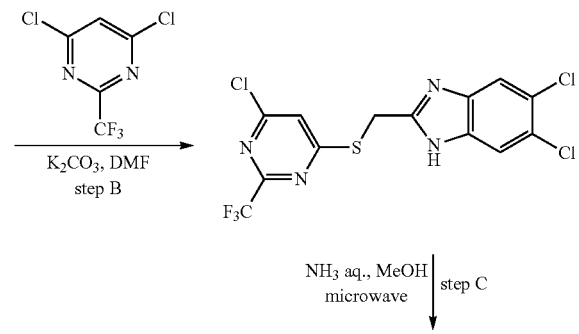

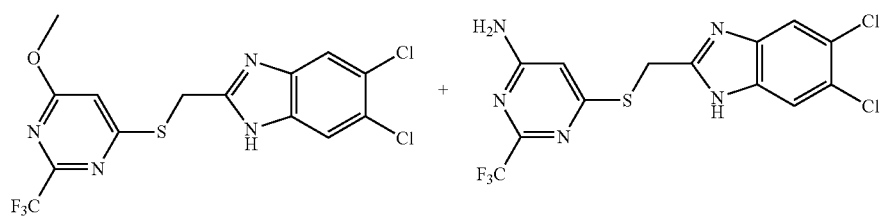

Step A. (5,6-Dichloro-1H-benzo[d]imidazol-2-yl)methanethiol 20 ml of 6N HCl was added to 500 mg of 4,5-dichlorobenzene-1,2-diamine in round bottom flask. Then add 250 μL of thioglycolicacid. This reaction mixture was refluxed for 4 hours. Excess solvent was evaporated under reduced pressure and to the remaining residue water (30 ml) was added and then extraction with ethyl acetate. The organic mmol) in methanol (3 ml) was added ammonia solution (3 ml). The reaction was heated under microwave activation, at 100-C for 20 min. After cooling, excess solvent was evaporated under reduced pressure and to the remaining residue water (30 ml) was added and then extraction with ethyl acetate. The organic solvent was then dried over anhydrous MgSO4 and evaporated under reduced pressure. The residue was purified by prep-HPLC using 5 acetonitrile and water as eluent to afford the desired compounds.

5,6-Dichloro-2-(((6-methoxy-2-(trifluoromethyl)pyrimidin-4-yl)thio)methyl)-1H-benzo[d]imidazole (116)

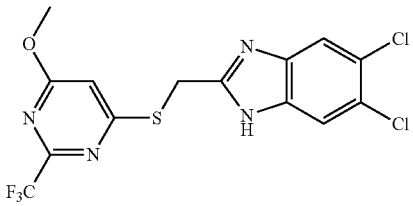 [SMILES: COc1cc(SCc2nc3cc(Cl)c(Cl)cc3[nH]2)nc(C(F)(F)F)n1]

$^1$H NMR (300 MHz, Acetone) δ 7.72 (s, 1H), 7.19 (s, 1H), 4.78 (s, 1H), 4.03 (s, 1H). LC.MS: m/z 411.02 (M+H)$^+$.

6-(((5,6-Dichloro-1H-benzo[d]imidazol-2-yl)methyl)thio)-2-(trifluoromethyl)pyrimidin-4-amine (117)

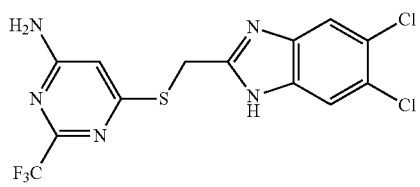 [SMILES: Nc1cc(SCc2nc3cc(Cl)c(Cl)cc3[nH]2)nc(C(F)(F)F)n1]

$^1$H NMR (300 MHz, Acetone) δ 7.70 (d, J=20.7 Hz, 2H), 6.88 (s, 2H), 6.71 (s, 1H), 4.68 (s, 2H). LC.MS: m/z 396.04 (M+H)$^+$.

10.2 6-(((5-Chloro-1H-benzo[d]imidazol-2-yl)methyl)thio)-2-(trifluoromethyl)pyrimidin-4-amine (118)

Compound 118 was synthesized based on the procedure described above for Compound 117.

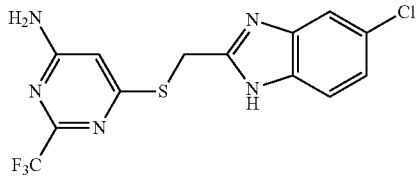 [SMILES: Nc1cc(SCc2nc3cc(Cl)ccc3[nH]2)nc(C(F)(F)F)n1]

LC.MS: m/z 360.02 (M+H)$^+$.

Example 11: Compounds 119 to 123

11.1 Preparation of 5,6-dichloro-2-(((2-(trifluoromethyl)pyridin-4-yl)thio)methyl)-1H-benzo[d]imidazole (119), 5,6-dichloro-2-(((2-(trifluoromethyl)pyridin-4-yl)oxy)methyl)-1H-benzo[d]imidazole (120), and N-((5,6-dichloro-1H-benzo[d]imidazol-2-yl)methyl)-2-(trifluoromethyl)pyridin-4-amine (121)

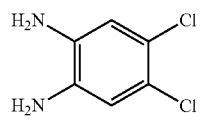

BrCH$_2$COOH
PPA step A

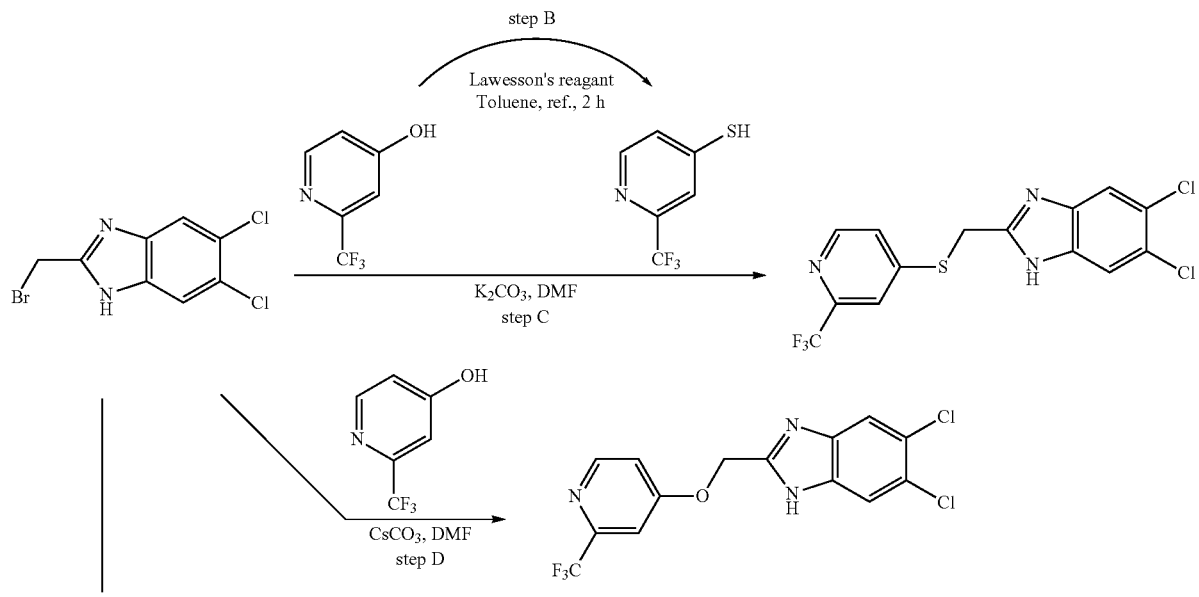

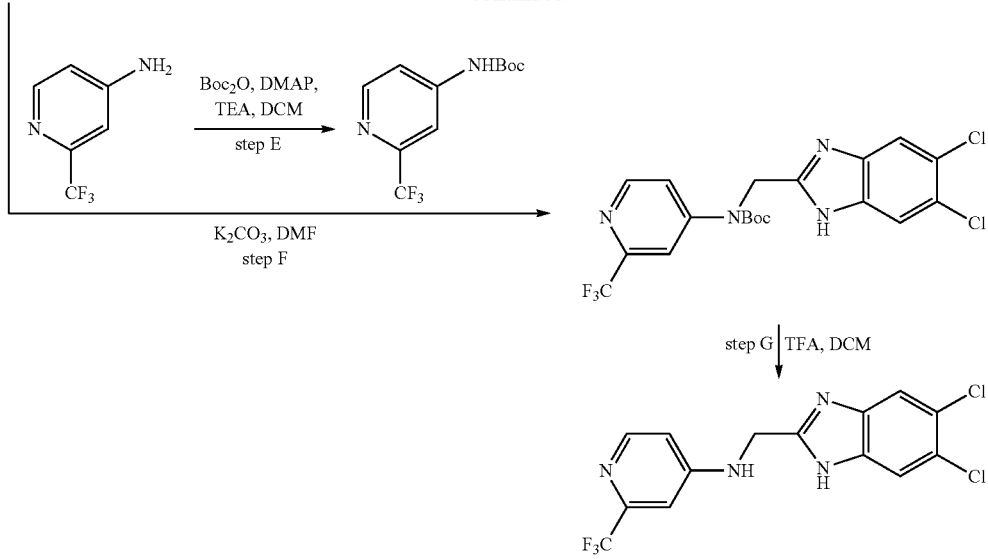

Step A. 2-(Bromomethyl)-5,6-dichloro-1H-benzo[d]imidazole

To a mixture of 4,5-dichlorobenzene-1,2-diamine (177 mg, 1 mmol) in polyphosphoric acid (1 g), bromoacetic acid (208 mg, 1.5 mmol) was added and stirred at 130° C. for 4 h. the reaction mixture was poured into ice water and stirred for 1 h to give a fine precipitate. The solid was collected by filtration, washed with cold water, dried, and used directly for the next step without further purification. LC.MS: m/z 280.97 (M+H)$^+$.

Step B. 2-(Trifluoromethyl)pyridine-4-thiol

A mixture of 2-(trifluoromethyl)pyridin-4-ol (100 mg, 0.61 mmol) and Lawesson's reagent (123.99 mg, 0.30 mmol) in toluene (10 mL) was refluxed for 2 hours. Excess solvent was evaporated under reduced pressure. The residue was purified was purified by column chromatography (DCM) to give the desired product (75 mg, 26% yield). LC.MS: m/z 180.08 (M+H)$^+$.

Step C. 5,6-Dichloro-2-(((2-(trifluoromethyl)pyridin-4-yl)thio)methyl)-1H-benzo[d]imidazole (119)

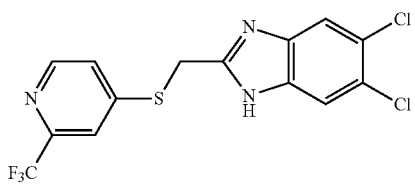

A mixture of 2-(bromomethyl)-5,6-dichloro-1H-benzo[d]imidazole (160 mg, 0.62 mmol), 2-(trifluoromethyl)pyridine-4-thiol (107 mg, 0.42 mmol) and K$_2$CO$_3$ (86 mg, 0.42 mmol) in DMF (10 mL) was stirred overnight at rt. Excess solvent was evaporated under reduced pressure and to the remaining residue water (30 ml) was added and then extraction with DCM. The organic solvent was then dried over anhydrous MgSO$_4$ and evaporated under reduced pressure. The residue was purified by prep-HPLC using acetonitrile and water as eluent to afford the desired compound. $^1$H NMR (300 MHz, Acetone) δ 8.54 (d, J=5.3 Hz, 1H), 8.00 (s, 2H), 7.94 (d, J=1.7 Hz, 1H), 7.78 (s, 1H), 7.73 (dd, J=5.3, 1.8 Hz, 1H), 4.78 (s, 2H). LC.MS: m/z 378.06 (M+H)$^+$.

Step D. 5,6-Dichloro-2-(((2-(trifluoromethyl)pyridin-4-yl)oxy)methyl)-1H-benzo[d]imidazole (120)

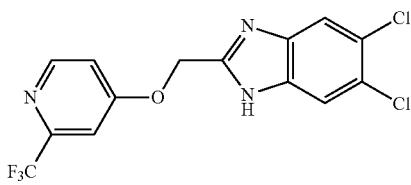 [SMILES: FC(F)(F)c1cc(SCc2nc3cc(Cl)c(Cl)cc3[nH]2)ccn1]

A mixture of 2-(bromomethyl)-5,6-dichloro-1H-benzo[d]imidazole (110 mg, 0.39 mmol), 2-(trifluoromethyl)pyridine-4-ol (77 mg, 0.47 mmol) and CsCO$_3$ (153 mg, 0.47 mmol) in DMF (10 mL) was stirred at 60° C. for 1 h. Excess solvent was evaporated under reduced pressure and to the remaining residue water (30 ml) was added and then extraction with DCM. The organic solvent was then dried over anhydrous MgSO$_4$ and evaporated under reduced pressure. The residue was purified by prep-HPLC using acetonitrile and water as eluent to afford the desired compound. $^1$H NMR (300 MHz, Acetone) δ 7.92 (d, J=7.8 Hz, 1H), 7.78 (s, 2H), 6.66 (d, J=2.8 Hz, 1H), 6.35 (dd, J=7.8, 2.8 Hz, 1H), 5.62 (s, 2H). LC.MS: m/z 362.09 (M+H)$^+$.

Step E. tert-Butyl (2-(trifluoromethyl)pyridin-4-yl)carbamate 2-(Trifluoromethyl)pyridin-4-amine (135 mg, 0.83 mmol), DMAP (10.25 mg, 0.08 mmol), Boc$_2$O (274.80 mg, 1.25 mmol) and Et$_3$N (152.83 µl, 1.09 mmol) were suspended in anhydrous DCM (3 mL) at rt, and stirred 2 h under argon atmosphere. The reaction mixture was diluted with CH$_2$C$_2$(25 mL) and washed with 0.1 N HCl (5 mL). The combined organic layers were dried over anhydrous MgSO$_4$ and concentrated under reduced pressure. The obtained residue was taken to the next step without further purification. $^1$H-NMR (300 MHz, CDCl$_3$): δ [ppm]=8.53 (d, J=5.6 Hz, 1H), 7.78 (d, J=2.0 Hz, 1H), 7.44 (dd, J=5.5 Hz, J=2.1 Hz, 1H), 6.92 (bs, 1H), 1.53 (s, 9H). LC.MS: m/z 207 (M+H-tBu)$^+$.

Step F. tert-Butyl ((5,6-dichloro-1H-benzo[d]imidazol-2-yl)methyl)(2-(trifluoromethyl)pyridin-4-yl) carbamate A mixture of 2-(bromomethyl)-5,6-dichloro-1H-benzo[d] imidazole (174 mg, 0.62 mmol), tert-butyl (2-(trifluoromethyl)pyridin-4-yl)carbamate (110 mg, 0.42 mmol) and K$_2$CO$_3$ (60 mg, 0.42 mmol) in DMF (10 mL) was stirred overnight at rt. Excess solvent was evaporated under reduced pressure and to the remaining residue water (30 ml) was added and then extraction with DCM. The organic solvent was then dried over anhydrous MgSO$_4$ and evaporated under reduced pressure. The remaining residue was taken directly for the next step and used without further purification. LC.MS: m/z 361.12 (M+H-tBu)$^+$.

Step G. N-((5,6-Dichloro-1H-benzo[d]imidazol-2-yl)methyl)-2-(trifluoromethyl)pyridin-4-amine (121)

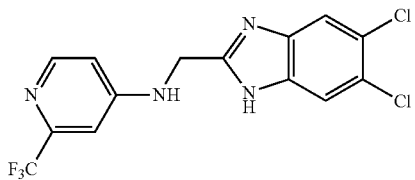 [SMILES: FC(F)(F)c1cc(NCc2nc3cc(Cl)c(Cl)cc3[nH]2)ccn1]

To crude tert-butyl ((5,6-dichloro-1H-benzo[d]imidazol-2-yl)methyl)(2-(trifluoromethyl)pyridin-4-yl)carbamate (60 mg, 0.13 mmol) dissolved in DCM (10 ml) was added TFA (2 ml). The reaction was stirred for 2 hours at room temp. Excess solvent was evaporated under reduced pressure and to the remaining residue was dissolved in DCM (10 ml×2) and evaporated again under reduced pressure. The residue was purified by prep-HPLC using acetonitrile and water as eluent to afford the desired compound. $^1$H NMR (300 MHz, Acetone) δ 8.21 (d, J=5.7 Hz, 1H), 7.72 (s, 2H), 7.12 (d, J=2.2 Hz, 1H), 7.03 (s, 1H), 6.83 (dd, J=5.7, 2.2 Hz, 1H), 4.81 (d, J=5.8 Hz, 2H). LC.MS: m/z 361.12 (M)$^+$.

11.2 Compounds 122 and 123

Compounds 122 and 123 were synthesized based on the procedure described above for Compound 119.

5,6-Difluoro-2-(((2-(trifluoromethyl)pyridin-4-yl) thio)methyl)-1H-benzo[d]imidazole. (122)

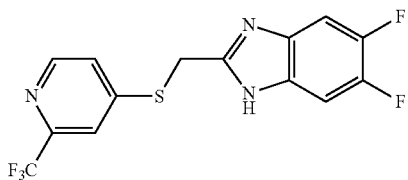 [SMILES: Fc1cc2nc(CSc3ccnc(C(F)(F)F)c3)[nH]c2cc1F]

$^1$H NMR (300 MHz, CDCl$_3$) δ 8.37 (d, J=5.3 Hz, 1H), 7.49 (d, J=1.5 Hz, 1H), 7.31 (dd, J=5.3, 1.5 Hz, 2H), 7.28-7.21 (m, 2H). LC.MS: m/z 346.12 (M+H)$^+$.

5-Chloro-2-(((2-(trifluoromethyl)pyridin-4-yl)thio) methyl)-1H-benzo[d]imidazole. (123)

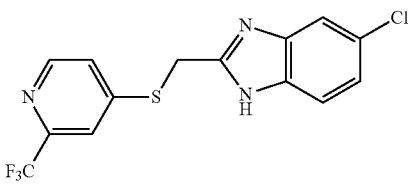 [SMILES: FC(F)(F)c1cc(SCc2nc3cc(Cl)ccc3[nH]2)ccn1]

LC.MS: m/z 344.04 (M+H)$^+$.

Example 12: Compounds 124 to 130

12.1 Preparation of 2-(((6-chloro-2-(trifluoromethyl)pyrimidin-4-yl)thio)methyl)-5-phenoxy-1H-benzo[d]imidazole (124), 6-(((5-phenoxy-1H-benzo[d]imidazol-2-ylmethylthio)-2-(trifluoromethyl) pyrimidin-4-amine (125), 2-(((6-methoxy-2-(trifluoromethyl)pyrimidin-4-yl)thio)methyl)-5-phenoxy-1H-benzo[d]imidazole (126), and 5-phenoxy-2-(((2-(trifluoromethyl)pyridin-4-yl)thio) methyl)-1H-benzo[d]imidazole (127)

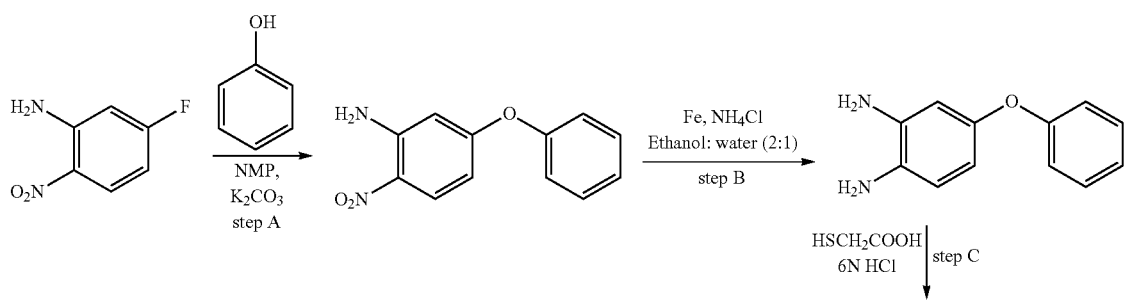

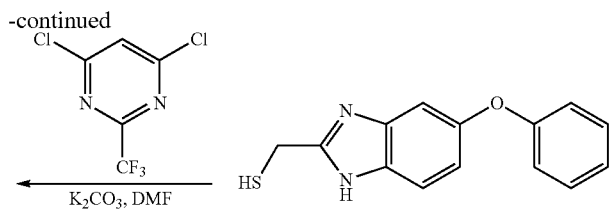

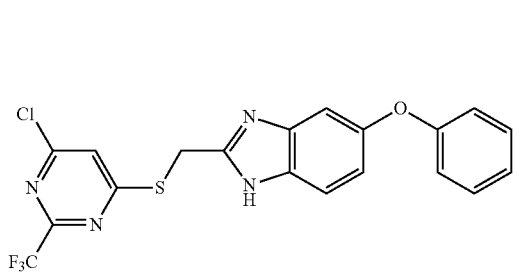

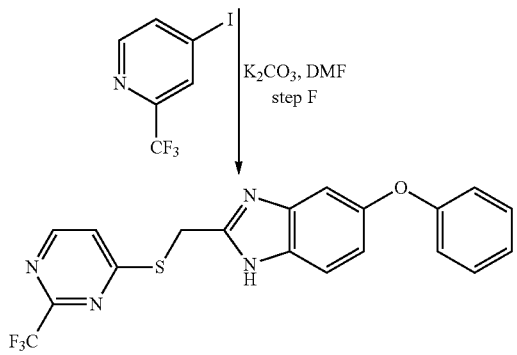

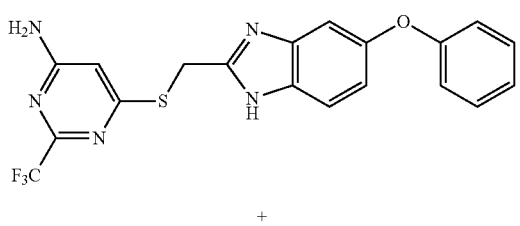

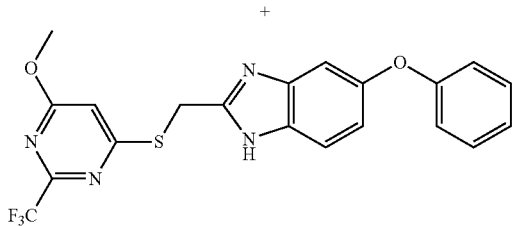

Step A. 2-Nitro-5-phenoxyaniline

To a mixture of 5-fluoro-2-nitroaniline (1560 mg, 10 mmol) in NMP (10 mL) were added phenol (1128 mg, 12 mmol) and $K_2CO_3$ (1656 mg, 12 mmol). The reaction mixture was stirred at 160° C. for 5 h. The reaction mixture was cooled to room temperature. The solid was collected by filtration, washed with cold water, dried, and used directly for the next step without further purification. LC.MS: m/z 231.07 $(M+H)^+$.

Step B. 4-Phenoxybenzene-1,2-diamine

A mixture of 2-nitro-5-phenoxyaniline (760 mg, 3.3 mmol), Fe (950 mg, 16.9 mmol) and ammonium chloride (90 mg, 1.6 mmol) was dissolved in an Ethanol/water (2:1) mixture. The mixture was heated at 100-C for 2 hours. Excess ethanol was evaporated under reduced pressure and to the remaining residue, water (50 ml) was added and then extraction with ethyl acetate. The organic solvent was then dried over $MgSO_4$ and evaporated under reduced pressure. The remaining residue was taken directly for the next step and used without further purification. LC.MS: m/z 201.19 $(M+H)^+$.

Step C. (5-Phenoxy-1H-benzo[d]imidazol-2-yl)methanethiol 20 ml of 6N HCl was added to 1000 mg of 4-phenoxybenzene-1,2-diamine in round bottom flask. Then add 500 µL of thioglycolicacid. This reaction mixture was refluxed for 4 hours. Excess solvent was evaporated under reduced pressure and to the remaining residue water (30 ml) was added and then extraction with ethyl acetate. The organic solvent was then dried over anhydrous $MgSO_4$ and evaporated under reduced pressure. The crude product was directly used in the next step without any further purification. LC.MS: m/z 257.06 $(M+H)^+$.

Step D. 2-(((6-Chloro-2-(trifluoromethyl)pyrimidin-4-yl)thio)methyl)-5-phenoxy-1H-benzo[d]imidazole (124)

A mixture of (5-phenoxy-1H-benzo[d]imidazol-2-yl)methanethiol (256 mg, 1 mmol), 4,6-dichloro-2-(trifluoromethyl)pyrimidine (217 mg 1 mmol), and $K_2CO_3$ (180 mg, 1.5 mmol) in DMF (10 mL) was stirred at rt for 2 h. Excess solvent was evaporated under reduced pressure and to the remaining residue water (30 ml) was added and then extraction with DCM. The organic solvent was then dried over anhydrous $MgSO_4$ and evaporated under reduced pressure. The residue was purified by prep-HPLC using acetonitrile and water as eluent to afford the desired compound.

Step E. 6-(((5-Phenoxy-1H-benzo[d]imidazol-2-yl)methyl)thio)-2-(trifluoromethyl)pyrimidin-4-amine (125) and 2-(((6-methoxy-2-(trifluoromethyl)pyrimidin-4-yl)thio)methyl)-5-phenoxy-1H-benzo[d]imidazole (126)

To 2-(((6-chloro-2-(trifluoromethyl)pyrimidin-4-yl)thio)methyl)-5-phenoxy-1H-benzo[d]imidazole (218 mg 0.5 mmol) in methanol (3 ml) was added ammonia solution (3 ml). The reaction was heated under microwave activation, at 100° C. for 20 min. After cooling, excess solvent was evaporated under reduced pressure. The residue was purified by prep-HPLC using acetonitrile and water as eluent to afford the desired compounds.

Step F. 5-Phenoxy-2-(((2-(trifluoromethyl)pyridin-4-yl)thio)methyl)-1H-benzo[d]imidazole (127)

A mixture of (5-phenoxy-1H-benzo[d]imidazol-2-yl)methanethiol (256 mg, 1 mmol), 2-(trifluoromethyl)pyridine-4-thiol (225 mg, 1.2 mmol) and K₂CO₃ (180 mg, 1.2 mmol) in DMF (10 mL) was stirred at 130° C. for 4 h. Excess solvent was evaporated under reduced pressure and to the remaining residue water (30 ml) was added and then extraction with DCM. The organic solvent was then dried over anhydrous MgSO₄ and evaporated under reduced pressure. The residue was purified by prep-HPLC using acetonitrile and water as eluent to afford the desired compound.

2-(((6-Chloro-2-(trifluoromethyl)pyrimidin-4-yl)thio)methyl)-5-phenoxy-1H-benzo[d]imidazole (124)

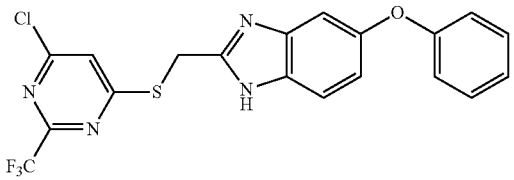 [SMILES: FC(F)(F)c1nc(Cl)cc(SCc2nc3cc(Oc4ccccc4)ccc3[nH]2)n1]

$^1$H NMR (300 MHz, Acetone) δ 8.08 (s, 1H), 7.55 (d, J=8.6 Hz, 1H), 7.40-7.29 (m, 2H), 7.14 (s, 1H), 7.12-7.02 (m, 1H), 7.01-6.89 (m, 3H), 4.86 (s, 2H). LC.MS: m/z 236.96 (M)⁺.

6-(((5-Phenoxy-1H-benzo[d]imidazol-2-yl)methyl)thio)-2-(trifluoromethyl)pyrimidin-4-amine (125)

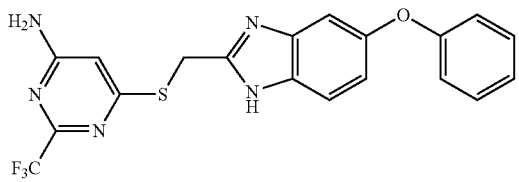 [SMILES: Nc1cc(SCc2nc3cc(Oc4ccccc4)ccc3[nH]2)nc(C(F)(F)F)n1]

$^1$H NMR (300 MHz, Acetone) δ 7.53 (d, J=8.7 Hz, 1H), 7.14 (d, J=2.2 Hz, 1H), 7.10-7.03 (m, 1H), 6.98 (q, J=1.8 Hz, 1H), 6.96-6.91 (m, 2H), 6.87 (br., 2H), 6.75 (s, 1H), 4.67 (s, 2H).
LC.MS: m/z 418.14 (M+H)⁺.

2-(((6-Methoxy-2-(trifluoromethyl)pyrimidin-4-yl)thio)methyl)-5-phenoxy-1H-benzo[d]imidazole (126)

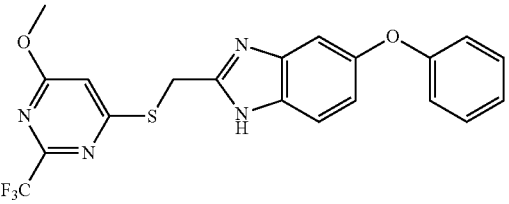 [SMILES: COc1cc(SCc2nc3cc(Oc4ccccc4)ccc3[nH]2)nc(C(F)(F)F)n1]

$^1$H NMR (300 MHz, Acetone) δ 7.54 (d, J=8.7 Hz, 1H), 7.39-7.30 (m, 2H), 7.25 (s, 1H), 7.14 (s, 1H), 7.11-7.03 (m, 1H), 7.00-6.90 (m, 3H), 4.76 (s, 2H), 4.03 (s, 3H). LC.MS: m/z 433.11 (M+H)⁺.

5-Phenoxy-2-(((2-(trifluoromethyl)pyridin-4-yl)thio)methyl)-1H-benzo[d]imidazole (127)

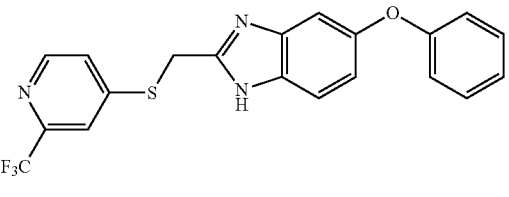 [SMILES: FC(F)(F)c1cc(SCc2nc3cc(Oc4ccccc4)ccc3[nH]2)ccn1]

$^1$H NMR (300 MHz, Acetone) δ 8.51 (d, J=5.3 Hz, 1H), 7.95 (d, J=1.7 Hz, 1H), 7.73 (dd, J=5.3, 1.8 Hz, 1H), 7.56 (d, J=8.7 Hz, 1H), 7.39-7.27 (m, 2H), 7.16 (d, J=2.3 Hz, 1H), 7.10-7.01 (m, 1H), 7.00-6.86 (m, 3H), 4.74 (s, 2H). LC.MS: m/z 402.00 (M+H)⁺.

12.2 Compounds 128 and 129

Compounds 128 to 129 were synthesized based on the procedure described above for Compound 125.

6-(((5-(m-Tolyloxy)-1H-benzo[d]imidazol-2-yl)methyl)thio)-2-(trifluoromethyl)pyrimidin-4-amine (128)

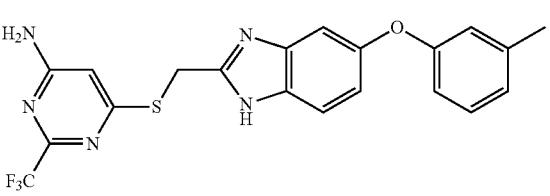 [SMILES: Cc1cccc(Oc2ccc3[nH]c(CSc4cc(N)nc(C(F)(F)F)n4)nc3c2)c1]

$^1$H NMR (300 MHz, Acetone) δ 7.50 (d, J=8.7 Hz, 1H), 7.15 (dd, J=8.7, 0.6 Hz, 2H), 7.08 (d, J=2.2 Hz, 1H), 6.94-6.81 (m, 5H), 6.73 (s, 1H), 4.66 (s, 2H), 2.29 (s, 3H). LC.MS: m/z 432.06 (M+H)⁺.

6-(((5-(3-Fluorophenoxy)-1H-benzo[d]imidazol-2-yl)methyl)thio)-2-(trifluoromethyl)pyrimidin-4-amine (129)

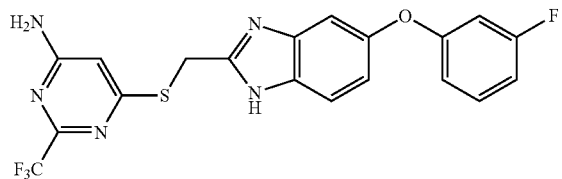 [SMILES: Nc1cc(SCc2nc3cc(Oc4cccc(F)c4)ccc3[nH]2)nc(C(F)(F)F)n1]

$^1$H NMR (300 MHz, Acetone) δ 7.51 (d, J=26.2 Hz, 1H), 7.26-7.04 (m, 3H), 7.05-6.84 (m, 5H), 6.75 (s, 1H), 4.66 (s, 2H). LC.MS: m/z 436.03 (M+H)$^+$.

12.3 Compound 130

Compound 130 was synthesized based on the procedure described above for Compound 127.

5-(3-Fluorophenoxy)-2-(((2-(trifluoromethyl)pyridin-4-yl)thio)methyl)-1H-benzo[d]imidazole (130)

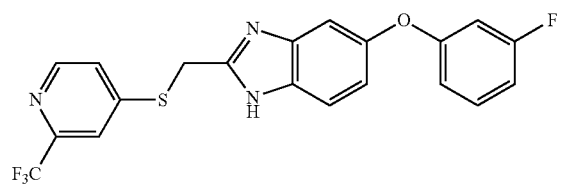 [SMILES: Fc1cccc(Oc2ccc3[nH]c(CSc4ccnc(C(F)(F)F)c4)nc3c2)c1]

$^1$H NMR (300 MHz, Acetone) δ 8.51 (d, J=5.3 Hz, 1H), 7.95 (d, J=1.6 Hz, 1H), 7.73 (dd, J=5.3, 1.6 Hz, 1H), 7.55 (d, J=8.7 Hz, 1H), 7.16-7.06 (m, 3H), 7.04-6.96 (m, 2H), 6.93 (dd, J=8.7, 2.3 Hz, 1H), 4.74 (s, 2H). LC.MS: m/z 419.95 (M+H)$^+$.

Example 13: Preparation of 5-isopropyl-2-(((2-(trifluoromethyl)pyridin-4-yl)thio)methyl)-1H-benzo[d]imidazole (131)

Step A. 2,2,2-Trifluoro-N-(4-isopropyl-2-nitrophenyl)acetamide

To a well-stirred solution of trifluoroacetic anhydride (10 mL) at 0° C. under nitrogen is added P-isopropylaniline (1000 mg, 7.39 mmol) dropwise via syringe. Stirring at 0° C. is continuated for 30 min. and potassium nitrate (896 mg, 8.86 mmol) is added as a solid. The slurry is stirred at 0° C. for 1 h and is allowed to warm to rt overnight. This mixture is poured onto ice (200 mL) and extracted with ethyl acetate (3×100). The organic solvent was then dried over anhydrous MgSO$_4$ and evaporated under reduced pressure. The remaining residue was taken directly for the next step and used without further purification. LC.MS: m/z 275.21 (M–H)$^-$.

Step B. 4-Isopropylbenzene-1,2-diamine 2,2,2-Trifluoro-N-(4-isopropyl-2-nitrophenyl)acetamide (276 mg, 1 mmol) in 60 mL of a mixture of methanol/water (2/1) was refluxed in 10% NaOH (5 mL) for 2 h. the reaction mixture was cooled and extracted with ethyl acetate (3×50). The organic solvent was then dried over anhydrous MgSO$_4$ and evaporated under reduced pressure. The remaining residue was taken directly for the next step and used without further purification. LC.MS: m/z 181.17 (M+H)$^+$.

Step C. 2-((2-(Trifluoromethyl)pyridin-4-yl)thio)acetic acid

A mixture of 4-iodo-2-(trifluoromethyl)pyridine (100 mg, 0.36 mmol), thioglycolic acid (50.5 mg, 0.55 mmol) and K$_2$CO$_3$ (202 mg, 1.5 mmol) in DMF (10 mL) was stirred at 130° C. for 4 h. Excess solvent was evaporated under reduced pressure and to the remaining residue water (30 ml) was added and the pH was adjusted to 5. The white solid was collected by filtration, washed with cold water, dried, and used directly for the next step without further purification. LC.MS: m/z 238.00 (M+H)$^+$.

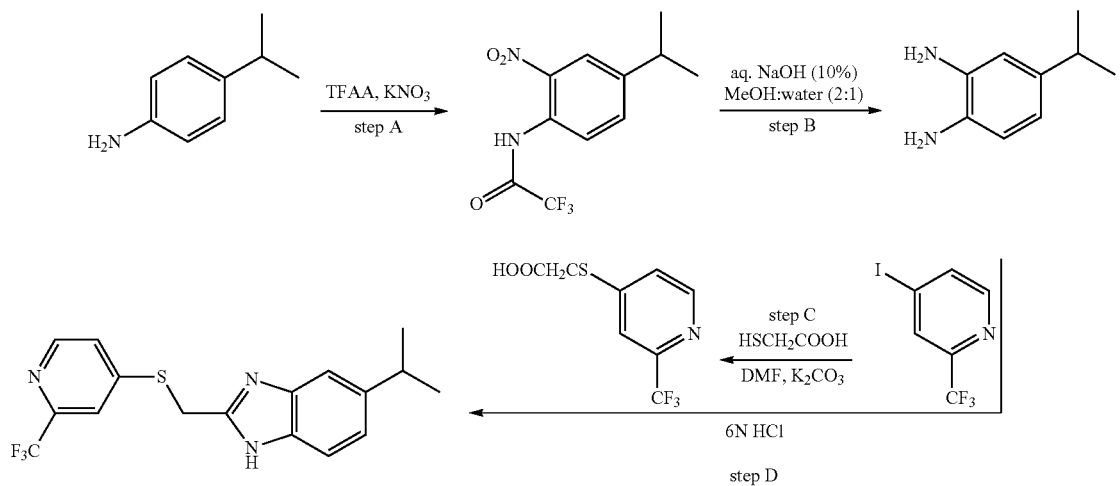

Step D. 5-Isopropyl-2-(((2-(trifluoromethyl)pyridin-4-yl)thio)methyl)-1H-benzo[d]imidazole (131)

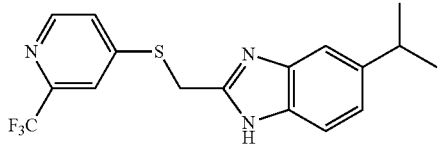 [SMILES: CC(C)c1ccc2[nH]c(CSc3ccnc(C(F)(F)F)c3)nc2c1]

20 ml of 6N HCl was added to 150 mg (1 mmol) of 4-isopropylbenzene-1,2-diamine in round bottom flask. Then add 200 mg (0.8 mmol) of 2-((2-(Trifluoromethyl)pyridin-4-yl)thio)acetic acid. This reaction mixture was refluxed on. Excess solvent was evaporated under reduced pressure and to the remaining residue water (30 ml) was added and then extraction with ethyl acetate. The organic solvent was then dried over anhydrous MgSO₄ and evaporated under reduced pressure. The residue was purified by prep-HPLC using acetonitrile and water as eluent to afford the desired compound. $^1$H NMR (500 MHz, CDCl₃) δ 8.47 (d, J=5.2 Hz, 1H), 7.60 (s, 1H), 7.44 (m, 3H), 7.17 (d, J=8.3 Hz, 1H), 4.53 (s, 2H), 3.02 (hept, J=6.7 Hz, 1H), 1.29 (d, J=6.9 Hz, 6H). LC.MS: m/z 352.18 (M+H)$^+$.

Example 14: Preparation of 6-phenoxy-2-(((2-(trifluoromethyl)pyridin-4-yl)thio)methyl)-benzo[d]oxazole (132), 6-phenoxy-2-(((2-(trifluoromethyl)pyridin-4-yl)oxy)methyl)-benzo[d]oxazole (133), and N-((6-phenoxybenzo[d]oxazol-2-yl)methyl)-2-(trifluoromethyl)-pyridin-4-amine (134)

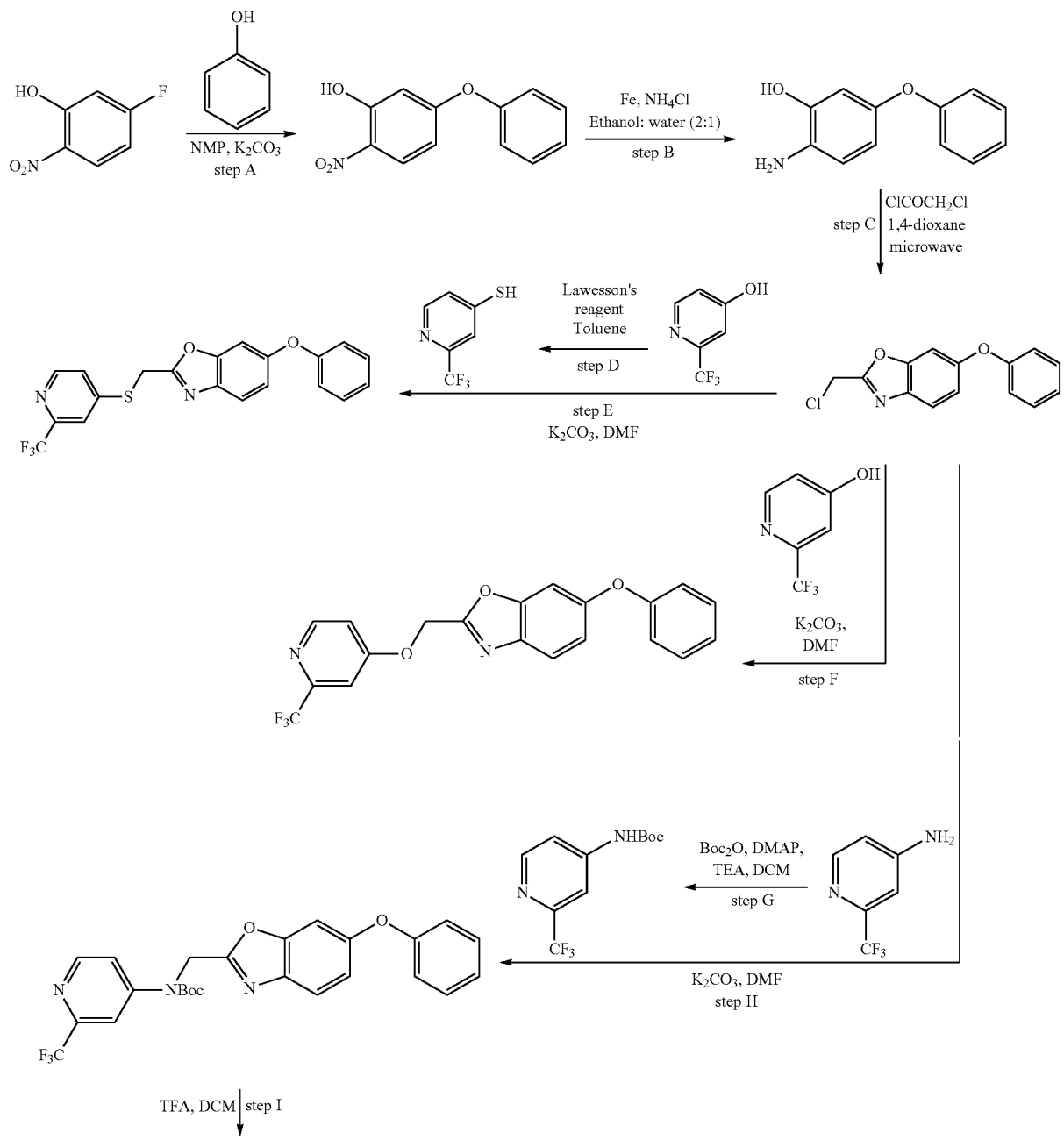

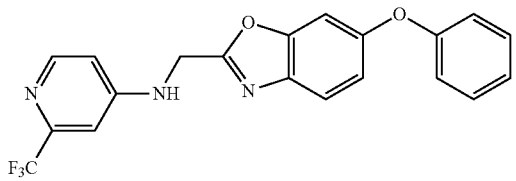

Step A. 2-Nitro-5-phenoxyphenol

To a mixture of 5-fluoro-2-nitrophenol (500 mg, 3.2 mmol) in NMP (10 mL) were added phenol (360 mg, 3.8 mmol) and $K_2CO_3$ (570 mg, 4.1 mmol). The reaction mixture was stirred at 160° C. for 5 h. The reaction mixture was cooled to room temperature. The solid was collected by filtration, washed with cold water, dried, and used directly for the next step without further purification. LC.MS: m/z 230.25 (M−H)⁻.

Step B. 2-Amino-5-phenoxyphenol

A mixture of 2-nitro-5-phenoxyphenol (500 mg, 2.1 mmol), Fe (595 mg, 10.8 mmol) and ammonium chloride (58 mg, 1.1 mmol) was dissolved in an Ethanol/water (2:1) mixture. The mixture was heated at 100-C for 2 hours. Excess ethanol was evaporated under reduced pressure and to the remaining residue, water (50 ml) was added and then extraction with ethyl acetate. The organic solvent was then dried over $MgSO_4$ and evaporated under reduced pressure. The obtained residue was purified using combi-flash (hexan:ethylacetate 30%). LC.MS: m/z 202.16 (M+H)⁺.

Step C. 2-(Chloromethyl)-6-phenoxybenzo[d]oxazole

To 2-amino-5-phenoxyphenol (201 mg 1 mmol) in Dioxane (3 ml) was added chloroacetyl chloride (113 mg, 1 mmol)). The reaction was heated under microwave activation, at 100-C for 90 min. After cooling, excess solvent was evaporated under reduced pressure. The remaining residue was taken directly for the next step and used without further purification. LC.MS: m/z 260.01 (M+H)⁺.

Step D. 2-(Trifluoromethyl)pyridine-4-thiol

A mixture of 2-(trifluoromethyl)pyridin-4-ol (100 mg, 0.613 mmol) and Lawesson's reagent (123.99 mg, 0.307 mmol) in toluene (10 mL) was refluxed for 2 hours. Excess solvent was evaporated under reduced pressure. The residue was purified was purified by column chromatography (DCM) to give the desired product. LC.MS: m/z 180.08 (M+H)⁺.

Step E. 6-Phenoxy-2-(((2-(trifluoromethyl)pyridin-4-yl)thio)methyl)benzo[d]oxazole (132)

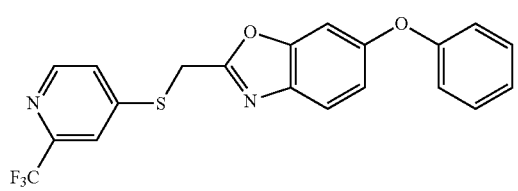 [SMILES: FC(F)(F)c1cc(OCc2nc3ccc(Oc4ccccc4)cc3o2)ccn1]

A mixture of 2-(chloromethyl)-6-phenoxybenzo[d]oxazole (260 mg, 1 mmol), 2-(trifluoromethyl)pyridine-4-thiol (179 mg, 1 mmol) and $K_2CO_3$ (138 mg, 1 mmol) in DMF (10 mL) was stirred overnight at rt. Excess solvent was evaporated under reduced pressure and to the remaining residue water (30 ml) was added and then extraction with DCM. The organic solvent was then dried over anhydrous $MgSO_4$ and evaporated under reduced pressure. The residue was purified by prep-HPLC using acetonitrile and water as eluent to afford the desired compound. ¹H NMR (300 MHz, Acetone) δ 8.56 (d, J=5.3 Hz, 1H), 7.94 (d, J=1.7 Hz, 1H), 7.74 (dd, J=5.3, 1.8 Hz, 1H), 7.66 (d, J=8.7 Hz, 1H), 7.43-7.33 (m, 2H), 7.23 (d, J=2.2 Hz, 1H), 7.18-7.09 (m, 1H), 7.08-6.98 (m, 3H), 4.80 (s, 2H). LC.MS: m/z 403.09 (M+H)⁺.

Step F. 6-Phenoxy-2-(((2-(trifluoromethyl)pyridin-4-yl)oxy)methyl)benzo[d]oxazole (133)

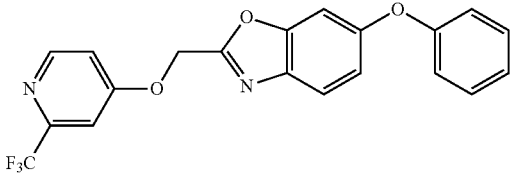

A mixture of 2-(chloromethyl)-6-phenoxybenzo[d]oxazole (260 mg, 1 mmol), 2-(trifluoromethyl)pyridine-4-ol (163 mg, 1 mmol) and $K_2CO_3$ (138 mg, 1 mmol) in DMF (10 mL) was stirred overnight at rt. Excess solvent was evaporated under reduced pressure and to the remaining residue water (30 ml) was added and then extraction with DCM. The organic solvent was then dried over anhydrous $MgSO_4$ and evaporated under reduced pressure. The residue was purified by prep-HPLC using acetonitrile and water as eluent to afford the desired compound. ¹H NMR (300 MHz, Acetone) δ 8.61 (d, J=5.7 Hz, 1H), 7.73 (d, J=8.7 Hz, 1H), 7.57 (d, J=2.4 Hz, 1H), 7.44-7.33 (m, 3H), 7.28 (d, J=2.2 Hz, 1H), 7.20-7.12 (m, 1H), 7.10 (dd, J=8.7, 2.3 Hz, 1H), 7.08-7.01 (m, 2H), 5.68 (s, 2H). LC.MS: m/z 387.13 (M+H)⁺.

Step G. tert-Butyl (2-(trifluoromethyl)pyridin-4-yl)carbamate 2-(Trifluoromethyl)pyridin-4-amine (135 mg, 0.83 mmol), DMAP (10.25 mg, 0.08 mmol), $Boc_2O$ (274.80 mg, 1.25 mmol) and $Et_3N$ (152.83 µl, 1.09 mmol) were suspended in anhydrous DCM (3 mL) at rt, and stirred 2 h under argon atmosphere. The reaction mixture was diluted with $CH_2Cl_2$ (25 mL) and washed with 0.1 N HCl (5 mL). The combined organic layers were dried over anhydrous $MgSO_4$ and concentrated under reduced pressure. The obtained residue was taken to the next step without further purification. ¹H-NMR (300 MHz, CDCl₃): δ [ppm]=8.53 (d, J=5.6 Hz, 1H), 7.78 (d, J=2.0 Hz, 1H), 7.44 (dd, J=5.5 Hz, J=2.1 Hz, 1H), 6.92 (bs, 1H), 1.53 (s, 9H). LC.MS: m/z 207 (M+H-tBu)⁺.

Step H. tert-Butyl ((6-phenoxybenzo[d]oxazol-2-yl)methyl)(2-(trifluoromethyl)pyridin-4-yl)carbamate A mixture of 2-(chloromethyl)-6-phenoxybenzo[d]oxazole (161 mg, 0.62 mmol), tert-butyl (2-(trifluoromethyl)pyridin-4-yl)carbamate (110 mg, 0.42 mmol) and K₂CO₃ (60 mg, 0.42 mmol) in DMF (10 mL) was stirred overnight at rt. Excess solvent was evaporated under reduced pressure and to the remaining residue water (30 ml) was added and then extraction with DCM. The organic solvent was then dried over anhydrous MgSO₄ and evaporated under reduced pressure. The remaining residue was taken directly for the next step and used without further purification.

LC.MS: m/z 386.12 (M+H-tBu)⁺.

Step I. N-((6-Phenoxybenzo[d]oxazol-2-yl)methyl)-2-(trifluoromethyl)pyridin-4-amine (134)

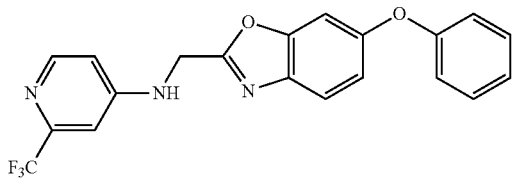 [SMILES: FC(F)(F)c1cc(NCc2nc3ccc(Oc4ccccc4)cc3o2)ccn1]

To crude tert-butyl ((6-phenoxybenzo[d]oxazol-2-yl)methyl)(2-(trifluoromethyl)pyridin-4-yl)carbamate (63 mg, 0.13 mmol) dissolved in DCM (10 ml) was added TFA (2 ml). The reaction was stirred for 2 hours at room temp. Excess solvent was evaporated under reduced pressure and to the remaining residue was dissolved in DCM (10 ml×2) and evaporated again under reduced pressure. The residue was purified by prep-HPLC using acetonitrile and water as eluent to afford the desired compound. ¹H NMR (300 MHz, Acetone) δ 8.56 (d, J=5.5 Hz, 1H), 8.47 (s, 1H), 8.06 (d, J=4.3 Hz, 1H), 7.44-7.32 (m, 2H), 7.22 (d, J=8.5 Hz, 1H), 7.17-7.08 (m, 1H), 7.06-6.91 (m, 3H), 6.69-6.58 (m, 1H), 6.53 (d, J=2.6 Hz, 1H), 4.71 (s, 2H). LC.MS: m/z 386.15 (M)⁺.

Example 15: Compounds 135 to 137

15.1 Preparation of 4-(((1-(4-chlorophenyl)-1H-pyrazol-3-yl)methyl)thio)-2-(trifluoromethyl)-pyridine (135)

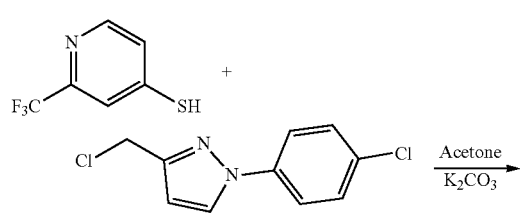

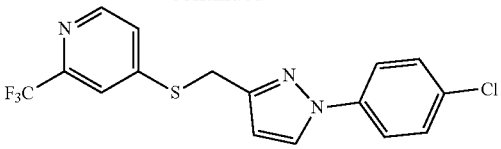

To a mixture of 2-(Trifluoromethyl)pyridine-4-thiol (60 mg, 0.335 mmol) and K₂CO₃ (55.54 mg, 0.402 mmol) in Acetone (20 ml) was added the 3-(chloromethyl)-1-(4-chlorophenyl)-1H-pyrazole (83.6 mg, 0.36 mmol). The reaction was heated at 50° C. for 15 hours. Excess solvent was evaporated under reduced pressure and to the remaining residue water (30 ml) was added and then extraction with Ethyl acetate. The organic solvent was then dried over anhydrous MgSO₄ and evaporated under reduced pressure. The residue was purified by automate column chromatography to give the desired product.

LC/MS: m/z 370 (M+H)⁺. ¹H-NMR (300 MHz, DMSO-d6) δ 8.60 (d, J=5.3 Hz, 1H), 8.02-7.99 (m, 1H), 7.96-7.90 (m, 2H), 7.76 (dd, J=5.5, 1.9 Hz, 1H), 7.70-7.64 (m, 2H), 4.96 (s, 2H). 13C NMR (75 MHz, DMSO-d6) δ 163.8, 163.5, 149.7, 149.4, 146.5 (d, J=33.7 Hz), 136.9 129.7, 128.2, 123.9, 121.90, 117.7, 23.6.

15.2 Compounds 136 and 137

Compounds 136 and 137 described below are further representative examples of compounds according to general formula (I) of the present invention. These compounds have been synthesized based on the procedure described above for Compound 135.

2-(4-Chlorophenyl)-5-(((2-(trifluoromethyl)pyridin-4-yl)thio)methyl)-1,3,4-oxadiazole (136)

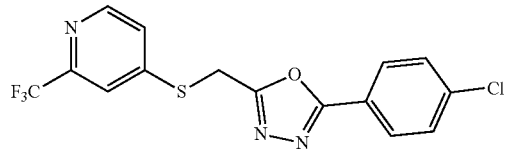 [SMILES: FC(F)(F)c1cc(SCc2nnc(-c3ccc(Cl)cc3)o2)ccn1]

LC/MS: m/z 372 (M+H)⁺. ¹H-NMR (300 MHz, DMSO-d6) δ 8.59-8.54 (m, 2H), 7.85-7.79 (m, 4H), 7.66 (dd, J=5.3, 1.8 Hz, 1H), 7.59-7.53 (m, 2H), 4.43 (s, 2H). 13C NMR (75 MHz, DMSO-d6) δ 151.04, 149.32, 141.13, 141.09, 137.93, 130.10, 129.18, 127.05, 123.08, 119.52, 117.89, 30.10.

3-(4-Chlorophenyl)-5-(((2-(trifluoromethyl)pyridin-4-yl)thio)methyl)-1,2,4-oxadiazole (137)

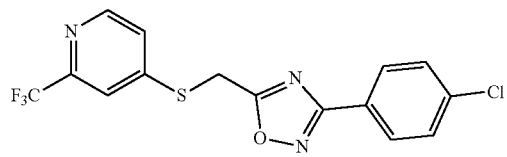 [SMILES: FC(F)(F)c1cc(SCc2nc(-c3ccc(Cl)cc3)no2)ccn1]

LC/MS: m/z 372 (M+H)⁺. ¹H-NMR (300 MHz, Chloroform-d) δ 8.50 (d, J=5.3 Hz, 1H), 7.90 (d, J=8.3 Hz, 2H), 7.69 (d, J=1.9 Hz, 1H), 7.44-7.30 (m, 3H), 4.39 (s, 2H).

Example 16: Preparation of 4-(((2-(4-chlorophenyl)-2H-tetrazol-5-yl)methyl)thio)-2-(trifluoromethyl)pyridine (138)

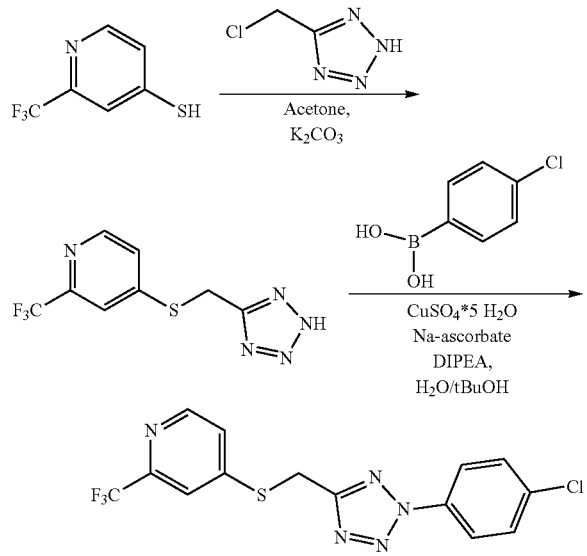

Step A. 4-(((2H-tetrazol-5-yl)methyl)thio)-2-(trifluoromethyl)pyridine

To a mixture of 2-(Trifluoromethyl)pyridine-4-thiol (60 mg, 0.335 mmol) and K₂CO₃ (55.54 mg, 0.402 mmol) in Acetone (20 ml) was added the 5-(chloromethyl)-2H-tetrazole (43.6 mg, 0.36 mmol). The reaction was heated at 50° C. for 15 hours. Excess solvent was evaporated under reduced pressure and to the remaining residue water (30 ml) was added and then extraction with Ethyl acetate. The organic solvent was then dried over anhydrous MgSO₄ and evaporated under reduced pressure. The residue was purified by automate column chromatography to give the desired product. LC/MS: m/z 262 (M+H)⁺.

Step B. 4-(((2-(4-Chlorophenyl)-2H-tetrazol-5-yl)methyl)thio)-2-(trifluoromethyl)pyridine (138)

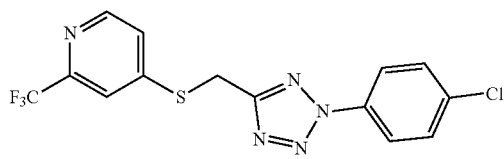 [SMILES: FC(F)(F)c1cc(SCc2nnn(-c3ccc(Cl)cc3)n2)ccn1]

K₂CO₃ (121 mg, 0.88 mmol), [Cu(OH)(TMEDA)]₂Cl₂ (45 mg, 0.09 mmol), and (4-chlorophenyl)boronic acid (275 mg, 1.76 mmol) were added to a solution of 4-(((2H-tetrazol-5-yl)methyl)thio)-2-(trifluoromethyl)pyridine (209 mg, 0.8 mmol) in CH₂Cl₂ (0.1-0.2M) at room temperature. The mixture was stirred for 16 h, then 10% aqueous NH₃ was added and extracted with CH₂Cl₂. The organic layer was washed with 10% aq. NaCL, dried over MgSO₄ and evaporated under reduced pressure. The residue was purified by automate column chromatography to give the desired product.

LC/MS: m/z 372 (M+H)⁺. ¹H-NMR (300 MHz, Acetone-d6) δ 8.43 (dd, J=5.3, 0.7 Hz, 1H), 7.98 (d, J=8.9 Hz, 2H), 7.81 (dd, J=2.0, 0.7 Hz, 1H), 7.56 (d, J=9.0 Hz, 2H), 4.73 (s, 3H).

Example 17: Preparation of N-((3-(4-phenoxyphenyl)isoxazol-5-yl)methyl)-2-(trifluoromethyl)pyridin-4-amine (139)

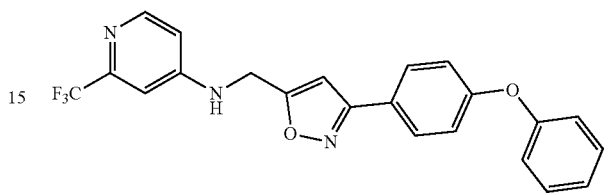

N-(Prop-2-yn-1-yl)-2-(trifluoromethyl)pyridin-4-amine (20 mg, 100 μmol) was dissolved in tBuOH/H₂O (1 mL) followed by the addition of (Z)—N-Hydroxy-4-phenoxybenzimidoyl chloride (25 mg, 100 μmol) and DIPEA (35 μL, 200 μmol). The reaction mixture was purged with Argon and Cu₂SO₄*5H₂O (10 mol %) and Na-ascorbate (10 mol %) were added. After stirring for 18 h at r.t. Saturated NH₄Cl solution was added and the reaction mixture was extracted with EtOAc. The combined organic layers were washed with Brine, dried over Na₂SO₄, filtered and concentrated under reduced pressure. The title compound (40 mg, 98 μmol, 98%) was yielded after prep-HPLC purification as a white solid.

LC-MS: m/z: 412 (M+H)⁺. ¹H-NMR (300 MHz, CDCl₃): δ [ppm]=4.62 (d, J=6.1 Hz, 2H), 5.02-5.06 (m, 1H), 6.46 (s, 1H), 6.66 (dd, J=5.7 Hz, J=2.3 Hz, 1H), 6.92 (d, J=2.3 Hz, 1H), 7.04-7.08 (m, 4H), 7.15-7.20 (m, 1H), 7.36-7.41 (m, 2H), 7.71-7.76 (m, 2H), 8.36 (d, J=5.7 Hz, 1H).

Example 17A: Compounds Nos. 140 to 184

The compounds Nos. 140 to 184 presented below are further representative examples of compounds according to general formula (I) of the present invention. These compounds have been synthesized using the methods described above, together with synthetic methods disclosed in the references cited herein or known in the art of synthetic organic chemistry, and variations thereon as appreciated by those skilled in the art. Each of the references cited herein in relation to the routes of synthesis described in Examples 1 to 17 is hereby incorporated by reference in its entirety in the present specification. In any event, those skilled in the art of organic synthesis will recognize the starting materials and reaction conditions including variations to produce the compounds. 2-chloro-N-((1-(4-isopropoxyphenyl)-1H-1,2,3-triazol-4-yl)methyl)-6-(trifluoromethyl)pyridin-4-amine (140)

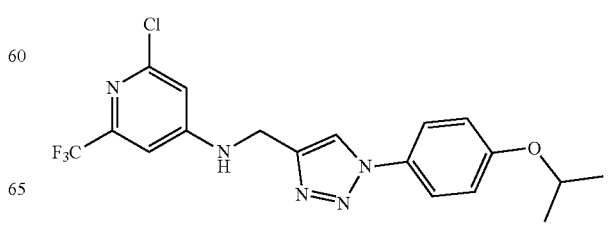

LC-MS: m/z: 412 (M+H)⁺. ¹H-NMR (300 MHz, acetone-d₆): δ [ppm]=1.21 (d, J=6.0 Hz, 6H), 4.50 (d, J=5.8 Hz, 2H), 4.58 (dq, J=6.0 Hz, 1H), 6.81 (d, J=1.8 Hz, 1H), 6.95-6.97 (m, 2H), 7.03 (d, J=1.9 Hz, 1H), 7.05 (bs, 1H), 7.59-7.62 (m, 2H), 8.34 (s, 1H).

2-chloro-N-((1-(4-(pyridin-3-yloxy)phenyl)-1H-1,2,3-triazol-4-yl)methyl)-6-(trifluoromethyl)pyridin-4-amine (141)

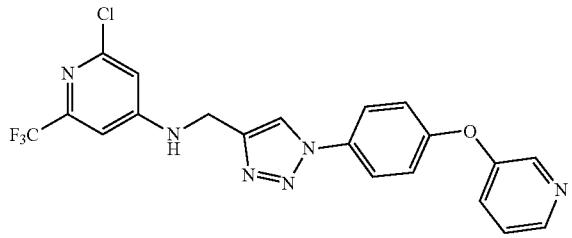 [SMILES: FC(F)(F)c1cc(NCc2cn(-c3ccc(Oc4cccnc4)cc3)nn2)cc(Cl)n1]

LC-MS: m/z: 447 (M+H)⁺. ¹H-NMR (500 MHz, acetone-d₆): δ [ppm]=4.70 (d, 5.8 Hz, 2H), 6.94 (d, J=2.0 Hz, 1H), 7.16 (d, J=2.0 Hz, 1H), 7.21 (bs, 1H), 7.25-7.27 (m, 2H), 7.43-7.46 (m, 1H), 7.49-7.52 (m, 1H), 7.89-7.92 (m, 2H), 8.43 (bs, 2H), 8.57 (s, 1H).

2-chloro-N-((1-(4-((2-fluoropyridin-3-yl)oxy)phenyl)-1H-1,2,3-triazol-4-yl)methyl)-6-(trifluoromethyl)pyridin-4-amine (142)

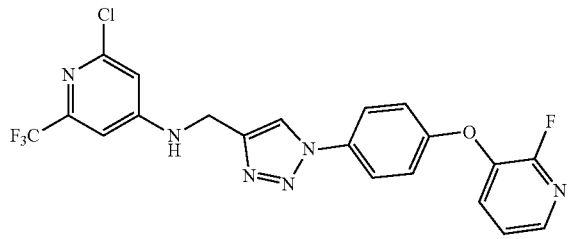 [SMILES: Fc1ncccc1Oc1ccc(-n2cc(CNc3cc(Cl)nc(C(F)(F)F)c3)nn2)cc1]

LC-MS: m/z: 465 (M+H)⁺. ¹H-NMR (300 MHz, CDCl₃): δ [ppm]=4.61 (s, 1H), 5.41 (bs, 1H), 6.70, (s, 1H), 6.87 (s, 1H), 7.13-7.15 (m, 2H), 7.24-7.26 (m, 1H), 7.53-7.57 (m, 1H), 7.70-7.72 (m, 2H), 7.96 (bs, 1H), 8.07-8.08 (m, 1H).

2-chloro-N-((1-(4-(2-fluorophenoxy)phenyl)-1H-1,2,3-triazol-4-yl)methyl)-6-(trifluoromethyl)pyridin-4-amine (143)

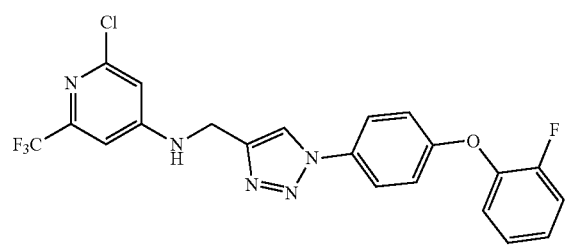 [SMILES: Fc1ccccc1Oc1ccc(-n2cc(CNc3cc(Cl)nc(C(F)(F)F)c3)nn2)cc1]

LC-MS: m/z: 464 (M+H)⁺. ¹H-NMR (500 MHz, CDCl₃): δ [ppm]=4.59 (s, 2H), 5.45 (bs, 1H), 6.69 (s, 1H), 6.86 (s, 1H), 7.10-7.11 (m, 2H), 7.15-7.26 (m, 4H), 7.63-7.66 (m, 2H), 7.68 (s, 1H).

N-((1-(4-(2-fluorophenoxy)phenyl)-1H-1,2,3-triazol-4-yl)methyl)-2-(trifluoromethyl)pyridin-4-amine (144)

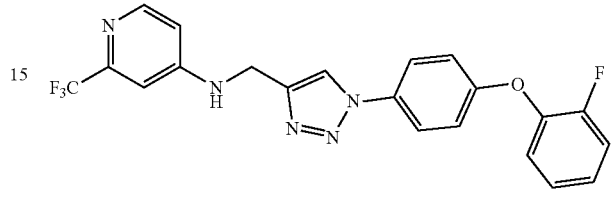

LC-MS: m/z: 430 (M+H)⁺. ¹H-NMR (300 MHz, CDCl₃): δ [ppm]=4.61 (d, J=5.5 Hz, 2H), 5.26 (bs, 1H), 6.69 (dd, J=5.8 Hz, J=2.3 Hz, 1H, 4-H), 6.93 (d, J=2.1 Hz, 1H), 7.09-7.12 (m, 2H), 7.14-7.24 (m, 4H), 7.63-7.66 (m, 2H), 7.87 (s, 1H), 8.33 (d, J=5.7 Hz, 1H).

N-((1-(4-(3-fluorophenoxy)phenyl)-1H-1,2,3-triazol-4-yl)methyl)-2-(trifluoromethyl)pyridin-4-amine (145)

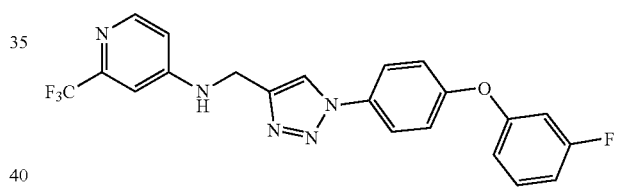

LC-MS: m/z: 430 (M+H)⁺. ¹H-NMR (500 MHz, CDCl₃): δ [ppm]=4.63 (d, J=5.3 Hz, 2H), 5.33 (bs, 1H), 6.70 (dd, J=5.7 Hz, J=1.9 Hz, 1H, 4H), 6.77 (ddd, J=9.9 Hz, J=2.4 Hz, 1H), 6.84 (dd, J=8.2 Hz, J=2.3 Hz, 1H), 6.89 (ddd, J=8.2 Hz, J=2.3 Hz, J=0.8 Hz 1H), 6.95 (d, J=2.1 Hz, 1H), 7.16-7.19 (m, 2H), 7.32-7.36 (m, 1H), 7.69-7.71 (m, 2H), 7.89 (s, 1H), 8.33 (d, J=5.3 Hz, 1H).

2-chloro-N-((1-(4-(4-fluoro-1H-indazol-1-yl)phenyl)-1H-1,2,3-triazol-4-yl)methyl)-6-(trifluoromethyl)pyridin-4-amine (146)

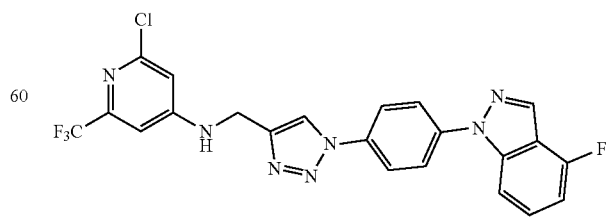

LC-MS: m/z: 488 (M+H)⁺.

N-((1-(3-chloro-4-(1H-pyrazolo[3,4-c]pyridin-1-yl)phenyl)-1H-1,2,3-triazol-4-yl)methyl)-2-trifluoromethyl)pyridin-4-amine (147)

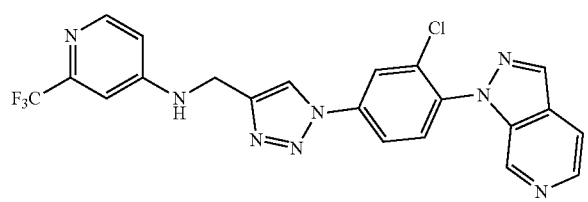 [SMILES: FC(F)(F)c1cc(NCc2cn(-c3ccc(-n4ncc5ccncc54)c(Cl)c3)nn2)ccn1]

LC-MS: m/z: 471 (M+H)⁺. 1H-NMR (500 MHz, CDCl₃): Shift [ppm]=4.68 (bs, 2H), 5.19 (bs, 1H), 6.70 (bs, 1H), 6.95 (bs, 1H), 7.75-7.76 (m, 2H), 7.87-7.89 (m, 1H), 8.03 (s, 1H), 8.11 (s, 1H), 8.36 (bs, 2H), 8.47 (bs, 1H), 8.86 (s, 1H).

N-((1-(4-(1H-pyrazolo[3,4-c]pyridin-1-yl)phenyl)-1H-1,2,3-triazol-4-yl)methyl)-2-(trifluoromethyl)pyridin-4-amine (148)

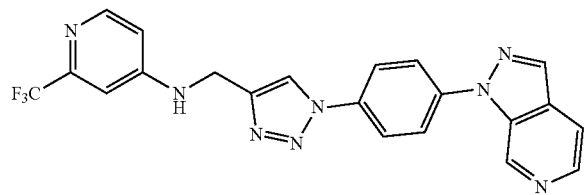 [SMILES: FC(F)(F)c1cc(NCc2cn(-c3ccc(-n4ncc5ccncc54)cc3)nn2)ccn1]

LC-MS: m/z: 437 (M+H)⁺. 1H-NMR (500 MHz, acetone-d6): δ [ppm]=4.70-4.71 (m, 2H), 6.87-6.92 (m, 2H), 7.13-7.16 (m, 1H), 7.74-7.75 (m, 1H), 7.88-7.89 (m, 1H), 8.13-8.17 (m, 2H), 8.23-8.26 (m, 2H), 8.41-8.42 (m, 1H), 8.46-8.47 (m, 1H), 8.68-8.69 (m, 1H), 9.42 (s, 1H).

N-((1-(4-(1H-pyrazolo[4,3-b]pyridin-1-yl)phenyl)-1H-1,2,3-triazol-4-yl)methyl)-2-(trifluoromethyl)pyridin-4-amine (149)

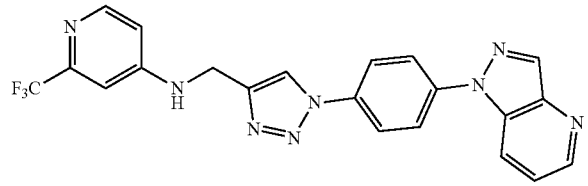 [SMILES: FC(F)(F)c1cc(NCc2cn(-c3ccc(-n4ncc5ncccc54)cc3)nn2)ccn1]

LC-MS: m/z: 437 (M+H)⁺. 1H-NMR (500 MHz, acetone-d6): δ [ppm]=4.00 (s, J=5.0 Hz, 2H), 4.77 (bs, 1H), 6.04-6.05 (m, 1H), 6.30 (s, 1H), 6.61-6.62 (m, 1H), 6.77-6.78 (m, 1H), 7.27-7.29 (m, 2H), 7.36-7.36 (m, 2H), 7.47-7.49 (m, 1H), 7.67-7.68 (m, 1H), 7.84 (s, 1H), 8.07 (bs, 1H).

N-((1-(4-(1H-indazol-1-yl)phenyl)-1H-1,2,3-triazol-4-yl)methyl)-2-chloro-6-(trifluoromethyl)pyridin-4-amine (150)

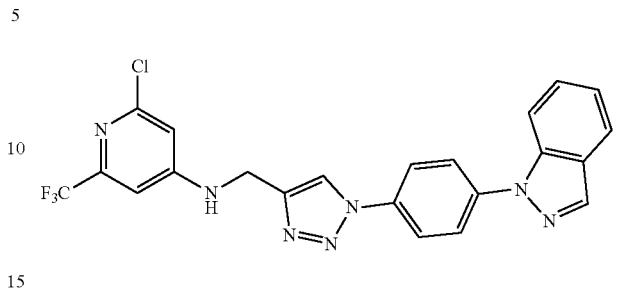

LC-MS: m/z: 470 (M+H)⁺. 1H-NMR (500 MHz, acetone-d6): δ [ppm]=4.75 (d, J=5.8 Hz, 2H), 6.96 (d, J=2.0 Hz, 1H), 7.18 (d, J=2.0 Hz, 1H), 7.21 (bs, 1H), 7.29-7.32 (m, 1H), 7.52-7.55 (m, 1 h), 7.91-7.92 (m, 1H), 7.94-7.96 (m, 1H), 8.04-8.06 (m, 2H), 8.09-8.11 (m, 2H), 8.34 (s, 1H), 8.69 (s, 1H).

N-((1-(4-(1H-pyrazolo[3,4-c]pyridin-1-yl)phenyl)-1H-1,2,3-triazol-4-yl)methyl)-2-chloro-6-(trifluoromethyl)pyridin-4-amine (151)

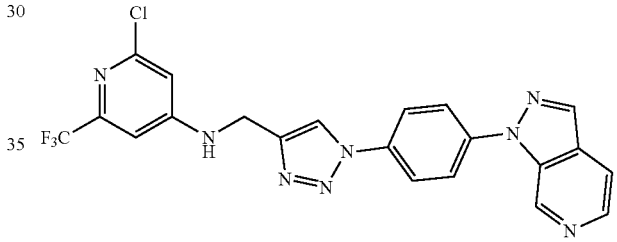

LC-MS: m/z: 471 (M+H)⁺. 1H-NMR (500 MHz, acetone-d6): δ [ppm]=4.75 (d, J=5.7 Hz, 2H), 6.96 (d, J=1.8 Hz, 1H), 7.18 (d, J=1.8 Hz, 1H), 7.26 (bs, 1H), 7.52-7.54 (m, 1H), 8.07-8.09 (m, 2H), 8.12-8.14 (m, 2H), 8.39-8.41 (m, 1H), 8.50 (s, 1H), 8.67-8.68 (m, 1H), 8.70 (s, 1H).

N-((1-(3-chloro-4-(oxetan-3-yloxy)phenyl)-1H-1,2,3-triazol-4-yl)methyl)-2-(trifluoromethyl)pyridin-4-amine (152)

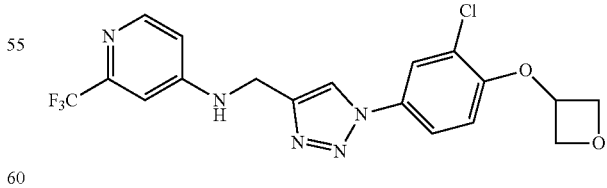

LC-MS: m/z: 426 (M+H)⁺. 1 H-NMR (500 MHz, CDCl₃): Shift [ppm]=4.61 (d, J=5.5 Hz, 2H), 4.84-4.86 (m, 2H), 5.01-5.04 (m, 2H), 5.27-5.32, (m, 1H), 6.61 (d, J=8.7 Hz, 1H), 6.66 (dd, J=5.7 Hz, J=2.0 Hz, 1H), 6.91 (d, J=2.0 Hz, 1H), 7.54 (dd, J=8.7 Hz, J=2.4 Hz, 1H), 7.78 (d, J=2.4 Hz, 1H), 7.84 (s, 1H), 8.31 (d, J=5.7 Hz, 1H).

N-((1-(3-chloro-4-((tetrahydrofuran-3-yl)oxy)phenyl)-1H-1,2,3-triazol-4-yl)methyl)-2-(trifluoromethyl)pyridin-4-amine (153)

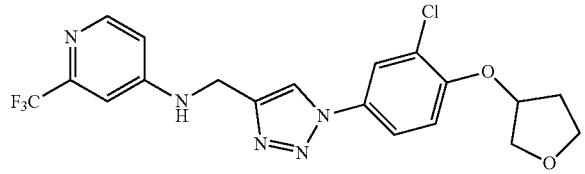 [SMILES: FC(F)(F)c1cc(NCc2cn(-c3ccc(OC4CCOC4)c(Cl)c3)nn2)ccn1]

LC-MS: m/z: 440 (M+H)⁺. 1H-NMR (500 MHz, CDCl₃): δ [ppm]=2.20-2.28 (m, 2H), 3.94-3.98 (m, 1H), 4.02-4.08 (m, 3H), 4.61 (d, J=5.3 Hz, 2H, 6-H), 5.02 (m, 1H), 5.35 (m, 1H), 6.66 (dd, J=5.7 Hz, J=1.8 Hz, 1H), 6.91 (d, J=1.8 Hz, 1H), 6.91 (d, J=8.3 Hz, 1H), 7.56 (dd, J=8.3 Hz, J=2.0 Hz, 1H), 7.75 (d, J=2.0 Hz, 1H), 7.85 (s, 1H), 8.31 (d, J=5.7 Hz, 1H).

N-((1-(3-chloro-4-cyclopropoxyphenyl)-1H-1,2,3-triazol-4-yl)methyl)-2-(trifluoromethyl)pyridin-4-amine (154)

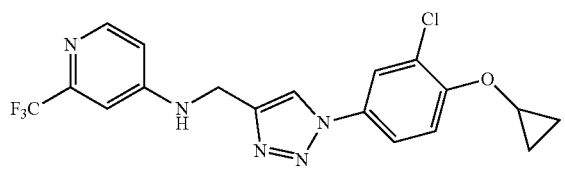 [SMILES: FC(F)(F)c1cc(NCc2cn(-c3ccc(OC4CC4)c(Cl)c3)nn2)ccn1]

LC-MS: m/z: 410 (M+H)⁺. 1H-NMR (500 MHz, CDCl₃): δ [ppm]=0.90 (m, 4H), 3.85-3.88 (m, 1H), 4.60 (d, J=4.7 Hz, 2H), 5.33 (bs, 1H), 6.67-6.68 (m, 1H), 6.62 (s, 1H), 7.43 (d, J=8.9 Hz, 1H), 7.58 (dd, J=8.9 Hz, J=2.4 Hz, 1H), 7.71 (d, J=2.3 Hz, 1H), 7.85 (bs, 1H), 8.32 (m, 1H).

N-((1-(4-((2-fluoropyridin-3-yl)oxy)phenyl)-1H-1,2,3-triazol-4-yl)methyl)-2-(trifluoromethyl)pyridin-4-amine (155)

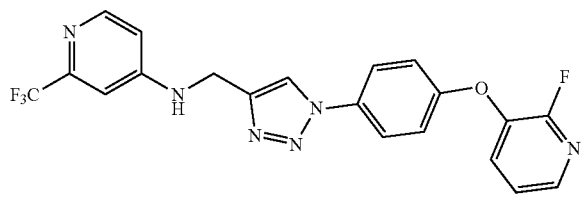 [SMILES: Fc1ncccc1Oc1ccc(-n2cc(CNc3ccnc(C(F)(F)F)c3)nn2)cc1]

LC-MS: m/z: 431 (M+H)⁺. 1H-NMR (500 MHz, acetone-d6): δ [ppm]=4.66 (d, J=5.7 Hz, 2H), 6.8 (bs, 1H), 6.88-6.89 (m, 1H), 7.12 (s, 1H), 7.25-7.27 (m, 2H), 7.40-7.42 (m, 1H), 7.73-7.77 (m, 1H), 7.89-.791 (m, 2H), 8.06 (m, 1H), 8.21-8.22 (m, 1H), 8.53 (s, 1H).

4-(((1-(3-chloro-4-isopropoxyphenyl)-1H-1,2,3-triazol-4-yl)methyl)amino)-6-(trifluoromethyl)picolinonitrile (156)

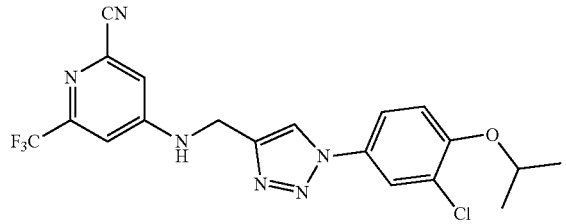 [SMILES: CC(C)Oc1ccc(-n2cc(CNc3cc(C#N)nc(C(F)(F)F)c3)nn2)cc1Cl]

¹H NMR (500 MHz, Acetone) δ 8.59 (s, 1H), 7.91 (d, J=2.7 Hz, 1H), 7.78 (dd, J=8.9, 2.7 Hz, 1H), 7.46 (d, J=1.7 Hz, 2H), 7.39 (d, J=2.2 Hz, 1H), 7.35 (d, J=9.0 Hz, 1H), 4.84-4.74 (m, 3H), 1.40 (d, J=6.0 Hz, 6H). LC-MS: m/z: 437 (M+H)⁺.

N-((1-(3-chloro-4-isopropoxyphenyl)-1H-1,2,3-triazol-4-yl)methyl)-2-nitropyridin-4-amine (157)

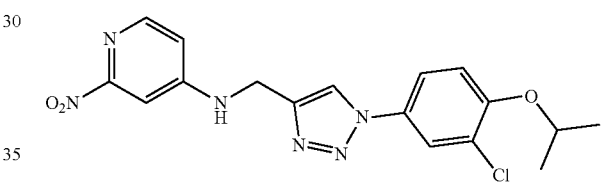

¹H NMR (500 MHz, Acetone) δ 8.42 (s, 1H), 7.97 (d, J=5.5 Hz, 1H), 7.76 (d, J=2.4 Hz, 1H), 7.63 (dd, J=8.9, 2.4 Hz, 1H), 7.42 (d, J=1.6 Hz, 1H), 7.19 (d, J=8.9 Hz, 1H), 7.01 (s, 1H), 6.92 (dd, J=5.4, 1.8 Hz, 1H), 4.66 (dt, J=12.0, 5.9 Hz, 1H), 4.57 (d, J=5.7 Hz, 2H), 1.24 (d, J=6.0 Hz, 6H).

LC-MS: m/z: 389 (M+H)⁺.

2,6-dichloro-N-((1-(3-chloro-4-isopropoxyphenyl)-1H-1,2,3-triazol-4-yl)methyl)pyridin-4-amine (158)

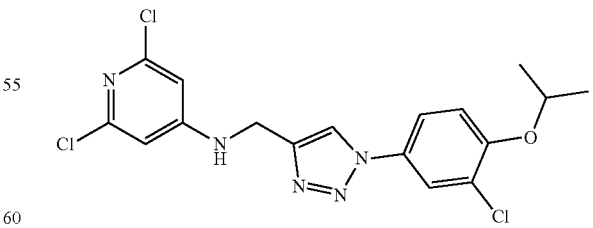

¹H NMR (500 MHz, Acetone) δ 8.41 (s, 1H), 7.78 (d, J=2.7 Hz, 1H), 7.64 (dd, J=8.9, 2.7 Hz, 1H), 7.20 (d, J=9.0 Hz, 1H), 6.83 (s, 1H), 6.61 (s, 2H), 4.65 (dt, J=12.1, 6.0 Hz, 1H), 4.49 (d, J=5.8 Hz, 2H), 1.25 (d, J=6.0 Hz, 6H). LC-MS: m/z: 412 (M+H)⁺.

4-(((1-(3-chloro-4-isopropoxyphenyl)-1H-1,2,3-triazol-4-yl)methyl)amino)pyridine-2,6-dicarbonitrile (159)

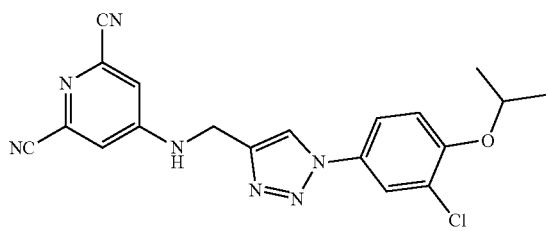 [SMILES: CC(C)Oc1ccc(-n2cc(CNc3cc(C#N)nc(C#N)c3)nn2)cc1Cl]

¹H NMR (500 MHz, Acetone) δ 8.46 (s, 1H), 7.76 (d, J=2.7 Hz, 1H), 7.63 (dd, J=8.9, 2.7 Hz, 1H), 7.39 (s, 1H), 7.32 (s, 2H), 7.20 (d, J=9.0 Hz, 1H), 4.70-4.58 (m, 3H), 1.25 (d, J=6.0 Hz, 6H).
LC-MS: m/z: 394 (M+H)⁺.

4-(((2-(3-Chloro-4-isopropoxyphenyl)thiazol-5-yl)methyl)amino)-6-(trifluoromethyl)picolinonitrile (160)

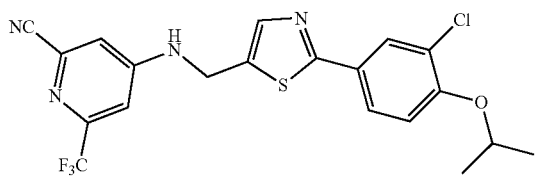 [SMILES: CC(C)Oc1ccc(-c2ncc(CNc3cc(C#N)nc(C(F)(F)F)c3)s2)cc1Cl]

¹H NMR (500 MHz, Acetone) δ 7.86-7.78 (m, 2H), 7.73 (s, 1H), 7.66 (dd, J=8.6, 2.2 Hz, 1H), 7.29 (d, J=2.1 Hz, 1H), 7.21 (d, J=2.2 Hz, 1H), 7.07 (d, J=8.7 Hz, 1H), 4.79 (d, J=3.9 Hz, 2H), 4.70-4.56 (m, 1H), 1.23 (d, J=6.0 Hz, 6H). LC-MS: m/z: 453.1 (M+H)⁺.

2-Chloro-N-((2-(4-isopropoxyphenyl)thiazol-5-yl)methyl)-6-(trifluoromethyl)pyridin-4-amine (161)

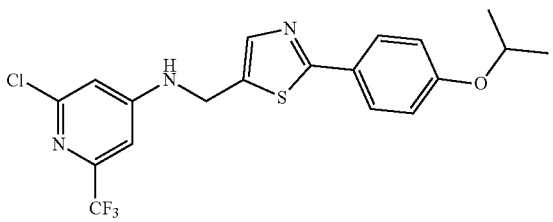 [SMILES: CC(C)Oc1ccc(-c2ncc(CNc3cc(Cl)nc(C(F)(F)F)c3)s2)cc1]

¹H NMR (500 MHz, Acetone) δ 7.88-7.83 (m, 2H), 7.80 (s, 1H), 7.27 (br., s, 1H), 7.14 (d, J=2.0 Hz, 1H), 7.03-6.97 (m, 2H), 6.92 (d, J=1.9 Hz, 1H), 4.88-4.80 (m, 2H), 4.71 (hept, J=6.0 Hz, 1H), 1.32 (d, J=6.0 Hz, 6H). LC.MS: m/z 428.2 (M+H)⁺.

2,6-Dichloro-N-((2-(4-isopropoxyphenyl)thiazol-5-yl)methyl)pyridin-4-amine (162)

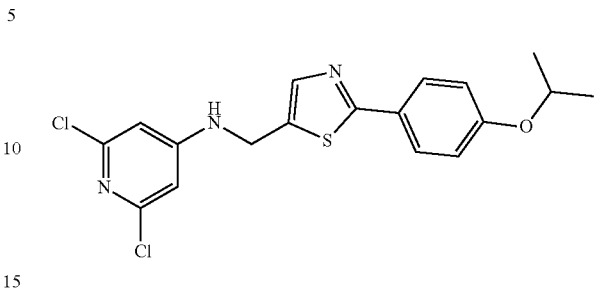

¹H NMR (500 MHz, DMSO) δ 7.41 (t, J=5.9 Hz, 1H), 7.35 (dt, J=5.2, 3.0 Hz, 3H), 6.58-6.49 (m, 2H), 6.25 (s, 2H), 4.28-4.15 (m, 3H), 0.83 (d, J=6.0 Hz, 6H). LC.MS: m/z 394.2 (M+H)⁺.

4-(((2-(4-Isopropoxyphenyl)thiazol-5-yl)methyl)amino)-6-(trifluoromethyl)picolinonitrile (163)

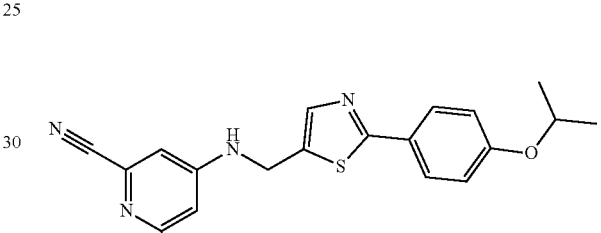

¹H NMR (500 MHz, Acetone) δ 7.88-7.80 (m, 3H), 7.52 (d, J=5.2 Hz, 1H), 7.44 (d, J=2.1 Hz, 1H), 7.35 (d, J=2.2 Hz, 1H), 7.04-6.95 (m, 2H), 4.92 (d, J=5.5 Hz, 2H), 4.76-4.66 (m, 1H), 1.32 (d, J=6.0 Hz, 6H). LC.MS: m/z 419.2 (M+H)⁺.

N-((2-(5-chloro-6-isopropoxypyridin-3-yl)pyrimidin-5-yl)methyl)-2-(trifluoromethyl)pyridin-4-amine (164)

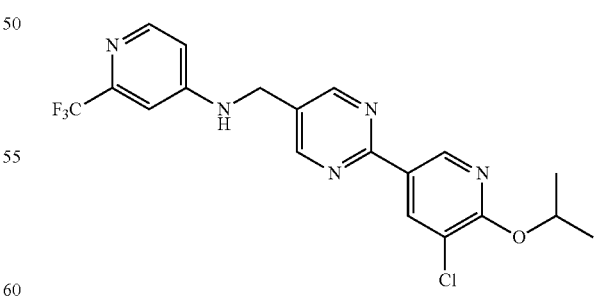

¹H NMR (500 MHz, Acetone) δ 9.10 (d, J=2.1 Hz, 1H), 8.94 (s, 2H), 8.65 (d, J=2.1 Hz, 1H), 8.25 (d, J=5.7 Hz, 1H), 7.12 (d, J=2.3 Hz, 1H), 6.95 (s, 1H), 6.87 (dd, J=5.7, 2.3 Hz, 1H), 5.49 (hept, J=6.2 Hz, 1H), 4.71 (d, J=5.9 Hz, 2H), 1.41 (d, J=6.2 Hz, 6H). LC-MS: m/z: 424 (M+H)⁺.

113

N-((5-(3-chloro-4-isopropoxyphenyl)pyridin-2-yl)methyl)-2-(trifluoromethyl)pyridin-4-amine (165)

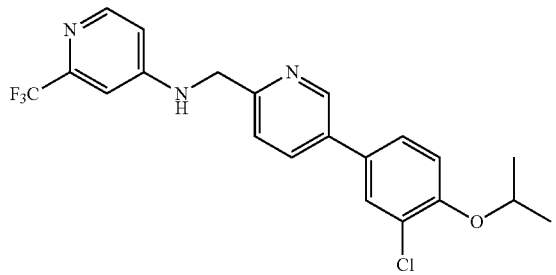 [SMILES: CC(C)Oc1ccc(-c2ccc(CNc3ccnc(C(F)(F)F)c3)nc2)cc1Cl]

$^{1}$H NMR (500 MHz, Acetone) δ 8.85 (d, J=2.2 Hz, 1H), 8.22 (d, J=5.7 Hz, 1H), 8.03 (dd, J=8.1, 2.4 Hz, 1H), 7.76 (d, J=2.3 Hz, 1H), 7.63 (dd, J=8.6, 2.3 Hz, 1H), 7.51 (d, J=8.1 Hz, 1H), 7.27 (d, J=8.6 Hz, 1H), 7.13 (d, J=1.7 Hz, 1H), 7.01 (s, 1H), 6.89-6.80 (m, 1H), 4.86-4.73 (m, 1H), 4.66 (d, J=5.7 Hz, 2H), 1.39 (d, J=6.0 Hz, 6H). LC-MS: m/z: 422 (M+H)$^{+}$.

2-chloro-N-((2-(3-chloro-4-isopropoxyphenyl)pyrimidin-5-yl)methyl)-6-trifluoromethyl)pyridin-4-amine (166)

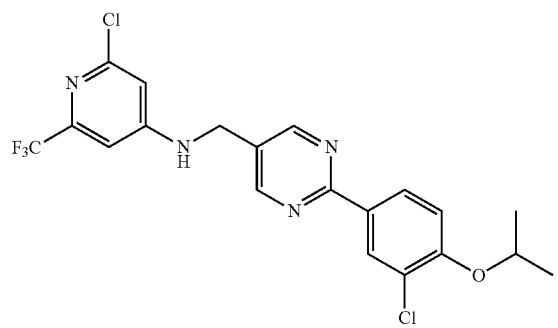 [SMILES: CC(C)Oc1ccc(-c2ncc(CNc3cc(Cl)nc(C(F)(F)F)c3)cn2)cc1Cl]

$^{1}$H NMR (500 MHz, Acetone) δ 8.77 (s, 2H), 8.33 (d, J=2.1 Hz, 1H), 8.24 (dd, J=8.7, 2.1 Hz, 1H), 7.12 (d, J=8.8 Hz, 2H), 7.00 (d, J=1.9 Hz, 1H), 6.76 (d, J=1.7 Hz, 1H), 4.74-4.64 (m, 1H), 4.58 (d, J=5.9 Hz, 2H), 1.26 (d, J=6.0 Hz, 6H). LC-MS: m/z: 457 (M+H)$^{+}$.

2-chloro-N-((2-(4-(2-fluorophenoxy)phenyl)pyrimidin-5-yl)methyl)-6-(trifluoromethyl)pyridin-4-amine (167)

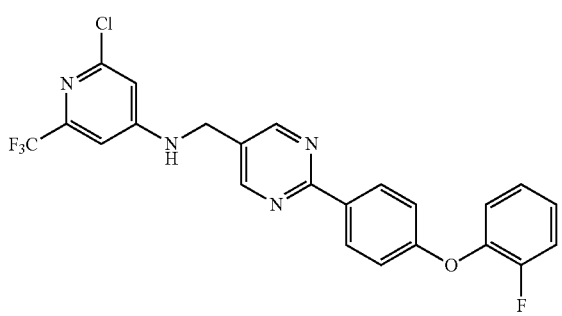 [SMILES: Fc1ccccc1Oc1ccc(-c2ncc(CNc3cc(Cl)nc(C(F)(F)F)c3)cn2)cc1]

114

$^{1}$H NMR (500 MHz, Acetone) δ 8.77 (s, 2H), 8.39-8.30 (m, 2H), 7.27-7.10 (m, 5H), 7.00 (d, J=1.9 Hz, 1H), 6.96-6.88 (m, 2H), 6.77 (d, J=1.7 Hz, 1H), 4.58 (d, J=5.8 Hz, 2H). LC-MS: m/z: 475 (M+H)$^{+}$.

2-chloro-N-((2-(4-isopropoxyphenyl)pyrimidin-5-yl)methyl)-6-(trifluoromethyl)pyridin-4-amine (168)

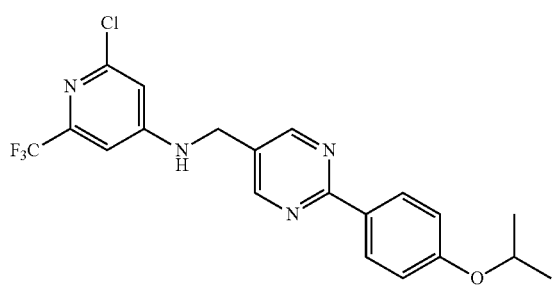 [SMILES: CC(C)Oc1ccc(-c2ncc(CNc3cc(Cl)nc(C(F)(F)F)c3)cn2)cc1]

$^{1}$H NMR (500 MHz, Acetone) δ 8.73 (s, 2H), 8.29-8.21 (m, 2H), 7.08 (s, 1H), 6.99 (d, J=1.9 Hz, 1H), 6.91-6.85 (m, 2H), 6.76 (d, J=1.8 Hz, 1H), 4.61 (dq, J=12.1, 6.0 Hz, 1H), 4.55 (d, J=5.8 Hz, 2H), 1.20 (d, J=6.0 Hz, 6H). LC-MS: m/z: 423 (M+H)$^{+}$.

2-chloro-N-((2-(4-chloro-3-nitrophenyl)pyrimidin-5-yl)methyl)-6-(trifluoromethyl)pyridin-4-amine (169)

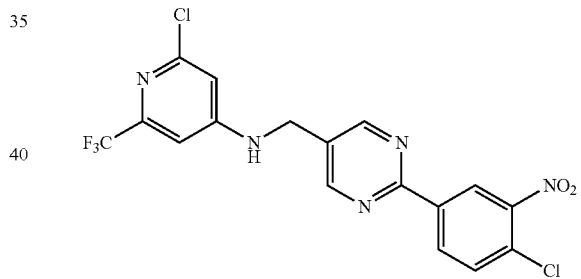

$^{1}$H NMR (500 MHz, Acetone) δ 8.90 (s, 2H), 8.85 (d, J=2.0 Hz, 1H), 8.59 (dd, J=8.5, 2.0 Hz, 1H), 7.76 (d, J=8.5 Hz, 1H), 7.20 (s, 1H), 7.01 (d, J=1.9 Hz, 1H), 6.77 (d, J=1.7 Hz, 1H), 4.67 (d, J=5.9 Hz, 2H). LC-MS: m/z: 444 (M+H)$^{+}$.

5-(3-fluorophenoxy)-2-(((2-(trifluoromethyl)pyridin-4-yl)thio)methyl)-1H-benzo[d]imidazole (170)

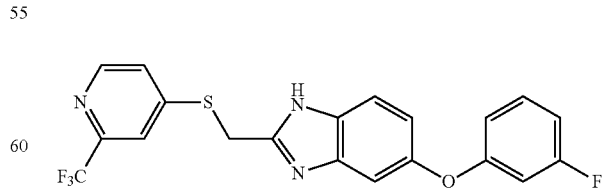

$^{1}$H NMR (500 MHz, DMSO-d6) δ 12.61 (s, 1H), 8.57 (d, J=5.3 Hz, 1H), 8.00 (d, J=1.9 Hz, 1H), 7.77 (dd, J=5.3, 1.9 Hz, 1H), 7.56 (d, J=8.7 Hz, 1H), 7.44-7.16 (m, 2H), 7.02-6.67 (m, 4H), 4.71 (s, 2H). LC.MS: m/z 420.3 (M+H)$^{+}$

115

6-(((5-(3-fluorophenoxy)-1H-benzo[d]imidazol-2-yl)methyl)thio)-2-(trifluoromethyl)pyrimidin-4-amine (171)

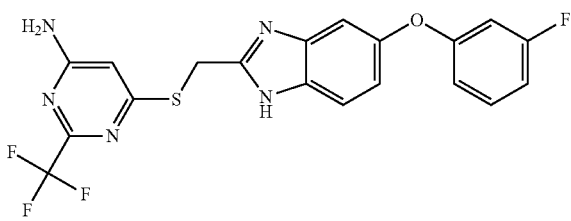 [SMILES: Nc1cc(SCc2nc3cc(Oc4cccc(F)c4)ccc3[nH]2)nc(C(F)(F)F)n1]

$^1$H NMR (500 MHz, DMSO-d6)) δ 12.48 (m, 1H), 7.67-7.44 (m, 3H), 7.44-7.08 (m, 2H), 7.02-6.69 (m, 4H), 6.59 (s, 1H), 4.60 (s, 2H). LC.MS: m/z 436.2 (M+H)$^+$

N-((5-(4-fluorophenoxy)-1H-benzo[d]imidazol-2-yl)methyl)-2-(trifluoromethyl)pyridin-4-amine (172)

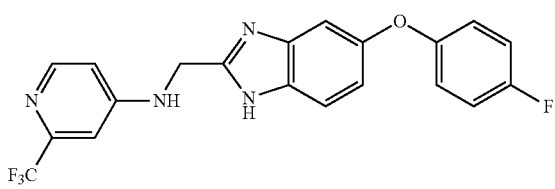 [SMILES: Fc1ccc(Oc2ccc3[nH]c(CNc4ccnc(C(F)(F)F)c4)nc3c2)cc1]

$^1$H NMR (500 MHz, DMSO-d6) 12.29 (s, 1H), 8.19 (d, J=5.7 Hz, 1H), 7.72 (app t, J=5.9 Hz, 1H), 7.54 (s, 1H), 7.24-6.93 (m, 6H), 6.88 (dd, J=11.0, 8.7 Hz, 1H), 6.81-6.75 (m, 1H), 4.62 (d, J=5.8 Hz, 2H). LC.MS: m/z 403.2 (M+H)$^+$ 5-(4-fluorophenoxy)-2-(((2-(trifluoromethyl)pyridin-4-yl)thio)methyl)-1H-benzo[d]imidazole (173)

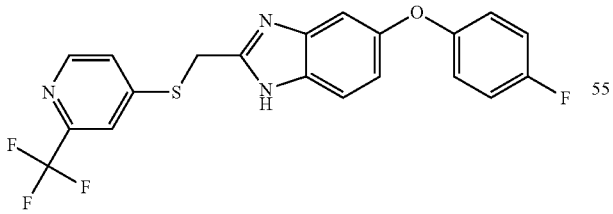

$^1$H NMR (500 MHz, DMSO-d6) δ 12.53 (s, 1H), 8.56 (d, J=5.3 Hz, 1H), 7.99 (d, J=1.7 Hz, 1H), 7.76 (dd, J=5.4, 1.8 Hz, 1H), 7.53 (d, J=8.2 Hz, 1H), 7.23-7.06 (m, 3H), 7.01 (dd, J=8.9, 4.5 Hz, 2H), 6.90 (d, J=8.6 Hz, 1H), 4.70 (d, J=1.3 Hz, 2H). LC.MS: m/z 420.1 (M+H)$^+$

116

6-(((5-(pyridin-3-yloxy)-1H-benzo[d]imidazol-2-yl)methyl)thio)-2-(trifluoromethyl)pyrimidin-4-amine (174)

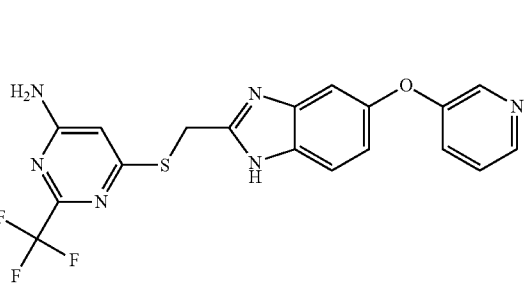 [SMILES: Nc1cc(SCc2nc3cc(Oc4cccnc4)ccc3[nH]2)nc(C(F)(F)F)n1]

$^1$H NMR (500 MHz, DMSO-d6) δ 12.47 (s, 1H), 8.40-8.26 (m, 2H), 7.54 (br s, 3H), 7.42-6.89 (m, 4H), 6.59 (s, 1H), 4.60 (s, 2H). LC.MS: m/z 419.1 (M+H)$^+$ 4-(((5-phenoxy-1H-benzo[d]imidazol-2-yl)methyl)thio)picolinonitrile (175)

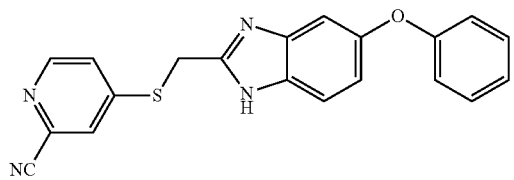 [SMILES: N#Cc1cc(SCc2nc3cc(Oc4ccccc4)ccc3[nH]2)ccn1]

1H NMR (500 MHz, DMSO-d6, 90° C.) δ 12.25 (s, 1H), 8.53 (d, J=5.4 Hz, 1H), 8.08 (d, J=1.9 Hz, 1H), 7.75 (dd, J=5.4, 2.0 Hz, 1H), 7.53 (s, 1H), 7.36 (app t, J=7.7 Hz, 2H), 7.10 (app q, J=10.6, 7.4 Hz, 2H), 6.99 (d, J=8.0 Hz, 2H), 6.92 (d, J=8.9 Hz, 1H), 4.65 (s, 2H). LC.MS m/z 359.2 (M+H)$^+$ 5-(phenylthio)-2-(((2-(trifluoromethyl)pyridin-4-yl)thio)methyl)-1H-benzo[d]imidazole (176) N

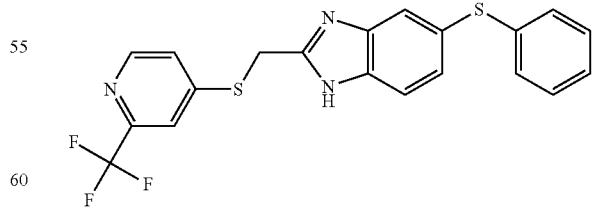

$^1$H NMR (500 MHz, DMSO-d$_6$) δ 8.56 (d, J=5.3 Hz, 1H), 7.92 (d, J=1.9 Hz, 1H), 7.73 (d, J=5.6 Hz, 1H), 7.63-7.51 (m, 2H), 7.41-7.07 (m, 6H), 4.68 (s, 2H). LC.MS m/z 418.2 (M+H)$^+$

5-phenoxy-2-(((2-(trifluoromethyl)pyridin-4-yl)oxy)methyl)-1H-benzo[d]imidazole (177)

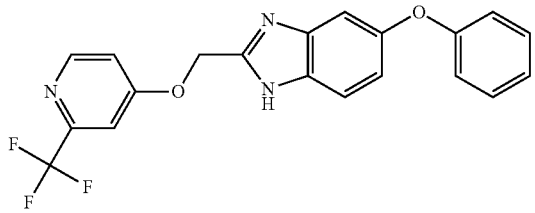 [SMILES: FC(F)(F)c1cc(OCc2nc3cc(Oc4ccccc4)ccc3[nH]2)ccn1]

$^1$H NMR (500 MHz, DMSO-d$_6$) δ 12.74 (s, 1H), 8.63 (d, J=5.7 Hz, 1H), 7.62 (d, J=2.4 Hz, 1H), 7.60 (s, 1H), 7.44 (dd, J=5.7, 2.5 Hz, 1H), 7.39-7.33 (m, 2H), 7.18 (s, 1H), 7.10 (app t, J=7.4 Hz, 1H), 6.97 (app t, J=7.7 Hz, 3H), 5.55 (s, 2H). LC.MS: m/z 386.3 (M+H)$^+$

2-(((2-chloropyridin-4-yl)thio)methyl)-5-phenoxy-1H-benzo[d]imidazole (178)

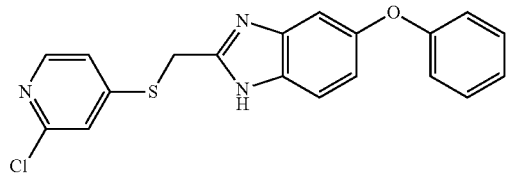 [SMILES: Clc1cc(SCc2nc3cc(Oc4ccccc4)ccc3[nH]2)ccn1]

Mixture of tautomers by NMR, ratio=1:0.7, shifts of major tautomer given:
$^1$H NMR (500 MHz, DMSO-d$_6$) δ 12.47 (s, 1H), 8.22 (s, 1H), 7.63 (d, J=1.7 Hz, 2H), 7.59 (d, J=8.8 Hz, 1H), 7.46 (d, J=1.7 Hz, 1H), 7.35 (s, 1H), 7.24-7.05 (m, 2H), 7.00-6.87 (m, 3H), 4.64 (s, 2H). LC.MS: m/z 368.2 (M+H)$^+$ methyl 4-((2-(((2-(trifluoromethyl)pyridin-4-yl)thio)methyl)-1H-benzo[d]imidazol-5-yl)oxy)benzonate (179)

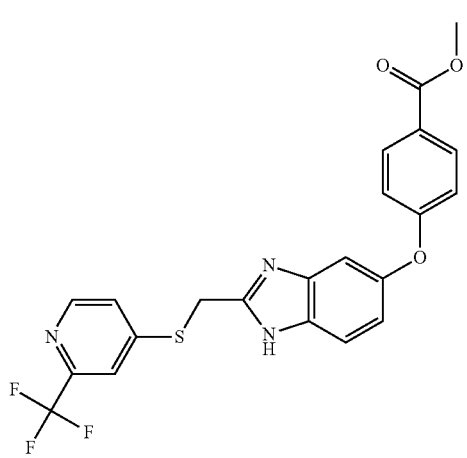 [SMILES: COC(=O)c1ccc(Oc2ccc3[nH]c(CSc4ccnc(C(F)(F)F)c4)nc3c2)cc1]

Mixture of tautomers by NMR, ratio=1:0.5, shifts of major tautomer given: H NMR (500 MHz, DMSO-d$_6$) δ 12.63 (s, 1H), 8.57 (d, J=5.3 Hz, 1H), 8.06-7.88 (m, 3H), 7.78 (dd, J=5.4, 1.9 Hz, 1H), 7.69-7.52 (m, 1H), 7.38-7.22 (m, 1H), 7.00 (d, J=8.4 Hz, 3H), 4.72 (s, 2H), 3.82 (s, 3H). LC.MS: m/z 460.2 (M+H)$^+$

6-chloro-5-fluoro-2-(((2-(trifluoromethyl)pyridin-4-yl)thio)methyl)-1H-benzo[d]imidazole (180)

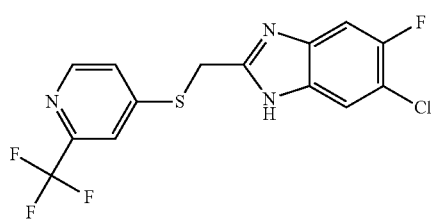 [SMILES: Fc1cc2nc(CSc3ccnc(C(F)(F)F)c3)[nH]c2cc1Cl]

$^1$H NMR (500 MHz, DMSO-d$_6$) δ 12.82 (s, 1H), 8.56 (d, J=5.3 Hz, 1H), 7.96 (d, J=1.8 Hz, 1H), 7.74 (dd, J=5.4, 1.9 Hz, 2H), 7.58 (d, J=9.7 Hz, 1H), 4.72 (s, 2H). LC.MS: m/z 362.1 (M+H)$^+$

6-((5-phenoxy-1H-benzo[d]imidazol-2-yl)methoxy)-2-(trifluoromethyl)pyrimidin-4-amine (181)

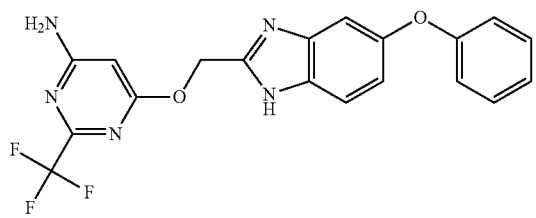

$^1$H NMR (500 MHz, DMSO-d$_6$, 90° C.) δ 12.32 (s, 1H), 7.56 (s, 1H), 7.41-7.30 (m, 2H), 7.16 (s, 1H), 7.12-7.07 (m, 3H), 7.00 (d, J=8.0 Hz, 2H), 6.97-6.91 (m, 1H), 6.04 (s, 1H), 5.52 (s, 2H). LC.MS: m/z 400.3 (M–H)

N-((5-phenoxy-1H-benzo[d]imidazol-2-yl)methyl)-2-(trifluoromethyl)pyridin-4-amine (182)

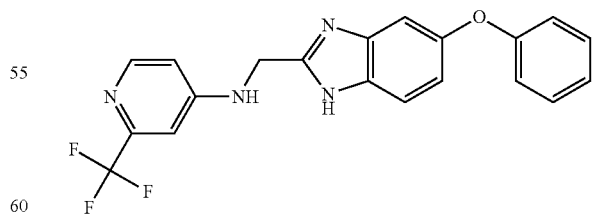

$^1$H NMR (500 MHz, DMSO-d6) δ 12.40 (s, 1H), 8.19 (d, J=5.7 Hz, 1H), 7.73 (app t, J=5.8 Hz, 1H), 7.53 (s, 1H), 7.40-7.31 (m, 2H), 7.28-7.04 (m, 3H), 6.95 (d, J=8.0 Hz, 2H), 6.93-6.86 (m, 1H), 6.79 (dd, J=5.9, 2.3 Hz, 1H), 4.63 (d, J=5.8 Hz, 2H). LC.MS: m/z 385.3 (M+H)$^+$ 4-(((5-phenoxy-1H-benzo[d]imidazol-2-yl)methyl)thio)-6-(trifluoromethyl)pyridin-2-amine (183)

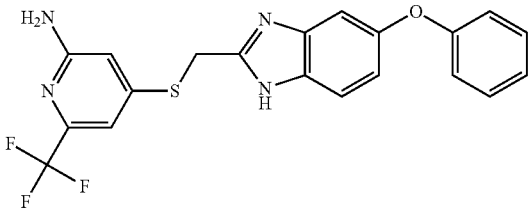

$^1$H NMR (500 MHz, DMSO-d$_6$) δ 12.51 (s, 1H) 7.53 (d, J=9.1 Hz, 1H), 7.35 (app q, J=7.4 Hz, 2H), 7.15-7.06 (m, 2H), 6.95 (d, J=4.9 Hz, 3H), 6.90 (d, J=9.1 Hz, 1H), 6.65 (d, J=4.1 Hz, 1H), 6.57 (d, J=4.6 Hz, 2H), 4.53 (d, J=5.0 Hz, 2H). LC.MS: m/z 417.3 (M+H)$^+$ 2-(((2-chloro-6-(trifluoromethyl)pyridin-4-yl)thio)methyl)-5-phenoxy-1H-benzo[d]imidazole (184)

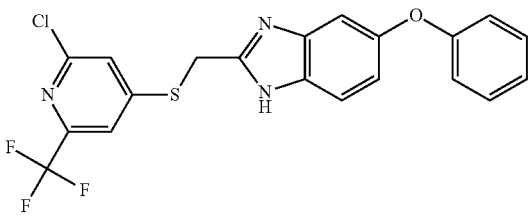 [SMILES: FC(F)(F)c1cc(SCc2nc3cc(Oc4ccccc4)ccc3[nH]2)cc(Cl)n1]

Mixture of tautomers by NMR, ratio=1:0.7, shifts of major tautomer given:
$^1$H NMR (500 MHz, DMSO-d$_6$) δ 12.50 (s, 1H), 8.06 (d, J=1.5 Hz, 1H), 7.98 (d, J=1.4 Hz, 1H), 7.56 (s, 1H), 7.35 (app t, J=7.8 Hz, 2H), 7.24-7.06 (m, 2H), 6.96 (s, 3H), 4.76 (s, 2H). LC.MS: m/z 436.6 (M+H)$^+$ Example 18: PqsR Inverse Agonistic Activity of Test Compounds (Reporter Gene Assay in E. coli)

Inhibition of pqsR-dependent gene expression of test compounds was determined in an E. coli based β-galactosidase reporter gene assay.[19] Escherichia coli DH5α was transfected with pEAL08-2 plasmid encoding pqsR under control of promoter tac and β-galactosidase reporter gene lacZ under control of promoter pqsA. Antagonistic effects of compounds were evaluated in the presence of/in competition to 50 nM PQS. A positive control was used to ensure the reliability of individual assays. First, PQS was diluted in methanol and added to the wells of a glass coated 96-deep-well plate, and the solvent was evaporated. Then, compounds were added in 5 μL DMSO to final concentrations of 0.001-10 μM. Overnight cultures of E. coli DH5αx pEAL08-2 were diluted 1:100 in LB medium with ampicillin (50 μg/ml) and incubated at 37° C. with shaking until it reached an OD600 of 0.2. Finally, 995 μL of culture was added to each well and the p-galactosidase activity was determined by ortho-nitrophenyl-p-galactoside conversion in permeabilized cells after a 2.5 h incubation period (37° C., 180 rpm). OD600, OD420, and OD550 were measured using POLARstar Omega (BMG Labtech, Ortenberg, Germany), and the activity was expressed as ratio of the slope of β-galactosidase activity between basal control (no PQS) and solvent control. IC$_{50}$ values of antagonists were determined by variation of the concentration of the test compounds.

Results of measurements of example test compounds are summarized below. The following Example Compounds showed an IC$_{50}$-value of equal to or below 50 nM towards PqsR-dependent transcription: 001, 004, 005, 007, 012, 016, 017, 018, 021, 022, 025, 026, 028, 030, 032, 033, 034, 035, 036, 037, 038, 041, 042, 043, 044, 047, 048, 049, 050, 051, 052, 053, 054, 061, 065, 071, 076, 077, 078, 080, 081, 082, 087, 088, 091, 092, 093, 094, 108, 125, 127, 128, 129, 130, 139, 141, 142, 143, 144, 145, 147, 148, 149, 152, 153, 154, 156, 157, 158, 159, 160, 161, 162, 164, 165, 166, 176, 182, 183, and 184.

The following Example Compounds showed an IC$_{50}$-value between 51 and 250 nM towards PqsR-dependent transcription: 003, 006, 008, 010, 011, 014, 015, 020, 024, 029, 040, 045, 046, 057, 058, 059, 063, 064, 066, 072, 073, 074, 083, 084, 089, 095, 096, 097, 098, 100, 101, 102, 104, 105, 106, 107, 112, 114, 117, 118, 119, 132, 178, and 181.

The following Example Compounds showed an IC$_{50}$-value between 251 nM and 1000 nM towards PqsR-dependent transcription: 002, 009, 013, 019, 023, 027, 039, 055, 056, 060, 062, 067, 075, 079, 085, 086, 090, 099, 109, 103, 110, 113, 115, 121, 120, 122, 123, 124, 126, 133, 134, 135, 136, 137, 138, 177, 179, and 180.

None of the tested compounds showed any bacteriostatic or bactericidal effects in the cell-based test system.

Example 19: Pyocyanin Assay

Inhibition of P. aeruginosa pyocyanin production by compounds was determined photometrically as described before.[20] In short, an overnight culture of PA14 in PPGAS medium was washed, diluted in medium to a start OD600 of 0.02, and incubated for 16 h (37° C., 200 rpm, relative humidity 75%) in the presence of test compounds. Then, cultures were extracted with chloroform and re-extracted with 0.2 M HCl. Protonated red colored pyocyanin was determined by measuring OD520 and normalizing to OD600.

Results of measurements of example test compounds are summarized below.

The following Example Compounds showed an IC$_{50}$-value of equal to or below 250 nM towards pyocyanin production: 001, 036, 042, 047, 048, 051, 052, 053, 065, 076, 077, 078, 081, 082, 087, 091, 094, 108, 127, 140, 141, 142, 143, 144, 145, 157, 158, 159, 160, 161, 162, 163, 166, 167, 168, 169, 170, 171, 183, and 184.

The following Example Compounds showed an IC$_{50}$-value between 251 and 1000 nM towards pyocyanin production: 005, 007, 017, 018, 022, 025, 028, 040, 046, 049, 054, 061, 071, 072, 074, 078, 092, 093, 095, 096, 097, 102, 105, 106, 107, 125, 129, 130, 132, 146, 147, 148, 150, 151, 153, 154, 156, 164, 165, 172, 173, 174, 175, 176, 178, and 182.

The following Example Compounds showed an IC$_{50}$-value 1001 and 5000 nM towards pyocyanin production: 004, 006, 012, 016, 021, 026, 045, 050, 063, 066, 073, 080, 103, 104, 112, 118, 119, 152, 177, 179, and 180.

Example 20: Biofilm Assays Regarding Effects on Biovolume and eDNA Content

Commonly used crystal violet (CV) assay procedures (PMID: 3905855, PMID: 10547784, PMID: 22488868)

were adapted for determination of biofilm mass. For the cultivation of biofilm in 96 well plates, the protocol described by Frei et al. (PMID: 22488868) was slightly modified by replacement of medium and *Pseudomonas* strain used. The experiment was performed using *P. aeruginosa* PA14 strain and PPGAS medium. CV staining was used to detect compound effects on the overall biofilm biomass. Impact on eDNA was assessed by incubation of biofilm with propidium iodine solution (0.05 mg ml$^{-1}$) for 24 h and detection of specific florescence at 620 nm (excitation 544 nm) after a thorough washing step with 18 MΩ H$_2$O. (PMID: 16430688)

Results of measurements of example test compounds are summarized below.

Example Compounds 001 and 017 showed an IC$_{50}$-value of equal to or below 500 nM towards biofilm formation.

Example Compound 001 showed an IC$_{50}$-value of below 500 nM towards eDNA content of the biofilm.

Example 21: Metabolic Stability Against Human Hepatic S9 Fraction

For the evaluation of combined phase I and phase II metabolic stability, the compound (1 μM) was incubated with 1 mg/mL pooled human liver S9 fraction (BD Gentest), 2 mM NADPH regenerating system, 1 mM UDPGA, 10 mM MgCl$_2$ and 0.1 mM PAPS at 37° C. for 0, 5, 15, 30 and 60 min. The metabolic stability of Testosterone (1 μM) and 7-hydroxycoumarin (1 μM) were determined in parallel to confirm the enzymatic activity of the S9 fraction. The incubation was stopped by precipitation of S9 enzymes with 2 volumes of cold acetonitrile containing internal standard (750 nM Diphenhydramine). Samples were stored on ice for 10 min and precipitated protein was removed by centrifugation (10 min, 4° C., 17,000 g). Concentration of the remaining test compound at the different time points was analyzed by LC-MS/MS (TSQ Quantum Access MAX, Thermo Fisher, Dreieich, Germany) and used to determine half-life (t/2).

Results of measurements of example test compounds are summarized below.

The following Example Compounds showed a half-life (t$_{1/2}$) above 60 min towards human hepatic S9 fraction: 054, 066, 071, 072, 076, 082, 087, 114, 118, 125, 132, and 134.

The following Example Compounds showed a half-life (t$_{1/2}$) between 41 min and 60 min towards human hepatic S9 fraction: 001, 017, and 081.

Example 22: Cytotoxicity Toward Human HepG2 and HEK293 Cell Lines

To obtain information regarding the toxicity of our compounds, their impact on the viability of human cells was investigated. HepG2 and HEK293 cells (2×10$^5$ per well) were seeded in 24-well, flat-bottomed culture plates. 24 h after seeding the cells the incubation was started by the addition of compounds in a final DMSO concentration of 1%. The living cell mass was determined 48 h after treatment with compounds by adding 0.1 volumes of 3-(4,5-dimethylthiazol-2-yl)-2,5-diphenyltetrazolium bromide (MTT) solution (5 mg per mL sterile PBS) (Sigma, St. Louis, MO) to the wells. After incubating the cells for 30 min at 37° C. (atmosphere containing 5% CO$_2$), MTT crystals were dissolved in a solution containing 10% SDS and 0.5% acetic acid in DMSO. The optical density (OD) of the samples was determined photometrically at 570 nm in a FLUOstar Omega plate reader (BMG labtech, Ortenberg, Germany). To obtain inhibition values for each sample, their ODs were related to those of DMSO controls.

Results of measurements of example test compounds are summarized below.

A. HepG2

The following Example Compounds showed an IC$_{50}$-value of equal to or above 50 μM towards HepG2 or at solubility maximum: 017, 054, 112, 118, 122, 123, 125, and 132.

The following Example Compounds showed an IC$_{50}$-value between 25 μM and 50 μM towards HepG2: 001, 022, 028, 071, 072, 077, 080, 097, 127, 128, and 129.

B. HEK293

The following Example Compounds showed an IC$_{50}$-value of equal to or above 50 μM towards HEK293 or at solubility maximum: 017, 054, 072, 112, 118, 122, 123, and 125.

The following Example Compounds showed an IC$_{50}$-value between 25 μM and 50 μM towards HEK293: 001, 012, 022, 028, 071, 080, 097, 127, 128, 129, and 132.

Example 23: Metabolic Stability Tests in Mouse Liver Microsomes (MLM)

For the evaluation of phase I metabolic stability, the compound (1 μM) was incubated with 0.5 mg/mL MLM (Corning) and 1 mM NADPH at 37° C. for 0, 5, 10, 15 and 30 min. The metabolic stability of Verapamil, Diphenhydramine and Benzydamine (1 μM each) were determined in parallel to confirm the enzymatic activity of the MLM. The incubation was stopped by addition of 2 volumes of acetonitrile containing internal standard (1 μM Leucine Enkephaline). Samples were centrifuged (15 min, 3,500 rpm). Concentration of the remaining test compound at the different time points was analyzed by HPLC-MS/MS and used to determine half-life (t$_{1/2}$).

Results of measurements of example test compounds are summarized below.

The following Example Compounds showed a half-life (t$_{1/2}$) above 60 min towards MLM: 004, 030, 032, 037, 050, 057, 068, 069, 072, 073, 076, 083, 088, 098, 106, 164, 165, and 181.

The following Example Compounds showed a half-life (t/2) between 31 min and 60 min towards MLM: 007, 022, 039, 040, 041, 045, 046, 048, 092, 093, 100, 102, 103, 105, 121, 129, 139, 144, 147, 160, 171, 172.

Example 24: Compound Solubility

Turbidimetric Aqueous Solubility at 37° C. for 2 h. Test compound was diluted in buffer to give a range of concentrations (typically 1, 3, 10, 30 and 100 μM, final DMSO concentration 1%) and incubated at 37° C. for 2 hr. Absorbance was measured at a wavelength of 620 nm and the solubility was estimated from the concentration of test compound that produces an increase in absorbance above the vehicle control (i.e., 1% DMSO in buffer). An estimated precipitation range (lower and upper bound) was provided as result.

Reference compound SPR-00305 showed a Turbidimetric Aqueous Solubility at 37° C. for 2 hr between 3 μM and 10 μM.

Example Compounds 017, 108, and 132 showed a Turbidimetric Aqueous Solubility at 37° C. for 2 hr between 10 μM and 30 μM.

Kinetic Turbidimetric Aqueous Solubility at room temperature for 5 min. Test compound was diluted in PBS buffer to give a range of concentrations (typically 0.4, 2, 4, 20, 40, 100, and 200 µM, final DMSO concentration 2%) and incubated at room temperature for 5 min. Absorbance was measured at a wavelength of 620 nm and the solubility was estimated from the concentration of test compound that produces an increase in absorbance above the vehicle control (i.e., 1% DMSO in buffer). Data was analyzed by fitting a four parameter sigmoidal function to the measured and normalized absorbances and AUC calculation providing access to Log S (decadic logarithm of the solubility).

The following Example Compounds showed a Kinetic Turbidimetric Aqueous Solubility at room temperature for 5 min above or equal to 100 µM: 035, 050, 073, 098, 121, 122, 134, and 174.

The following Example Compounds showed a Kinetic Turbidimetric Aqueous Solubility at room temperature for 5 min above 50 µM: 017, 039, 051, 102, 117, 120, 147, 180, 181, and 182.

The following Example Compounds showed a Kinetic Turbidimetric Aqueous Solubility at room temperature for 5 min above 25 µM: 004, 022, 031, 033, 036, 038, 040, 043, 045, 046, 047, 056, 069, 070, 072, 074, 079, 084, 095, 100, 101, 106, 108, 112, 119, 125, 128, 129, 144, 145, 153, 161, 164, 165, 166, 172, 173, 175, 177, and 183.

The following Example Compounds showed a Kinetic Turbidimetric Aqueous Solubility at room temperature for 5 min above 10 µM: 037, 041, 042, 044, 068, 077, 078, 080, 087, 096, 097, 104, 105, 107, 111, 127, 154, 157, 160, 171, 176, and 179.

REFERENCES

1. Frei R, Breitbach A S, Blackwell H E (2012) Angew Chem Int Ed Engl 51:5226-5229
2. Yang L, Rybtke M T, Jakobsen T H, Hentzer M, Bjarnsholt T, Givskov M, Tolker-Nielsen T (2009) Antimicrob Agents Chemother 53:2432-2443
3. O'Loughlin C T, Miller L C, Siryaporn A, Drescher K, Semmelhack M F, Bassler B L (2013) Proc Natl Acad Sci USA 110:17981-17986
4. Hentzer M, Wu H, Andersen J B, Riedel K, Rasmussen T B, Bagge N, Kumar N, Schembri M A, Song Z, Kristoffersen P, Manefield M, Costerton J W, Molin S, Eberl L, Steinberg P, Kjelleberg S, Hoiby N, Givskov M (2003) EMBO J 22:3803-3815
5. Hentzer M, Riedel K, Rasmussen T B, Heydorn A, Andersen J B, Parsek M R, Rice S A, Eberl L, Molin S, Hoiby N, Kjelleberg S, Givskov M (2002) Microbiology 148:87-102
6. Rasmussen T B, Skindersoe M E, Bjarnsholt T, Phipps R K, Christensen K B, Jensen P O, Andersen J B, Koch B, Larsen T O, Hentzer M, Eberl L, Hoiby N, Givskov M (2005) Microbiology 151:1325-1340
7. Jakobsen T H, van G M, Phipps R K, Shanmugham M S, Christensen L D, Alhede M, Skindersoe M E, Rasmussen T B, Friedrich K, Uthe F, Jensen P O, Moser C, Nielsen K F, Eberl L, Larsen T O, Tanner D, Hoiby N, Bjarnsholt T, Givskov M (2012) Antimicrob Agents Chemother 56:2314-2325
8. Hinsberger S, de Jong J C, Groh M, Haupenthal J, Hartmann R W (2014) Eur J Med Chem 76C:343-351
9. Storz M P, Brengel C, Weidel E, Hoffmann M, Hollemeyer K, Steinbach A, Muller R, Empting M, Hartmann R W (2013) ACS Chem Biol 8:2794-2801
10. Sahner J H, Brengel C, Storz M P, Groh M, Plaza A, Muller R, Hartmann R W (2013) J Med Chem 56:8656-8664
11. Weidel E, de Jong J C, Brengel C, Storz M P, Braunshausen A, Negri M, Plaza A, Steinbach A, Muller R, Hartmann R W (2013) J Med Chem 56:6146-6155
12. Calfee M W, Coleman J P, Pesci E C (2001) Proc Natl Acad Sci USA 98:11633-11637
13. Pistorius D, Ullrich A, Lucas S, Hartmann R W, Kazmaier U, Muller R (2011) Chembiochem 12:850-853
14. Lesic B, Lepine F, Deziel E, Zhang J, Zhang Q, Padfield K, Castonguay M H, Milot S, Stachel S, Tzika A A, Tompkins R G, Rahme L G (2007) PLoS Pathog 3:1229-1239
15. Storz M P, Maurer C K, Zimmer C, Wagner N, Brengel C, de Jong J C, Lucas S, Musken M, Haussler S, Steinbach A, Hartmann R W (2012) J Am Chem Soc 134:16143-16146
16. Coleman J P, Hudson L L, McKnight S L, Farrow J M, III, Calfee M W, Lindsey C A, Pesci E C (2008) J Bacteriol 190:1247-1255
17. Klein T, Henn C, de Jong J C, Zimmer C, Kirsch B, Maurer C K, Pistorius D, Muller R, Steinbach A, Hartmann R W (2012) ACS Chem Biol 7:1496-1501
18. Zender M, Klein T, Henn C, Kirsch B, Maurer C K, Kail D, Ritter C, Dolezal O, Steinbach A, Hartmann R W (2013) J Med Chem 56:6761-6774
19. Lu C, Kirsch B, Zimmer C, de Jong J C, Henn C, Maurer C K, Musken M, Haussler S, Steinbach A, Hartmann R W (2012) Chem Biol 19:381-390
20. Lu C, Maurer C K, Kirsch B, Steinbach A, Hartmann R W (2014) Angew Chem Int Ed Engl 53:1109-1112
21. Ilangovan A, Fletcher M, Rampioni G, Pustelny C, Rumbaugh K, Heeb S, Camara M, Truman A, Chhabra S R, Emsley J, Williams P (2013) PLoS Pathog 9:e1003508
22. Maurer C K, Steinbach A, Hartmann R W (2013) J Pharm Biomed Anal 86C:127-134
23. Zhang Y, Miller R M (1992) Appl Environ Microbiol 58:3276-3282

Overall, the results presented herein show that compounds of the invention are anti-pathogenic compounds exhibiting both anti-virulence and anti-biofilm activity allowing for an effective treatment of bacterial infections and their application in in vivo.

The features of the present invention disclosed in the specification and/or the claims may both separately and in any combination thereof be material for realizing the invention in various forms thereof.

The invention claimed is:
1. A compound having the formula (I):

or a pharmacologically acceptable salt thereof,
wherein
A represents a group:

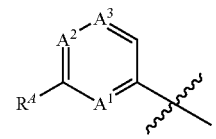

wherein
said group A is as defined in (i) or (ii):
(i) $A^1$ is CH; $A^2$ is N;
$A^3$ is N or C—$R^{A3}$,
$R^{A3}$ represents a hydrogen atom, a halogen atom, $CF_3$, CN, C(=O)$NH_2$, C(=O)OH, $CH_2$OH, $CH_2NH_2$, OH, OMe, or $NH_2$; and
$R^A$ represents $CF_3$, CN, Cl, $NO_2$ or F; or
(ii) $A^1$ is N; $A^2$ is N; $A^3$ is C—$NH_2$; and $R^A$ represents $CF_3$, CN, Cl, $NO_2$ or F;
L is a group represented by formula (L-1) or (L-2):

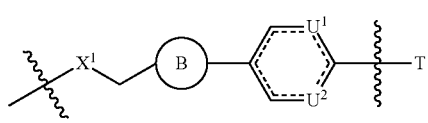
(L-1)

wherein
$X^1$ is NH or S;
ring B is a partially unsaturated or aromatic, 5-membered heterocyclic ring represented by formula (B-1) or 6-membered heterocyclic ring represented by formula (B-2):

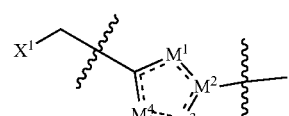
(B-1)

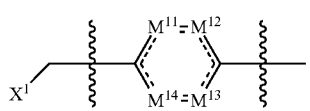
(B-2)

wherein
the ring represented by formula (B-1) is:
(i) a ring, wherein $M^1$ is CH; $M^2$ is C or N; and each of $M^3$ and $M^4$, independently of one another, is N or NH; or
(ii) a ring, wherein $M^1$ is S; $M^2$ is C; $M^3$ is N; and $M^4$ is CH;
$M^{11}$, $M^{12}$, $M^{13}$, and $M^{14}$ each, independently of one another, represents CH or N;
at least one of $M^{11}$, $M^{12}$, $M^{13}$, and $M^{14}$ being a group with a heteroatom as defined above;
$U^1$ and $U^2$ each, independently of one another, represents N or C(R');
$R^1$, at each occasion independently, represents a hydrogen atom, a halogen atom, OH, CN, $CF_3$, $CH_2$—OH, $OCH_3$, $OCF_3$; or an alkyl, alkenyl, alkynyl, heteroalkyl, cycloalkyl, heterocyclo-alkyl, alkylcycloalkyl, heteroalkylcycloalkyl, aryl, heteroaryl, aralkyl or heteroaralkyl group;
each " ---- ", independently of one another, represents a single bond or a double bond, wherein at least one " --- " in each of the rings of formulae (L-1), (B-1) and (B-2) is a double bond;

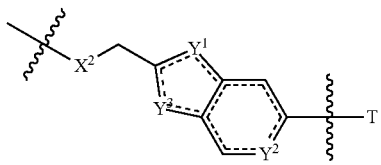
(L-2)

wherein
$X^2$ is NH, O or S;
$Y^1$ represents N, NH, S or O;
$Y^2$ represents N or C($R^{11}$);
$Y^3$ represents N or NH;
$R^{11}$ represents a hydrogen atom, a halogen atom, OH, CN, $CF_3$, $CH_2$—OH, $OCH_3$, $OCF_3$; or an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group;
each " ---- " independently of one another, represents a single bond or a double bond, wherein at least one " --- " in the ring of formula (L-2) is a double bond;
T is $R^2$ or a group: —Y—$R^3$, wherein
$R^2$ is a hydrogen atom, a halogen atom, CN, $CF_3$, $CH_2$—OH; $NR^{T1}R^{T2}$; or an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which groups may optionally be substituted;
$R^{T1}$ and $R^{T2}$ each, independently of one another, represents a hydrogen atom or a ($C_1$-$C_3$)alkyl group, which may be substituted by one or more, identical or different, group(s) selected from a halogen atom, OH, =O, and $NH_2$;
Y is —O— or —S—; and
$R^3$ is a hydrogen atom; or an alkyl, alkenyl, alkynyl, heteroalkyl, cycloalkyl, heterocyclo-alkyl, alkylcycloalkyl, heteroalkylcycloalkyl, aryl, heteroaryl, aralkyl or heteroaralkyl group, all of which groups may optionally be substituted.

2. The compound according to claim 1, or a pharmacologically acceptable salt thereof, wherein A is a group selected from:

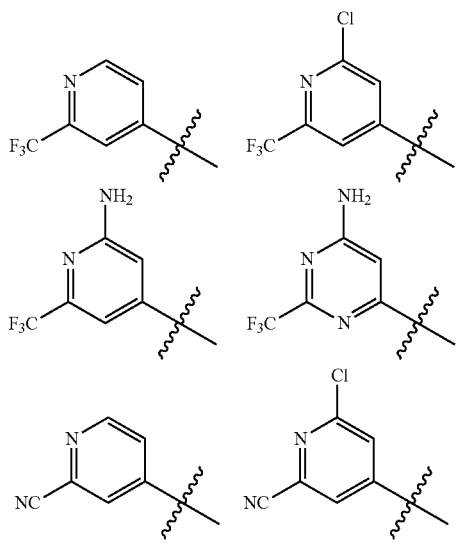

-continued

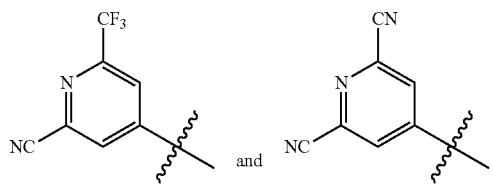 and 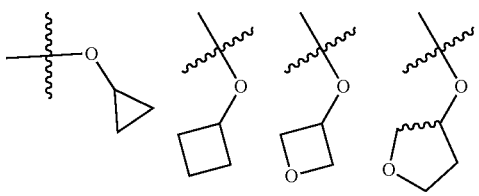

3. The compound according to claim 1, or a pharmacologically acceptable salt thereof, wherein L is a group of formula (L-1).

4. The compound according to claim 3, or a pharmacologically acceptable salt thereof, wherein the ring B is a ring represented by formula (B-1).

5. The compound according to claim 3, or a pharmacologically acceptable salt thereof, wherein the ring B is a ring represented by formula (B-2).

6. The compound according to claim 5, or a pharmacologically acceptable salt thereof, wherein the ring represented by formula (B-2) is:

(i) a ring, wherein $M^{11}$ is N and each of $M^{12}$, $M^{13}$ and $M^{14}$ is CH; or (ii) a ring, wherein $M^{11}$ and $M^{14}$ are CH, and $M^{12}$ and $M^{13}$ are N.

7. The compound according to claim 1, or a pharmacologically acceptable salt thereof, wherein L is a group of formula (L-2).

8. The compound according to claim 7, or a pharmacologically acceptable salt thereof, wherein the group represented by formula (L-2) is a group selected from:

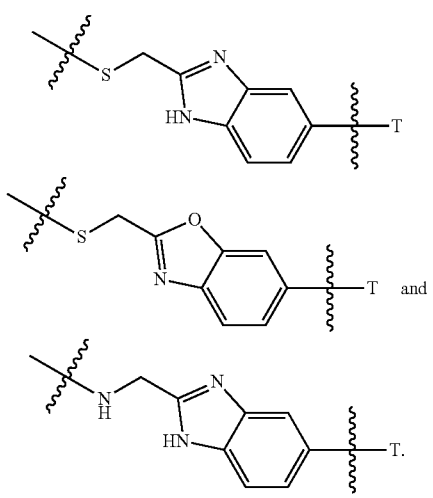

9. The compound according to claim 1, or a pharmacologically acceptable salt thereof, wherein T is selected from:

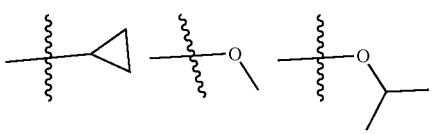

-continued and Cl.

10. The compound according to claim 1, or a pharmacologically acceptable salt thereof, wherein the compound is selected from the group consisting of:

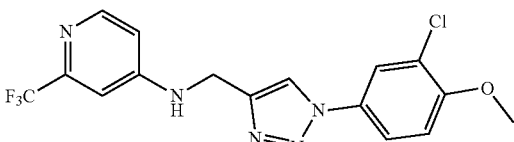

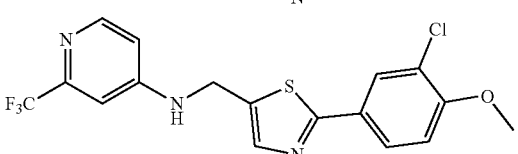

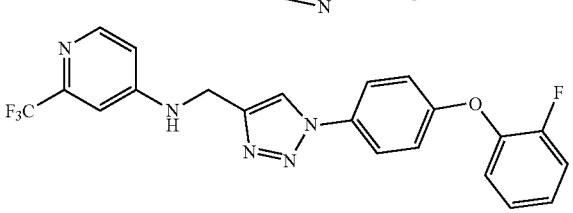

-continued
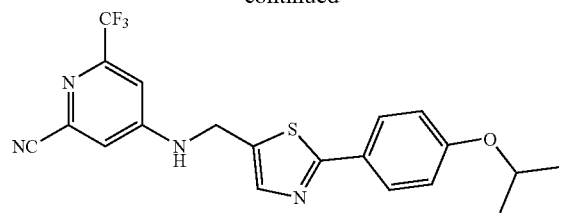
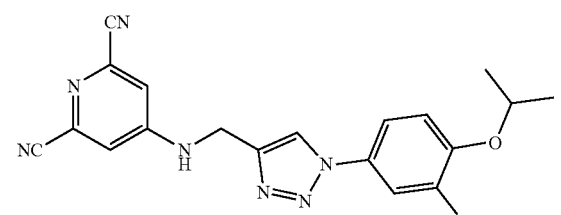
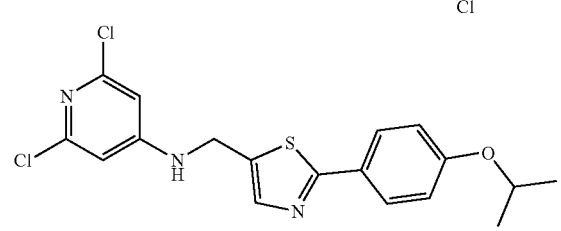
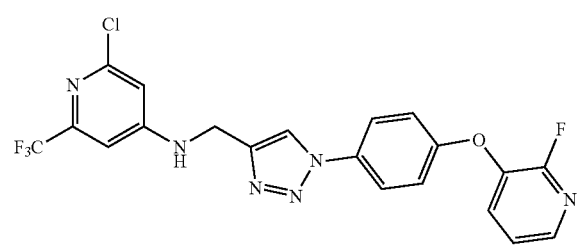
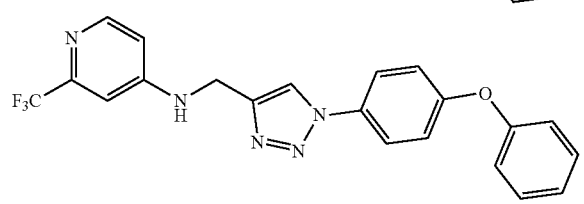
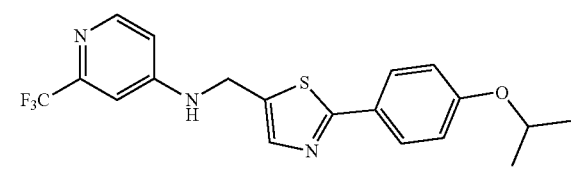
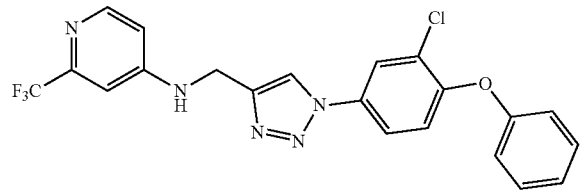
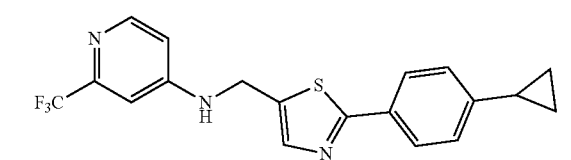
-continued
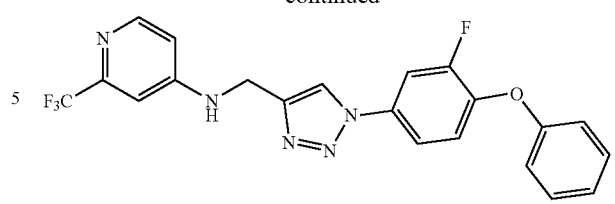
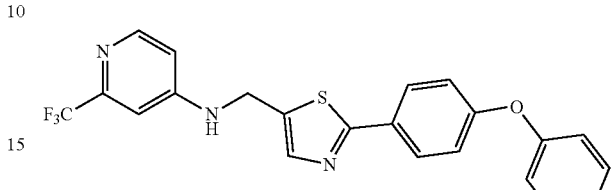
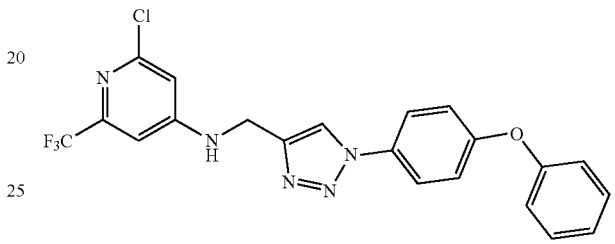
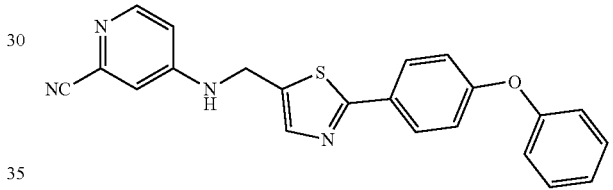
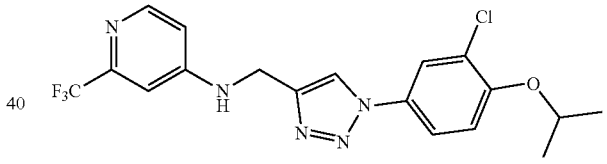
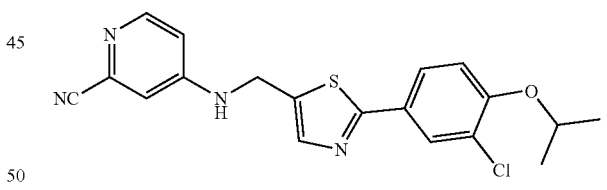
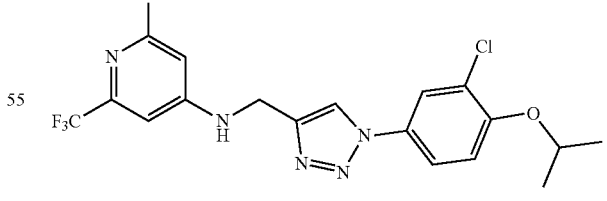
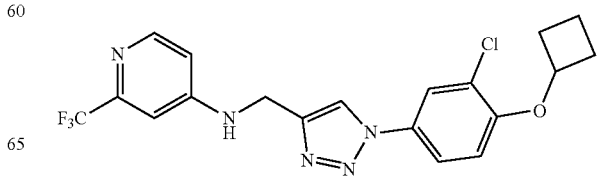

-continued
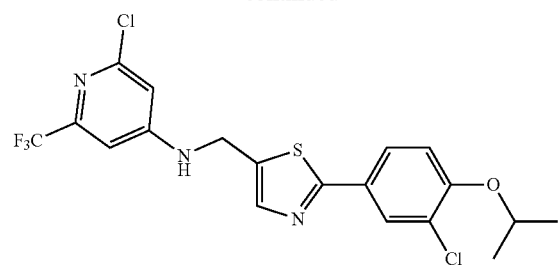
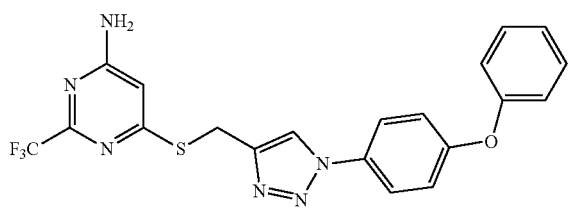
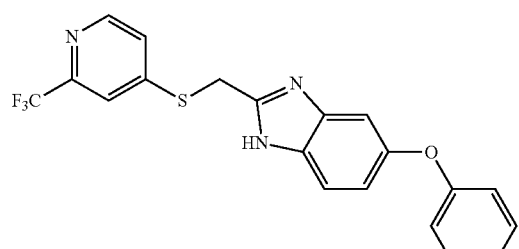
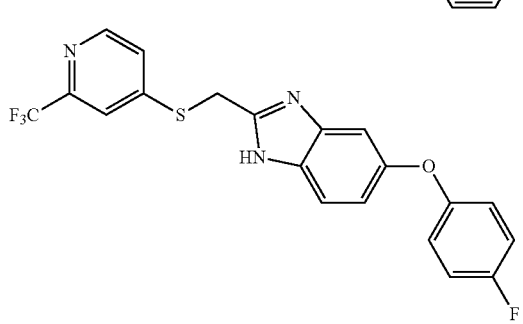
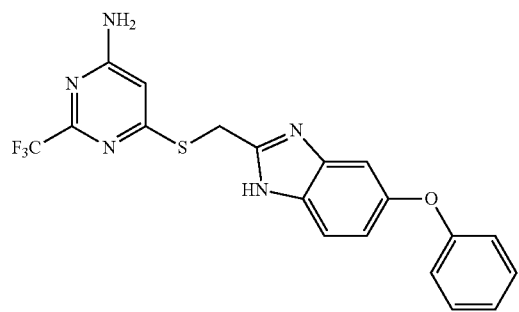
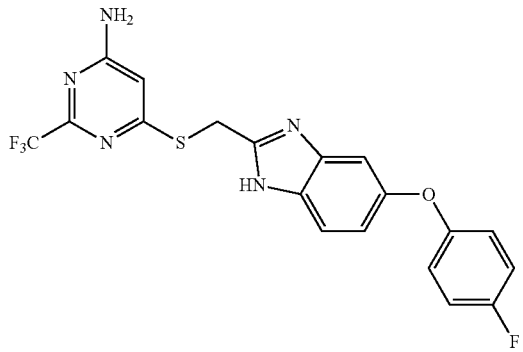
-continued
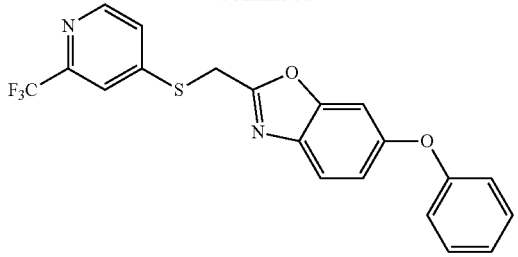
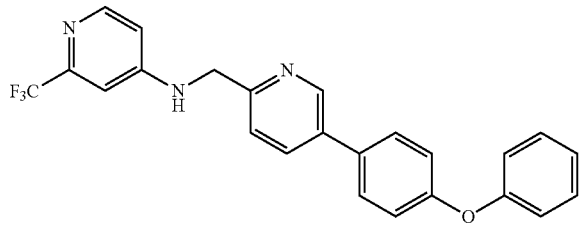
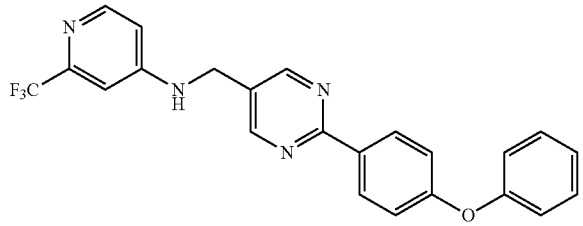
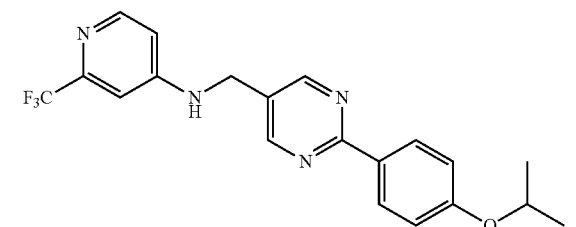
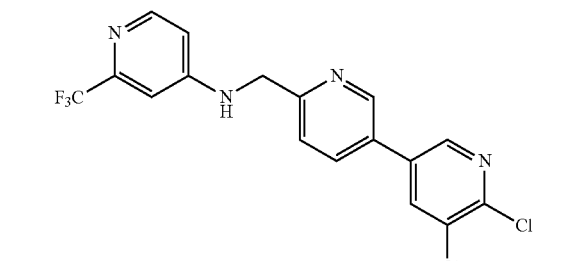
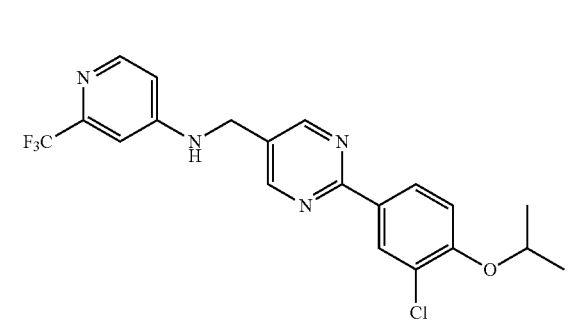

-continued

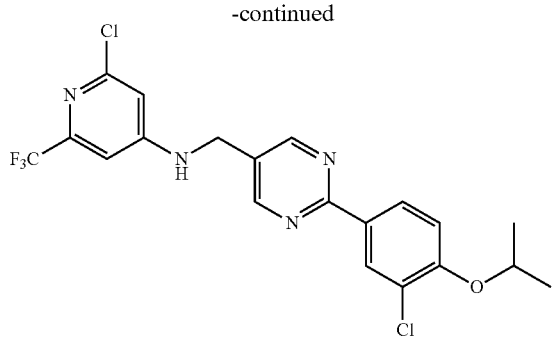

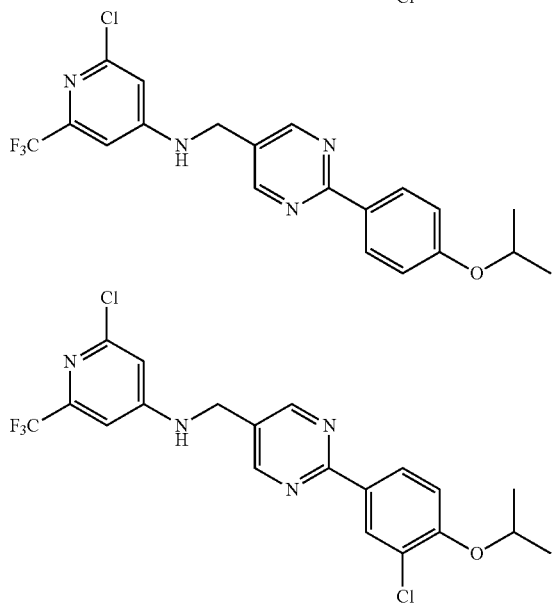

-continued
and

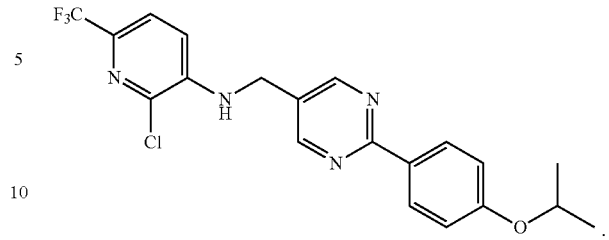

11. A pharmaceutical composition that comprises one or more compound(s) according to claim 1 and, optionally, at least one carrier substance, excipient and/or adjuvant.

12. A combination preparation comprising at least one compound according to claim 1, and at least one antibiotic as a further active ingredient.

13. A coating for medicinal devices containing at least one compound according to claim 1.

14. A method for treating a respiratory condition in a subject, the method comprising:
 administering to said subject an effective amount of the compound according to claim 1, thereby treating the respiratory condition.

15. The method of claim 14 wherein the respiratory condition is cystic fibrosis (CF).

16. The method of claim 14 wherein the respiratory condition is chronic obstructive pulmonary disease (COPD).

17. The method of claim 14 wherein the respiratory condition is primary ciliary dyskinesia.

* * * * *